US012195481B2

(12) United States Patent
Takiguchi et al.

(10) Patent No.: US 12,195,481 B2
(45) Date of Patent: Jan. 14, 2025

(54) PROCESS FOR PREPARING 7H-PYRROLO[2,3-D]PYRIMIDINE DERIVATIVES AND SYNTHETIC INTERMEDIATES THEREOF

(71) Applicants: JAPAN TOBACCO INC., Tokyo (JP); LEO Pharma A/S, Ballerup (DK)

(72) Inventors: Hiromu Takiguchi, Takatsuki (JP); Akinobu Higashi, Takatsuki (JP); Takashi Inaba, Takatsuki (JP); Takashi Watanabe, Takatsuki (JP); Tsubasa Takeichi, Takatsuki (JP); Anders Klarskov Petersen, Ballerup (DK); Per Vedsoe, Ballerup (DK); Kim Lebek Jensen, Ballerup (DK); Jan Bornholdt, Ballerup (DK); Soren Ebdrup, Ballerup (DK)

(73) Assignees: Japan Tobacco Inc., Tokyo (JP); Leo Pharma A/S, Ballerup (DK)

( * ) Notice: Subject to any disclaimer, the term of this patent is extended or adjusted under 35 U.S.C. 154(b) by 0 days.

(21) Appl. No.: 18/136,661

(22) Filed: Apr. 19, 2023

(65) Prior Publication Data
US 2024/0140967 A1    May 2, 2024

Related U.S. Application Data

(63) Continuation of application No. 16/470,888, filed as application No. PCT/JP2017/045729 on Dec. 20, 2017, now Pat. No. 11,673,900.

(30) Foreign Application Priority Data

Dec. 21, 2016   (JP) .................................. 2016247607

(51) Int. Cl.
| C07D 519/00 | (2006.01) |
| C07C 271/22 | (2006.01) |
| C07D 487/10 | (2006.01) |
| C07C 269/00 | (2006.01) |
| C07C 269/06 | (2006.01) |
| C07D 205/08 | (2006.01) |
| C07D 307/33 | (2006.01) |
| C07D 403/06 | (2006.01) |
| C07D 491/10 | (2006.01) |
| C07D 491/107 | (2006.01) |

(52) U.S. Cl.
CPC .......... C07D 519/00 (2013.01); C07C 271/22 (2013.01); C07D 487/10 (2013.01); *C07B 2200/13* (2013.01)

(58) Field of Classification Search
CPC ............ C07B 2200/13; C07B 2200/07; C07D 519/00; C07D 487/10; C07D 205/08; C07D 307/33; C07D 403/06; C07D 491/107; C07D 491/10; C07C 271/22; C07C 269/00; C07C 269/06
See application file for complete search history.

(56) References Cited

U.S. PATENT DOCUMENTS

| 8,609,647 | B2* | 12/2013 | Noji ......................... A61P 1/04 |
|           |     |         | 514/210.16 |
| 2004/0053331 | A1 | 3/2004 | Kahn et al. |
| 2006/0128789 | A1 | 6/2006 | Chand et al. |
| 2008/0076753 | A1 | 3/2008 | Xiang et al. |
| 2011/0136778 | A1 | 6/2011 | Satoru et al. |
| 2014/0256702 | A1 | 9/2014 | Fenster et al. |
| 2019/0062346 | A1 | 2/2019 | Yamasaki et al. |

FOREIGN PATENT DOCUMENTS

| CN | 103570601 | 2/2014 |
| EP | 2460806 | 6/2012 |
| EP | 3321271 | 5/2018 |
| JP | 2010504351 | 2/2010 |
| JP | 2016512195 | 4/2016 |
| WO | WO2004/108731 | 12/2004 |
| WO | WO2008/036755 | 3/2008 |
| WO | WO2011/013785 | 3/2011 |
| WO | WO2012/098033 | 7/2012 |
| WO | WO2014/138053 | 9/2014 |
| WO | WO2017/006968 | 1/2017 |
| WO | WO2018/117152 | 6/2018 |
| WO | WO2018/117153 | 6/2018 |

OTHER PUBLICATIONS

Alcaide et al., "Synthesis of Functionalized Azetidines through Chemoselective Zinc-Catalyzed Reduction of B-Lactams with Silanes", Adv. Synth. Catal., 2013, 355:2089-2094.
Arnett et al., "A Spectacular Example of the Importance of Rotational Barriers: The Ionization of Meldrum's Acid", Journal of American Chem. Soc., 1987, 109:809-812.
Bańkowski et al., "Synthesis, biological activity and resistance to proteolytic digestion of new cyclic dermorphin/deltorphin analogues," European Journal of Medicinal Chemistry, (2013), 63:457-467.
Baxendale et al., "Application of Polymer-Supported Enzymes and Reagents in the Synthesis of y-Aminobutyric Acid (GABA) Analogues", Letter from University of Cambridge, Dept. of Chemistry, Jul. 2002, 1641-1644.

(Continued)

*Primary Examiner* — Sun Jae Yoo
(74) *Attorney, Agent, or Firm* — Fish & Richardson P.C.

(57) ABSTRACT

The present invention provides processes for preparing 7H-pyrrolo[2,3-d]pyrimidine derivatives, which are useful as a Janus kinase (JAK) inhibitor, intermediates thereof, and processes for preparing the intermediates. The present invention provides processes for preparing 3-[(3S,4R)-3-methyl-6-(7H-pyrrolo[2,3-d]pyrimidin-4-yl)-1,6-diazaspiro[3.4]octan-1-yl]-3-oxopropanenitrile using salts of (3S,4R)-1-benzyl-3-methyl-1,6-diazaspiro[3.4]octane with organic acids.

6 Claims, 15 Drawing Sheets

(56) References Cited

OTHER PUBLICATIONS

Berge, et al., "Pharmaceutical Salts," Journal of Pharmaceutical Sciences, Jan. 1977, 66(1):1-19.
Bhattacharya et al., "Polymorphism in Pharmaceutical Solids", Drugs and the Pharmaceutical Sciences, Second Edition, 2009, 192:334.
Bhattacharya et al., "Thermoanalytical and Crystallographic Methods", Polymorphism in Pharmaceutical Solids, 2009, p. 334.
Chigorina et al., "1-Cyanoacetyl-3,5-dimethylpyrazole", Synlett Spotlight 458, 2014, 453-454.
Drouillat et al., "Insight into the Regioselectivity of Nucleophilic Ring-Opening of Azetidinium Ions Containing Quaternary Carbon Atoms," European Journal of Organic Chemistry, (2012), 2012(30):6005-6012.
English translation of International Preliminary Report on Patentability in International Application No. PCT/JP2017/045729.
EPO Partial Supplementary European Search Report in European Application No. 16821437.7, dated Jan. 31, 2019, 11 pages.
Extended European Search Report in EP Application No. 17885424.6, dated Sep. 24, 2020, 14 pages.
Handbook, Hirayama et al., Organic Compound Crystal Production, 2008, pp. 10, 11, 57-72 and 78-81 (English Summary).
Igarashi et al., "Transition-Metal Complex-Catalyzed Reduction of Amides with Hydrosilanes: A Facile Transformation of Amides to Amines", Tetrahedron Letters, 2001, 42:1945-1947.
International Search Report in International Application No. PCT/JP2016/070046, dated Sep. 27, 2016, 2 pages (English Translation).
International Search Report in International Application No. PCT/JP2017/045729, dated Mar. 20, 2018, 5 pages (English Translation).
Katamoto et al., "Novel Probes Showing Specific Fluorescence Enhancement on Binding to a Hexahistidine Tag", Chemistry—A European Journal, 2008, 14(26):8004-8012.
Kawabata et al., "Stereochemical Diversity in Asymmetric Cyclization via Memory of Chirality," Journal of the American Chemical Society, Nov. 9, 2006, 128(48):15394-15395.
Kunz et al., "Formation of 4-, 5- and 6-membered heterocycles by ambidoselective cyclization of enolate anions," Helvetica Chimica Acta, (1979), 62(3):872-881 (with English Abstract).
Loh et al., "A remote substituent as a control element in indium-mediated allylation reactions in aqueous media: highly diastereoselective synthesis of 1,3-amino alcohols," Tetrahedron Letters, (2000), 41:6511-6515.

Majer et al., "Synthesis and Absolute Configuration of 1,7-diazaspiro[4,4]nonane-2,6-dione," Collection of Czechoslovak Chemical Communications, (1982), 47(3):950-960.
More et al., "Inhibition of Glyoxalase I: The First Low-Nanomolar Tight-Binding Inhibitors", Journal of Medicinal Chemistry, 2009, 52(15):4650-4656.
Núñez-Villanueva et al., "Quaternary α,α-2-Oxoazepane α-Amino Acids: Synthesis from Ornithine-Derived β-Lactams and Incorporation into Model Dipeptides," Journal of Organic Chemistry, (2011), 76:6592-6603.
Ojima et al., "Azetidines and Bisazetidines: Their Synthesis and Use as the Key Intermediates to Enantiomerically Pure Diamines, Amino Alcohols, and Polyamines", Journal of Organic Chemistry, 1991, 56:5263-5277.
Perez-Faginas et al., "Exceptional Stereoselectivity in the Synthesis of 1, 3, 4-Trisubstituted 4-Carboxy B-Lactam Derivatives from Amino Acids", Organic Letters, Mar. 2007, 9(8):1593-1596.
Perez-Faginas et al., "Synthesis and SAR studies on azetidine-containing dipeptides as HCMV inhibitors", Bioorganic & Medicinal Chemistry, 2011, pp. 1155-1161.
Ravinder et al., "Amide Activation by TMSCI: Reduction of Amides to Amines by LiAlH4 under Mild Conditions", Tetrahedron Letters, 2013, 54:4908-4913.
Stacy et al., "Synthesis and biological evaluation of triazole-containng N-acyl homoserine lactones as quorum sensing modulators", Org. Biomol. Chem., Feb. 2013, 11(6):938-954.
Talbot et al., "Synthesis of 4-Aminobutyric Acid and 2,4-Diaminobutyric Acid from Butyrolactone", Canadian Journal of Chemistry, Apr. 1958, 36(4):593-596.
Van Nispen et al., "Synthesis and Biological Activities of Two Acth-Analogues Containing L-Norarginine in Position 8," International Journal of Peptide and Protein Research, (1977), 9(3):193-202.
Wiberg et al., "Acidity of (Z)- and €-Methyl Acetates: Relationship to Meldrum's Acid", Journal of American Chem. Soc., 1988, 110:1872-1874.
Written Opinion in International Application No. PCT/JP2016/070046, dated Sep. 27, 2016, 7 pages (English Translaton).
Written Opinion in International Application No. PCT/JP2017/045729, dated Mar. 20, 2018, 7 pages (Machine Translation).
Yamashita et al., "Effective Route to Azetidines from Azetidin-2-ones Using Hydroalanes as Specific Reducing Agents", American Chemical Society, 1983, 105:6339-6342.

* cited by examiner

[Fig. 9]
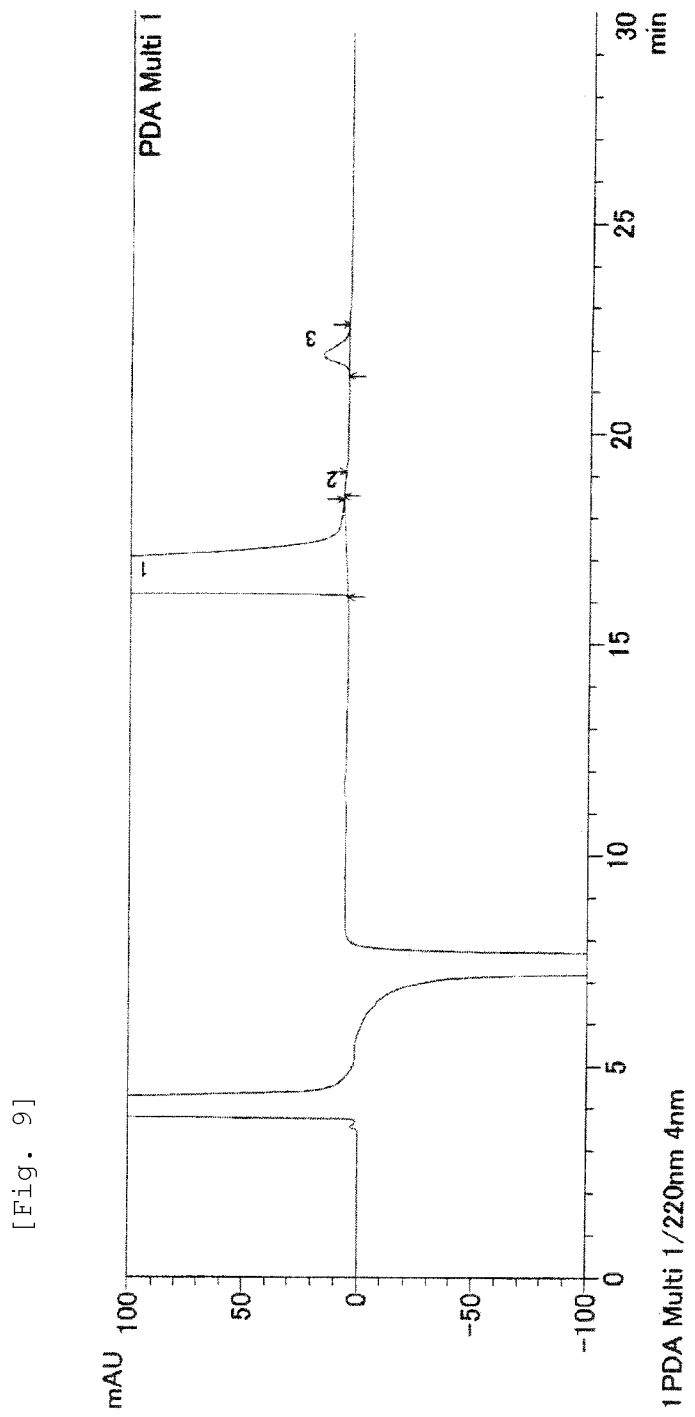

[Fig. 10]
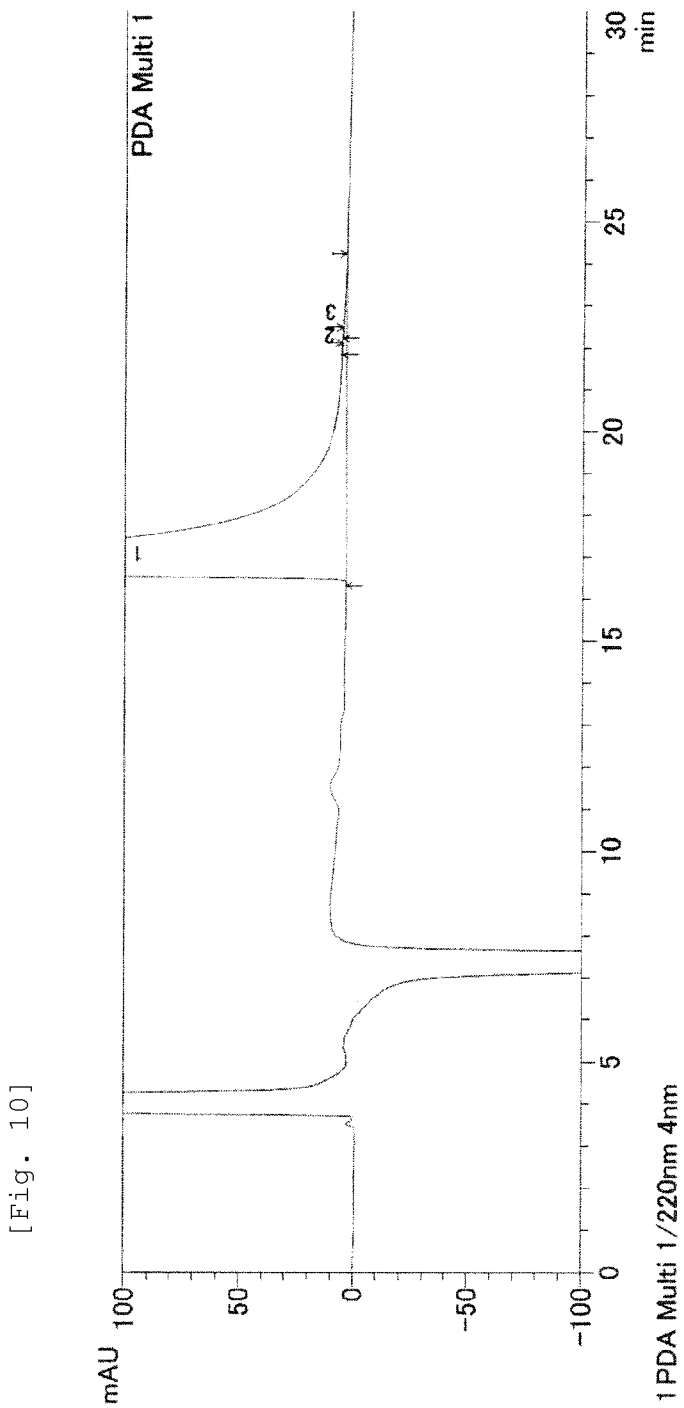

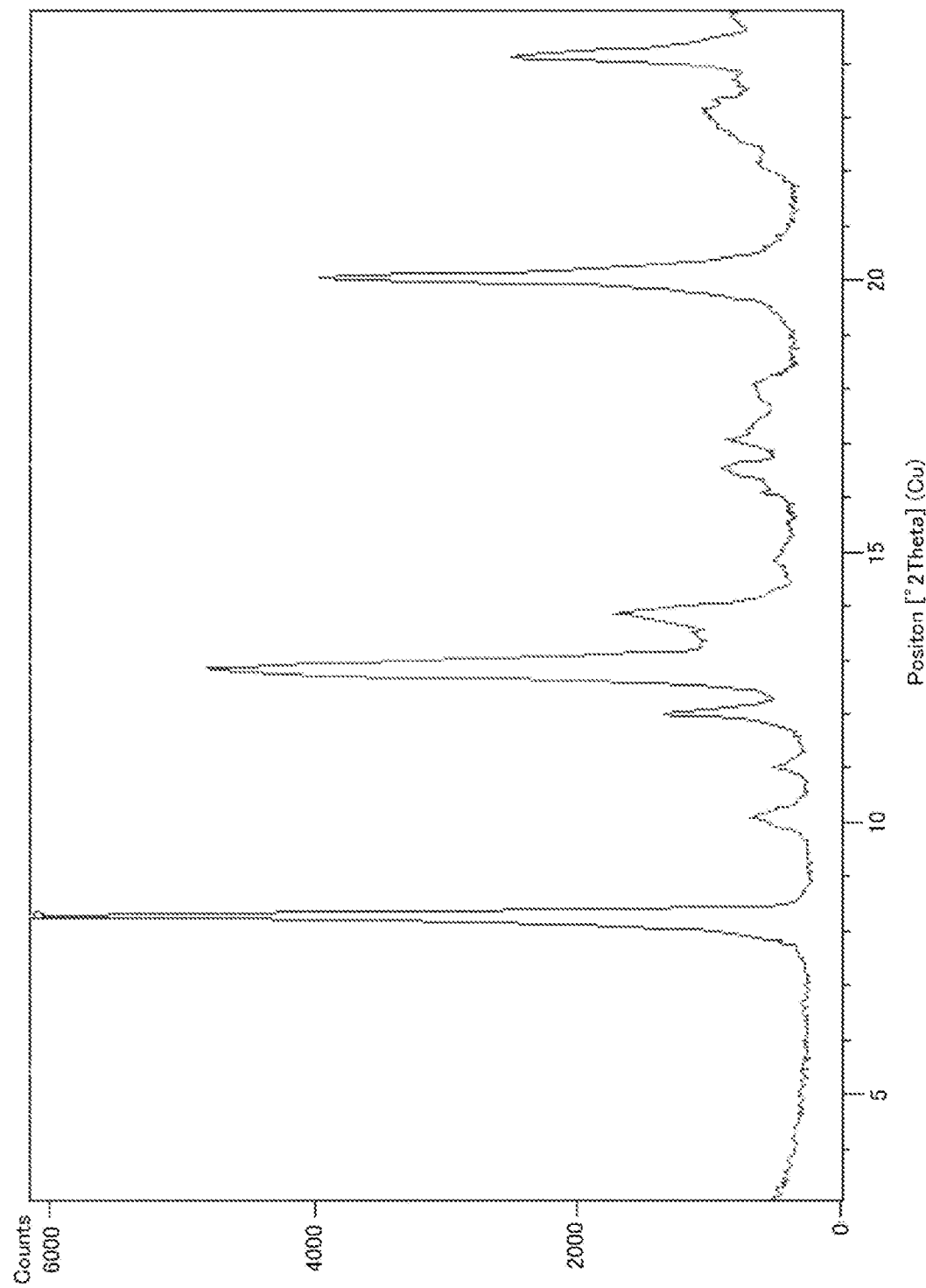

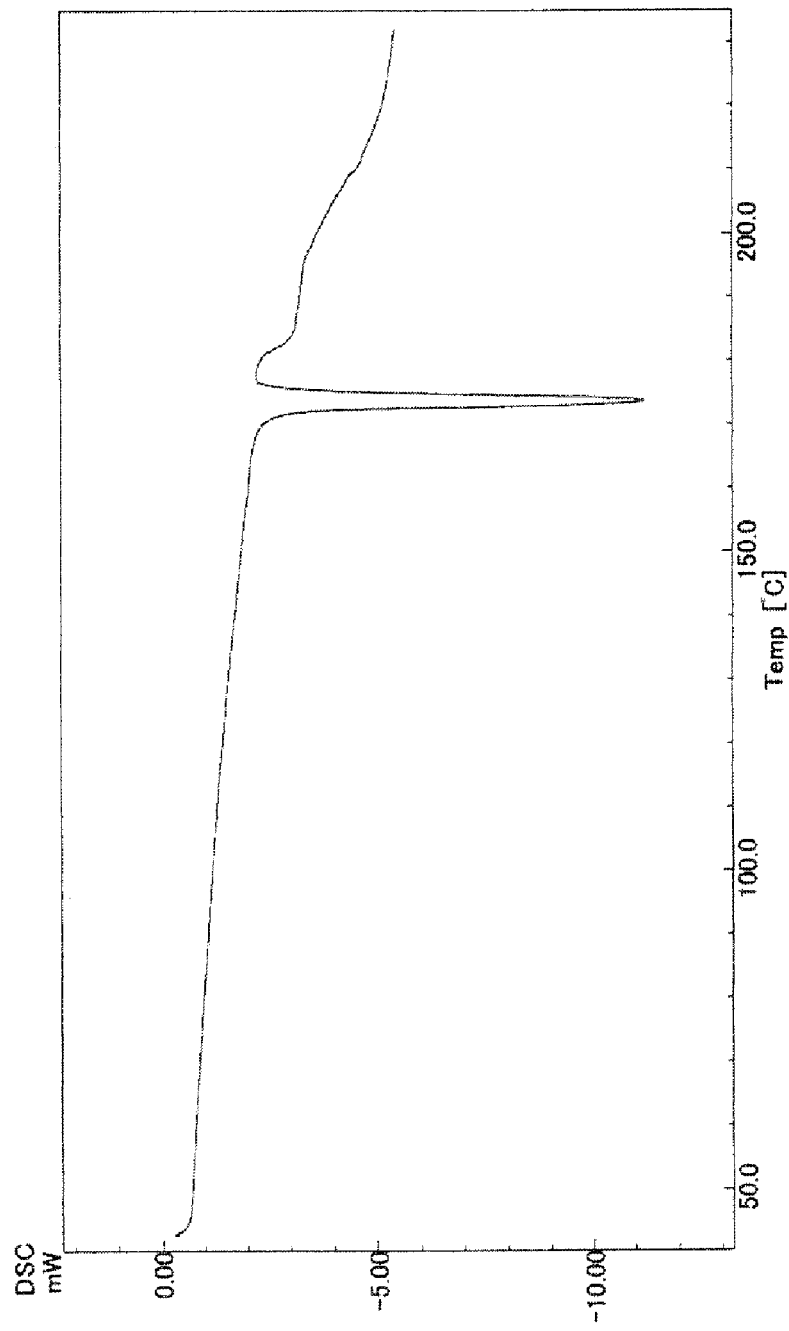
[Fig. 12]

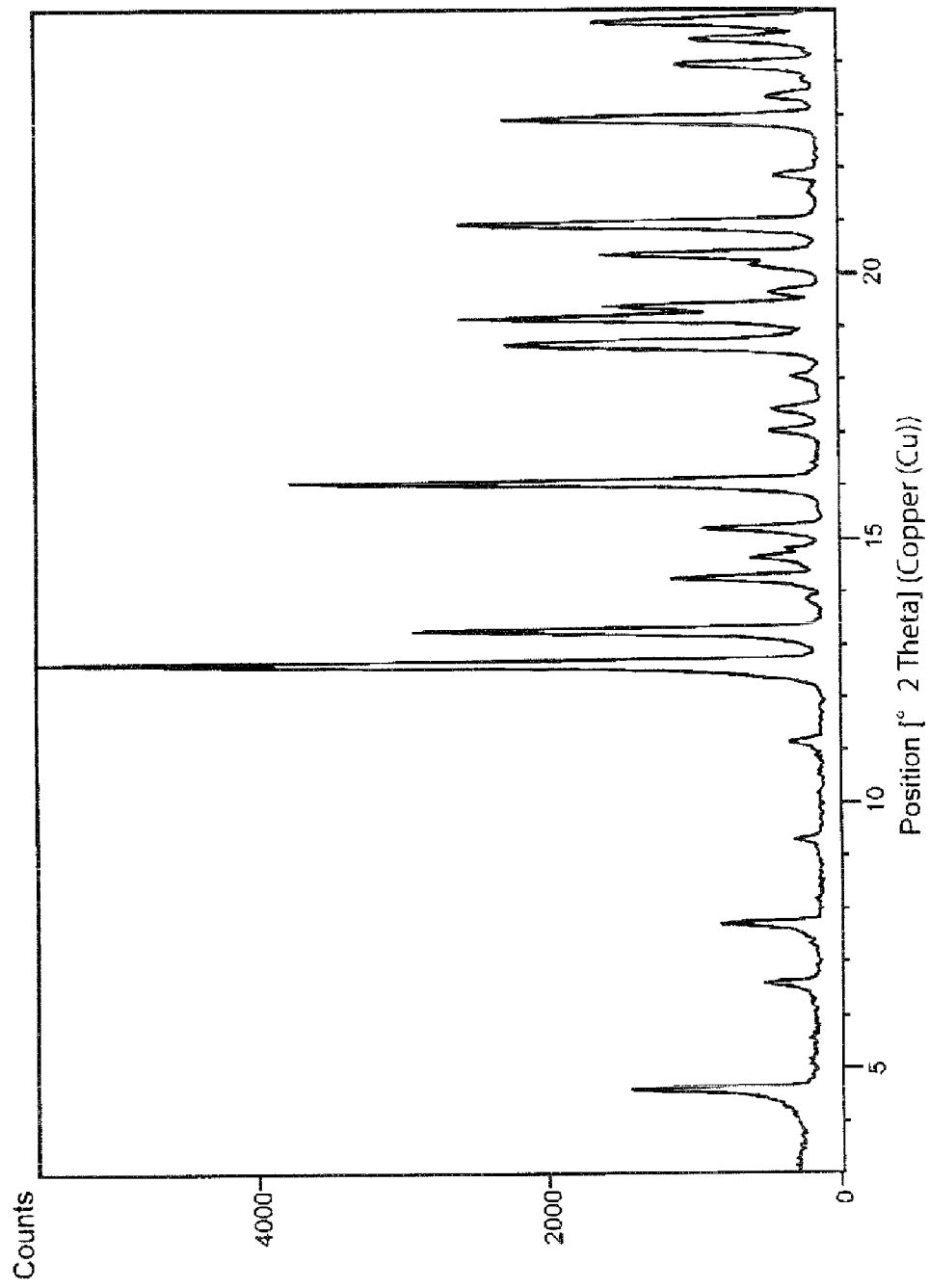
[Fig. 13]

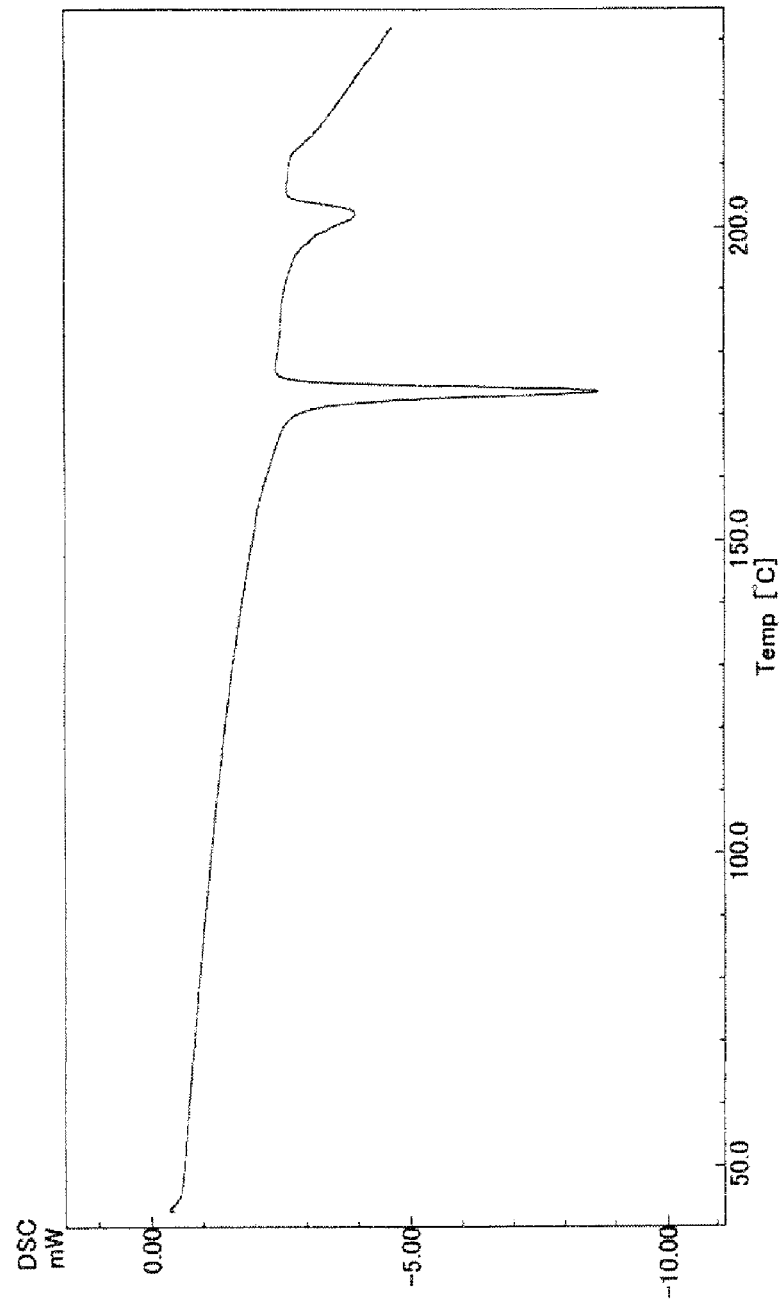
[Fig. 14]

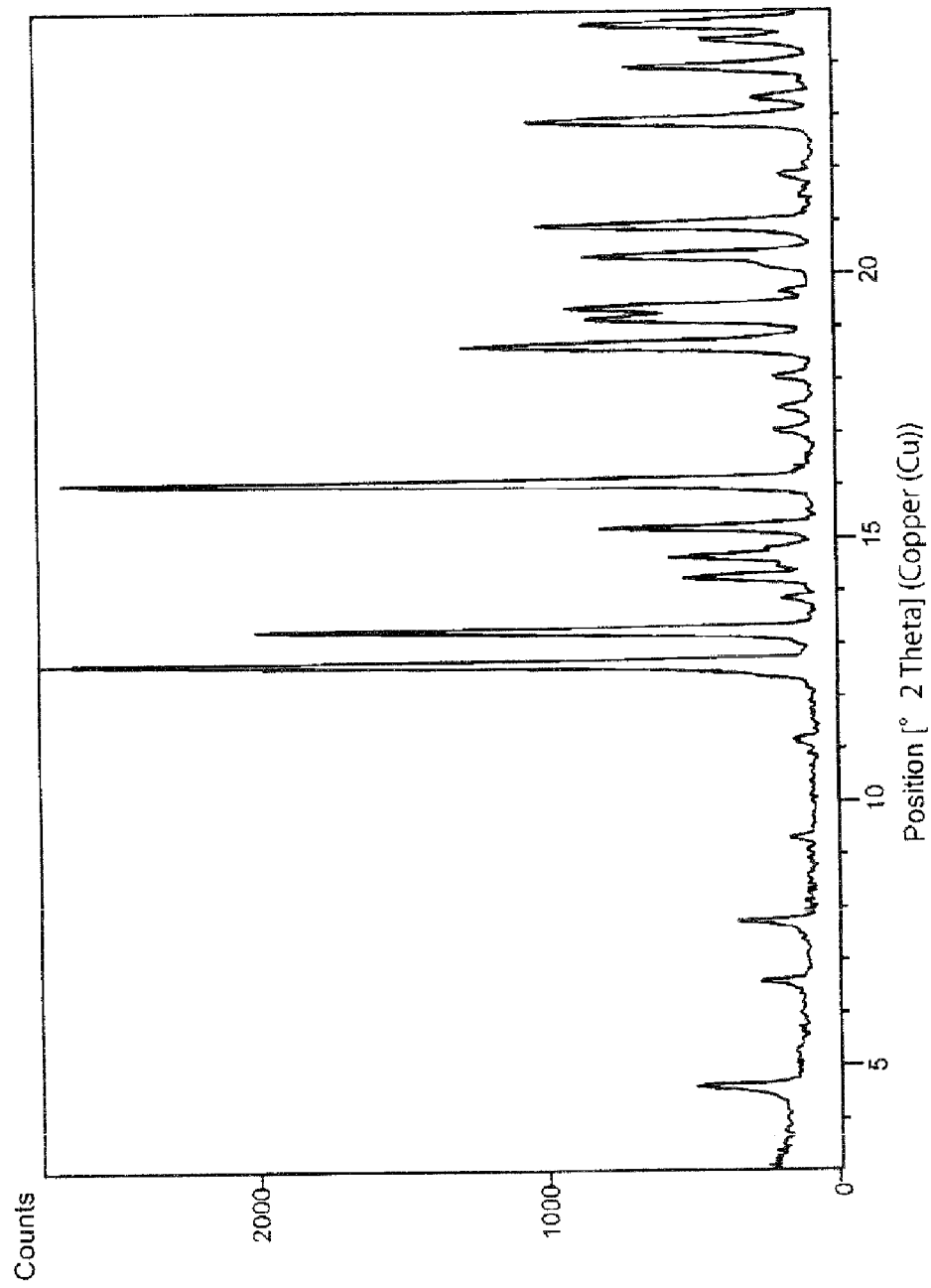
[Fig. 15]

PROCESS FOR PREPARING 7H-PYRROLO[2,3-D]PYRIMIDINE DERIVATIVES AND SYNTHETIC INTERMEDIATES THEREOF

CROSS-REFERENCE TO RELATED APPLICATIONS

This application is a continuation application of and claims the benefit of priority to U.S. application Ser. No. 16/470,888, filed on Jun. 18, 2019, which is a U.S. National Application claiming priority to PCT Application no. PCT/JP2017/045729 filed on Dec. 20, 2017, which claims priority to Japanese Application No. 2016-247607 filed Dec. 21, 2016, the contents of which are hereby incorporated by reference.

TECHNICAL FIELD

The present invention relates to process for preparing 7H-pyrrolo[2,3-d]pyrimidine derivatives which are useful as a Janus kinase (JAK) inhibitor, synthetic intermediates thereof, and process for preparing the intermediates.

BACKGROUND ART

JAK is a member of a cytoplasmic protein tyrosine kinase family, and for example, includes JAK1, JAK2, JAK3, and TYK2.

Patent Literature 1 discloses Compound A (Compound [17]: 3-[(3S,4R)-3-methyl-6-(7H-pyrrolo[2,3-d]pyrimidin-4-yl)-1,6-diazaspiro[3.4]octan-1-yl]-3-oxopropanenitrile) which is useful as a JAK inhibitor.

CITATION LIST

Patent Literature

[PTL 1] WO 2011/013785

Non Patent Literature

[NPL 1] STACY, D M et al. Synthesis and biological evaluation of triazole-containing N-acyl homoserine lactones as quorum sensing modulators. Org Biomol Chem. Feb. 14, 2013, Vol. 11, No. 6, pages 938-954.

SUMMARY OF INVENTION

The present invention provides processes for preparing 7H-pyrrolo[2,3-d]pyrimidine derivatives which are useful as a JAK inhibitor, synthetic intermediates of the derivatives, and processes for preparing the synthetic intermediates.

The present invention includes the following embodiment:

A process for preparing a compound of formula [17]:

[Chem. 1]

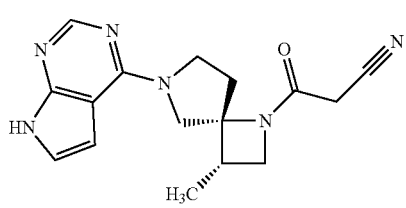

[17]

or its salt with using a compound of formula [13]:

[Chem. 2]

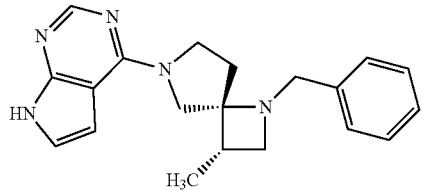

[13]

or its salt, comprising the following steps:
(1) the benzyl is removed from the compound of formula [13] or its salt to give a compound of formula [14]:

[Chem. 3]

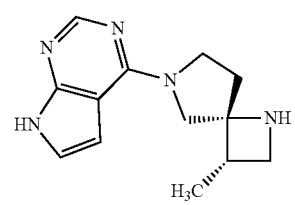

[14]

or its salt, and
(2) the compound of formula [14] or its salt is reacted with a compound of formula [18]:

[Chem. 4]

[18]

to give the compound of formula [17] or its salt.

BRIEF DESCRIPTION OF DRAWINGS

FIG. 9 shows analytical results of HPLC for crude SR-MDBN-DSU [11-1] obtained in Example 9. Absorbance (AU) is shown in the vertical axis, and retention time (min) is shown in the horizontal axis.

FIG. 10 shows analytical results of HPLC for SR-MDBN-DSU [11-1] obtained via the purification step in Example 9. Absorbance (AU) is shown in the vertical axis, and retention time (min) is shown in the horizontal axis.

FIG. 11 shows a multiple record for powder X-ray diffraction pattern of 1-ethanolate of Compound A (Compound [17]). Diffraction intensity (cps: counts per second) is shown in the vertical axis, and diffraction angle 2θ (°) is shown in the horizontal axis.

FIG. 12 shows a differential scanning calorimetry (DSC) curve for a co-crystal (2:1, molar ratio) (Compound [33]) of Compound A (Compound [17]) with 3,5-dimethylpyrazole as a seed crystal.

FIG. 13 shows a multiple record for powder X-ray diffraction pattern of a co-crystal (2:1, molar ratio) (Compound [33]) of Compound A (Compound [17]) with 3,5-dimethylpyrazole as a seed crystal. Diffraction intensity (cps: counts per second) is shown in the vertical axis, and diffraction angle 2θ (°) is shown in the horizontal axis.

FIG. 14 shows a differential scanning calorimetry (DSC) curve for a co-crystal (2:1, molar ratio) (Compound [33]) of Compound A (Compound [17]) with 3,5-dimethylpyrazole.

FIG. 15 shows a multiple record for powder X-ray diffraction pattern of a co-crystal (2:1, molar ratio) (Compound [33]) of Compound A (Compound [17]) with 3,5-dimethylpyrazole. Diffraction intensity (cps: counts per second) is shown in the vertical axis, and diffraction angle 2θ (°) is shown in the horizontal axis.

DESCRIPTION OF EMBODIMENTS

Figure 1:
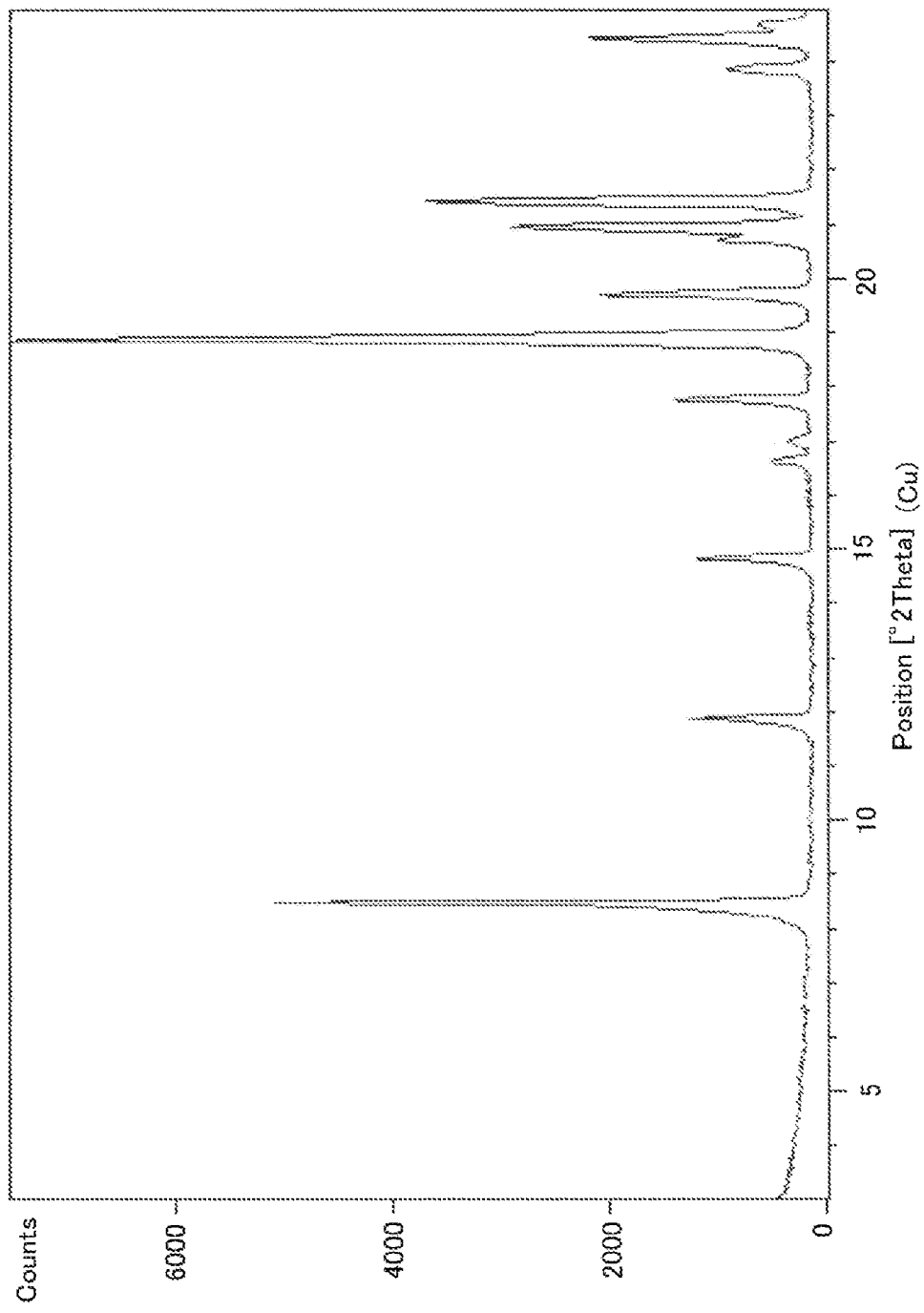
FIG. 1 shows a multiple record for powder X-ray diffraction pattern of BABL-HC [3]. Diffraction intensity (cps: counts per second) is shown in the vertical axis, and diffraction angle 2θ (°) is shown in the horizontal axis.

The definitions of the terms herein are as below.

A compound of formula [17] may be, for example, referred to as Compound [17] herein.

Examples of halogen include fluorine, chlorine, bromine, and iodine.

$C_{1-4}$ alkyl refers to a straight or branched chain alkyl of 1 to 4 carbons, and includes, for example, methyl, ethyl, propyl, isopropyl, butyl, isobutyl, sec-butyl, or tert-butyl.

Salts of compounds may be any salts if such salts can be formed with the compound of the present invention, and includes, for example, salts with inorganic acids, salts with organic acids, salts with inorganic bases, salts with organic bases, salts with amino acids.

The inorganic acids include, for example, hydrochloric acid, nitric acid, sulfuric acid, phosphoric acid, hydrobromic acid. A preferable inorganic acid is hydrochloric acid.

The organic acids include, for example, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid, 10-camphorsulfonic acid. Preferable organic acids are oxalic acid, L-tartaric acid, D-tartaric acid, succinic acid, (+)-10-camphorsulfonic acid and (−)-10-camphorsulfonic acid. More preferable organic acids are oxalic acid, succinic acid, L-tartaric acid, D-tartaric acid, (+)-10-camphorsulfonic acid.

The salts with inorganic bases include, for example, sodium salt, potassium salt, calcium salt, magnesium salt, ammonium salt.

The organic bases include, for example, methylamine, diethylamine, trimethylamine, triethylamine, ethanolamine, diethanolamine, triethanolamine, ethylenediamine, tris(hydroxymethyl)methylamine, dicyclohexylamine, N,N-dibenzylethylenediamine, guanidine, pyridine, picoline, choline, cinchonine, meglumine.

The amino acids include, for example, lysine, arginine, aspartic acid, glutamic acid.

According to known methods, the compound of the present invention may be reacted with inorganic bases, organic bases, inorganic acids, organic acids, or amino acids to give salts of the compound of the present invention.

The chlorinating agent includes, for example, thionyl chloride, oxalyl chloride, phosphoryl chloride. A preferable chlorinating agent is thionyl chloride.

The compound or its salt of the present invention may exist as its solvate.

The solvate is a compound where a molecule of a solvent coordinates to the compound or its salt of the present invention, and includes a hydrate. The preferable solvate is a pharmaceutically acceptable solvate, and includes, for example, a hydrate, an ethanolate, a solvate with DMSO, a 1-propanolate, a 2-propanolate, a solvate with chloroform, a solvate with dioxane, a solvate with anisole, a solvate with acetone, a solvate with ethyleneglycol, or a solvate with dimethylacetamide of the compound or its salt of the present invention.

According to known methods, a solvate of the compound or its salt of the present invention may be obtained.

The compound of the present invention may exist as a tautomer. In such case, the compound of the present invention may exist as a single tautomer or a mixture of individual tautomers.

The compound of the present invention may have a carbon-carbon double bond. In such case, the compound of the present invention may exist as E form, Z form, or a mixture of E form and Z form.

The compound of the present invention may exist as a stereoisomer to be identified as a cis/trans isomer. In such case, the compound of the present invention may exist as a cis form, trans form, or a mixture of a cis form and a trans form.

The compound of the present invention may have one or more asymmetric carbon atoms. In such case, the compound of the present invention may exist as a single enantiomer, a single diastereomer, a mixture of enantiomers, or a mixture of diastereomers.

The compound of the present invention may exist as an atropisomer. In such case, the compound of the present invention may exist as a single atropisomer, or a mixture of individual atropisomers.

The compound of the present invention may simultaneously include several structural features causing the above isomers. The compound of the present invention may include the above isomers in any ratios.

In the absence of other references such as annotation and the like, the formulae, chemical structures and compound names indicated in the present specification without specifying the stereochemistry thereof encompass all the above-mentioned isomers that may exist.

The chemical bond shown in a wavy line represents that the compound is a mixture of stereoisomers or any of stereoisomers. For example, a compound of formula [6]:

[Chem. 5]

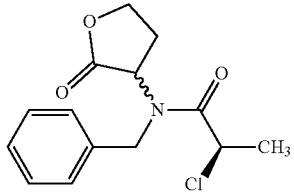

[6]

represents a mixture of formulae [6-1] and [6-2]:

[Chem. 6]

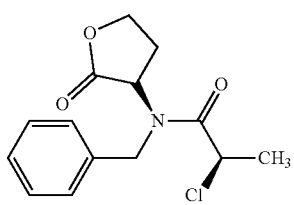

[6-1]

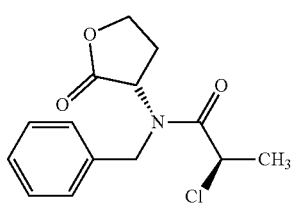

[6-2]

or any one of the compounds.

A diastereomeric mixture may be separated into each diastereomer by a conventional method such as chromatography or crystallization. Each diastereomer may be also obtained by using a stereochemically pure starting material or by a synthetic method using a stereoselective reaction.

A separation of enantiomeric mixture into each single enantiomer may be carried out by well-known methods in the field.

For example, according to a standard method such as fractional crystallization or chromatography, a diastereomer with a higher isomeric ratio or a substantially pure single diastereomer may be separated from a diastereomeric mixture which is formed by reacting an enantiomeric mixture with a chiral auxiliary which is a substantially pure enantiomer. The separated diastereomer may be converted into the desired enantiomer by removing off the added chiral auxiliary in a cleavage reaction.

The desired enantiomer may be also obtained by directly separating an enantiomeric mixture by a chromatography using a chiral solid phase well known in the field.

Alternatively, the desired enantiomer may be also obtained by using a substantially pure optically active starting material or by a stereoselective synthesis using a chiral auxiliary or asymmetric catalyst to a prochiral synthetic intermediate, i.e. asymmetric induction.

An absolute configuration may be determined by X-ray crystal analysis of a crystalline final product or synthetic intermediate. If necessary, an absolute configuration may be determined by using a crystalline final product or synthetic intermediate derivatized with a reagent having an asymmetric center of which a steric configuration is known. The configuration herein was specified by X-ray crystal analysis of a crystalline chloroformate of Compound [17].

The compound of the present invention may be crystalline or amorphous.

The compound of the present invention may be labelled with an isotope including $^{3}H$, $^{14}C$, $^{35}S$.

Processes for preparing the compound of the present invention or its salt, or a solvate thereof is illustrated as below.

In each step, the reaction may be carried out in a solvent.

The compound obtained in each step may be isolated and purified by a known method such as distillation, recrystallization, column chromatography, if needed, or may be optionally used in a subsequent step without isolation or purification.

The room temperature herein represents a condition wherein a temperature is not controlled, and includes 1° C. to 40° C. as one embodiment. The reaction temperature may include the temperature as described ±5° C., preferably ±2° C.

An example of a process for preparing the compound of the present invention or its salt, or a solvate thereof is shown in the following Scheme 1. Specifically, a scheme via compound [8a] is shown.

In the scheme, $X^1$ is chlorine or bromine; $R^1$ is $C_{1-4}$ alkyl or benzyl; $X^2$ is halogen; Y is an acid; n is any number of 0.5 to 2; and m is any number of 0.4 to 0.5.

Scheme 1
[Chem. 7]
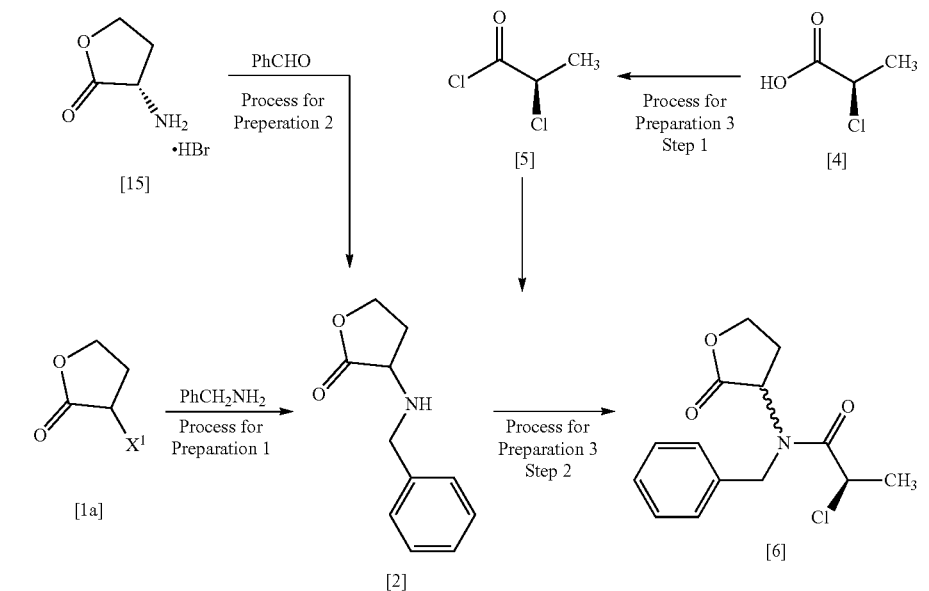
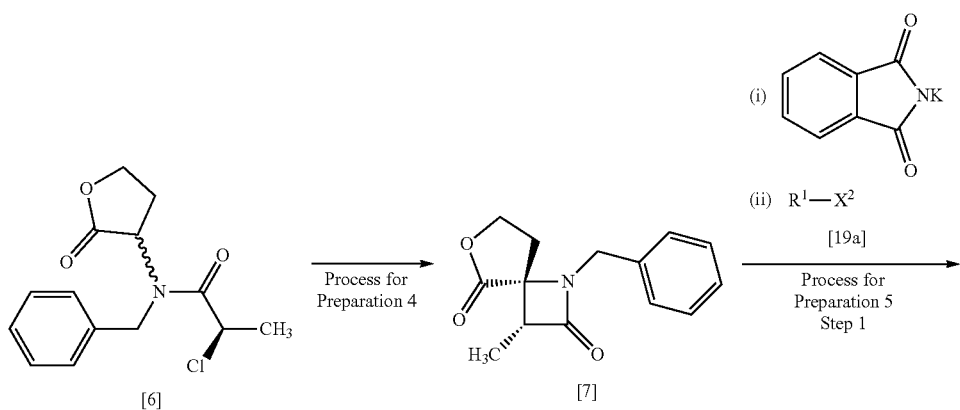
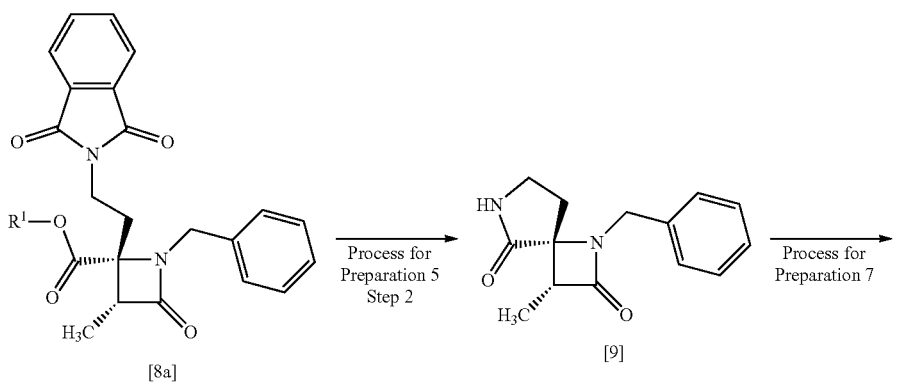

-continued
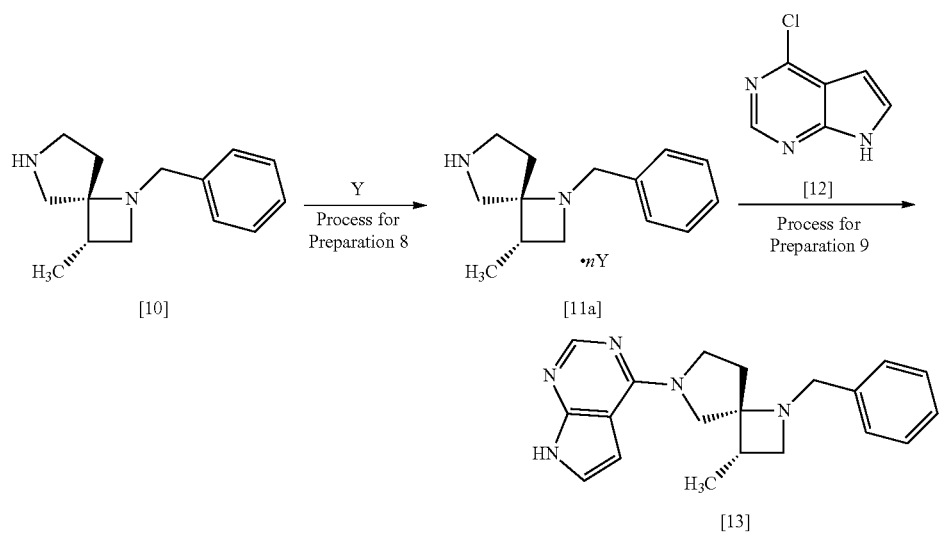
[Chem. 8]
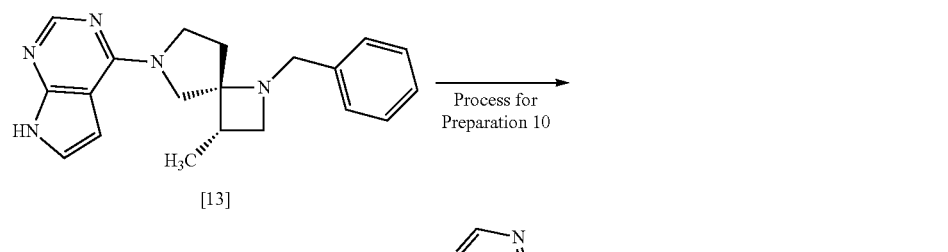
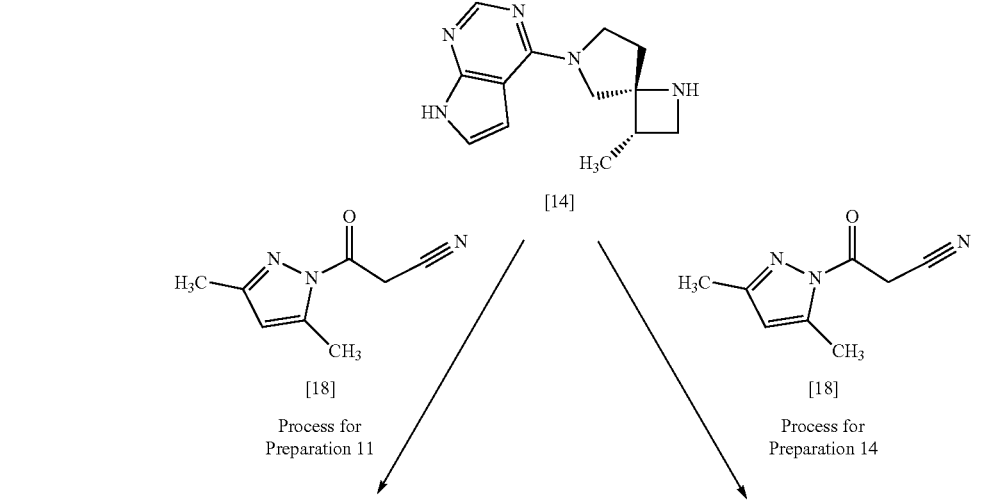
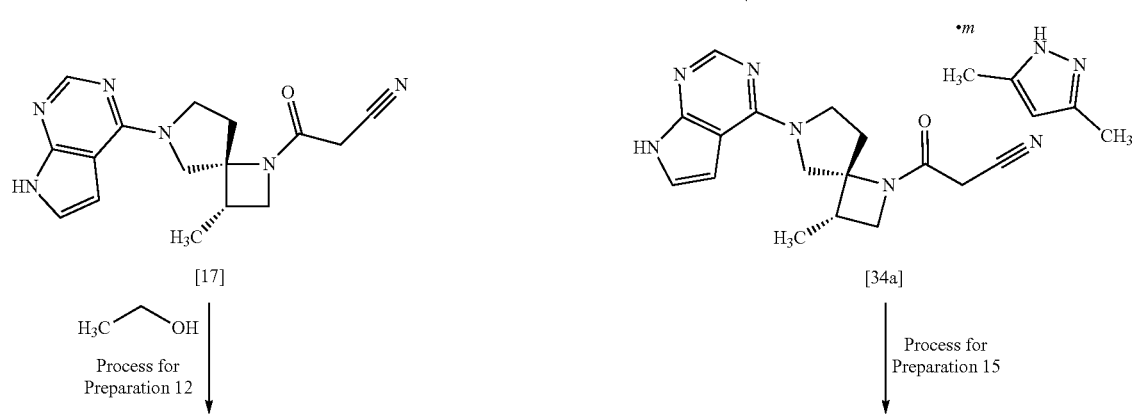

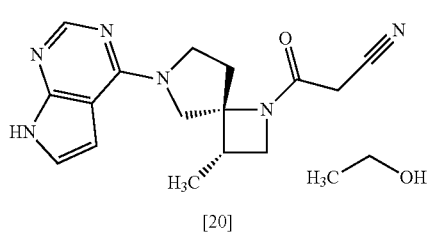
[20]
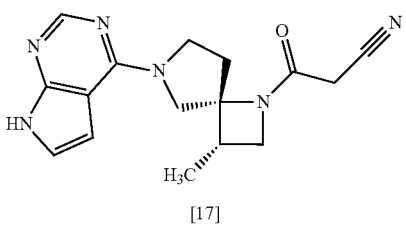
[17]
Another example of the process for preparing the compound of the present invention or its salt, or a solvate thereof is shown in the following Scheme 2. Specifically, a scheme via compound [16a] is shown.
In the scheme, $X^1$ is chlorine or bromine; $R^1$ is $C_{1-4}$ alkyl or benzyl; $X^2$ is halogen; Y is an acid; n is any number of 0.5 to 2; and m is any number of 0.4 to 0.5.
Scheme 2
[Chem. 9]
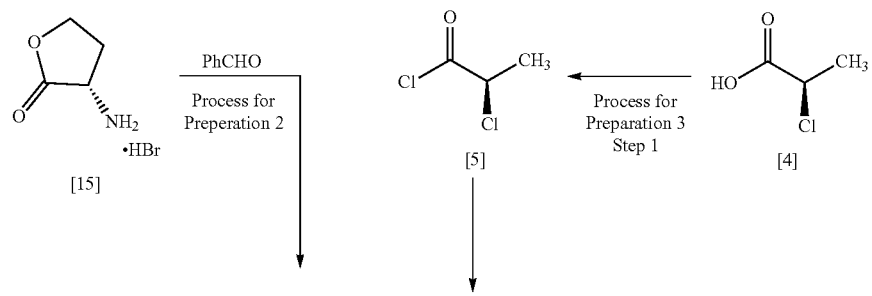
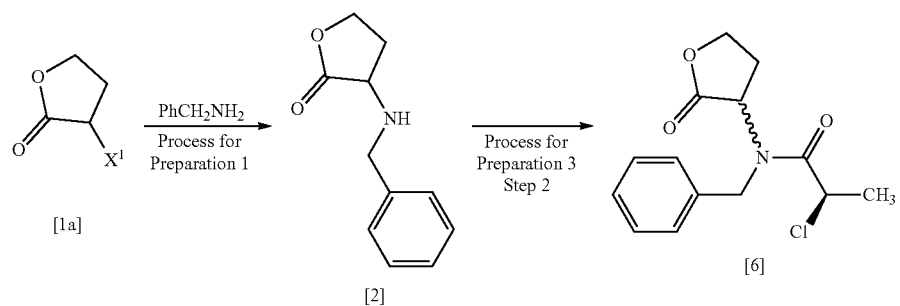
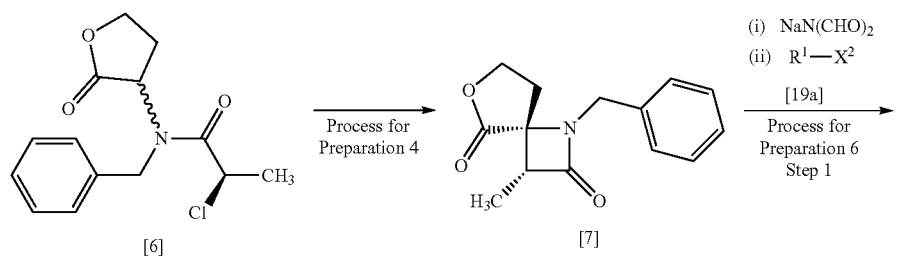

-continued
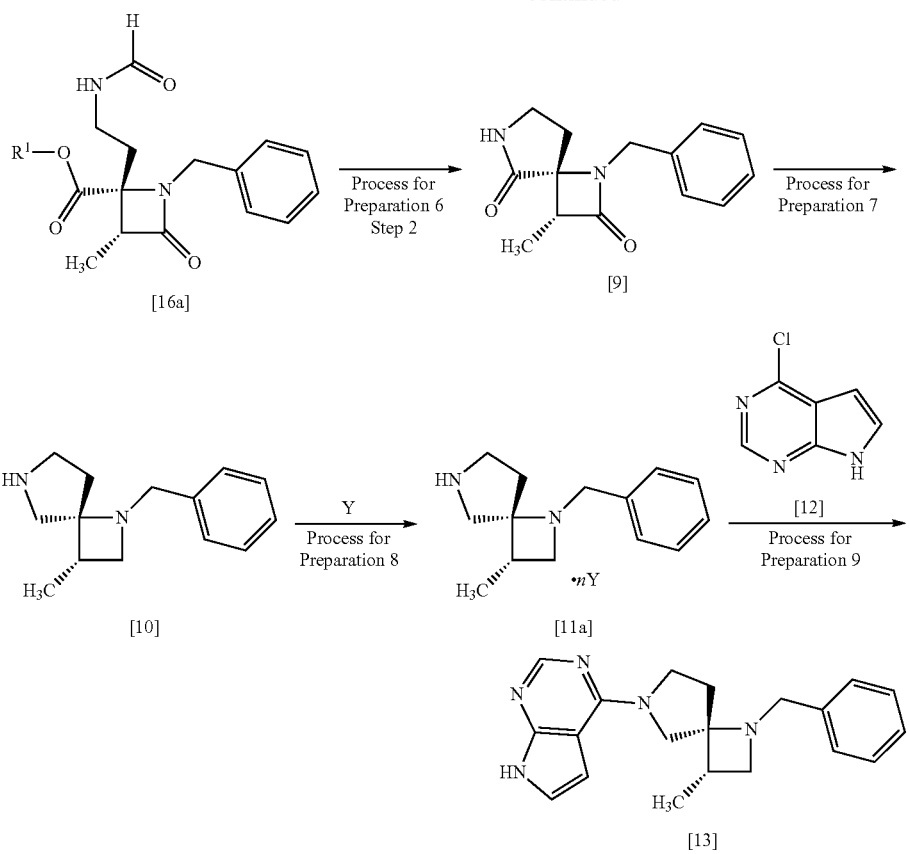
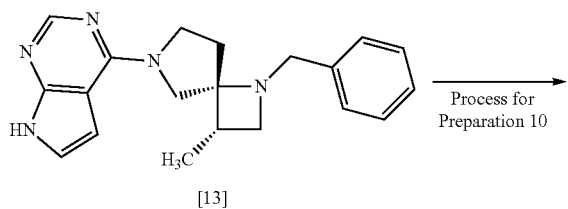
[Chem. 10]
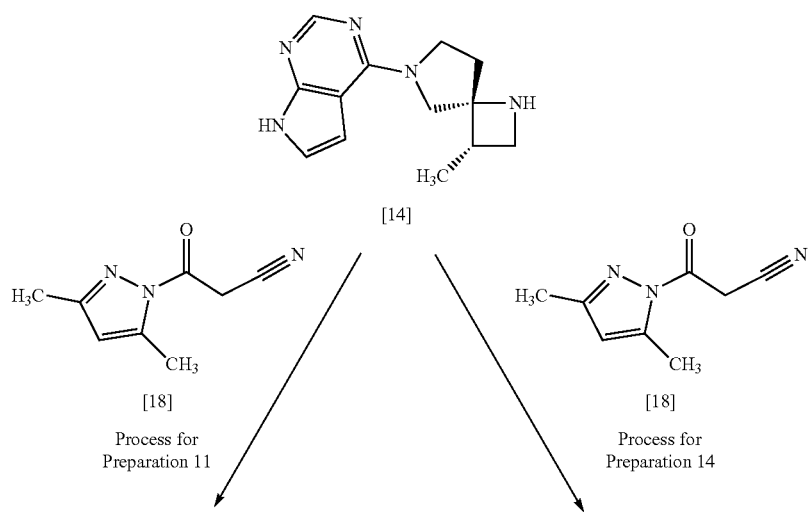

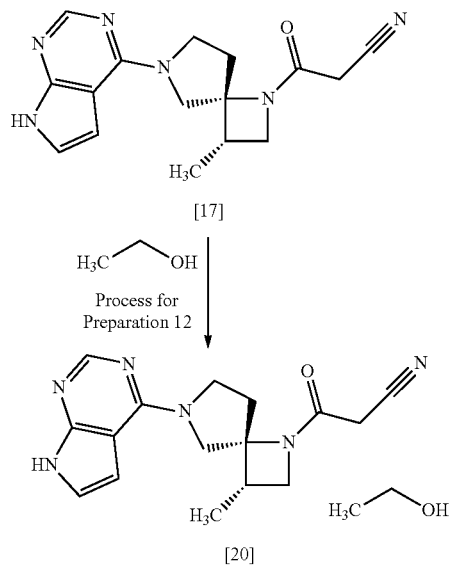
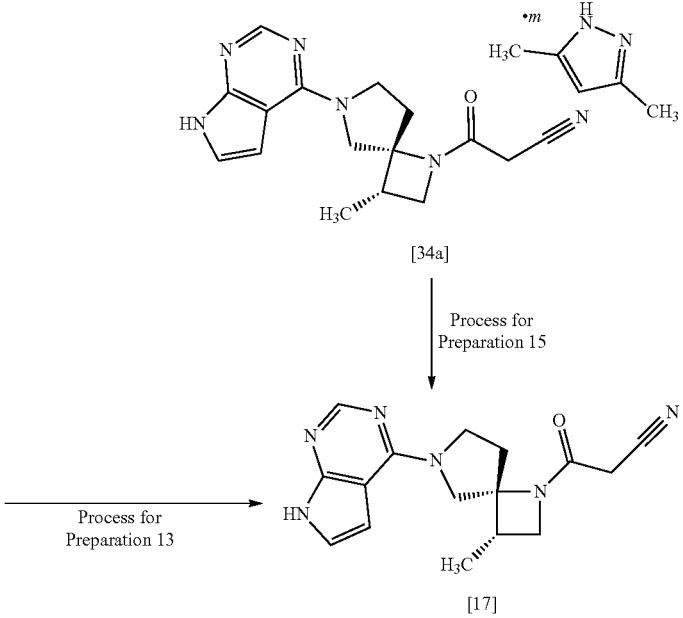
Another example of the process for preparing the compound of the present invention or its salt, or a solvate thereof is shown in the following Scheme 3-1 and Scheme 3-2. Specifically, a scheme via compound [26a] is shown.
In the scheme, $R^2$ is methyl, ethyl or benzyl; $R^3$ is methyl, ethyl or benzyl; Y is an acid; and n is any number of 0.5 to 2.
Scheme 3-1
[Chem. 11]
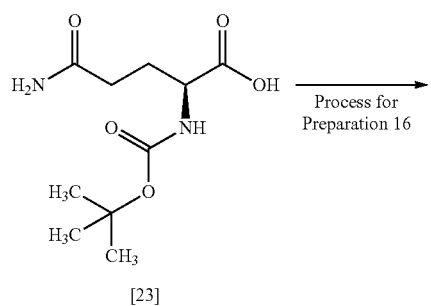
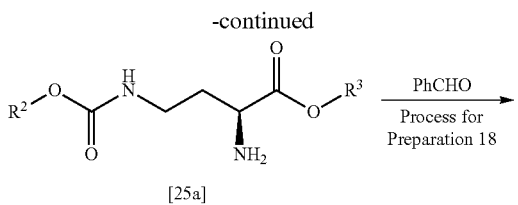
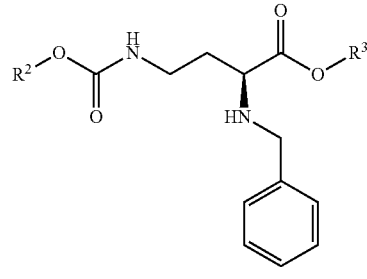

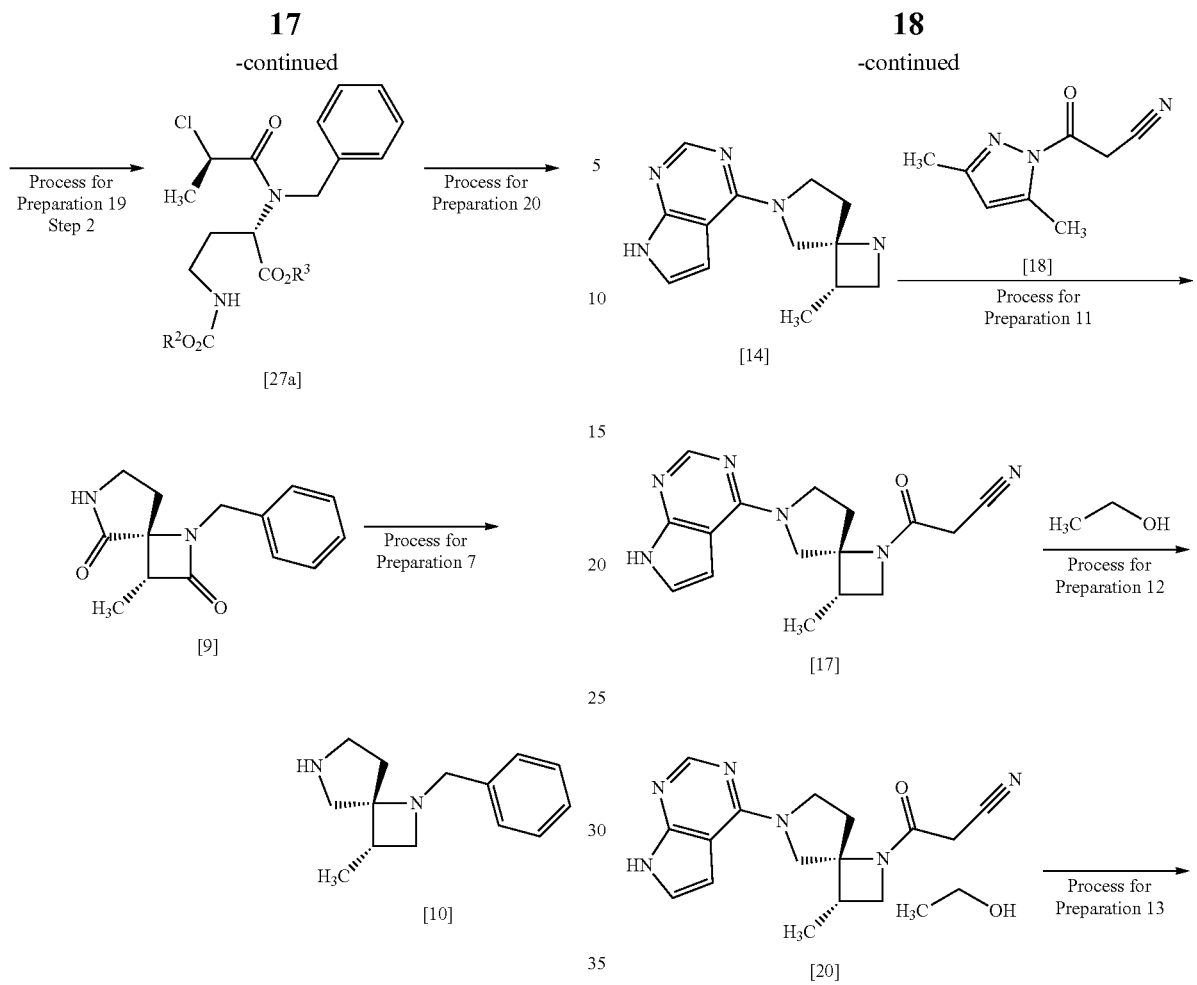
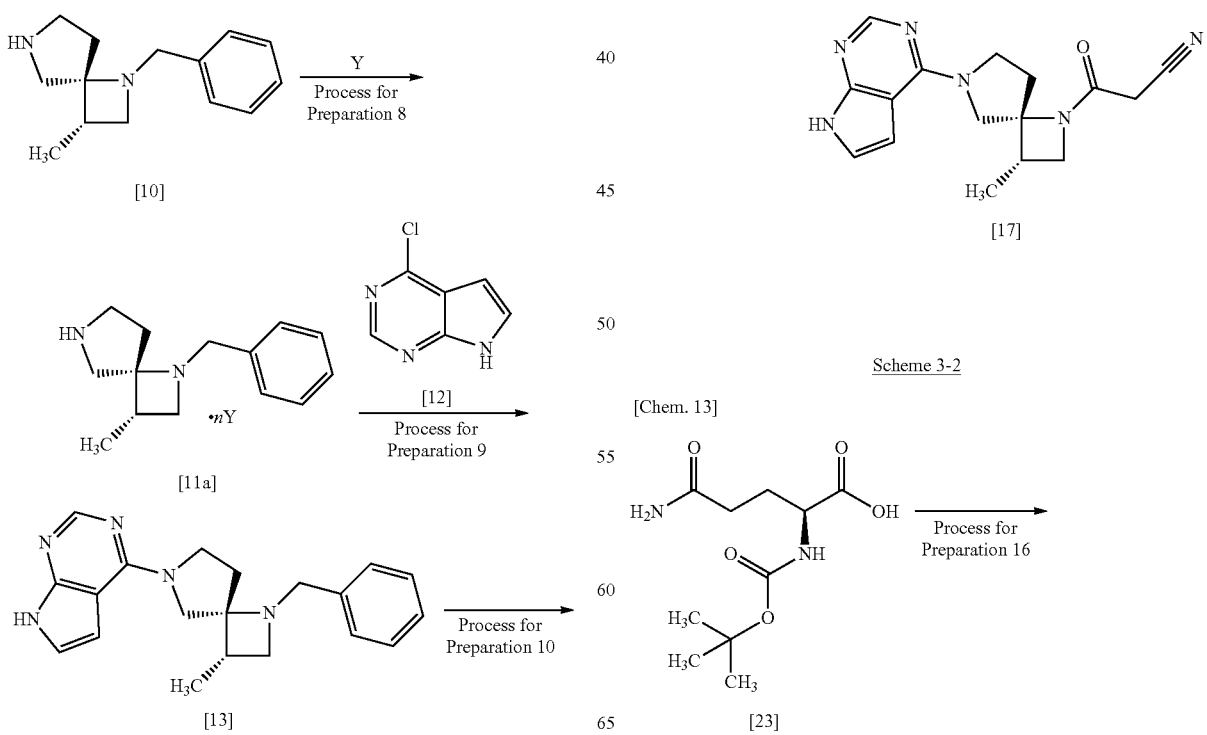
Scheme 3-2
[Chem. 13]

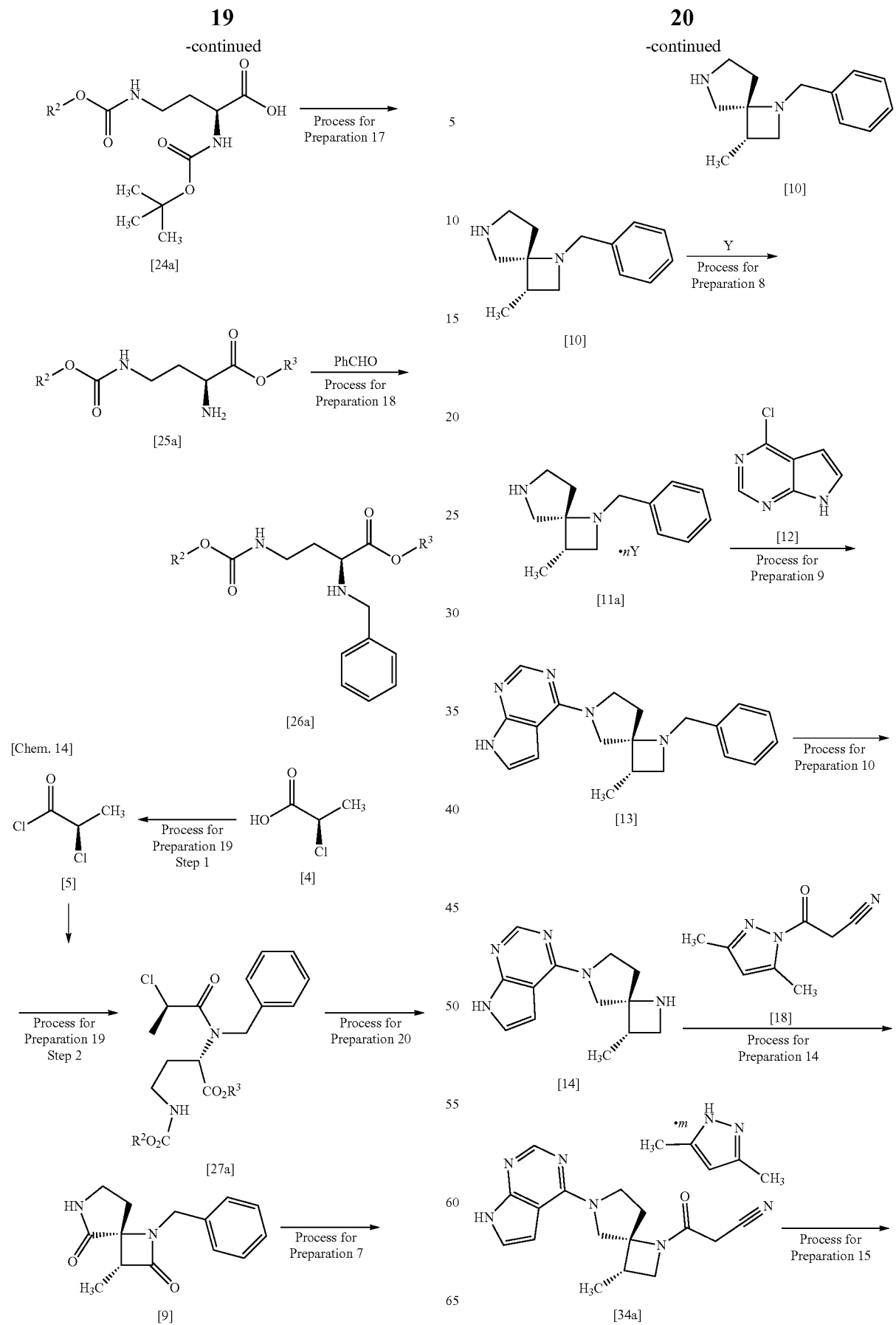

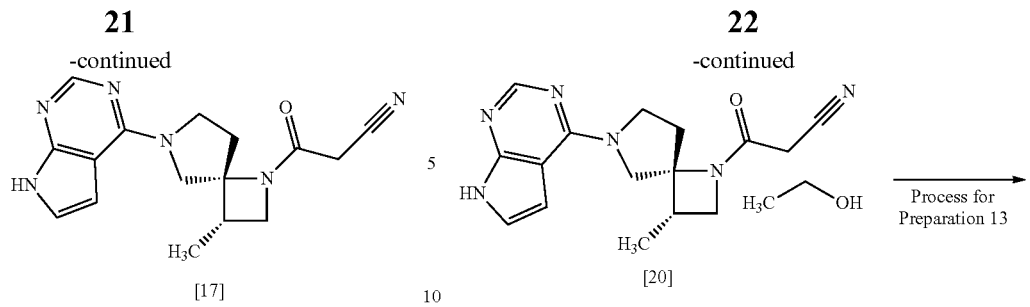
Other examples of the process for preparing the compound of the present invention or its salt, or a solvate thereof are shown in the following Schemes 4-1 to 6-2. Specifically, schemes via compound [30a] are shown.
In the schemes, Y is an acid; and n is any number of 0.5 to 2.
Scheme 4-1
[Chem. 15]
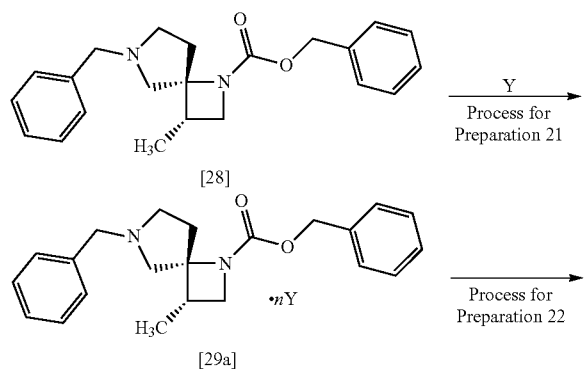
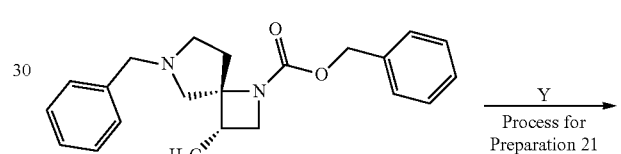
Scheme 4-2
[Chem. 16]
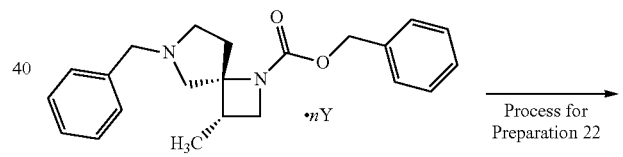
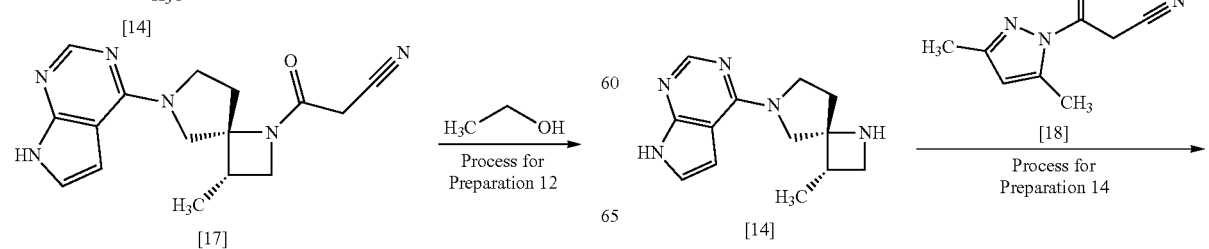

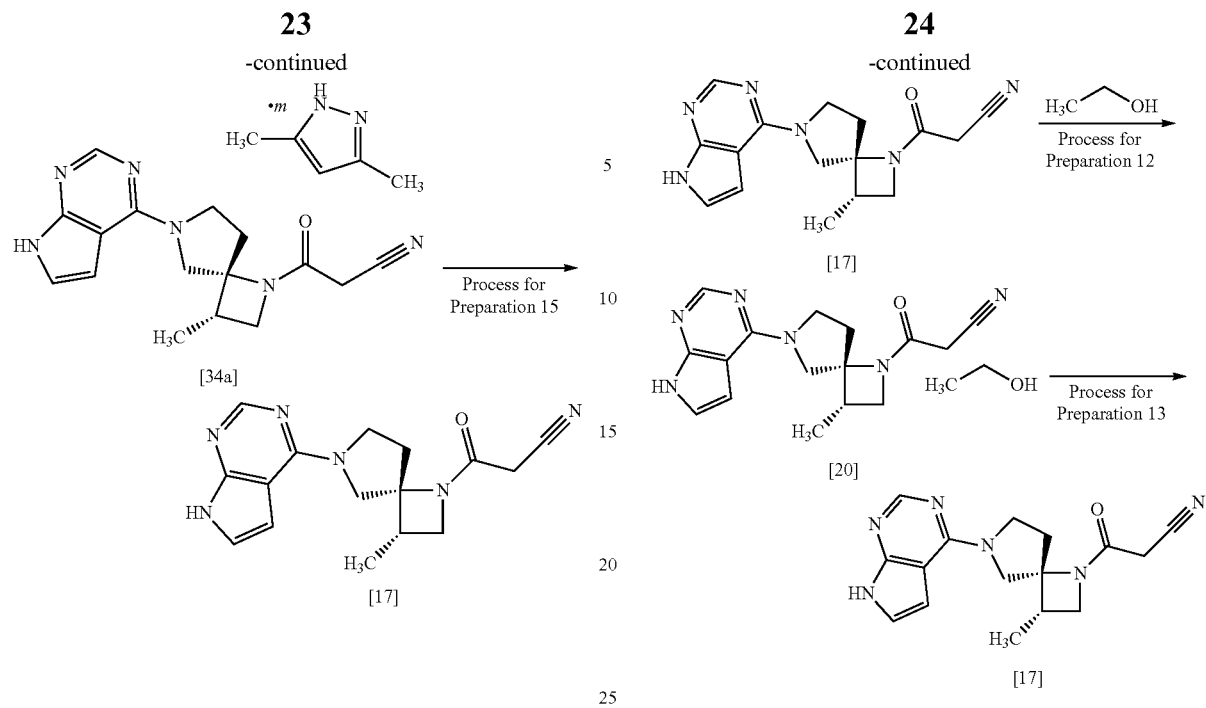
Scheme 5-1
[Chem. 17]
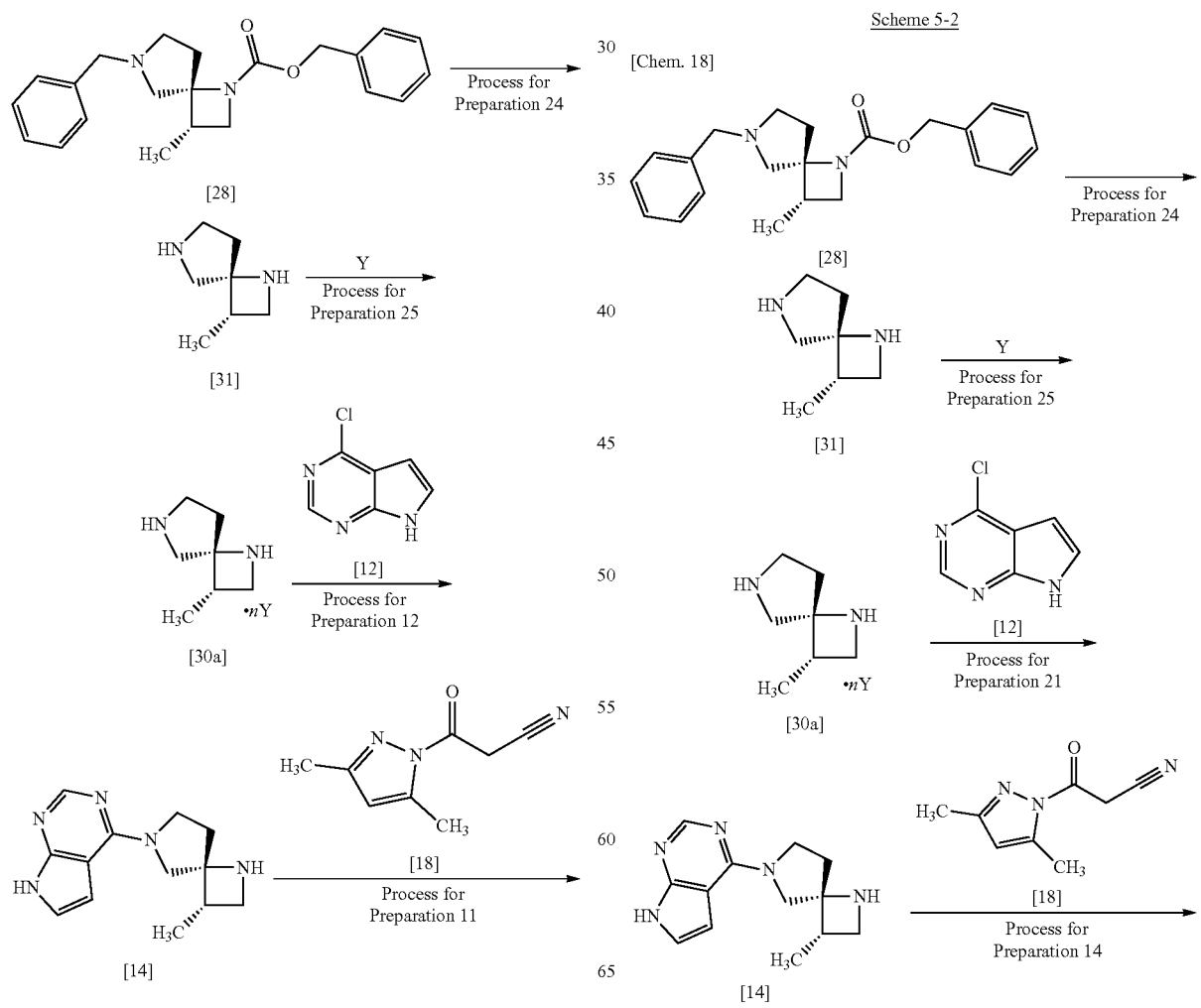
Scheme 5-2
[Chem. 18]

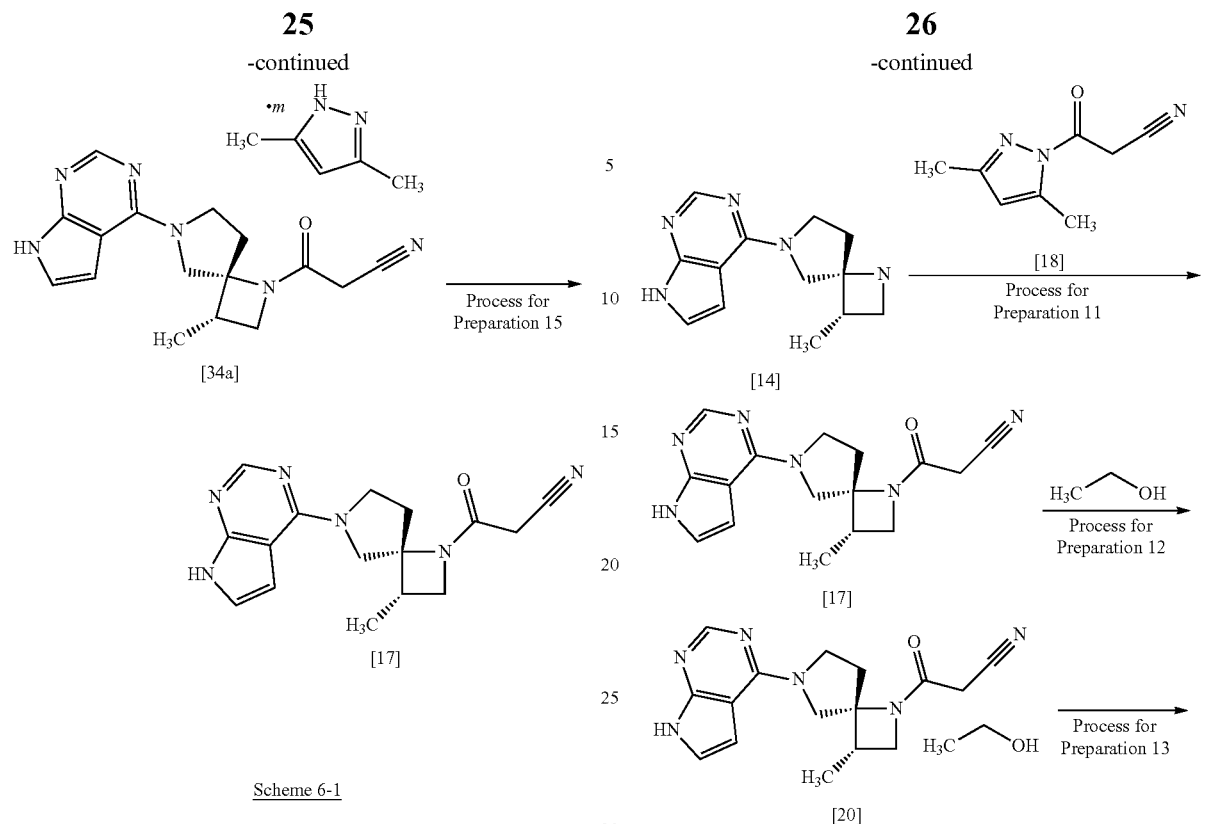
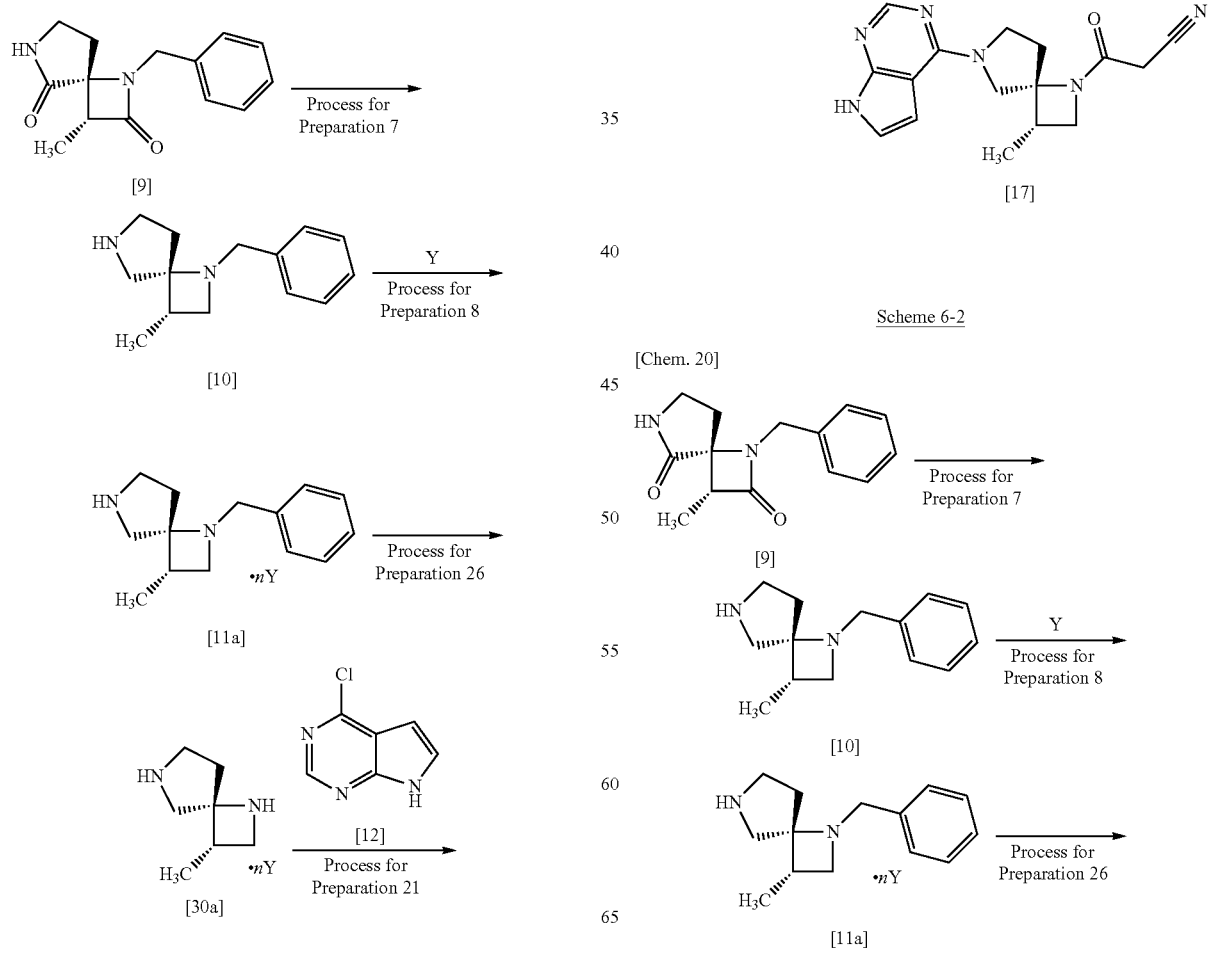

-continued

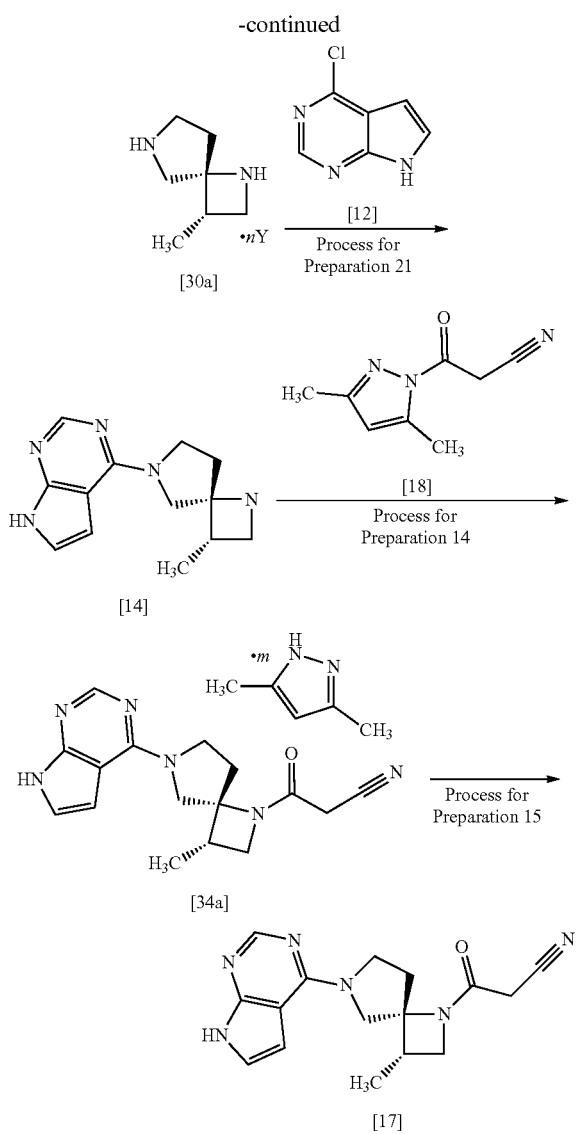

Below is detailed explanations of the processes shown in the above Schemes 1 to 6-2.

[Process for Preparation 1] Preparation of the Compound of Formula [2] or a Salt Thereof

[Chem. 21]

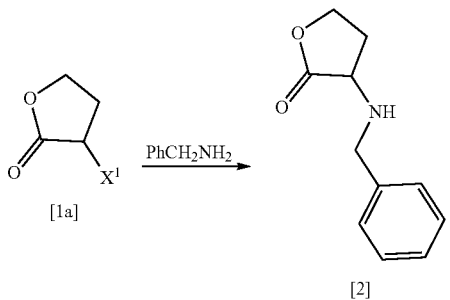

wherein $X^1$ is chlorine or bromine.

The compound of formula [2] may be prepared by reacting the compound of formula [1a] with benzylamine in the presence of a base. Optionally, 4-chlorobenzylamine, 3-chlorobenzylamine, 4-methoxybenzylamine, 3-methoxybenzylamine, 4-methylbenzylamine, 3-methylbenzylamine, benzhydrylamine, triphenylmethylamine or the like may be used in place of benzylamine.

Examples of the compound of formula [1a] include BBL and 3-chlorodihydrofuran-2-one. A preferable compound of formula [1a] is BBL.

Examples of the solvent include, for example, THF, acetonitrile, DMF, dimethylacetamide, N-methylpyrrolidone and DMSO. A preferable solvent is acetonitrile.

Examples of the base include, for example, tripotassium phosphate, potassium carbonate and cesium carbonate. A preferable base is tripotassium phosphate. The base may be used, for example, in an amount of from 2.0 to 5.0 equivalents relative to the compound of formula [1a], preferably 3.0±0.5 equivalents.

The reaction temperature is in the range of, for example, room temperature and 60° C., preferably 45° C.±5° C. Another preferable embodiment is 50° C.±5° C.

The reaction time is, for example, between 5 hr and 48 hr, preferably between 5 hr and 30 hr.

The compound of formula [2] can be form a salt with an acid.

The acid includes, for example, organic or inorganic acids.

The organic acids include, for example, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

The inorganic acids include, for example, hydrochloric acid, nitric acid, sulfuric acid, phosphoric acid, hydrobromic acid and the like. A preferable inorganic acid is hydrochloric acid.

A salt of the compound of formula [2] is, preferably, a monohydrochloride.

The compound of formula [2] may be obtained as a crystal by means of forming a salt with an inorganic acid.

The salt of the compound of formula [2] is, for example, the monohydrochloride, which is the crystal showing the X-ray powder diffraction pattern having at least one (for example, at least 1, 2, 3, 4, or 5) peak at 8.5°±0.2°, 18.9°±0.2°, 21.0°±0.2°, 21.4°±0.2° or 24.4°±0.2° of the diffraction angle (2θ) measured by using CuKα radiation.

Preferably, the salt of the compound of formula [2] is the monohydrochloride, which is the crystal showing the X-ray powder diffraction pattern having at least one (for example, at least 1, 2, 3, 4, or 5) peak at 8.5°±0.10, 18.9°±0.1°, 21.0°±0.1°, 21.4°±0.10 or 24.4°±0.10 of the diffraction angle (2θ) measured by using CuKα radiation.

More preferably, the salt of the compound of formula [2] is the monohydrochloride, which is the crystal showing the X-ray powder diffraction pattern having at least one (for example, at least 1, 2, 3, 4, or 5) peak at 8.5°±0.06°, 18.9°±0.06°, 21.0°±0.06°, 21.4°±0.06° or 24.4°±0.06° of the diffraction angle (2θ) measured by using CuKα radiation.

[Process for Preparation 2] Preparation of the Compound of Formula [2-2] or a Salt Thereof

[Chem. 22]

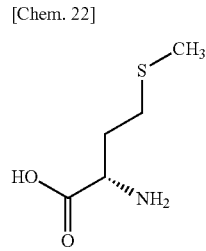

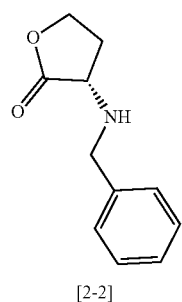

The compound of formula [2-2] may be prepared by reacting the compound of formula [15], which may be synthesized from L-methionine according to the method described in Non Patent Literature 1, with benzaldehyde under an acidic condition followed by a reduction of thus obtained compound. Optionally, 4-methoxybenzaldehyde or the like may be used in place of benzaldehyde.

Examples of the solvent include, for example, DMSO, DMF, dimethylacetamide, N-methylpyrrolidone, chloroform and THF. A preferable solvent is DMF.

Examples of the acid include acetic acid.

Examples of the reducing agent include, for example, sodium triacetoxyborohydride and sodium cyanoborohydride. A preferable reducing agent is sodium triacetoxyborohydride. The reducing agent may be used, for example, in an amount of from 1.0 to 3.0 equivalents relative to the compound of formula [15], preferably 1.2±0.2 equivalents.

The reaction temperature is in the range of, for example, 0° C. and 60° C., preferably room temperature.

The reaction time is, for example, between 0.5 hr and 24 hr, preferably between 1 hr and 5 hr.

[Process for Preparation 3] Preparation of the Compound of Formula [6]

[Chem. 23]

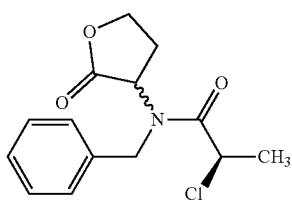

Step 1

[Chem. 24]

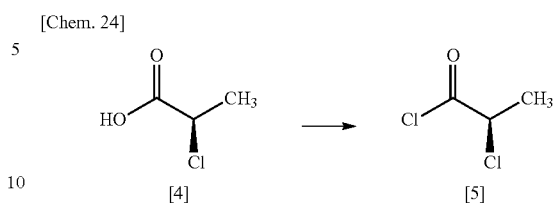

The compound of formula [5] may be prepared by reacting the compound of formula [4] with a chlorinating agent.

Examples of the solvent include, for example, toluene, THF, DMF, acetonitrile, a mixed solvent of acetonitrile and DMF, and a mixed solvent of toluene and DMF. A preferable solvent is toluene, acetonitrile, a mixed solvent of acetonitrile and DMF or a mixed solvent of toluene and DMF. The compound of formula [5] may be prepared without any solvent.

Examples of the chlorinating agent include, for example, thionyl chloride, oxalyl chloride and phosphoryl chloride. A preferable chlorinating agent is thionyl chloride. The chlorinating agent may be used, for example, in an amount of from 0.9 to 1.5 equivalents relative to the compound of formula [4], preferably 0.95 to 1.15 equivalents.

The reaction temperature may be optionally adjusted on the basis of common knowledge. The reaction temperature in the case where oxalyl chloride is used as the chlorinating agent is in the range of, for example, −20° C. and 10° C., preferably from −10° C. to 0° C. The reaction temperature in the case where thionyl chloride is used as the chlorinating agent is in the range of, for example, 45° C. and 75° C., preferably 65° C.±5° C. Another preferable reaction temperature in the case where thionyl chloride is used as the chlorinating agent is in the range of −20° C. and 10° C., preferably from −20° C. to 0° C.

The reaction time is, for example, between 0.5 hr and 5 hr, preferably between 0.5 hr and 3 hr, more preferably between 1 hr and 2 hr.

The compound of formula [5] may be purified by distillation, for example, under reduced pressure or atmospheric pressure, preferably at atmospheric pressure.

Step 2

[Chem. 25]

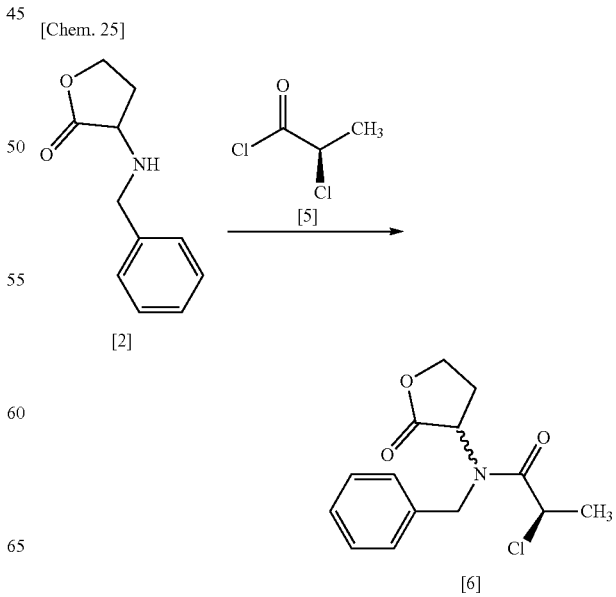

The compound of formula [6] may be prepared by reacting the compound of formula [2] or a salt thereof with the compound of formula [5] in the presence of a base. In this step, the compound [2-2] or a salt thereof may be used in place of the compound [2] or a salt thereof. In this case, the compound [6-2]

[Chem. 26]

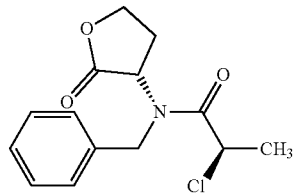

[6-2]

may be prepared.

Examples of the solvent include, for example, toluene, ethyl acetate, THF and any mixed solvent thereof. A preferable solvent is a mixed solvent of toluene and ethyl acetate.

Examples of the base include, for example, 2,6-lutidine and N,N-diisopropylethylamine. A preferable base is 2,6-lutidine. The base may be used, for example, in an amount of from 1.0 to 5.0 equivalents relative to the compound of formula [2], preferably 3.0±0.5 equivalents. It may be used, for example, in an amount of from 2.0 to 5.0 equivalents relative to a salt of the compound of formula [2], preferably 4.0±0.5 equivalents.

The reaction temperature is in the range of, for example, −20° C. and 20° C., preferably from −10° C. to 10° C.

The reaction time is, for example, between 1 hr and 5 hr, preferably between 2 hr and 3 hr.

The compound of formula [6] may be obtained in a crystalline form. Examples of the solvent used for crystallization include, for example, toluene; 2-propanol; CPME; ethyl acetate; a mixture of two or more solvents selected from toluene, 2-propanol, CPME, and ethyl acetate; a mixed solvent of 2-propanol and water; and a mixed solvent of toluene, 2-propanol, CPME or ethyl acetate, and heptane. A preferable solvent is a mixed solvent of toluene and heptane, or a mixed solvent of 2-propanol and heptane.

[Process for Preparation 4] Preparation of the Compound of Formula [7]

[Chem. 27]

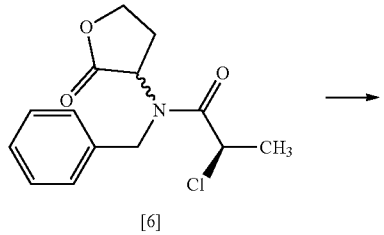

The compound of formula [7] may be prepared by a cyclization reaction of the compound of formula [6] in the presence of a base. In this Process for preparation, the compound [6-2] may be used in place of the compound [6] to prepare the compound [7].

Examples of the solvent include, for example, THF, acetonitrile, toluene, DMSO, DMF, dimethylacetamide, N-methylpyrrolidone and any mixed solvent thereof. A preferable solvent is DMSO, THF, or a mixed solvent of toluene and THF.

Examples of the base include, for example, 1,8-diazabicyclo[5.4.0]-7-undecene, lithium hexamethyldisilazide, sodium hexamethyldisilazide, potassium hexamethyldisilazide, lithium diisopropylamide, tripotassium phosphate, cesium carbonate and tert-butylimino-tri(pyrrolidino)phosphorane. A preferable base is lithium hexamethyldisilazide, cesium carbonate or tripotassium phosphate. A more preferable base is lithium hexamethyldisilazide.

When lithium hexamethyldisilazide is used as the base, the base may be used, for example, in an amount of from 0.9 to 1.2 equivalents relative to the compound of formula [6], preferably 1.0±0.05 equivalents. The reaction temperature is in the range of, for example, −20° C. and 5° C., preferably from −15° C. to 0° C. The reaction time is, for example, between 0.5 hr and 5 hr, preferably between 1 hr to 3 hr.

When cesium carbonate or tripotassium phosphate is used as the base, the base may be used, for example, in an amount of from 2.0 to 5.0 equivalents relative to the compound of formula [6], preferably 3.0±0.5 equivalents. The reaction temperature is in the range of, for example, room temperature and 60° C., preferably room temperature. The reaction time is, for example, between 10 hr and 30 hr, preferably between 10 hr and 24 hr.

[Process for Preparation 5] Preparation of the Compound of Formula [9]

[Chem. 28]

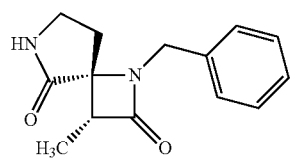

[9]

Step 1

[Chem. 29]

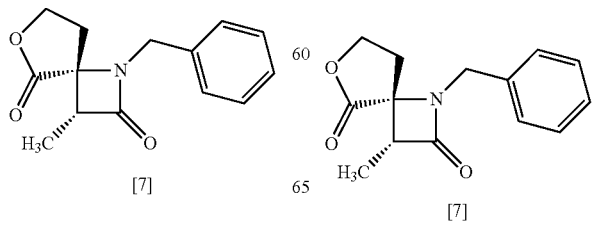

-continued

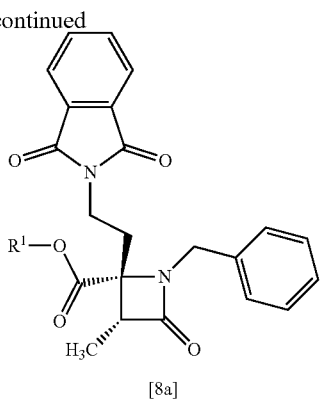

[8a]

wherein R[1] is $C_{1-4}$ alkyl or benzyl; and X[2] is halogen.

The compound of formula [8a] may be prepared by reacting the compound of formula [7] with potassium phthalimide, then esterifying the obtained compound by using the compound of formula [19a]. Potassium phthalimide may be used, for example, in an amount of from 1.0 to 2.0 equivalents relative to the compound of formula [7], preferably 1.1±0.05 equivalents.

Examples of the compound of formula [19a] include, for example, methyl iodide, ethyl iodide and benzyl bromide. A preferable compound of formula [19a] is ethyl iodide. The compound of formula [19a] may be used, for example, 1.0 to 2.0 equivalents relative to the compound of formula [7], preferably 1.3±0.05 equivalents.

Examples of the solvent include, for example, DMF, dimethylacetamide, DMSO, N-methylpyrrolidone, toluene, and any mixed solvent thereof. A preferable solvent is DMF, DMSO, or a mixed solvent of DMSO and toluene.

The reaction temperature for the reaction with potassium phthalimide is in the range of, for example, 80° C. and 150° C., preferably from 90° C. to 115° C. For the esterification, the temperature is in the range of, for example, room temperature and 80° C., preferably from room temperature to 60° C.

The reaction time for the reaction with potassium phthalimide is, for example, between 10 hr and 30 hr, preferably between 10 hr and 24 hr. For the esterification, the reaction time is, for example, between 1 hr and 6 hr, preferably between 4 hr and 5 hr. Another preferable reaction time for the esterification is between 1 hr and 2 hr.

The compound of formula [8a] may be also prepared by isolating the compound of formula [22]

[Chem. 30]

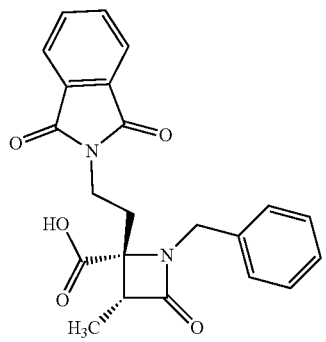

[22]

or a salt thereof, followed by esterification. The esterification may be carried out according to known methods.

Step 2

[Chem. 31]

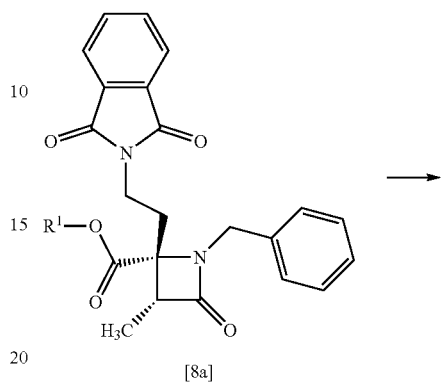

wherein R[1] is $C_{1-4}$ alkyl or benzyl.

The compound of formula [9] may be prepared by the removal of phthaloyl in the compound of formula [8a]. Any known method may be used for removing phthaloyl, for example, the compound of formula [9] may be prepared by reacting the compound of formula [8a] with ethylenediamine or diethylenetriamine.

Ethylenediamine or diethylenetriamine may be used, for example, in an amount of from 1.0 to 10 equivalents relative to the compound of formula [8a], preferably 5.0±0.5 equivalents.

Examples of the solvent include, for example, methanol, ethanol, 1-propanol, 2-propanol, 1-butanol, 2-butanol and 2-methyl-2-propanol. A preferable solvent is 2-butanol.

The reaction temperature is in the range of, for example, 60° C. and 105° C., preferably from 80° C. to 95° C.

The reaction time is, for example, between 1 hr and 6 hr, preferably between 2 hr and 5 hr.

The compound of formula [9] may be obtained as a crystal by means of recrystallization. For example, the crystal of the compound of formula [9] may be obtained by dissolving the compound of formula [9] in CPME with heating and then adding diisopropyl ether to the solution, or by dissolving the compound of formula [9] in toluene with heating and then adding heptane to the solution.

The temperature for dissolving the compound [9] into a solvent for recrystallization is in the range of, for example, 40° C. and 80° C. A preferable temperature is in the range of 50° C. and 60° C. when CPME is used, and in the range of 65° C. and 75° C. when toluene is used.

The time for recrystallization is, for example, between 3 hr and 10 hr, preferably between 3 hr and 5 hr.

The compound of formula [9] is a crystal, for example, showing the X-ray powder diffraction pattern having at least one (for example, at least 1, 2, 3, 4, or 5) peak at 10.6°±0.2°, 16.0°±0.2°, 17.5°±0.2°, 18.3°±0.2° or 19.2°±0.2° of the diffraction angle (2θ) measured by using CuKα radiation.

Preferably, the compound of formula [9] is a crystal showing the X-ray powder diffraction pattern having at least one (for example, at least 1, 2, 3, 4, or 5) peak at 10.6°±0.1°, 16.0°±0.10, 17.5°±0.10, 18.3°±0.10 or 19.2°±0.1° of the diffraction angle (2θ) measured by using CuKα radiation.

More preferably, the compound of formula [9] is a crystal showing the X-ray powder diffraction pattern having at least one (for example, at least 1, 2, 3, 4, or 5) peak 10.6°±0.06°, 16.0°±0.06°, 17.5°±0.06°, 18.3°±0.06° or 19.2°±0.06° of the diffraction angle (2θ) measured by using CuKα radiation.

[Process for Preparation 6] Alternative Process for Preparing the Compound of Formula [9]

[Chem. 32]

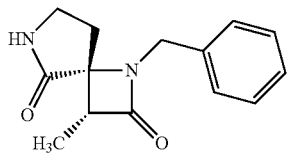

[9]

Step 1

[Chem. 33]

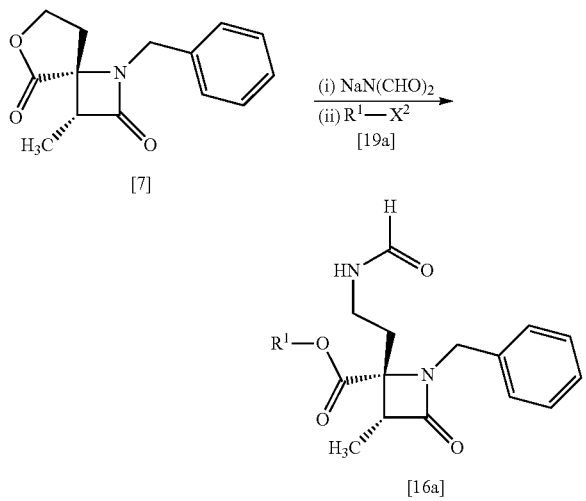

wherein R¹ is $C_{1-4}$ alkyl or benzyl; and $X^2$ is halogen.

The compound of formula [16a] may be prepared by reacting the compound of formula [7] with sodium diformylamide, and then esterifying the resulting compound by using the compound of formula [19a]. Sodium diformylamide may be used, for example, in an amount of from 2.0 to 5.0 equivalents relative to the compound of formula [7], preferably 3.0±0.5 equivalents.

Examples of the compound of formula [19a] include, for example, methyl iodide, ethyl iodide and benzyl bromide. A preferable compound of formula [19a] is ethyl iodide. The compound of formula [19a] may be used, for example, in an amount of from 2.0 to 5.0 equivalents relative to the compound of formula [7], preferably 3.0±0.5 equivalents.

Examples of the solvent include, for example, DMSO, dimethylacetamide and N-methylpyrrolidone. A preferable solvent is DMSO.

The reaction temperature for the reaction with sodium diformylamide is in the range of, for example, 80° C. and 150° C., preferably 100° C.±5° C. For the esterification, the temperature is in the range of, for example, room temperature and 80° C., preferably from room temperature to 50° C.

The reaction time for the reaction with sodium diformylamide is, for example, between 10 hr and 30 hr, preferably between 10 hr and 24 hr. For the esterification, the reaction time is, for example, between 3 hr and 6 hr, preferably between 4 hr and 5 hr.

Step 2

[Chem. 34]

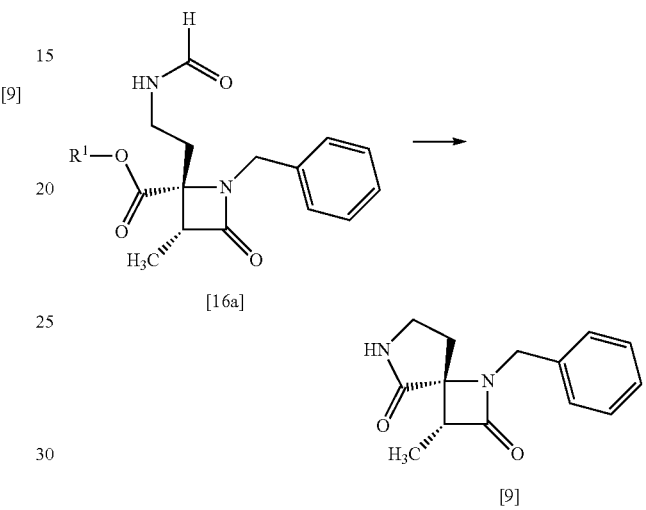

wherein R¹ is $C_{1-4}$alkyl or benzyl.

The compound of formula [9] may be prepared by the removal of formyl in the compound of formula [16a] in the presence of a base.

Examples of the solvent include, for example, acetonitrile, THF, DMF, DMSO, dimethylacetamide, DMSO, and N-methylpyrrolidone. A preferable solvent is acetonitrile.

Examples of the base include, for example, lithium hexamethyldisilazide, sodium hexamethyldisilazide, potassium hexamethyldisilazide, lithium diisopropylamide, cesium carbonate, tripotassium phosphate, and tert-butylimino-tri(pyrrolidino)phosphorane. A preferable base is cesium carbonate. The base may be used, for example, in an amount of from 1.0 to 2.0 equivalents relative to the compound of formula [16a], preferably 1.5±0.05 equivalents.

The reaction temperature is in the range of, for example, 0° C. and 50° C., preferably room temperature.

The reaction time is, for example, between 3 hr and 6 hr, preferably between 4 hr and 5 hr.

[Process for Preparation 7] Preparation of the Compound of Formula [10]

[Chem. 35]

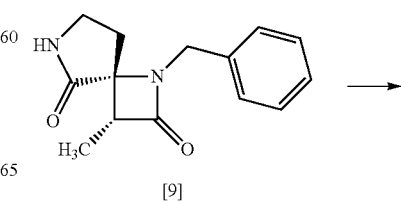

[9]

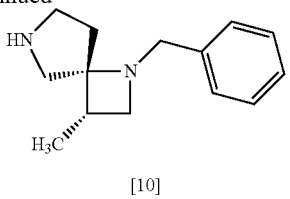

[10]

The compound of formula [10] may be prepared by the reduction of the compound of formula [9].

Examples of the solvent include, for example, toluene, CPME, THF, and 2-methyl tetrahydrofuran. A preferable solvent is toluene, THF or a mixture thereof.

Examples of the reducing agent include, for example, TMDS which is used in the presence of triruthenium dodecacarbonyl catalyst or zinc trifluoromethanesulfonate catalyst, and lithium aluminium hydride which is used in the presence of an acid. Examples of the acid include, for example, sulfuric acid, aluminum chloride, zinc chloride, and chlorotrimethylsilane. A preferable reducing agent is TMDS which is used in the presence of triruthenium dodecacarbonyl catalyst, or lithium aluminum hydride which is used in the presence of chlorotrimethylsilane or aluminum chloride.

[Process for Preparation 7-1] the Case where TMDS is Used in the Presence of a Catalyst The reducing agent may be used, for example, in an amount of from 3.0 to 15.0 equivalents relative to the compound of formula [9], preferably 10.0±0.5 equivalents.

The catalyst may be used, for example, in an amount of from 0.05 to 0.5 equivalents relative to the compound of formula [9], preferably 0.1 to 0.3 equivalents.

An additive may be further added to the reaction when triruthenium dodecacarbonyl catalyst is used. Examples of the additive include, for example, TMEDA and N,N,N',N'-tetramethyl-1,3-diaminopropane. A preferable additive is TMEDA. The additive may be used, for example, in an amount of 0.05 to 0.5 equivalents relative to the compound of formula [9], preferably 0.1 to 0.3 equivalents.

The reaction temperature is in the range of, for example, 40° C. and 100° C., preferably from 60° C. to 80° C.

The reaction time is, for example, between 10 hr and 50 hr, preferably between 35 hr and 45 hr.

[Process for Preparation 7-2] the Case where Lithium Aluminium Hydride is Used in the Presence of an Acid The reducing agent may be added at one time or in two or more divided portions. Preferably, the reducing agent is added in two or more divided portions.

(1) When the reducing agent is added at one time, the reducing agent may be used in the presence of an acid, for example, in an amount of from 1.0 to 5.0 equivalents relative to the compound of formula [9], preferably 3.0±0.5 equivalents. A preferable acid in this case is aluminum chloride or chlorotrimethylsilane. Aluminum chloride or chlorotrimethylsilane may be used, for example, in an amount of from 1.0 to 5.0 equivalents relative to the compound of formula [9], preferably 3.0±0.5 equivalents.

The reaction temperature is in the range of, for example, room temperature and 60° C., preferably from 40° C. to 50° C. The reaction time is, for example, between 10 hr and 30 hr, preferably between 15 hr and 24 hr.

(2) When the reducing agent is added in two or more divided portions, the reducing agent in a first portion may be used in the presence of an acid in an amount of, for example, from 1.0 to 5.0 equivalents relative to the compound of formula [9], preferably 2.5±0.5 equivalents. A preferable acid in this case is chlorotrimethylsilane. Chlorotrimethylsilane may be used, for example, in an amount of from 1.0 to 5.0 equivalents relative to the compound of formula [9], preferably 2.5±0.5 equivalents. The reducing agent in a second portion may be used, for example, in an amount of from 0.3 to 3.0 equivalents relative to the compound of formula [9], preferably 0.5±0.1 equivalents.

The reaction temperature is in the ranges of, for example, −20° C. and 10° C., preferably from −20° C. to 5° C., for the first portion, and for example, room temperature and 60° C., preferably from 40° C. to 50° C., for the second portion. Another preferable reaction temperature for the second portion is from 45° C. to 55° C.

The reaction time is, for example, between 0.5 hr and 3 hr, preferably between 1 hr and 2 hr, for the first portion, and for example, between 5 hr and 30 hr, preferably between 5 hr and 24 hr, for the second portion.

[Process for Preparation 8] Preparation of a Salt of a Compound of Formula [11a]

[Chem. 36]

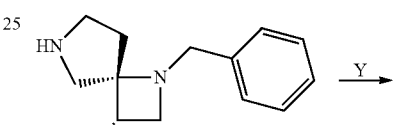

[10]

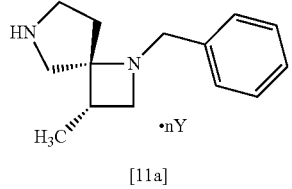

[11a]

wherein Y is an acid, n is any number between 0.5 to 2, for example, 0.5, 1 or 2.

The compound of formula [11a] may be prepared by forming a salt of the compound of formula [10] with using an acid.

Examples of the solvent include, for example, water, methanol, ethanol, 1-propanol, 2-propanol, THF and any mixed solvent thereof. A preferable solvent is 2-propanol.

The acid includes, for example, an organic or inorganic acid.

Examples of the organic acid includes, for example, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid, 10-camphorsulfonic acid and the like. Preferable organic acids are oxalic acid, L-tartaric acid, D-tartaric acid, succinic acid, (+)-10-camphorsulfonic acid or (−)-10-camphorsulfonic acid. More preferable organic acids are oxalic acid, succinic acid, L-tartaric acid, D-tartaric acid or (+)-10-camphorsulfonic acid.

Examples of the inorganic acid include, for example, hydrochloric acid, nitric acid, sulfuric acid, phosphoric acid, hydrobromic acid and the like.

The reaction temperature is in the range of, for example, room temperature and 80° C., preferably from room temperature to 70° C.

The reaction time is, for example, between 6 hr and 15 hr, preferably between 8 hr and 12 hr.

Example of the compound of formula [11a] is preferably a disuccinate salt of the compound of formula [10].

The compound of formula [11a] is, for example, a disuccinate salt of the compound of formula [10], which is a crystal showing the X-ray powder diffraction pattern having at least one (for example, at least 1, 2, 3, 4, or 5) peak at 4.8°±0.2°, 11.2°±0.2°, 16.2°±0.2°, 18.1°±0.2° or 20.1°±0.2° of the diffraction angle (2θ) measured by using CuKα radiation.

Preferably, the compound of formula [11a] is the disuccinate salt of the compound of formula [10], which is a crystal showing the X-ray powder diffraction pattern having at least one (for example, at least 1, 2, 3, 4, or 5) peak at 4.8°±0.1°, 11.2°±0.1°, 16.2°±0.1°, 18.1°±0.1° or 20.1°±0.1° of the diffraction angle (2θ) measured by using CuKα radiation.

More preferably, the compound of formula [11a] is the disuccinate salt of the compound of formula [10] which is a crystal showing the X-ray powder diffraction pattern having at least one (for example, at least 1, 2, 3, 4, or 5) peak at 4.8°±0.06°, 11.2°±0.06°, 16.2°±0.06°, 18.1°±0.06° or 20.1°±0.06° of the diffraction angle (2θ) measured by using CuKα radiation.

Another example of the compound of formula [11a] is preferably a hemi-oxalate salt of the compound of formula [10].

The compound of formula [11a] may be purified by recrystallization or stirring a mixed solution in which the compound of formula [11a] is suspended in a solvent (referred to as "slurry stirring" hereinafter). Alternatively, the compound of formula [11a] may be purified by recrystallization and slurry stirring, either of which may be carried out first. A preferable purification is slurry stirring.

Examples of the solvent used for the recrystallization and the slurry stirring include, for example, methanol, ethanol, 1-propanol, 2-propanol, THF, toluene, and a mixed solvent thereof. A preferable solvent for the recrystallization is a mixed solvent of methanol and toluene. A preferable solvent for the slurry stirring is 2-propanol.

The temperature for the slurry stirring is in the range of, for example, 0° C. and 60° C., preferably from 30° C. to 35° C. Another preferable temperature for the slurry stirring is from 35° C. to 40° C.

The time for the slurry stirring is, for example, between 1 hr and 15 hr, preferably between 2 hr and 12 hr.

[Process for Preparation 9] Preparation of the Compound of Formula [13]

[Chem. 37]

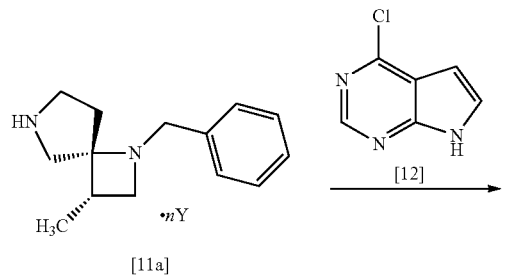

[11a]

[12]

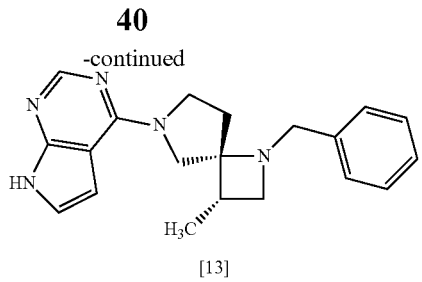

[13]

The compound of formula [13] may be prepared by condensing the compound of formula [11a] with 4-chloro-7H-pyrrolo[2,3-d]pyrimidine (CPPY) [12] or its salt in the presence of a base. The compound of formula [10] may be used in place of the compound of formula [11a]. The compound of formula [13] may be in its salt form, and the formation of a salt from the free form or the formation of the free form from a salt can be performed according to any one of the methods known in the art.

Examples of the solvent include, for example, tert-butanol, water, ethanol, methanol, 2-propanol and any mixed solvent thereof. A preferable solvent is a mixed solvent of tert-butanol or 2-propanol and water.

Examples of the base include, for example, alkali-phosphates such as tripotassium phosphate, alkali-carbonates such as potassium carbonate, alkali-hydroxides such as potassium hydroxide or a mixture thereof. A preferable base is tripotassium phosphate or a mixture of tripotassium phosphate and potassium hydroxide. The base may be used, for example, in an amount of from 4.0 to 10.0 equivalents relative to the compound of formula [11a], preferably 5.0 to 8.0 equivalents.

CPPY [12] may be used, for example, in an amount of from 0.95 to 1.10 equivalents relative to the compound of formula [11a], preferably 1.02±0.02 equivalents.

The reaction temperature is in the range of, for example, room temperature and 85° C., preferably 80° C.±5° C. Another preferable reaction temperature is 75° C.±5° C.

The reaction time is, for example, between 1 hr and 10 hr, preferably between 2 hr and 8 hr.

[Process for Preparation 10] Preparation of the Compound of Formula [14]

[Chem. 38]

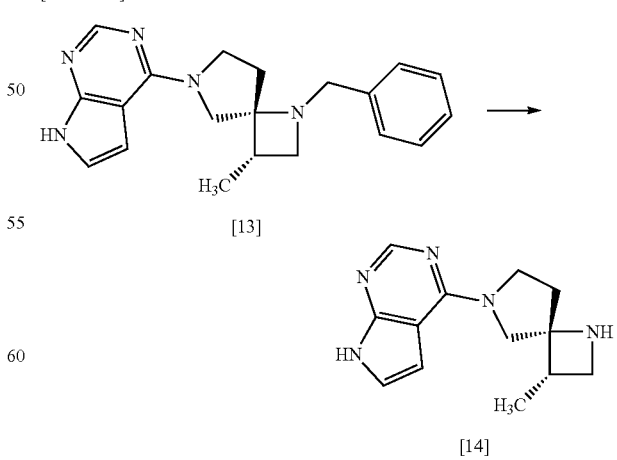

The compound of formula [14] may be prepared by the removal of the protecting group (benzyl) from the compound of formula [13]. Any of known methods may be used for the deprotection, for example, the compound of formula [14] may be prepared by adding hydrogen to the compound of formula [13] in the presence of a catalyst under an acidic condition. The compound of formula [13] and the compound of formula [14] may be in their salt forms, and the formation of a salt from the free form or the formation of the free form from a salt can be performed according to any one of the methods known in the art.

Examples of the solvent include, for example, tert-butanol, water, ethanol, 2-propanol and any mixed solvent thereof. A preferable solvent is a mixed solvent of tert-butanol and water or a mixed solvent of 2-propanol and water.

Examples of the catalyst include, for example, 5% palladium on carbon (50% water-containing product), 10% palladium on carbon (50% water-containing product), palladium on carbon, palladium hydroxide on carbon, palladium black and palladium on silica gel. A preferable catalyst is 5% palladium on carbon (50% water-containing product) or 10% palladium on carbon (50% water-containing product). The catalyst may be used, for example, in an amount of from 0.01 fold to 0.5 fold relative to the weight of the compound of formula [13], preferably 0.05 fold to 0.2 fold.

An example of the acid includes acetic acid.

Preferably, hydrogen gas pressure is atmospheric pressure. Pressurization of around 0.1 MPa may be applied.

The reaction temperature is in the range of, for example, room temperature and 80° C., preferably 55° C.±5° C. Another preferable embodiment is 50° C.±5° C.

The reaction time is, for example, between 2 hr and 10 hr, preferably between 3 hr and 8 hr.

[Process for Preparation 11] Preparation of the Compound of Formula [17]

[Chem. 39]

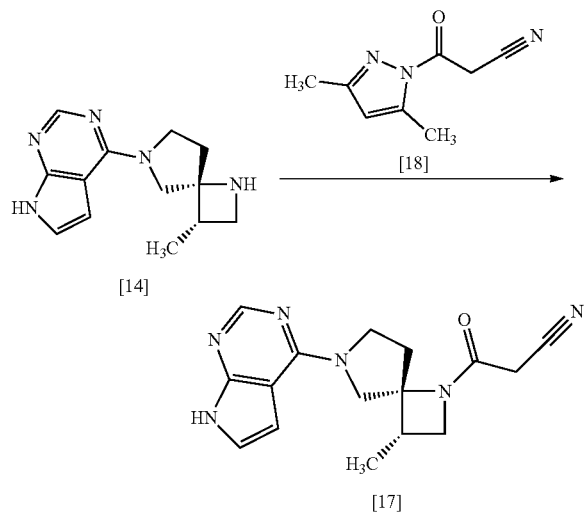

The compound of formula [17] may be prepared by condensing the compound of formula [14] with 1-cyano-acetyl-3,5-dimethyl-1H-pyrazole (DPCN) [18] in the presence of a base. The compound of formula [14] and the compound of formula [17] may be in their salt forms, and the formation of a salt from the free form or the formation of the free form from a salt can be performed according to any one of the methods known in the art.

Examples of the solvent include, for example, acetonitrile and THF. A preferable solvent is acetonitrile.

Examples of the base include, for example, triethylamine and N,N-diisopropylethylamine. A preferable base is triethylamine.

DPCN [18] may be used, for example, in an amount of from 0.95 to 1.2 equivalents relative to the compound of formula [17], preferably 1.05±0.10 equivalents.

The reaction temperature is in the range of, for example, room temperature and 80° C., preferably from 40° C. to 50° C.

The reaction time is, for example, between 1 hr and 12 hr, preferably between 2 hr and 6 hr.

In this reaction, the compound of formula [17] may be also prepared by condensing the compound of formula [14] with 1-cyanoacetyl-3,5-dimethyl-1H-pyrazole (DPCN) [18] without using the base. The compounds of formula [14] and formula [17] may be respectively replaced with their salts. Such salts may be formed from their free forms according to known methods, and vice versa.

The solvent used in this procedure includes, for example, acetonitrile and tetrahydrofuran. A preferable solvent is acetonitrile.

DPCN may be used, for example, in an amount of 0.95 to 1.2 equivalents relative to the compound of formula [14], preferably 1.05±0.05 equivalents.

The reaction temperature is in the range of, for example, room temperature and 80° C., preferably from 70° C. to 80° C.

The reaction time is, for example, between 0.5 hr and 12 hr, preferably between 0.5 hr and 6 hr.

The compound of formula [17] may be prepared by reacting the compound of formula [14] with a compound of formula [35a]:

[Chem. 40]

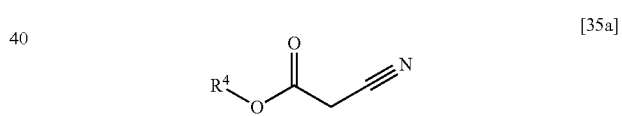

wherein $R^4$ is hydrogen, methyl or ethyl
or its salt, instead of 1-cyanoacetyl-3,5-dimethyl-1H-pyrazole (DPCN) [18]. The compound of formula [14] and the compound of formula [17] may be in their salt forms, and the formation of such a salt from the free form or the formation of the free form from such a salt can be performed according to any one of the methods known in the art.

When $R^4$ is hydrogen, the compound of formula [17] may be prepared by reacting the compound of formula [14] with the compound of formula [35a] or its salt in the presence of a base and a condensing agent.

Examples of the condensing agent include, for example, a combination of 1-ethyl-3-(3-dimethylaminopropyl)-carbodiimide hydrochloride (WSC·HCl) and 1-hydroxybenzotriazole (HOBt), and (benzotriazol-1-yloxy)tripyrrolidinophosphonium hexafluorophosphate (PyBOP) A preferable condensing agent is PyBOP.

When $R^4$ is methyl or ethyl, the compound of formula [17] may be prepared by condensing the compound of formula [14] with the compound of formula [35a]. The reaction is preferably performed in the presence of 3,5-dimethyl-1H-pyrazole and a catalytic amount of diazabicycloundecene (DBU).

[Process for Preparation 12] Preparation of the Compound of Formula [20]

[Chem. 41]

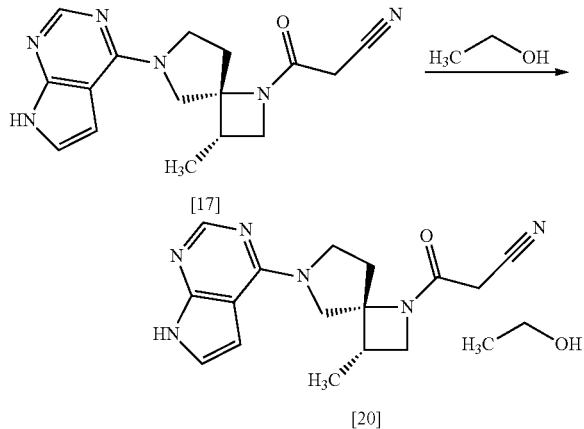

[17]

[20]

The compound of formula [20] may be prepared by crystallizing the compound of formula [17] by using a solvent. 1-Propanol, 2-propanol, chloroform, dioxane, anisole, acetone, ethylene glycol, dimethylacetamide or water may be used in place of ethanol in the compound of formula [20].

Examples of the solvent include, for example, ethanol, 1-propanol, 2-propanol, chloroform, dioxane, anisole, acetone, ethylene glycol, dimethylacetamide and water. A preferable solvent is ethanol.

Although this step is not necessarily required for the preparation of the compound [17], it may be optionally performed for the purpose of improving the purity of the compound [17].

The compound of formula [20] is, for example, the crystal showing the X-ray powder diffraction pattern having at least one (for example, at least 1, 2, 3, 4, or 5) peak at 8.3°±0.2°, 12.7°±0.2°, 13.0°±0.2°, 20.0°±0.2° or 24.1°±0.2° of the diffraction angle (2θ) measured by using CuKα radiation.

Preferably, the compound of formula [20] is the crystal showing the X-ray powder diffraction pattern having at least one (for example, at least 1, 2, 3, 4, or 5) peak at 8.3°±0.1°, 12.7°±0.1°, 13.0°±0.10, 20.0°±0.10 or 24.1°±0.1° of the diffraction angle (2θ) measured by using CuKα radiation.

More preferably, the compound of formula [20] is the crystal showing the X-ray powder diffraction pattern having at least one (for example, at least 1, 2, 3, 4, or 5) peak at 8.3°±0.06°, 12.7°±0.06°, 13.0°±0.06°, 20.0°±0.06° or 24.1°±0.06° of the diffraction angle (2θ) measured by using CuKα radiation.

[Process for Preparation 13] Purification of the Compound of Formula [17]

[Chem. 42]

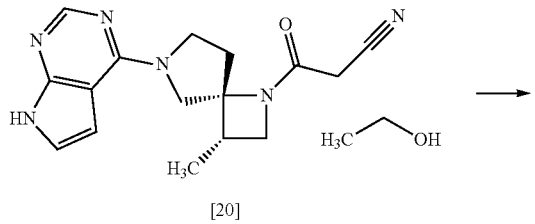

[20]

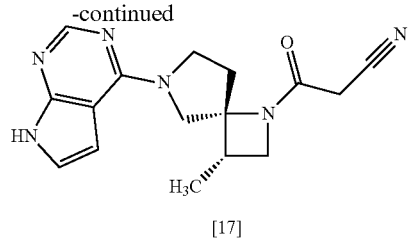

[17]

The compound of formula [17] can be purified by crystallization after dissolving the compound of formula [20].

Examples of the solvent for crystallization include, for example, 1-butanol, 1-propanol and 2-methyl-2-butanol. A preferable solvent is 1-butanol. The solvent may be used, for example, in an amount of from 8.0 fold to 20 fold relative to the weight of the compound of formula [20], preferably 8.5 fold±0.5 fold.

The temperature for dissolving the compound [20] into a solvent for crystallization is in the range of, for example, 100° C. and 117° C., preferably 110° C.±5° C.

The time for crystallization is, for example, between 15 hr and 48 hr, preferably between 18 hr and 24 hr.

The compound of formula [17] may be also purified by recrystallizing the compound of formula [17].

The solvent used in this procedure includes, for example, 1-butanol, 1-propanol and 2-methyl-2-butanol. A preferable solvent is 1-butanol. The solvent may be used, for example, in an amount of 18 fold to 22 fold relative to the weight of the compound of formula [17], preferably 20 fold±0.5 fold.

The temperature that the crystal dissolves is in the range of, for example, 85° C. and 100° C., preferably from 90° C. to 100° C.

The time for recrystallization is, for example, between 10 hr and 48 hr, preferably between 10 hr and 24 hr.

[Process for Preparation 14] Preparation of the Compound of Formula [34a]

[Chem. 43]

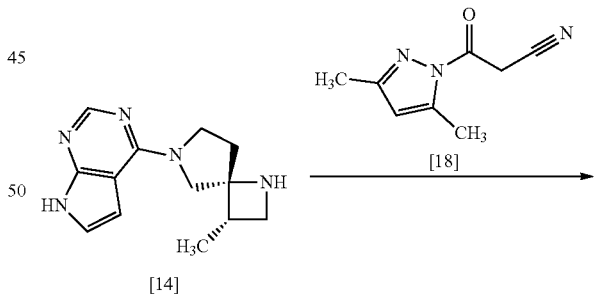

[14]

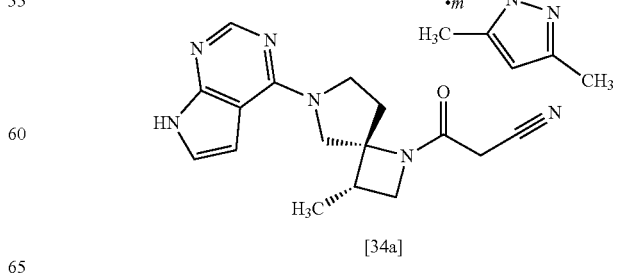

[34a]

wherein m is any number of 0.4 to 0.5.

The compound of formula [34a] may be prepared by condensing the compound of formula [14] with 1-cyanoacetyl-3,5-dimethyl-1H-pyrazole (DPCN) [18]. The compound of formula [14] may be in its salt form, and the formation of such a salt from the free form or the formation of the free form from such a salt can be performed according to any one of the methods known in the art.

A preferable solvent is acetonitrile.

DPCN [18] may be used, for example, in an amount of 0.95 to 1.2 equivalents relative to the compound of formula [14], preferably 1.1±0.05 equivalents. Another preferable embodiment is 1.05±0.05 equivalents.

The reaction temperature is in the range of, for example, room temperature and 80° C., preferably from 70° C. to 80° C.

The reaction time is, for example, between 0.5 hr and 12 hr, preferably between 0.5 hr and 6 hr.

Although this step is not necessarily required for the preparation of the compound [17], it may be optionally performed for the purpose of improving the purity of the compound [17].

The compound of formula [34a] may be, for example, the crystal showing the X-ray powder diffraction pattern having at least one (for example, at least 1, 2 or 3) peak at 4.6°±0.2°, 18.6°±0.2° or 20.9°±0.2° of the diffraction angle (2θ) measured by using CuKα radiation.

Preferably, the compound of formula [34a] may be the crystal showing the X-ray powder diffraction pattern having at least one (for example, at least 1, 2 or 3) peak at 4.6°±0.1°, 18.6°±0.1° or 20.9°±0.1° of the diffraction angle (2θ) measured by using CuKα radiation.

More preferably, the compound of formula [34a] may be the crystal showing the X-ray powder diffraction pattern having at least one (for example, at least 1, 2 or 3) peak at 4.6°±0.06°, 18.6°±0.06° or 20.9°±0.06° of the diffraction angle (2θ) measured by using CuKα radiation.

Further, the compound of formula [34a] may also be, for example, the crystal showing the X-ray powder diffraction pattern having at least one (for example, at least 1, 2, 3, 4, or 5) peak at 4.6°±0.2°, 12.6°±0.2°, 16.1°±0.2°, 18.6°±0.2° or 20.9°±0.2° of the diffraction angle (2θ) measured by using CuKα radiation.

Preferably, the compound of formula [34a] may also be the crystal showing the X-ray powder diffraction pattern having at least one (for example, at least 1, 2, 3, 4, or 5) peak at 4.6°±0.1°, 12.6°±0.1°, 16.1°±0.1°, 18.6°±0.1° or 20.9°±0.1° of the diffraction angle (2θ) measured by using CuKα radiation.

More preferably, the compound of formula [34a] may also be the crystal showing the X-ray powder diffraction pattern having at least one (for example, at least 1, 2, 3, 4, or 5) peak at 4.6°±0.06°, 12.6°±0.06°, 16.1°±0.06°, 18.6°±0.06° or 20.9°±0.06° of the diffraction angle (2θ) measured by using CuKα radiation.

[Process for Preparation 15] Purification of the Compound of Formula [17]

[Chem. 44]

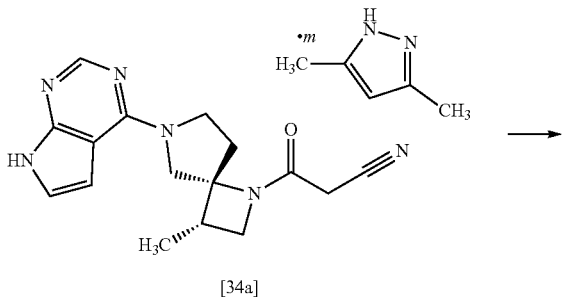

[34a]

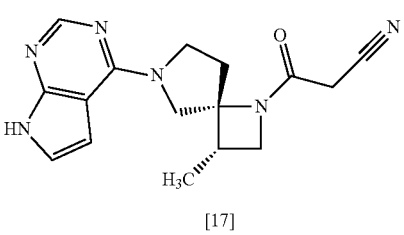 [SMILES: C[C@H]1CN(C(=O)CC#N)[C@]12CCN(c1ncnc3[nH]ccc13)C2]

[17]

wherein m has the same meaning as defined above.

The compound of formula [17] may be prepared by crystallization after dissolving the compound of formula [34a]. The purification may be performed by the addition of 2,6-di-tert-butyl-4-methylphenol (BHT) during the crystallization.

Examples of the solvent for crystallization include, for example, 1-butanol, 1-propanol and 2-methyl-2-butanol. A preferable solvent is 1-butanol. The solvent may be used, for example, in an amount of from 8.0 folds to 20 folds relative to the weight of the compound of formula [34a], preferably 8.5 folds±0.5 folds.

The temperature for dissolving the compound [34a] into the solvent for crystallization is in the range of, for example, 100° C. and 117° C., preferably 110° C.±5° C.

The time for crystallization is, for example, between 15 hr and 48 hr, preferably between 18 hr and 24 hr.

[Process for Preparation 16] Preparation of the Compound of Formula [24a]

[Chem. 45]

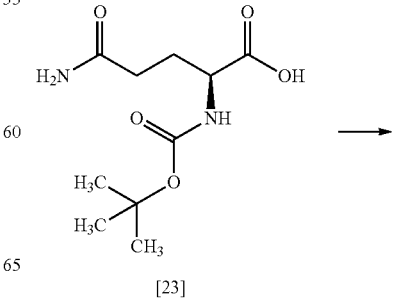

[23]

-continued

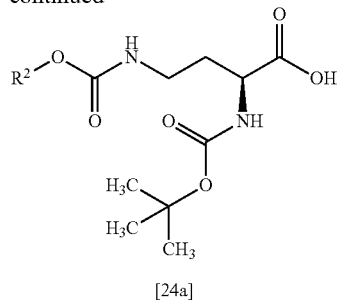

[24a]

wherein R² is methyl, ethyl or benzyl.

The compound of formula [24a] may be prepared by reacting the compound of formula [23] with methanol, ethanol or benzyl alcohol; and an oxidant. The compound of formula [23] and the compound of formula [24a] may be in their salt forms, and the formation of a salt from the free form or the formation of the free form from a salt can be performed according to any one of the methods known in the art.

Examples of the solvent include, for example, methanol, ethanol or benzyl alcohol; and a mixed solvent of methanol and water, THF or toluene. A preferable solvent is methanol.

Examples of the oxidant include, for example, bromine, sodium hypochlorite, oxone and (diacetoxyiodo)benzene. A preferable oxidant is sodium hypochlorite or bromine. The oxidant may be used, for example, in an amount of from 0.9 to 2.0 equivalents relative to the compound of formula [23], preferably 1.1±0.05 equivalents.

The reaction temperature is in the range of, for example, 0° C. and 60° C., preferably from 40° C. to 50° C.

The reaction time is, for example, between 1 hour and 5 hours, preferably 2 hours.

[Process for Preparation 17] Preparation of the Compound of Formula [25a] or a Salt Thereof

[Chem. 46]

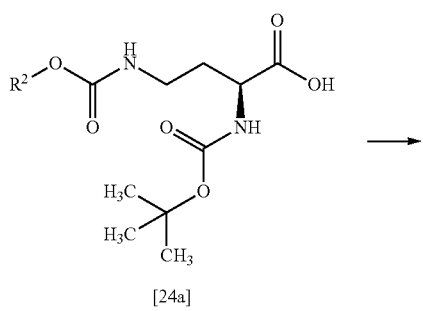

wherein R² has the same meaning as defined above and R³ is independently methyl, ethyl or benzyl.

The compound of formula [25a] or a salt thereof may be prepared by reacting the compound of formula [24a] with methanol, ethanol or benzyl alcohol; and an acid. The compound of formula [24a] may be in its salt form, and the formation of a salt from the free form or the formation of the free form from a salt can be performed according to any one of the methods known in the art.

Examples of the solvent include, for example, methanol, ethanol or benzyl alcohol; and a mixed solvent of methanol and water, THF or toluene. A preferable solvent is methanol.

Examples of the acid or acid precursor include, for example, hydrochloric acid, acetyl chloride, thionyl chloride, phosphoryl chloride, oxalyl chloride. A preferable acid or acid precursor is hydrochloric acid or thionyl chloride, respectively. A more preferable acid or acid precursor is thionyl chloride. The acid or acid precursor may be used, for example, in an amount of from 1.0 to 20.0 equivalents relative to the compound of formula [24a], preferably 2.0 equivalents.

The reaction temperature is in the range of, for example, 0° C. and 50° C., preferably from 15° C. to 25° C.

The reaction time is, for example, between 2 hours and 21 hours, preferably 2 hours.

[Process for Preparation 18] Preparation of the Compound of Formula [26a] or a Salt Thereof

[Chem. 47]

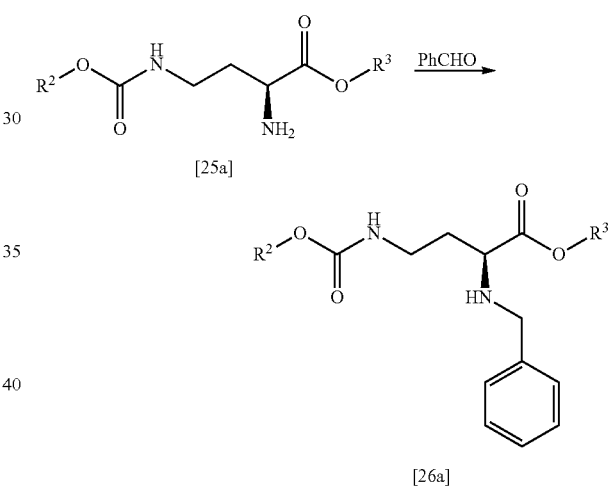

wherein R² and R³ each have the same meanings as defined above.

The compound of formula [26a] or a salt thereof may be prepared by reacting the compound of formula [25a] or a salt thereof with benzaldehyde and a base, followed by reduction of thus obtained compound. The compound of formula [25a] and the compound of formula [26a] may be also used or prepared in their salt forms, and the formation of a salt from the free form or the formation of the free form from a salt can be performed according to any one of the methods known in the art.

Examples of the solvent include, for example, methanol, ethanol, 2-propanol, acetonitrile, and 1,2-dichloroethane. A preferable solvent is methanol.

Examples of the base include, for example, triethylamine and N,N-diisopropylethylamine. A preferable base is triethylamine.

Examples of the reducing agent include, for example, sodium borohydride, sodium triacetoxyborohydride, sodium cyanoborohydride and hydrogen gas. A preferable reducing agent is sodium borohydride. The reducing agent may be used, for example, in an amount of from 0.95 to 1.2 equivalents relative to the compound of formula [25a], preferably 1.1±0.05 equivalents.

The reactant benzaldehyde may be used, for example, in an amount of from 0.95 to 2.0 equivalents relative to the compound of formula [25a], preferably 1.1±0.05 equivalents.

The reaction temperature during the addition of sodium borohydride is in the range of, for example, −30 to −5° C., preferably −20° C. to −15° C. Following the addition of sodium borohydride, the reaction temperature is between 0° C. and 25° C., preferably between 20° C. and 25° C.

The reaction time is, for example, between 2 hours and 21 hours, preferably between 3 hours and 6 hours.

An example of a salt of the compound of formula [26a] is a hydrogen chloride salt.

Examples of the solvent for the formation of the hydrogen chloride salt include, for example, methyl tert-butyl ether, 2-propanol, ethyl acetate, and 2-propyl acetate. A preferable solvent is ethyl acetate or 2-propyl acetate. A more preferable solvent is 2-propyl acetate.

The acid, hydrogen chloride, used for the formation of the hydrogen chloride salt may be used, for example, in an amount from 0.95 to 5.0 equivalents relative to the compound of formula [26a], preferably 1.5 to 2.5 equivalents.

The reaction temperature is in the range of, for example, −10° C. to 50° C., preferably 0° C. to 10° C.

The reaction time is, for example, between 30 minutes and 3 hours, preferably between 1 hour and 2 hours.

The hydrogen chloride salt of the compound of formula [26a] may be purified by slurry stirring with heating.

Examples of the solvent for the purification include, for example, methanol, ethanol, 2-propanol, 1-butanol, and 2-propyl acetate. A preferable solvent is 2-propyl acetate.

The purification temperature is in the range of, for example, room temperature to 60° C., preferably 40° C. to 50° C.

The purification time is, for example, between 2 hours and 12 hours, preferably between 3 hours and 6 hours.

[Process for Preparation 19] Preparation of the Compound of Formula [27a]

[Chem. 48]

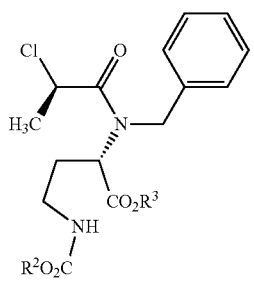

[27a]

wherein $R^2$ and $R^3$ each have the same meanings as defined above.

Step 1

[Chem. 49]

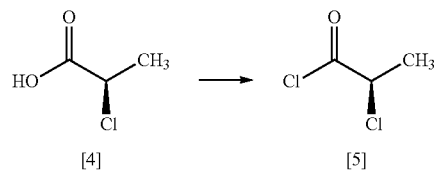

[4]         [5]

The compound of formula [5] may be prepared in the same manner as Step 1 of Process for preparation 3.

Step 2

[Chem. 50]

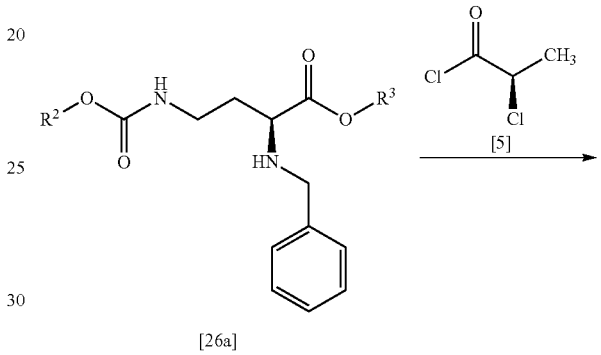

[26a]

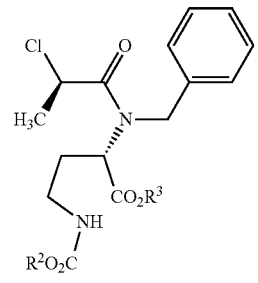

[27a]

wherein $R^2$ and $R^3$ each have the same meanings as defined above.

The compound of formula [27a] may be prepared by reacting the compound of formula [26a] or a salt thereof with the compound of formula [5] in the presence of a base. In this step, the compound [26b]

[Chem. 51]

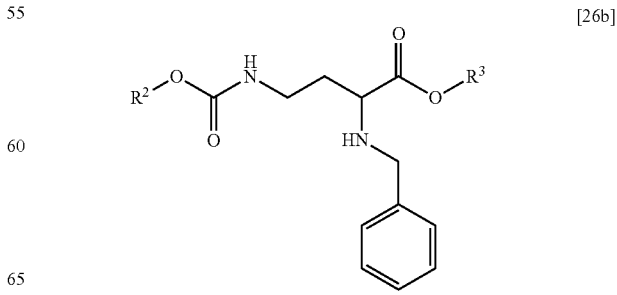

[26b]

or a salt thereof may be used in place of the compound [26a] or a salt thereof. When the compound [26b] is used in this step, the compound [27b]

[Chem. 52]

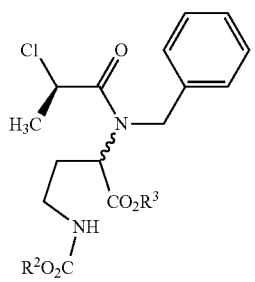

[27b]

may be prepared.

Examples of the solvent include, for example, toluene, ethyl acetate, THF, methyl tert-butyl ether, acetonitrile and any mixed solvent thereof. A preferable solvent is acetonitrile, toluene or a mixture of toluene and water.

Examples of the base include, for example, 2,6-lutidine, N,N-diisopropylethylamine, triethylamine, pyridine, tripotassium phosphate, and potassium carbonate. A preferable base is potassium carbonate or a combination of 2,6-lutidine and N,N-diisopropylethylamine. The base may be used, for example, in an amount from 1.0 to 5.0 equivalents relative to the compound of formula [26a], preferably 3.0 to 4.0 equivalents.

The reaction temperature is in the range of, for example, –20° C. and 20° C., preferably from –10° C. to 5° C.

The reaction time is, for example, between 1 hour and 5 hours, preferably between 1 hour and 3 hours.

[Process for Preparation 20] Preparation of the Compound of Formula [9]

[Chem. 53]

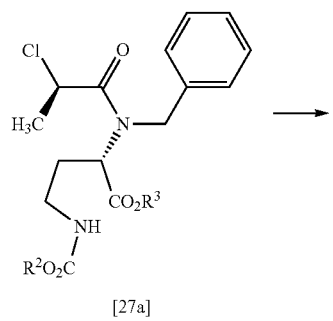

[27a]

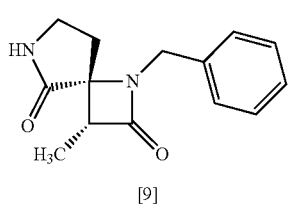

[9]

wherein $R^2$ and $R^3$ each have the same meanings as defined above.

The compound of formula [9] may be prepared by a double cyclization reaction of the compound of formula [27a] in the presence of a base. Alternatively, a mixture of stereoisomers of the compound [27a] may be used to prepare the compound [9] as a mixture of enantiomers, which is subsequently separated by chiral techniques.

Examples of the solvent include, for example, THF, acetonitrile, toluene, DMSO, DMF, dimethylacetamide, N-methylpyrrolidone, dimethylcarbonate and any mixed solvent thereof. A preferable solvent is acetonitrile or DMSO.

Examples of the base include, for example, lithium hexamethyldisilazide, sodium hexamethyldisilazide, potassium hexamethyldisilazide, lithium diisopropylamide, tripotassium phosphate, cesium carbonate, tert-butylimino-tri(pyrrolidino)phosphorane, potassium tert-butoxide and lithium 2-methyl-2-butoxide. A preferable base is lithium hexamethyldisilazide, cesium carbonate or lithium 2-methyl-2-butoxide. A more preferable base is lithium 2-methyl-2-butoxide.

When lithium 2-methyl-2-butoxide is used as the base, the base may be used, for example, in an amount of from 1.0 to 3.0 equivalents relative to the compound of formula [27a], preferably 3.0 equivalents. In that case, the reaction temperature is in the range of, for example, –20° C. to 5° C., preferably –10° C. to 0° C., and the reaction time is, for example, between 1 hour and 5 hours.

When cesium carbonate is used as the base, the base may be used, for example, in an amount of from 2.0 to 5.0 equivalents relative to the compound of formula [27a], preferably 2.5 equivalents. In that case, the reaction temperature is in the range of, for example, 15° C. and 50° C., preferably from 20° C. to 25° C., and the reaction time is, for example, between 10 hours and 30 hours, preferably between 15 hours and 20 hours.

[Process for Preparation 21] Preparation of the Compound of Formula [29a]

[Chem. 54]

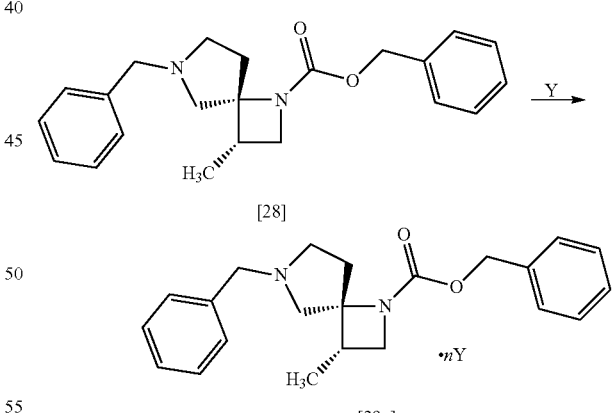

wherein Y is an acid, and n is any number between 0.5 to 1, for example, 0.5 or 1.

The compound of formula [29a] may be prepared by forming a salt of the compound of formula [28] with using an acid.

Examples of the solvent include, but are not limited to, water, methanol, ethanol, 1-propanol, isopropanol, acetonitrile, acetone, toluene, methyl tert-butyl ether, tetrahydrofuran, and any mixed solvent thereof. A preferable solvent is a mixture of tetrahydrofuran and toluene.

The acid includes, for example, an organic or inorganic acid.

Examples of the organic acid include, for example, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid, 10-camphorsulfonic acid and the like. A preferable organic acid is oxalic acid.

Examples of the inorganic acid include, for example, hydrochloric acid, nitric acid, sulfuric acid, phosphoric acid, hydrobromic acid and the like.

The reaction temperature is in the range of, for example, 0° C. to 80° C., preferably 30° C. to 60° C. The reaction time is, for example, between 30 mins and 24 hours, preferably between 1 hour and 3 hours.

An example of the compound of formula [29a] is preferably oxalate salt of the compound of formula [28].

[Process for Preparation 22] Preparation of the Compound of Formula [30a]

[Chem. 55]

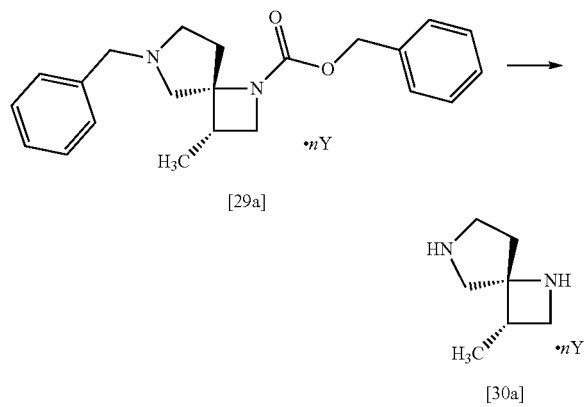

[29a]

[30a]

wherein Y is an acid, and n is any number between 0.5 to 2, for example, 0.5, 1 or 2.

The compound of formula [30a] may be prepared by the removal of the protecting groups (i.e., benzyloxycarbonyl and benzyl) from the compound of formula [29a]. Any of known methods may be used for the deprotection, for example, the compound of formula [30a] may be prepared by adding hydrogen gas to the compound of formula [29a] in the presence of a catalyst under neutral, basic or acidic conditions. The compound of formula [29a] and the compound of formula [30a] may be also used or prepared in their free forms, and the formation of a salt from the free form or the formation of the free form from a salt can be performed according to any one of the methods known in the art.

Examples of the solvent include, for example, tert-butanol, water, isopropanol, 1-propanol, ethanol and any mixed solvent thereof.

Examples of the catalyst include, for example, 5% palladium on carbon (50% water-containing product), 10% palladium on carbon (50% water-containing product), palladium on carbon, palladium hydroxide on carbon and palladium black. A preferable catalyst is 5% palladium on carbon (50% water-containing product) or 10% palladium on carbon (50% water-containing product). The catalyst may be used, for example, in an amount of from 0.01 fold to 0.5 fold relative to the weight of the compound of formula [29a], preferably 0.05 fold to 0.2 fold.

Hydrogen gas pressure is the range of 1 to 5 bar. Preferable hydrogen gas pressure is in the range of 2 to 4 bar.

The reaction temperature is in the range of, for example, room temperature to 80° C., preferably 40° C.±20° C.

The reaction time is, for example, between 2 hours and 24 hours, preferably between 12 hours and 24 hours.

Examples of organic acids for salt formation include, oxalic acid, malonic acid, maleic acid, citric acid, fumaric acid, terephthalic acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid, 10-camphorsulfonic acid and the like. Preferable organic acids are oxalic acid and succinic acid.

[Process for Preparation 23] Preparation of the Compound of Formula [14] or a Salt Thereof

[Chem. 56]

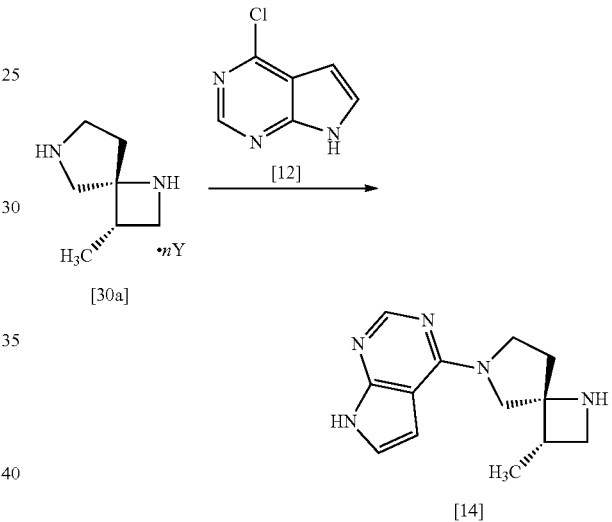

[14]

wherein Y is an acid, and n is any number between 0.5 to 2, for example, 0.5, 1 or 2.

The compound of formula [14] may be prepared by condensing the compound of formula [30a] with 4-chloro-7H-pyrrolo[2,3-d]pyrimidine (CPPY) [12] or its salt in the presence of a base. The compound of formula [30a] may be also used as its free form. The compound of formula [14] may be also prepared in its salt form, and the formation of a salt from the free form or the formation of the free form from a salt can be performed according to any one of the methods known in the art.

Examples of the solvent include, for example, ethanol, 2-propanol, 1-propanol, 2-propanol, tert-butanol, acetonitrile, THF and a mixture thereof with water. A preferable solvent is a mixture of tert-butanol and water.

Examples of the base include, for example, potassium phosphate, potassium carbonate, potassium hydroxide, triethylamine and N,N-diisopropylethylamine. A preferable base is potassium phosphate alone or in combination with potassium hydroxide.

The reactant CPPY [12] may be used, for example, in an amount of from 0.95 to 1.05 equivalents relative to the compound of formula [30a], preferably 1.0±0.02 equivalents.

The reaction temperature is in the range of, for example, room temperature to 80° C., preferably 40° C. to 50° C.

The reaction time is, for example, between 2 hours and 48 hours, preferably between 12 hours and 24 hours.

[Process for Preparation 24] Preparation of the Compound of Formula [31]

[Chem. 57]

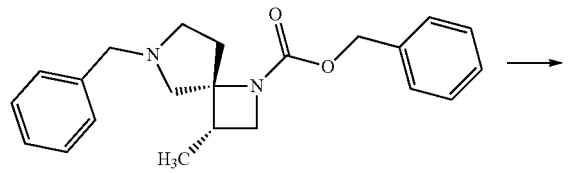

The compound of formula [31] may be prepared in the same manner as Process for preparation 22.

[Process for Preparation 25] Preparation of the Compound of Formula [30a]

[Chem. 58]

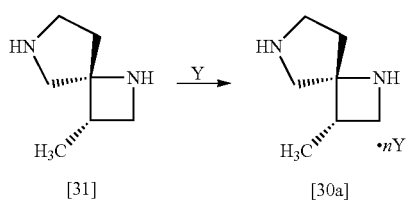

wherein Y is an acid, and n is any number between 0.5 to 2, for example, 0.5, 1 or 2.

The compound of formula [31] may be prepared in the same manner as Process for preparation 21.

A preferable organic acid used in this step is succinic acid.

The process for preparing the compound or its salt, or a solvate thereof in the present invention may have the following advantages over the Preparation 6 in Patent Literature 1.

(1) The present process can prepare compound A (compound [17]) in fewer steps.

(2) The present process is a preparation method avoiding ozone oxidation reaction and a reaction under ultracold conditions which are unsuitable for a large-scale synthesis.

(3) BABL [2] is obtained as a main product by virtue of suppression of cleavage of the lactone ring in Process for preparation 1, which can improve yield of compound A (compound [17]).

(4) Removal of a bisbenzyl-adduct and an unreacted benzylamine and the like in the isolation step utilizing a salt of BABL [2] can reduce side reactions in Process for preparation 3-Step 2, which can improve yield of compound A (compound [17]).

(5) The present process which contains forming RR-AOBL [7] can stereoselectively produce the β-lactam ring without using any special equipment or any special reagent.

(6) RR-AOPE [8a] and compound [16a] can be produced by virtue of the use of potassium phthalimide or sodium diformylamide as a nitrogen source in the process for preparing RR-MDDO [9], followed by the cleavage at position 7 of RR-AOBL [7], which can reduce the number of preparation steps and improve yield of compound A (compound [17]).

(7) The preparation of compound A (compound [17]) with a chemically high purity and an optically high purity can be achieved via the isolation step utilizing RR-MDDO [9].

(8) The preparation of compound A (compound [17]) with an optically high purity can be achieved via the isolation step utilizing a salt of SR-MDBN [10].

(9) Procedures for isolation and purification by extraction and silica gel column chromatography can be unnecessary by virtue of the highly stable compound [34a] which can be directly isolated from a reaction mixture. Compound A (compound [17]) can be prepared with a chemically high purity.

Embodiments of the present invention include the following embodiments:

Item 1: A process for preparing a compound of formula [17]:

[Chem. 59]

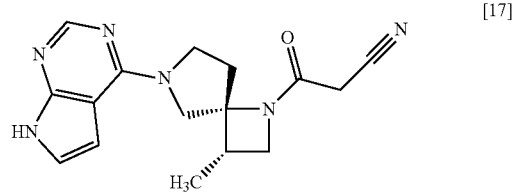

or its salt with using a compound of formula [13]:

[Chem. 60]

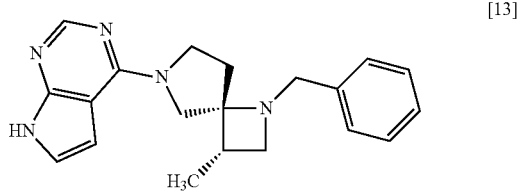

or its salt, comprising the following steps of:

(1) removing benzyl from a compound of formula [13] or its salt to give a compound of formula [14]:

[Chem. 61]

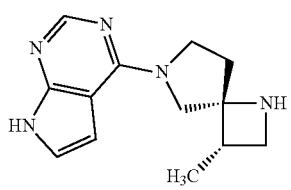

or its salt, and (2) cyanoacetylating the compound of formula [14] or its salt to give a compound of formula [17] or its salt.

Item 2: The process of Item 1, further comprising the step of reacting a compound of formula [10]:

[Chem. 62]

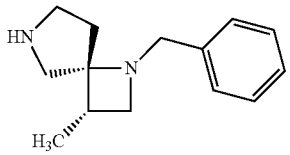

[10]

or its salt with an organic acid with a compound of formula [12]:

[Chem. 63]

[12]

or its salt to give the compound of formula [13] or its salt.

Item 3: The process of Item 2, further comprising the step of adding an organic acid to the compound of formula [10] to give a salt of the compound of formula [10] with the organic acid.

Item 4: The process of Item 2 or 3, wherein the salt of the compound of formula [10] with the organic acid is a disuccinate, an oxalate or a hemi-oxalate.

Item 5: The process of Item 2 or 3, wherein the salt of the compound of formula [10] with the organic acid is a hemi-oxalate.

Item 6: The process of any one of Items 2 to 5, further comprising the step of reducing a compound of formula [9]:

[Chem. 64]

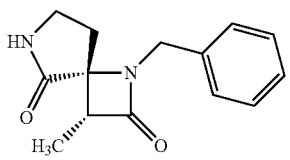

[9]

to give the compound of formula [10] or its salt with an organic acid.

Item 7: The process of Item 6, wherein the reduction is carried out in the presence of an acid and lithium aluminum hydride.

Item 8: The process of Item 6 or 7, further comprising the step of removing phthaloyl from a compound of formula [8a]:

[Chem. 65]

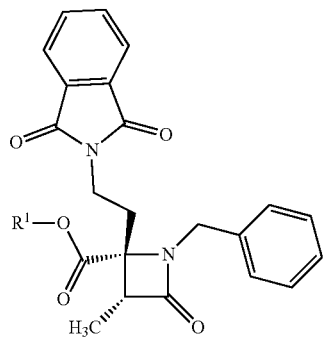

[8a]

wherein $R^1$ is $C_{1-4}$ alkyl or benzyl;
to give the compound of formula [9].

Item 9: The process of Item 6 or 7, further comprising the step of removing formyl from a compound of formula [16a]:

[Chem. 66]

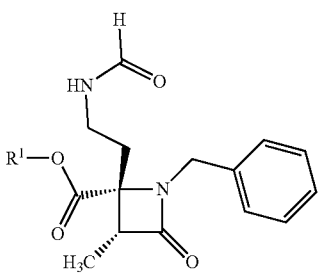

[16a]

wherein $R^1$ is $C_{1-4}$ alkyl or benzyl;
to give the compound of formula [9].

Item 10: The process of Item 8, further comprising the step of reacting a compound of formula [7]:

[Chem. 67]

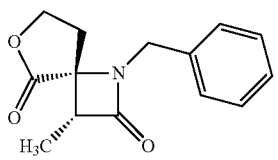

[7]

with potassium phthalimide followed by esterification to give the compound of formula [8a].

Item 11: The process of Item 9, further comprising the step of reacting a compound of formula [7]:

[Chem. 68]

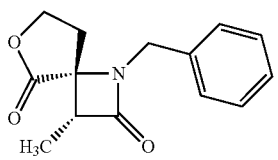

[7]

with sodium diformylamide followed by esterification to give the compound of formula [16a].

Item 12: The process of Item 10 or 11, further comprising the step of reacting a compound of formula [6]:

[Chem. 69]

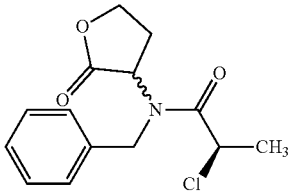

[6]

with a base to give the compound of formula [7].

Item 13: The process of Item 12, wherein the base is lithium hexamethyldisilazide.

Item 14: A process for preparing a salt of a compound of formula [10]:

[Chem. 70]

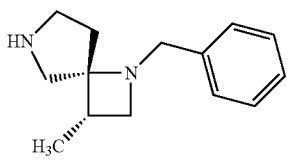

[10]

with an organic acid, comprising the step of adding an organic acid to a compound of formula [10] to give a salt of a compound of formula [10] with an organic acid.

Item 15: The process of Item 14, wherein the salt with an organic acid is disuccinate, an oxalate or a hemi-oxalate.

Item 16: The process of Item 14, wherein the salt with an organic acid is a hemi-oxalate.

Item 17: The process of Items 14 to 16, further comprising the step of reducing a compound of formula [9]:

[Chem. 71]

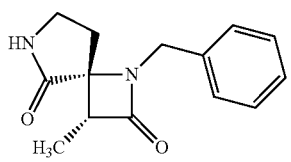

[9]

to give a compound of formula [10] or its salt with an organic acid.

Item 18: The process of Item 17, wherein the reduction is carried out in the presence of an acid and lithium aluminum hydride.

Item 19: The process of Item 17 or 18, further comprising the step of removing phthaloyl from a compound of formula [8a]:

[Chem. 72]

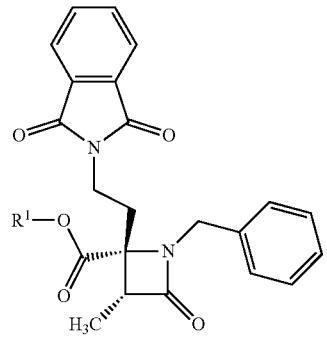

[8a]

wherein $R^1$ is $C_{1-4}$ alkyl or benzyl;

to give a compound of formula [9].

Item 20: The process of Item 17 or 18, further comprising the step of removing formyl from a compound of formula [16a]:

[Chem. 73]

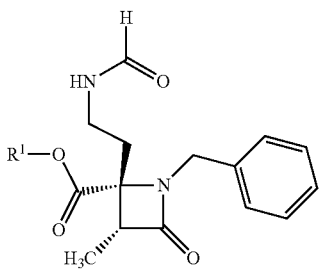

[16a]

wherein $R^1$ is $C_{1-4}$ alkyl or benzyl;

to give a compound of formula [9].

Item 21: The process of Item 19, further comprising reacting a compound of formula [7]:

[Chem. 74]

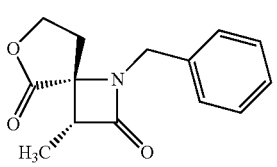

[7]

with potassium phthalimide followed by esterification to give a compound of formula [8a].

Item 22: The process of Item 19, further comprising the step of reacting a compound of formula [7]:

[Chem. 75]

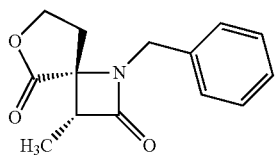

[7]

with sodium diformylamide followed by esterification to give a compound of formula [16a].

Item 23: The process of Item 21 or 22, further comprising the step of reacting a compound of formula [6]:

[Chem. 76]

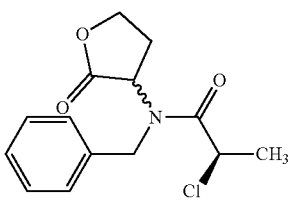

[6]

with a base to give a compound of formula [7].

Item 24: The process of Item 23, wherein the base is lithium hexamethyldisilazide.

Item 25: The process of Item 23 or 24, further comprising reacting a compound of formula [2]:

[Chem. 77]

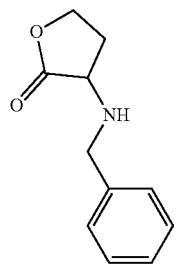

[2]

or its salt with a compound of formula [5]:

[Chem. 78]

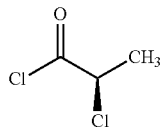

[5]

in the presence of a base to give a compound of formula [6]

Item 26: The process of Item 25, wherein the base is 2,6-lutidine.

Item 27: The process of Item 25 or 26, further comprising the step of adding an inorganic acid to a compound of formula [2] to give a salt of a compound of formula [2] with the inorganic acid.

Item 28: The process of any one of Items 25, 26 and 27, further comprising the step of reacting a compound of formula [4]:

[Chem. 79]

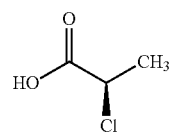

[4]

with a chlorinating agent to give a compound of formula [5]

Item 29: The process of Item 28, further comprising the step of reacting a compound of formula [1a]:

[Chem. 80]

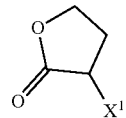

[1a]

wherein $X^1$ is chlorine or bromine;
with benzylamine in the presence of a base to give a compound of formula [2] or its salt.

Item 30: The process of Item 29, wherein the base is tripotassium phosphate.

Item 31: A process for preparing a compound of formula [9]:

[Chem. 81]

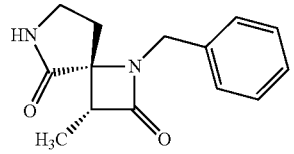

[9]

comprising the step of removing phthaloyl from a compound of formula [8a]:

[Chem. 82]

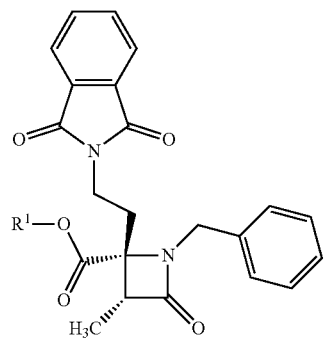

[8a]

wherein $R^1$ is $C_{1-4}$ alkyl or benzyl;
to give a compound of formula [9].

Item 32: A process for preparing a compound of formula [9]:

[Chem. 83]

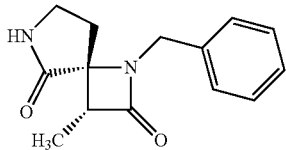

[9]

comprising the step of removing formyl from a compound of formula [16a]:

[Chem. 84]

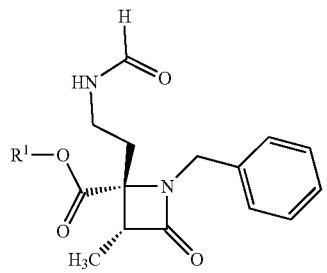

[16a]

wherein $R^1$ is $C_{1-4}$ alkyl or benzyl;
to give a compound of formula [9].

Item 33: The process of Item 31, further comprising the step of reacting a compound of formula [7]:

[Chem. 85]

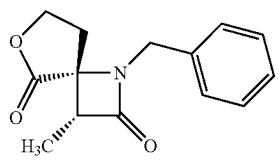

[7]

with potassium phthalimide followed by esterification to give a compound of formula [8a].

Item 34: The process of Item 32, further comprising the step of reacting a compound of formula [7]:

[Chem. 86]

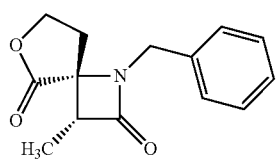

[7]

with sodium diformylamide followed by esterification to give a compound of formula [16a].

Item 35: The process of Item 33 or 34, further comprising the step of reacting a compound of formula [6]:

[Chem. 87]

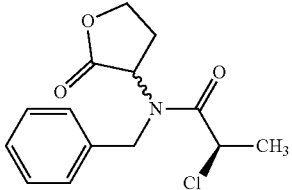

[6]

with a base to give a compound of formula [7].

Item 36: The process of Item 35, wherein the base is lithium hexamethyldisilazide.

Item 37: The process of Item 35 or 36, further comprising the step of reacting a compound of formula [2]:

[Chem. 88]

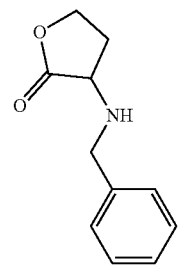

[2]

or its salt with a compound of formula [5]:

[Chem. 89]

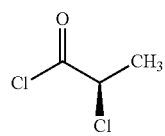

[5]

in the presence of a base to give a compound of formula [6]

Item 38: The process of Item 37, wherein the base is 2,6-lutidine.

Item 39: The process of Item 37 or 38, further comprising the step of adding an inorganic acid to a compound of formula [2] to give a salt of a compound of formula [2] with an inorganic acid.

Item 40: The process of any one of Items 37, 38 and 39, further comprising the step of reacting a compound of formula [4]:

[Chem. 90]

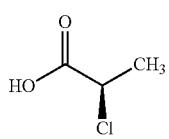

[4]

with a chlorinating agent to give a compound of formula [5]

Item 41: The process of Item 40, further comprising the step of reacting a compound of formula [1a]:

[Chem. 91]

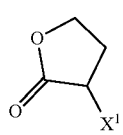
[1a]

wherein X¹ is chlorine or bromine;
with benzylamine in the presence of a base to give a compound of formula [2] or its salt.

Item 42: The process of Item 41, wherein the base is tripotassium phosphate.

Item 43: A process for preparing a compound of formula [7]:

[Chem. 92]

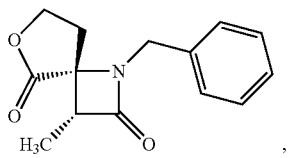
[7]

comprising the step of reacting a compound of formula [6]:

[Chem. 93]

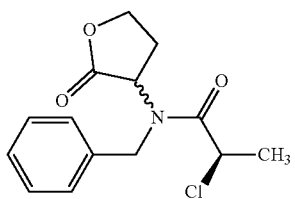
[6]

with a base to give a compound of formula [7].

Item 44: The process of Item 43, wherein the base is lithium hexamethyldisilazide.

Item 45: The process of Item 43 or 44, further comprising the step of reacting a compound of formula [2]:

[Chem. 94]

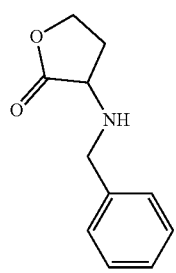
[2]

or its salt with a compound of formula [5]:

[Chem. 95]

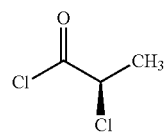
[5]

in the presence of a base to give a compound of formula [6]

Item 46: The process of Item 45, wherein the base is 2,6-lutidine.

Item 47: The process of Item 45 or 46, further comprising the step of adding an inorganic acid to a compound of formula [2] to give a salt of a compound of formula [2] with the inorganic acid.

Item 48: The process of any one of Items 45, 46 and 47, further comprising the step of reacting a compound of formula [4]:

[Chem. 96]

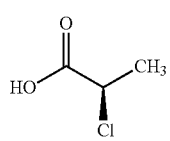
[4]

with a chlorinating agent to give a compound of formula [5]

Item 49: The process of Item 48, further comprising the step of reacting a compound of formula [1a]:

[Chem. 97]

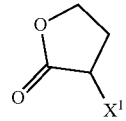
[1a]

wherein X¹ is chlorine or bromine;
with benzylamine in the presence of a base to give a compound of formula [2] or its salt.

Item 50: The process of Item 49, wherein the base is tripotassium phosphate.

Item 51: The process of Item 6 or 17, further comprising the step of cyclizing a compound of formula [27a]:

[Chem. 98]

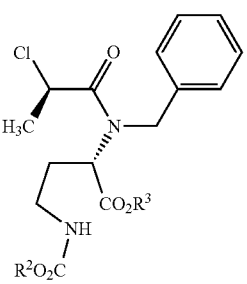
[27a]

wherein $R^2$ and $R^3$ are each independently methyl, ethyl or benzyl;
to give a compound of formula [9].

Item 52: The process of Item 51, further comprising the step of reacting a compound of formula [26a]:

[Chem. 99]

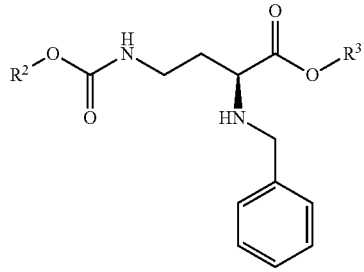

[26a]

wherein $R^2$ and $R^3$ are the same as defined above; or its salt with a compound of formula [5]:

[Chem. 100]

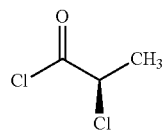

[5]

in the presence of a base to give a compound of formula [27a].

Item 53: The process of Item 52, further comprising the step of reacting a compound of formula [4]:

[Chem. 101]

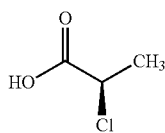

[4]

with a chlorinating agent to give a compound of formula [5].

Item 54: The process of Item 52 or 53, further comprising the step of reacting a compound of formula [25a]:

[Chem. 102]

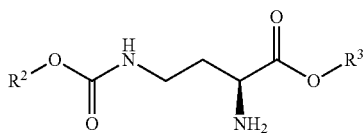

[25a]

wherein $R^2$ and $R^3$ are the same as defined above; or its salt with benzaldehyde to give a compound of formula [26a] or its salt.

Item 55: The process of Item 54, further comprising the step of esterifying a compound of formula [24a]:

[Chem. 103]

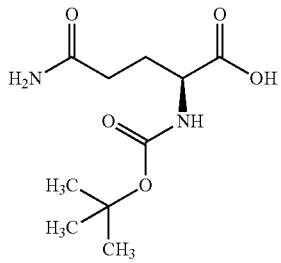

[24a]

wherein $R^2$ is the same as defined above;
or its salt to give a compound of formula [25a] or its salt.

Item 56: The process of Item 55, further comprising the step of obtaining a compound of formula [24a] or its salt from a compound of formula [23]:

[Chem. 104]

[23]

or its salt.

Item 57: A process for preparing a compound of formula [9]:

[Chem. 105]

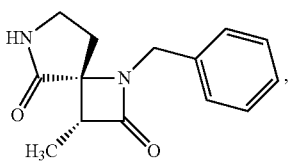

[9]

comprising the step of cyclizing a compound of formula [27a]:

[Chem. 106]

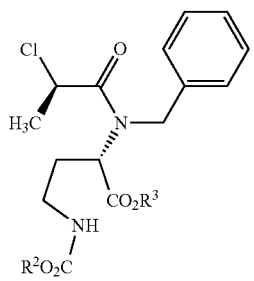

[27a]

wherein R² and R³ are each independently methyl, ethyl or benzyl;
to give a compound of formula [9].

Item 58: The process of Item 57, further comprising the step of reacting a compound of formula [26a]:

[Chem. 107]

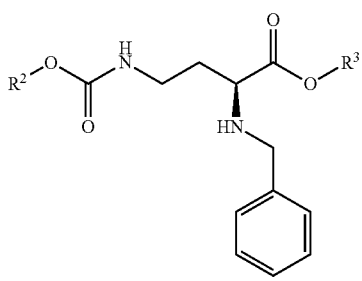

[26a]

wherein R² and R³ are the same as defined above; or its salt with a compound of formula [5]:

[Chem. 108]

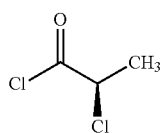

[5]

in the presence of a base to give a compound of formula [27a].

Item 59: The process of Item 58, further comprising the step of reacting a compound of formula [4]:

[Chem. 109]

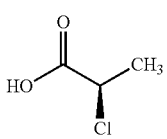

[4]

with a chlorinating agent to give a compound of formula [5]

Item 60: The process of Item 59, further comprising the step of reacting a compound of formula [25a]:

[Chem. 110]

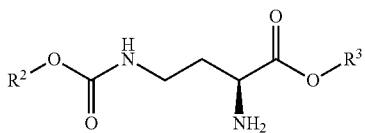

[25a]

wherein R² and R³ are the same as defined above;
or its salt with benzaldehyde to give a compound of formula [26a] or its salt.

Item 61: The process of Item 60, further comprising the step of esterifying a compound of formula [24a]:

[Chem. 111]

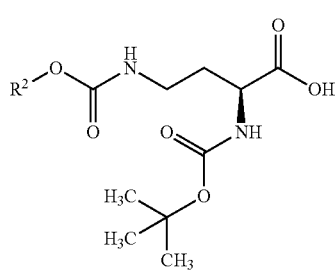

[24a]

wherein R² is the same as defined above;
or its salt to give a compound of formula [25a] or its salt.

Item 62: The process of Item 61, further comprising the step of obtaining a compound of formula [24a] or its salt from a compound of formula [23]:

[Chem. 112]

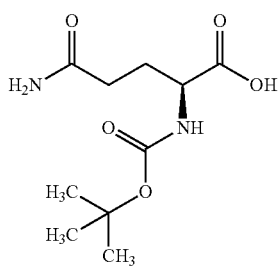

[23]

or its salt.

Item 63: A process for preparing a compound of formula [26a]:

[Chem. 113]

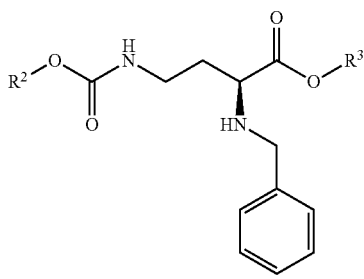

[26a]

wherein R² and R³ are the same as defined above;
or its salt, comprising the step of reacting a compound of formula [25a]:

[Chem. 114]

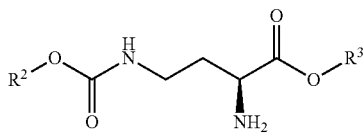

[25a]

wherein R² and R³ are the same as defined above;
or its salt with benzaldehyde to give a compound of formula [26a] or its salt.

Item 64: The process of Item 63, further comprising the step of esterifying a compound of formula [24a]:

[Chem. 115]

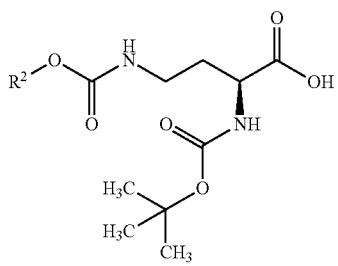

[24a]

wherein R² is the same as defined above;
or its salt to give a compound of formula [25a] or its salt.

Item 65: The process of Item 64, further comprising the step of obtaining a compound of formula [24a] or its salt from a compound of formula [23]:

[Chem. 116]

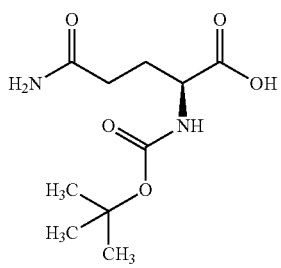

[23]

or its salt.

Item 66: A process for preparing a compound of formula [17]:

[Chem. 117]

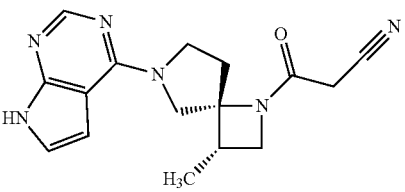

[17]

or its salt with using a compound of formula [31]:

[Chem. 118]

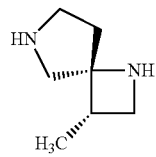

[31]

or its salt with an organic acid, comprising the following steps of:

(1) reacting a compound of formula [31] or its salt with an organic acid with a compound of formula [12]:

[Chem. 119]

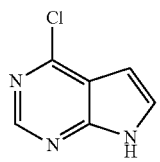

[12]

or its salt to give a compound of formula [14]:

[Chem. 120]

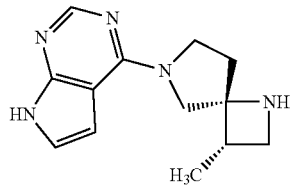

[14]

or its salt; and (2) cyanoacetylating a compound of formula [14] or its salt to give a compound of formula [17] or its salt.

Item 67: The process of Item 66, further comprising the step of adding an organic acid to a compound of formula [31] to give a salt of a compound of formula [31] with the organic acid.

Item 68: The process of Item 66 or 67, wherein the salt with an organic acid is a disuccinate or an oxalate.

Item 69: The process of any one of Items 66, 67 and 68, further comprising the step of obtaining a compound of formula [31] or its salt with an organic acid from a compound of formula [28]:

[Chem. 121]

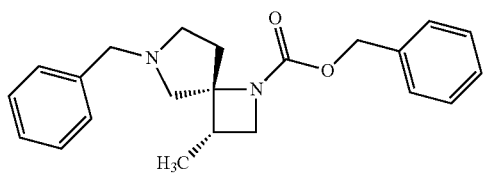

[28]

or its salt with an organic acid.

Item 70: The process of Item 69, further comprising the step of adding an organic acid to a compound of formula [28] to give a salt of a compound of formula [28] with the organic acid.

Item 71: The process of Item 69 or 70, wherein the salt of a compound of formula [28] with an organic acid is an oxalate.

Item 72: A process for preparing a salt of a compound of formula [31]:

[Chem. 122]

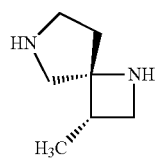

[31]

with an organic acid, comprising the step of adding an organic acid to a compound of formula [31] to give a salt of a compound of formula [31] with the organic acid.

Item 73: The process of Item 72, wherein the salt of a compound of formula [31] with an organic acid is a disuccinate or an oxalate.

Item 74: The process of Item 72 or 73, further comprising the step of obtaining a compound of formula [31] or its salt with an organic acid from a compound of formula [28]:

[Chem. 123]

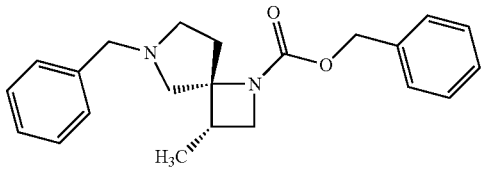

[28]

or its salt with an organic acid.

Item 75: The process of Item 74, further comprising the step of adding an organic acid to a compound of formula [28] to give a salt of a compound of formula [28] with the organic acid.

Item 76: The process of Item 74 or 75, wherein the salt of a compound of formula [28] with an organic acid is an oxalate.

Item 77: A compound of formula [13]:

[Chem. 124]

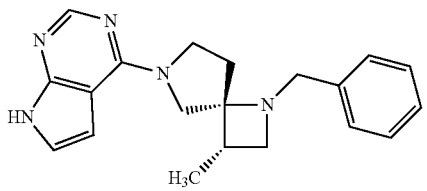

[13]

or its salt.

Item 78: A compound of formula [10]:

[Chem. 125]

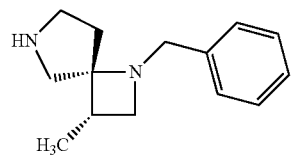

[10]

or its salt with an organic acid.

Item 79: The salt of Item 78, wherein the salt with an organic acid is a disuccinate, an oxalate or a hemi-oxalate.

Item 80: The salt of Item 78, wherein the salt with an organic acid is a hemi-oxalate.

Item 81: A crystal of a disuccinate of a compound of formula [10]:

[Chem. 126]

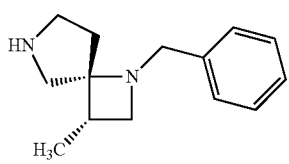

showing a X-ray powder diffraction pattern having at least one peak at 4.8°±0.2°, 11.2°±0.2°, 16.2°±0.2°, 18.1°±0.2° or 20.1°±0.2° of a diffraction angle (2θ) measured by using CuKα radiation.

Item 82: A compound of formula [9]:

[Chem. 127]

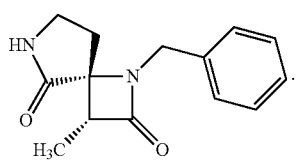

[9]

Item 83: A crystal of a compound of formula [9]:

[Chem. 128]

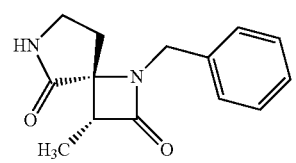

[9]

showing a X-ray powder diffraction pattern having at least one peak at 10.6°±0.2°, 16.0°±0.2°, 17.5°±0.2°, 18.3°±0.2° or 19.2°±0.2° of a diffraction angle (2θ) measured by using CuKα radiation.

Item 84: A compound of formula [8a]:

[Chem. 129]

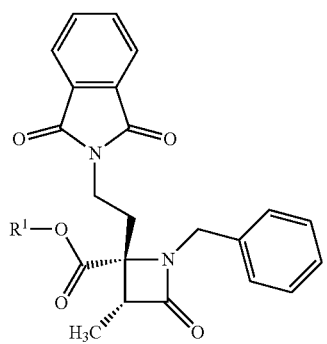

[8a]

wherein $R^1$ is $C_{1-4}$ alkyl or benzyl.

Item 85: A compound of formula [16a]:

[Chem. 130]

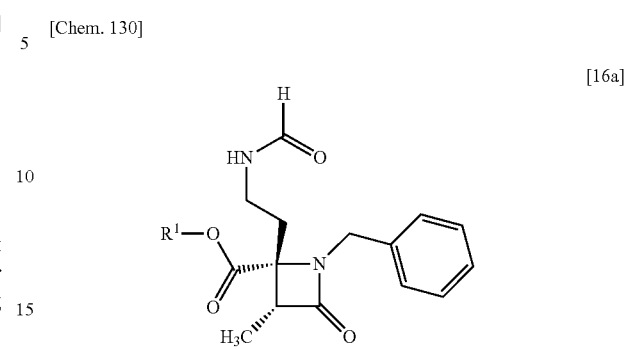

[16a]

wherein $R^1$ is $C_{1-4}$ alkyl or benzyl.

Item 86: A compound of formula [7]:

[Chem. 131]

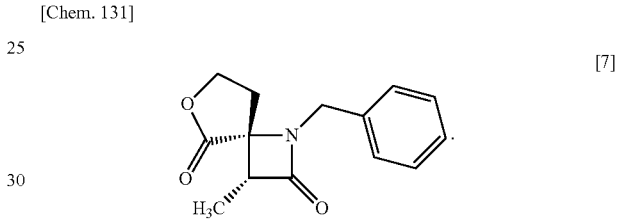

[7]

Item 87: A compound of formula [6]:

[Chem. 132]

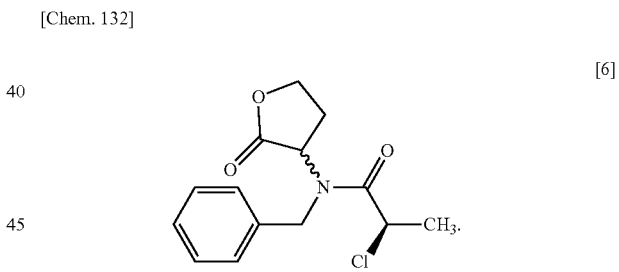

[6]

Item 88: A compound of formula [27a]:

[Chem. 133]

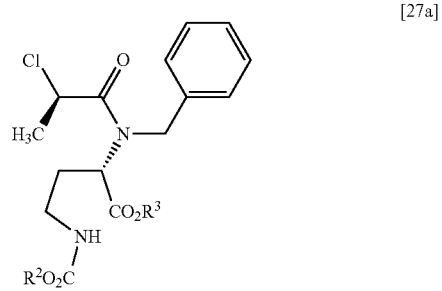

[27a]

wherein $R^2$ and $R^3$ are the same as defined above.

Item 89: A compound of formula [26a]:

[Chem. 134]

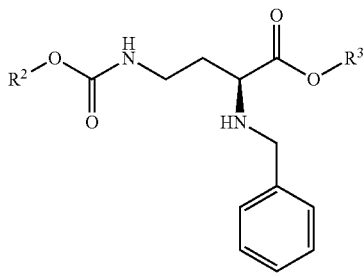
[26a]

wherein R² and R³ are the same as defined above; or its salt.

Item 90: A compound of formula [25a]:

[Chem. 135]

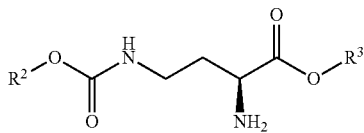
[25a]

wherein R² and R³ are the same as defined above; or its salt.

Item 91: A compound of formula [24a]:

[Chem. 136]

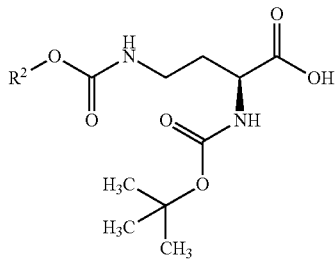
[24a]

wherein R² is the same as defined above; or its salt.

Item 92: A compound of formula [31]:

[Chem. 137]

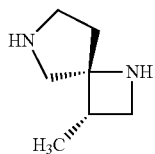
[31]

or its salt with an organic acid.

Item 93: The salt of Item 92, wherein the salt with an organic acid is a disuccinate or an oxalate.

Item 94: A salt of a compound of formula [28]:

[Chem. 138]

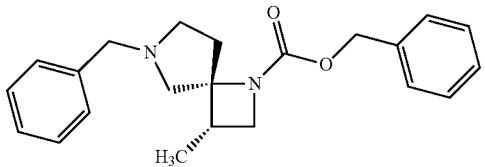
[28]

with an organic acid.

Item 95: The salt of Item 94, wherein the salt with an organic acid is an oxalate.

EXAMPLES

Specific processes for preparing compounds of the present invention or their salts, or solvates thereof are illustrated as examples hereinafter. However, the present invention is not restricted by these Examples.

In the crystallization steps in the preparation of the compound [9] (Example 4), the compound [20] (Example 13), the compound [29] (Example 36), the compound [30-2](Example 39) and Compound A (the compound [17]) (Examples 15 and 41), and the purification of Compound A (compound [17]) (Examples 14, 16, and 20), seed crystals were used to facilitate the crystallization. The crystals of these compounds can be obtained according to the methods described in the Examples even without employing seed crystals.

The meanings of the abbreviations used in the specification are shown below.

BBL: 3-bromodihydrofuran-2-one
BABL: 3-benzylaminodihydrofuran-2-one
BABL-HC: 3-benzylaminodihydrofuran-2-one monohydrochloride
BHT: 2,6-di-tert-butyl-4-methylphenol
R-CPRA: (R)-2-chloropropionic acid
R-CPRC: (R)-2-chloropropionyl chloride
R-CPBL: (R)—N-benzyl-2-chloro-N-(2-oxotetrahydrofuran-3-yl)-propionyl amide
RR-AOBL: (3R,4R)-1-benzyl-3-methyl-6-oxa-1-azaspiro[3.4]octane-2,5-dione
RR-AOPE: (2R,3R)-1-benzyl-2-[2-(1,3-dioxo-1,3-dihydroisoindol-2-yl)-ethyl]3-methyl-4-oxoazetidine-2-carboxylic acid ethyl ester
RR-AOPA: (2R,3R)-1-benzyl-2-[2-(1,3-dioxo-1,3-dihydroisoindol-2-yl)-ethyl]3-methyl-4-oxoazetidine-2-carboxylic acid
RR-MDDO: (3R,4R)-1-benzyl-3-methyl-1,6-diazaspiro[3.4]octane-2,5-dione)
SR-MDBN: (3S,4R)-1-benzyl-3-methyl-1,6-diazaspiro[3.4] octane
SR-MDBN-DSU: (3S,4R)-1-benzyl-3-methyl-1,6-diazaspiro[3.4]octane disuccinate
SR-MDBP: 4-[(3S,4R)-1-benzyl-3-methyl-1,6-diazaspiro[3.4] oct-6-yl]-7H-pyrrolo[2,3-d]pyrimidine
SR-MDOP: 4-[(3S,4R)-3-methyl-1,6-diazaspiro[3.4]-octan-6-yl]-7H-pyrrolo[2,3-d]pyrimidine
Compound A (Compound [17]): 3-[(3S,4R)-3-methyl-6-(7H-pyrrolo[2,3-d]pyrimidine-4-yl)-1,6-diazaspiro[3.4]octan-1-yl]-3-oxopropanenitrile
CPPY: 4-chloro-7H-pyrrolo[2,3-d]pyrimidine DPCN: 1-cyanoacetyl-3,5-dimethyl-1H-pyrazole
THF: tetrahydrofuran
CPME: cyclopentylmethyl ether
DMF: dimethylformamide
DMSO: dimethylsulfoxide
TMDS: 1,1,3,3-tetramethyldisiloxane
TMEDA: N,N,N',N'-tetramethylethylenediamine
TMSCl: chlorotrimethylsilane
LHMDS: lithium hexamethyldisilazide
TBBA: bromoacetic acid tert-butyl ester
Boc-Gln-OH: (tert-butoxycarbonyl)-L-glutamine
Boc-Dab(MeOCO)—OH: (S)-2-((tert-butoxycarbonyl)amino)-4-((methoxycarbonyl)amino)butanoic acid
SR-ZMDB: benzyl (3S,4R)-6-benzyl-3-methyl-1,6-diazaspiro[3.4]octane-1-carboxylate
SR-ZMDB-OX: benzyl (3S,4R)-6-benzyl-3-methyl-1,6-diazaspiro[3.4]octane-1-carboxylate oxalate
S-BAPO: (S)-2-(benzylamino) propan-1-ol
S-BBMO: tert-butyl (S)—N-benzyl-N-(1-hydroxypropan-2-yl)glycinate
R-BCAB: tert-butyl (R)—N-benzyl-N-(2-chloropropyl)glycinate
S-MABB: tert-butyl (3S)-1-benzyl-3-methylazetidine-2-carboxylate
S-MABB-HC: tert-butyl (3S)-1-benzyl-3-methylazetidine-2-carboxylate hydrochloride
S-MACB-HC: tert-butyl (3S)-3-methylazetidine-2-carboxylate hydrochloride
S-ZMAB: 1-benzyl 2-(tert-butyl) (3S)-3-methylazetidine-1,2-dicarboxylate
RS-ZMBB: 1-benzyl 2-(tert-butyl) (2R,3S)-2-(2-(tert-butoxy)-2-oxoethyl)-3-methylazetidine-1,2-dicarboxylate
RS-ZMAA: (2R,3S)-1-((benzyloxy)carbonyl)-2-(carboxymethyl)-3-methylazetidine-2-carboxylic acid
RS-ZMAA-DN·2H$_2$O: disodium (2R,3S)-1-((benzyloxy)carbonyl)-2-(carboxymethyl)-3-methylazetidine-2-carboxylate di-hydrate
RS-ZMOO: benzyl (2R,3S)-2-(2-hydroxyethyl)-2-(hydroxymethyl)-3-methylazetidine-1-carboxylate
RS-ZMSS: benzyl (2R,3S)-3-methyl-2-(2-((methylsulfonyl)oxy)ethyl)-2-(((methylsulfonyl)oxy)methyl)azetidine-1-carboxylate The measuring instruments and measuring conditions used in the Examples are shown below.

$^1$H-NMR spectrum are measured in CDCl$_3$, DMSO-d$_6$ or deuterium oxide using tetramethylsilane as an internal standard, and all δ values are reported as ppm. The measurement was performed by using NMR instrument at 400 MHz, unless otherwise specified.

Symbols in Examples have the meanings as shown below.
s: singlet
d: doublet
t: triplet
q: quartet
dd: double doublet
dq: double quartet
ddd: double double doublet
brs: broad singlet
m: multiplet
J: coupling constant The X-ray powder diffraction patterns of the samples were measured by means of the powder X-ray diffractometry. Measuring instrument: X'Pert Pro (SPECTRIS)

Measuring Condition:
Anticathode: Cu
Tube current and voltage of X-ray tube bulb: 45 kV, 40 mA
Rotary speed of sample: each 1 sec.
Incident-beam Soller slit: 0.02 rad
Incident-beam Vertical divergence slit: 15 mm
Incident-beam Divergence slit: Auto, Irradiation width 15 mm
Incident-beam Scattering slit: 1°
Diffracted-beam Filter: Nickel filter
Diffracted-beam Soller slit: 0.02 rad
Diffracted-beam Divergence slit: Auto, Irradiation width 15 mm
Detector: X'Celerator
Detector mode: Scanning
Effective width of Detector: 2.122°
Scan axis: Gonio.
Scan mode: Continuing
Scan range: 3°-60°
Time of unit step: 10 sec.

Each weight % of carbon, hydrogen and nitrogen in samples was determined by elemental analysis.

The average of measured values three times for a sample solution was an ion content in the sample.
Measuring instrument: Ion chromatograph LC-20 system (Shimadzu Corporation)
Measuring condition: Electrical-conductivity detector SHIMADZU CDD-10A VP
Column for analysis of anions SHIMADZU SHIM-PAC IC-A3
Column for analysis of cations SHIMADZU SHIM-PAC IC-C1

The content of water in a sample was determined by Karl Fischer titration.
Measuring instrument: Coulometric titrator for measurement of water contents CA-06 (Mitsubishi Chemical Corporation)
Measuring condition: Sample amount: about 20 mg
Reagent: Anode solution Aquamicron AX (API Corporation)
Cathode solution Aquamicron CXU (API Corporation)

[Example 1] Preparation of BABL-HC (Compound [3])

[Chem. 139]

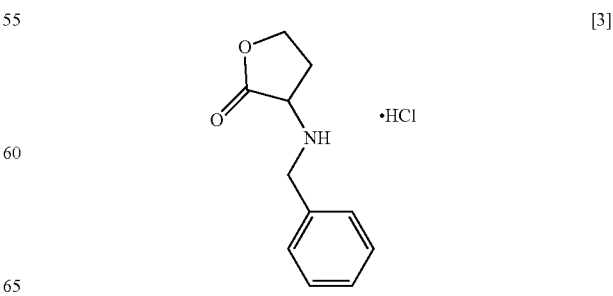

[3]

Step 1

[Chem. 140]

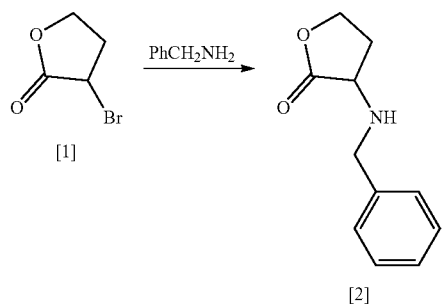

Under nitrogen atmosphere, tripotassium phosphate (1466.7 g, 6.9 mol), acetonitrile (3.8 L), benzylamine (246.8 g, 2.30 mol) and BBL [1] (380 g, 2.30 mol) were added sequentially to a reaction vessel at room temperature. The reaction mixture was stirred at 40° C. to 45° C. for 21 hr, and then cooled to room temperature. Any insoluble materials in the reaction mixture were filtered off and washed with acetonitrile (760 mL). The filtrate combined with the washing was concentrated under reduced pressure. To this concentrated residue were added toluene (3.8 L), 20% brine (1.14 L) and acetic acid (20.75 g) and, after stirring the mixture, the organic layer was separated. The resulting organic layer was washed with a mixture of 20% brine (760 mL) and 5% aqueous sodium bicarbonate (380 mL), and the solvent in the organic layer was distilled off under reduced pressure. To the concentrated residue was added toluene (380 mL). Any insoluble materials were filtered off and washed with toluene (380 mL). The filtrate combined with the washing was concentrated under reduced pressure. The procedure of adding ethyl acetate (1.52 L) to the concentrated residue followed by concentration was repeated twice, and ethyl acetate (760 mL) was added to the concentrate to give a solution of BABL [2] in ethyl acetate (440 g, equivalent to 2.30 mol). The resulting solution of BABL [2] in ethyl acetate was used in the next step assuming that the yield was 100%.

The crude BABL [2] prepared by the same process was concentrated to dryness for measuring MS.

MS: m/z=192 [M+H]$^+$

Step 2

[Chem. 141]

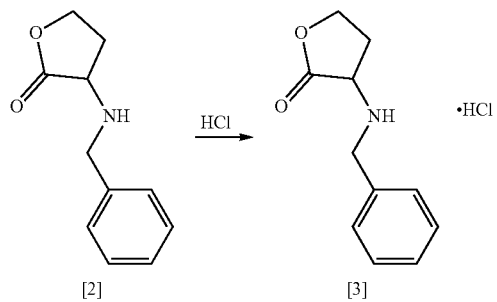

Under nitrogen atmosphere, to the solution of BABL [2] in ethyl acetate (440 g, equivalent to 2.30 mol) was added methanol (380 mL) at room temperature. To this mixture was added a solution of 4 N hydrochloric acid in ethyl acetate (575 mL, 2.30 mol) at 0° C., and the reaction mixture was stirred at 0° C. for 1.5 hr. The precipitated solid was collected on the filter, and the resulting solid was washed twice with ethyl acetate (760 mL). The resulting wet solid was dried under reduced pressure to give BABL-HC [3] (385.1 g, 1.69 mol) in a yield of 73.4%.

Using BABL-HC [3] prepared by the same process, NMR and melting point were measured, and elemental analysis was performed.

$^1$H-NMR (DMSO-d$_6$) δ: 10.11 (1H, brs), 7.55-7.41 (5H, m), 4.47 (1H, t, J=8.8 Hz), 4.36-4.22 (4H, m), 3.31 (1H, brs), 2.61-2.54 (1H, m), 2.49-2.41 (1H, m).

Melting Point: 206° C. to 208° C.

Elemental analysis: C, 58.1 wt %, H, 6.2 wt % and N, 6.1 wt %

(Theoretical value: C, 58.0 wt %, H, 6.2 wt % and N, 6.2 wt %)

Using BABL-HC [3] prepared by the same process, the diffraction angle 2θ and the diffraction intensity were measured by the powder X-ray diffractometry. The resulting spectrum is shown in FIG. 1.

The respective peaks in FIG. 1 are as shown in the following table.

TABLE 1

| Diffraction angle [2θ (°)] | Relative intensity [%] | Diffraction intensity [cps] |
| --- | --- | --- |
| 8.4720 | 65.46 | 4970.48 |
| 11.8659 | 14.93 | 1133.49 |
| 14.8286 | 14.45 | 1096.96 |
| 16.6274 | 4.93 | 374.50 |
| 17.0114 | 2.78 | 211.08 |
| 17.7705 | 16.90 | 1283.55 |
| 18.8793 | 100.00 | 7593.69 |
| 19.7206 | 25.67 | 1949.02 |
| 20.7055 | 11.10 | 842.77 |
| 20.9531 | 36.78 | 2792.92 |
| 21.4266 | 47.81 | 3630.51 |
| 23.8737 | 10.23 | 777.18 |
| 24.4323 | 27.55 | 2091.80 |
| 24.7131 | 6.23 | 473.16 |

[Example 2] Preparation of BABL (Compound [2-2])

Step 1

[Chem. 142]

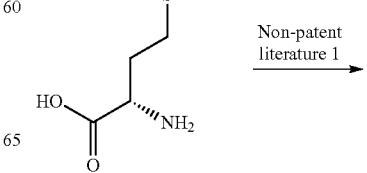

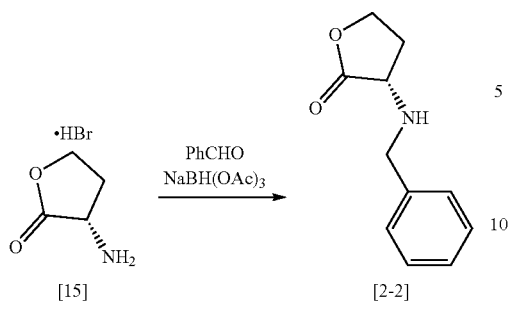

[15]  [2-2]

Aminolactone bromate [15] (1.0 g, 5.49 mmol) synthesized according to the method described in Non Patent Literature 1, DMF (15 mL), acetic acid (0.1 mL) and benzaldehyde (0.62 mL, 6.04 mmol) were added sequentially to a reaction vessel, and the mixture was cooled to 0° C. To the reaction mixture was added sodium triacetoxyborohydride (1.39 g, 6.59 mmol), and the mixture was stirred at room temperature for 1 hr. To the reaction mixture was added 1 M hydrochloric acid, and the mixture was washed with toluene. To the resulting aqueous layer was added saturated aqueous sodium bicarbonate, and the product was extracted with ethyl acetate three times. The combined organic layer was washed with a saturated brine and concentrated under reduced pressure to give BABL [2-2] (976 mg, equivalent to 5.11 mmol).

The crude BABL [2-2] prepared by the same process was concentrated to dryness for measuring MS.

MS: m/z=192 [M+H]$^+$

[Example 3] Preparation of RR-MDDO (Compound [9])

[Chem. 143]

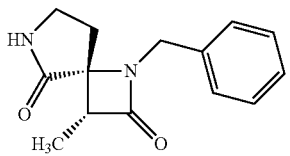

[9]

Step 1

[Chem. 144]

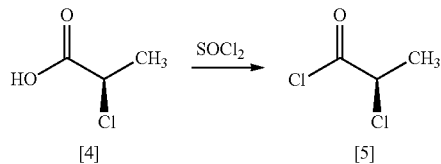

[4]  [5]

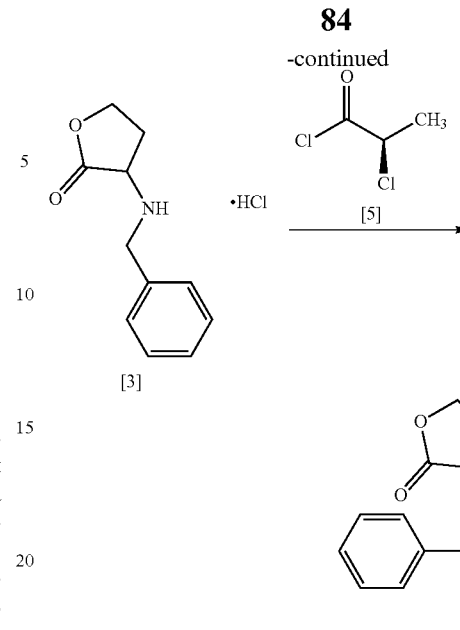

[3]  [6]

Under nitrogen atmosphere, to DMF (260 mL) was added thionyl chloride (107.8 mL, 1.48 mol) at 0° C., and the mixture was stirred at the same temperature for 30 min. To this solution, a solution of R-CPRA [4] (148.7 g, 1.37 mol) in toluene (260 mL) was added dropwise at 0° C., and the mixture was stirred at the same temperature for 1 hr to give a solution of R-CPRC [5] (equivalent to 1.37 mol) in toluene.

Under nitrogen atmosphere, BABL-HC [3] (260 g, 1.14 mol), ethyl acetate (2 L) and 2,6-lutidine (489.4 g, 4.57 mol) were added sequentially in a reaction vessel, and the mixture was stirred at room temperature for 20 min. The mixture was cooled to 0° C., to which the previously obtained solution of R-CPRC [5] (equivalent to 1.37 mol) in toluene was added dropwise at the temperature below 5° C., and the mixture was stirred at the same temperature for 2 hr. To the reaction mixture was added 1 M hydrochloric acid (1.3 L) and, after stirring, the organic layer was separated and washed sequentially twice with 5% aqueous sodium bicarbonate (1.3 L) and then water (1.3 L). The resulting organic layer was concentrated under reduced pressure, and then toluene (780 mL) was added to the concentrated residue, and the mixture was concentrated under reduced pressure again. The procedure was repeated once again. DMSO (750 mL) was added to the concentrated residue to give a solution of the crude R-CPBL [6] in DMSO (1187.94 g, equivalent to 1.14 mol). The resulting R-CPBL [6] was used in the next step assuming that the yield was 100%.

An aliquot of the solution of crude R-CPBL [6] in toluene prepared by the same process was concentrated to dryness for measuring NMR, MS and melting point, and performing the elemental analysis.

$^1$H-NMR (DMSO-$d_6$) δ: (3:2 diastereomer mixture) 5.03 and 4.99 (1H, q, J=6.5 Hz, proton at the joint of chlorine), 1.51 and 1.47 (3H, d, J=6.5 Hz, proton of methyl).

MS: m/z=282 [M+H]$^+$

Melting Point: 101° C. to 104° C.

Elemental analysis: C, 59.8 wt %, H, 5.7 wt % and N, 4.9 wt %

(Theoretical value: C, 59.7 wt %, H, 5.7 wt % and N, 5.0 wt %)

Step 2

[Chem. 145]

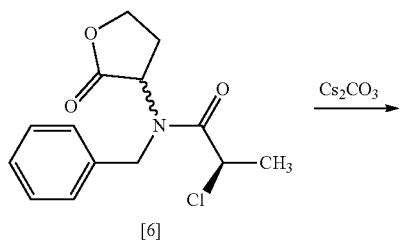

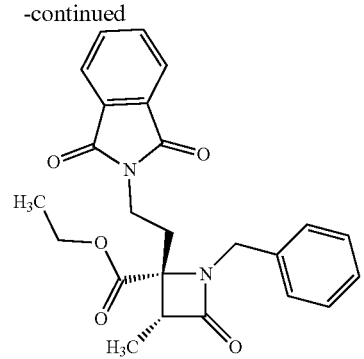

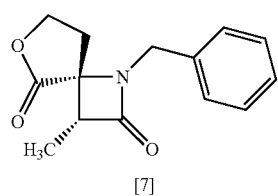

Under nitrogen atmosphere, to the previously obtained solution of crude R-CPBL [6] in DMSO (1161.8 g, equivalent to 1.12 mol), DMSO (250 mL) and cesium carbonate (728.1 g, 2.23 mol) were added sequentially at room temperature, and the mixture was stirred at room temperature overnight. To 2 M hydrochloric acid (1.78 L) cooled below 20° C., the reaction mixture was added dropwise, and the product was extracted with ethyl acetate (2.5 L). The resulting organic layer was washed sequentially with 5% aqueous sodium bicarbonate (1.3 L) and twice with 20% brine (1.3 L) and concentrated under reduced pressure to give the crude RR-AOBL [7] (353.9 g, equivalent to 1.12 mol, diastereomer ratio 97:3). The resulting crude RR-AOBL [7] was used in the next step assuming that the yield was 100%.

The crude RR-AOBL [7] prepared by the same process was concentrated to dryness for measuring NMR and MS.

$^1$H-NMR (CDCl$_3$) δ: 7.37-7.27 (5H, m), 4.86 (1H, d, J=15.3 Hz), 4.21 (1H, ddd, J=9.9, 5.2, 4.0 Hz), 4.13-4.06 (1H, m), 4.02 (1H, d, J=15.3 Hz), 3.36 (1H, q, J=7.5 Hz), 2.13-2.10 (2H, m), 1.31 (3H, d, J=7.3 Hz).

MS: m/z=246 [M+H]$^+$

Step 3

[Chem. 146]

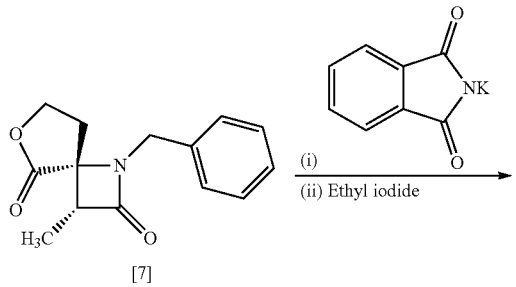

Under nitrogen atmosphere, the crude RR-AOBL [7] (220.15 g, equivalent to 0.97 mol), DMF (1.5 L) and potassium phthalimide (232.81 g, 1.26 mol) were added sequentially at room temperature to a reaction vessel, and the mixture was stirred at 80° C. to 100° C. overnight. After this reaction mixture was cooled to about 50° C., ethyl iodide (226.21 g, 1.45 mol) was added dropwise to the mixture, and the mixture was stirred at 40° C. to 50° C. for 4 hr. After the reaction mixture was cooled to about 0° C., 20% brine (1.1 L) was added to the mixture, and the product was extracted with toluene (1.1 L). The resulting organic layer was washed sequentially with 20% brine (1.1 L) and water (1.1 L), and then concentrated under reduced pressure. To the concentrated residue was added 2-butanol (1.1 L), and the mixture was concentrated under reduced pressure. This procedure was repeated once again to give a solution of the crude RR-AOPE [8] in 2-butanol (809.67 g, equivalent to 0.97 mol). The resulting solution of RR-AOPE [8] in 2-butanol was used in the next step assuming that the yield was 100%.

The crude RR-AOPE [8] prepared by the same process was concentrated to dryness for measuring NMR and MS.

$^1$H-NMR (CDCl$_3$) δ: 7.83-7.80 (2H, m), 7.73-7.69 (2H, m), 7.37-7.32 (4H, m), 7.29-7.25 (1H, m), 4.79 (1H, d, J=15.7 Hz), 4.40 (1H, d, J=15.7 Hz), 4.15-4.06 (2H, m), 3.68-3.61 (1H, m), 3.52-3.44 (1H, m), 3.37 (1H, q, J=7.5 Hz), 2.27-2.12 (2H, m), 1.26-1.22 (6H, m).

MS: m/z=421 [M+H]$^+$

Step 4

[Chem. 147]

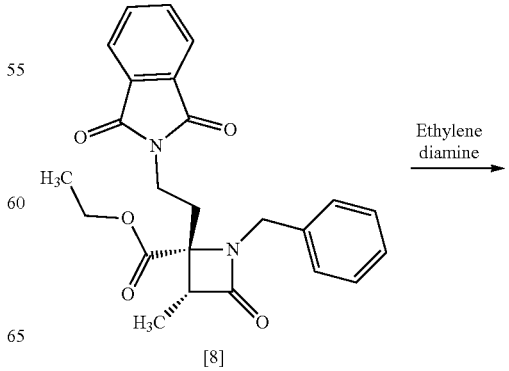

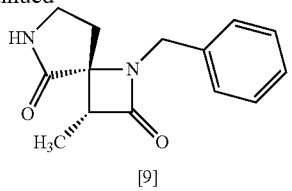

[9]

Under nitrogen atmosphere, to the solution of RR-AOPE [8] in 2-butanol (36.78 g, equivalent to 43.9 mmol) was added ethylenediamine (10.56 g, 175.6 mmol) at room temperature, and the mixture was stirred at 80° C. to 90° C. for 4 hr. This reaction mixture was cooled to about 50° C., THF (120 mL) was added thereto, and the mixture was stirred at 40° C. to 50° C. for 1 hr, and then at room temperature overnight. Any insoluble materials were filtered off, and then 25% aqueous potassium hydrogen sulfate solution (170 mL) was added to the filtrate, and the layers were separated. The resulting organic layer was washed with a mixture of 7.5% aqueous sodium bicarbonate and saturated brine (1/4, 50 mL), and concentrated under reduced pressure. To the concentrated residue were added ethyl acetate (200 mL) and CARBORAFFIN 20 (0.5 g, Japan EnviroChemicals, Ltd.), and the mixture was stirred at room temperature for 30 min. Any insoluble materials in the mixture were filtered off, and the filtrate was concentrated, and to the concentrated residue was added CPME (50 mL) and then the mixture was concentrated (crude RR-MDDO [9]). To the resulting concentrated residue was added CPME (40 mL), and the mixture was heated at 50° C. to 60° C. To this mixture, diisopropyl ether (40 mL) was added dropwise, and the mixture was stirred at the same temperature for 1 hr, and then for 2 hr after cooling to room temperature. The precipitated solid was collected on the filter, the resulting solid was washed with a mixture of CPME/diisopropyl ether (1:1, 20 mL), and dried at 50° C. under reduced pressure to give RR-MDDO [9] (6.70 g, 27.4 mmol) in a yield of 62.5% from BABL-HC [3].

Using RR-MDDO [9] prepared by the same process, NMR, MS and melting point were measured, and elemental analysis was performed.

$^1$H-NMR (CDCl$_3$) δ: 7.33-7.26 (5H, m), 5.92 (1H, brs), 4.85 (1H, d, J=15.5 Hz), 3.99 (1H, d, J=15.5 Hz), 3.27-3.18 (2H, m), 3.16-3.10 (1H, m), 2.07-1.99 (2H, m), 1.28 (3H, d, J=7.6 Hz).

MS: m/z=245 [M+H]$^+$

Melting Point: 125° C. to 127° C.

Elemental analysis: C, 68.9 wt %, H, 6.6 wt % and N, 11.4 wt %

(Theoretical value: C, 68.8 wt %, H, 6.6 wt % and N, 11.5 wt %)

Using RR-MDDO [9] prepared by the same process, the diffraction angle 2θ and the diffraction intensity were measured by the powder X-ray diffractometry. The resulting spectrum is shown in FIG. 2.

Figure 2:
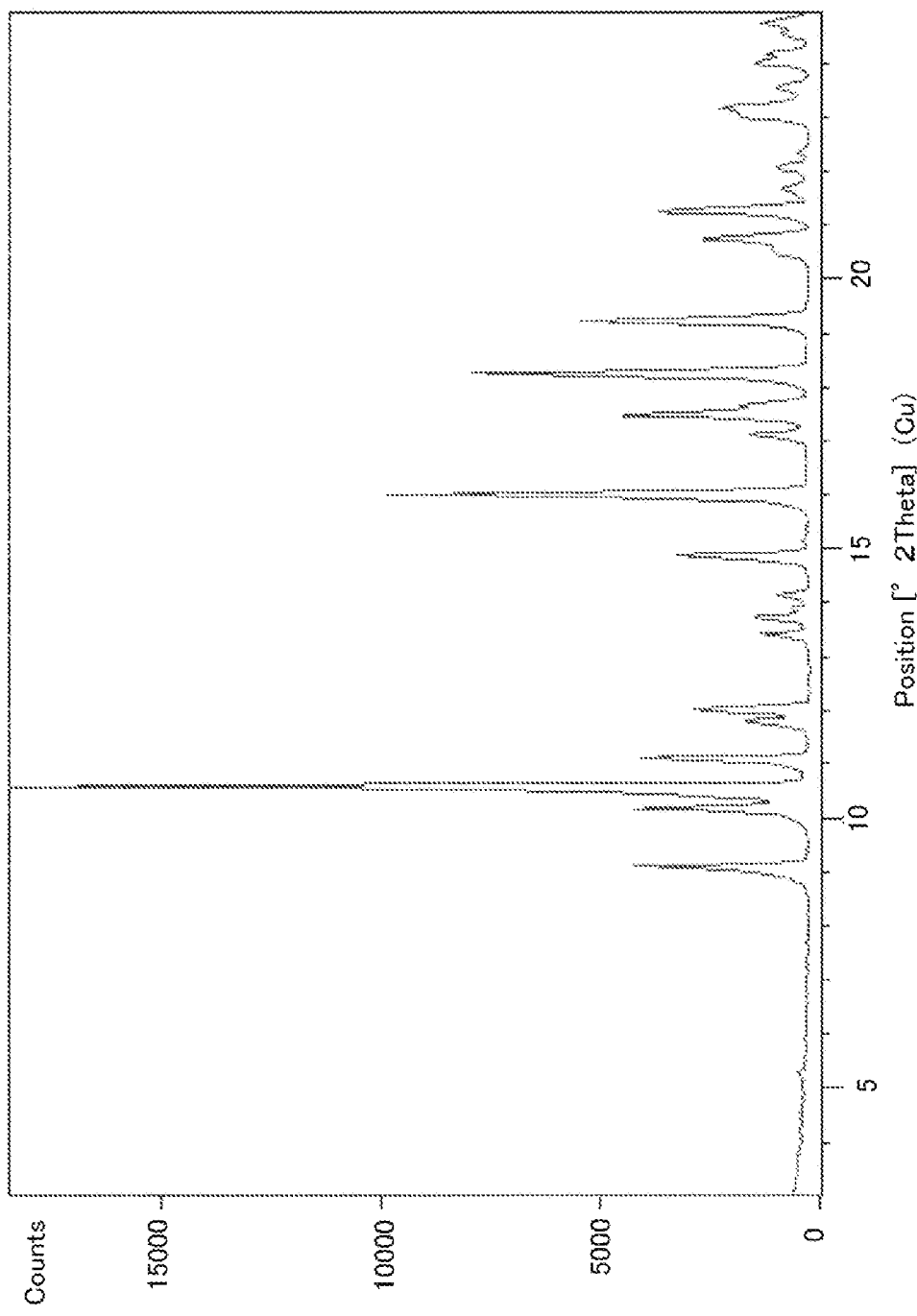
FIG. 2 shows a multiple record for powder X-ray diffraction pattern of RR-MDDO [9]. Diffraction intensity (cps: counts per second) is shown in the vertical axis, and diffraction angle 2θ (°) is shown in the horizontal axis.

The respective peaks in FIG. 2 are as shown in the following table.

TABLE 2

| Diffraction angle [2θ (°)] | Relative intensity [%] | Diffraction intensity [cps] |
|---|---|---|
| 9.0979 | 21.90 | 4009.37 |
| 10.1864 | 21.77 | 3984.95 |

TABLE 2-continued

| Diffraction angle [2θ (°)] | Relative intensity [%] | Diffraction intensity [cps] |
|---|---|---|
| 10.5858 | 100.00 | 18308.77 |
| 11.1145 | 21.00 | 3844.56 |
| 11.7820 | 7.79 | 1426.10 |
| 12.0289 | 14.60 | 2672.35 |
| 13.4150 | 6.21 | 1136.91 |
| 13.7219 | 6.74 | 1234.41 |
| 14.1371 | 4.12 | 754.46 |
| 14.8721 | 16.29 | 2983.07 |
| 15.1409 | 0.92 | 169.18 |
| 16.0216 | 53.20 | 9740.15 |
| 17.1231 | 7.20 | 1319.00 |
| 17.4922 | 23.90 | 4376.64 |
| 17.6960 | 7.72 | 1412.88 |
| 18.2720 | 41.92 | 7675.44 |
| 19.2469 | 28.89 | 5289.35 |
| 20.4687 | 3.92 | 718.21 |
| 20.7692 | 13.66 | 2501.28 |
| 21.2746 | 18.60 | 3405.92 |
| 21.6985 | 3.31 | 605.42 |
| 22.0927 | 3.97 | 726.82 |
| 22.3675 | 1.53 | 279.23 |
| 23.0181 | 8.09 | 1480.46 |
| 23.2134 | 10.64 | 1947.43 |
| 23.5762 | 3.74 | 684.16 |
| 24.0124 | 6.62 | 1212.01 |
| 24.2166 | 5.08 | 930.76 |
| 24.7758 | 6.22 | 1138.51 |

The crude RR-MDDO [9] obtained in Example 3 and the RR-MDDO [9] obtained via the crystallization step were analyzed by HPLC.

The measuring instrument and condition for HPLC are shown below.

Instrument: Nexera system (Shimadzu)

Condition:

Column: CHIRAL PAK IF-3: 3 um, 250 mm×4.6 mm (Daicel)

Column temperature: 40° C.

Flow rate: 1.0 mL/min

Analysis time: 35 min

Detector wave length: UV (220 nm)

Mobile phase: Hexane/2-propanol=80/20

The retention time of RR-MDDO [9] under above described HPLC measuring condition was about 14.6 min. The retention time of each stereoisomer was about 10.9 min for SS form, about 16.5 min for RS form, and about 18.6 min for SR form.

Figure 3:
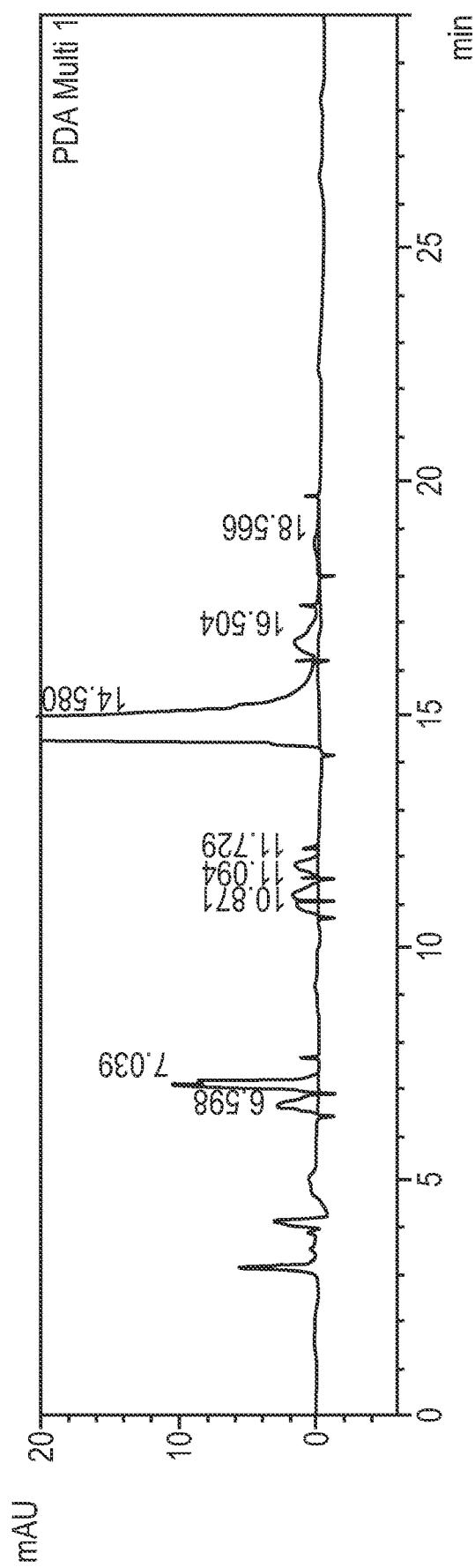
FIG. 3 shows analytical results of HPLC for a crude RR-MDDO [9] in Example 3. Absorbance (AU) is shown in the vertical axis, and retention time (min) is shown in the horizontal axis.

The result of HPLC analysis of the crude RR-MDDO [9] obtained in Example 3 is shown in FIG. 3 and in the following table.

TABLE 3

| | Retention time (min) | Area | Height | % Area | Configuration |
|---|---|---|---|---|---|
| 1 | 6.598 | 41404 | 3008 | 1.704 | |
| 2 | 7.039 | 108861 | 10591 | 4.481 | |
| 3 | 10.871 | 23189 | 1775 | 0.955 | SS |
| 4 | 11.094 | 31718 | 1945 | 1.306 | |
| 5 | 11.729 | 30699 | 1923 | 1.264 | |
| 6 | 14.580 | 2143972 | 95372 | 88.251 | RR |
| 7 | 16.504 | 35162 | 1479 | 1.447 | RS |
| 8 | 18.566 | 14399 | 314 | 0.593 | SR |

Figure 4:
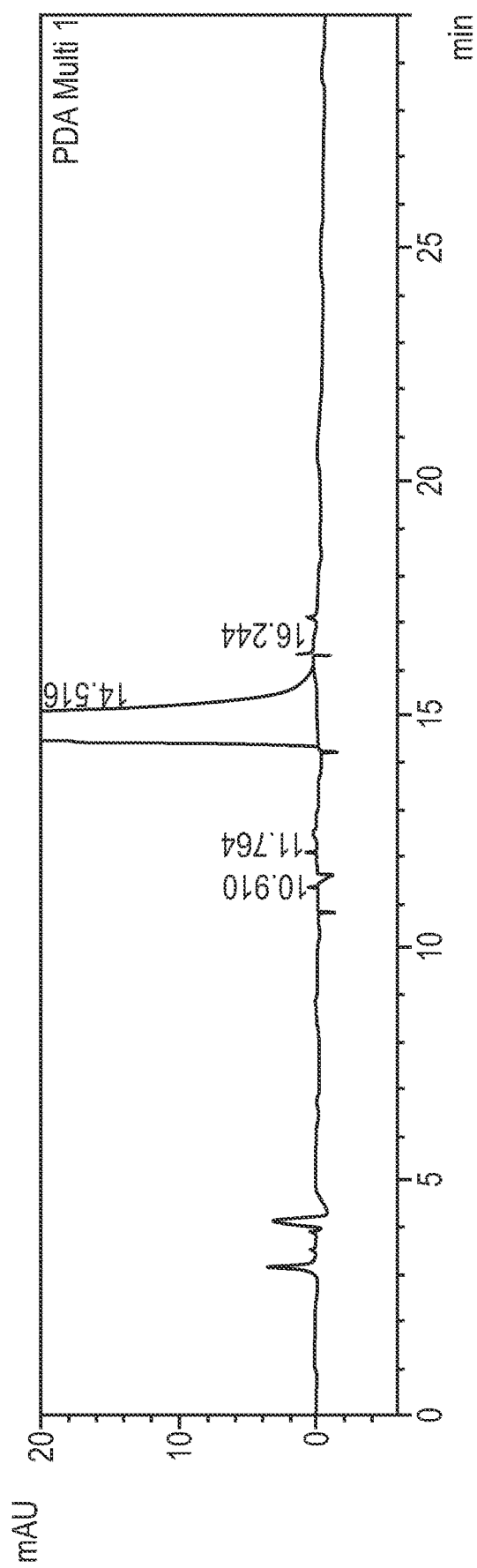
FIG. 4 shows analytical results of HPLC for RR-MDDO [9] obtained via the crystallization step in Example 3. Absorbance (AU) is shown in the vertical axis, and retention time (min) is shown in the horizontal axis.

The result of HPLC analysis of the RR-MDDO [9] obtained via the crystallization step is shown in FIG. 4 and in the following table.

TABLE 4

| | Retention time (min) | Area | Height | % Area | Configuration |
|---|---|---|---|---|---|
| 1 | 10.910 | 1761 | 114 | 0.041 | SS |
| 2 | 11.764 | 3750 | 257 | 0.087 | |
| 3 | 14.516 | 4302521 | 189506 | 99.832 | RR |
| 4 | 16.244 | 1714 | 5 | 0.040 | RS |

The crystallization step of RR-MDDO [9] is useful for a removal of its diastereomer, RS-MDDO. The diastereomer ratio in the crude RR-MDDO [9] was [RR-MDDO/RS-MDDO=88.25%/1.45% (HPLC Area percentage)], while the diastereomer ratio in the RR-MDDO [9] obtained via the crystallization step was [RR-MDDO/RS-MDDO=99.83%/0.04% (HPLC Area percentage)].

[Example 4] Preparation of RR-MDDO (Compound [9])

[Chem. 148]

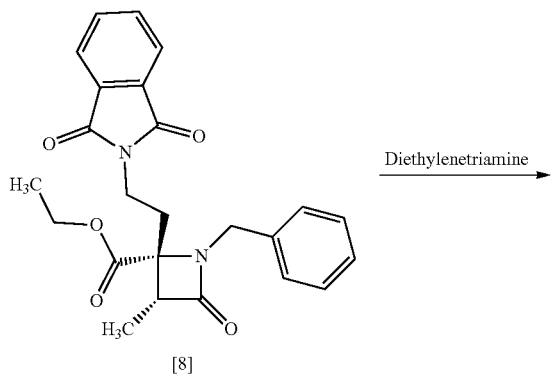

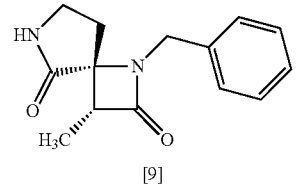

Under nitrogen atmosphere, to a solution of RR-AOPE [8] in 2-butanol (equivalent to 177.5 mmol) was added diethylenetriamine (91.72 g, 889.0 mmol) at room temperature, and the mixture was stirred at 85° C. to 95° C. for 2 hr. This reaction mixture was cooled to 10° C. or below, and then thereto were added dropwise concentrated hydrochloric acid (160 mL) and 25% brine (150 mL). The product was extracted after the addition of ethyl acetate (500 mL). The obtained organic layer was washed with a mixture of 7.5% aqueous sodium bicarbonate and brine (1/3, 200 mL) and concentrated under a reduced pressure. Toluene was added to the concentrated residue to adjust the total amount to 200 mL, and thereto were added ethyl acetate (400 mL) and CARBORAFFIN 20 (3.0 g, Japan EnviroChemicals, Ltd.). The mixture was stirred at room temperature overnight. Any insoluble materials were removed from the mixed solution, and the filtrate was concentrated. Toluene (250 mL) was added to the concentrated residue and the mixture was concentrated, which was repeated twice. Toluene was added to the obtained concentrated residue to adjust the total amount to 250 mL, and the mixture was dissolved with heating at 55° C. to 65° C. A seed crystal of RR-MDDO [9] (51 mg) was added to this solution, and the mixture was stirred at the same temperature for 1 hr. Then, thereto was added dropwise n-heptane (125 mL), and the mixture was stirred at the same temperature for 1 hr and cooled to room temperature to stir overnight. The precipitated solid was collected on a filter, and the obtained solid was washed with a mixture of toluene/n-heptane (2/1, 150 mL), and then dried at 50° C. under a reduced pressure to give RR-MDDO [9](31.07 g, 127.2 mmol) in a yield of 71.6% from R-CPBL [6].

NMR and MS were performed for the obtained RR-MDDO [9].

$^1$H-NMR (DMSO-D$_6$) δ: 8.10 (1H, brs), 7.35-7.24 (5H, m), 4.55 (1H, d, J=16.0 Hz), 3.95 (1H, d, J=16.0 Hz), 3.35 (1H, q, J=7.6 Hz), 3.15-3.05 (2H, m), 2.17-2.12 (1H, m), 2.07-1.99 (1H, m), 1.07 (3H, d, J=7.4 Hz).

MS: m/z=245 [M+H]$^+$

[Example 5] Isolation by Crystallization of R-CPBL (Compound [6])

[Chem. 149]

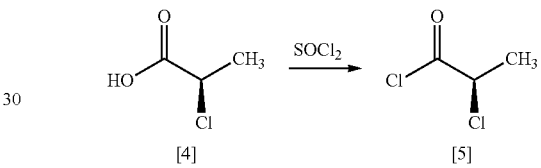

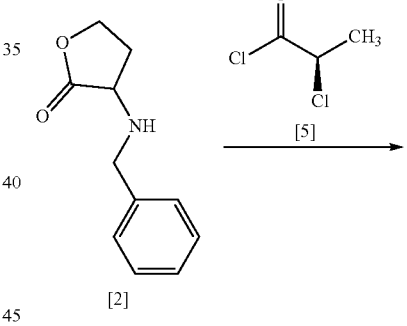

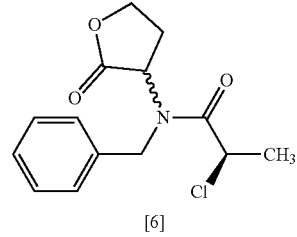

Under nitrogen atmosphere, to DMF (1.4 mL) was added thionyl chloride (0.57 mL, 7.88 mmol) at 0° C., and the mixture was stirred at the same temperature for 30 min. To this solution, a solution of R-CPRA [4] (789 mg, 7.27 mmol) in toluene (1.4 mL) was added dropwise at 0° C., and the mixture was stirred at the same temperature for 1 hr to give a solution of R-CPRC [5] (923 mg, equivalent to 7.88 mmol) in toluene.

Under nitrogen atmosphere, BABL [2] (1.16 g, 6.06 mmol), ethyl acetate (9 mL) and 2,6-lutidine (1.95 g, 18.18 mmol) were added sequentially to a reaction vessel, and the mixture was stirred at room temperature for 20 min. The mixture was cooled to 0° C., and to which the previously obtained solution of R-CPRC [5] (923 mg, equivalent to 7.88 mmol) in toluene was added dropwise at the temperature below 5° C., and the mixture was stirred at the same temperature for 2 hr. To the reaction mixture was added 1 M hydrochloric acid (5 mL) and, after stirring, the organic layer was separated and washed sequentially twice with 7.5% aqueous sodium bicarbonate (6 mL) and with water (6 mL). To the resulting organic layer was added CARBORAFFIN 20 (0.2 g, Japan EnviroChemicals, Ltd.), and the mixture was stirred at room temperature overnight. Any insoluble materials were filtered off, and washed with ethyl acetate. The filtrate combined with the washings was concentrated under reduced pressure. The resulting concentrated residue was crystallized by using toluene (6 mL) and heptane (6 mL) to give R-CPBL [6] (1.19 g, 4.22 mmol) in a yield of 98.2%.

Using R-CPBL [6] prepared by the same process, NMR, MS and melting point were measured, and elemental analysis was performed.

$^1$H-NMR (DMSO-$d_6$) δ: (3:2 diastereomer mixture) 5.03 and 4.99 (1H, q, J=6.5 Hz, proton at the joint of chlorine), 1.51 and 1.47 (3H, d, J=6.5 Hz, proton of methyl).

MS: m/z=282 [M+H]$^+$

Melting Point: 101° C. to 104° C.

Elemental analysis: C, 59.8 wt %, H, 5.7 wt % and N, 4.9 wt %

(Theoretical value: C, 59.7 wt %, H, 5.7 wt % and N, 5.0 wt %)

[Example 6] Preparation of RR-AOBL (Compound [7])

[Chem. 150]

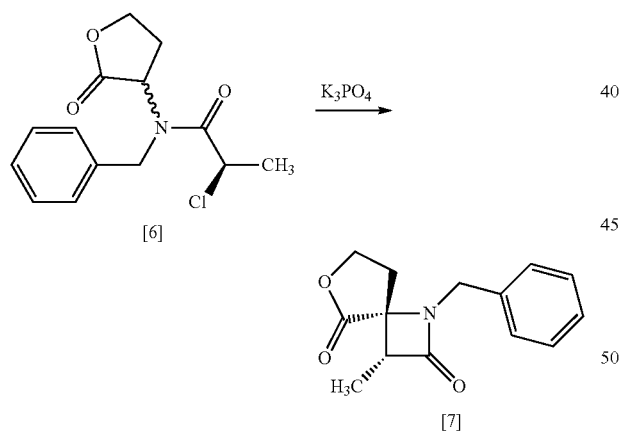

Under nitrogen atmosphere, R-CPBL [6] (5.58 g, equivalent to 24.5 mmol), DMSO (22 mL) and tripotassium phosphate (15.6 g, 73.5 mmol) were added sequentially to a reaction vessel at room temperature, and the mixture was stirred at 30° C. to 40° C. for 24 hr. To 3 M hydrochloric acid (33.5 mL), the reaction mixture cooled to room temperature was added dropwise, and the product was extracted with ethyl acetate. The resulting organic layer was washed sequentially once with 7.5% aqueous sodium bicarbonate and twice with 20% brine, and then concentrated under reduced pressure. To the concentrated residue was added toluene (400 mL), and the mixture was concentrated to give a solution of RR-AOBL [7] in toluene (6.44 g, equivalent to 24.5 mmol). The resulting solution of RR-AOBL [7] in toluene was used in the next step assuming that the yield was 100%.

The crude RR-AOBL [7] prepared by the same process was concentrated to dryness for measuring NMR and MS.

$^1$H-NMR (CDCl$_3$) δ: 7.37-7.27 (5H, m), 4.86 (1H, d, J=15.3 Hz), 4.21 (1H, ddd, J=9.9, 5.2, 4.0 Hz), 4.13-4.06 (1H, m), 4.02 (1H, d, J=15.3 Hz), 3.36 (1H, q, J=7.5 Hz), 2.13-2.10 (2H, m), 1.31 (3H, d, J=7.3 Hz).

MS: m/z=246 [M+H]$^+$

[Example 7] Preparation of RR-MDDO (Compound [9])

[Chem. 151]

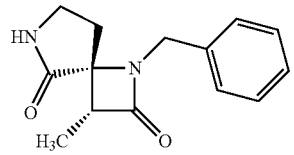

Step 1

[Chem. 152]

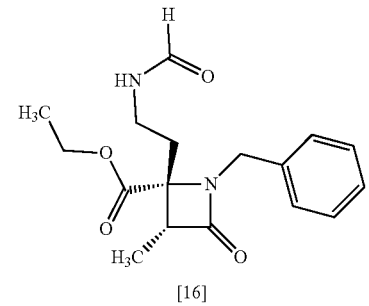

Under nitrogen atmosphere, RR-AOBL [7] (3.0 g, 12.2 mmol), DMSO (20 mL), and sodium diformylamide (3.48 g, 36.6 mmol) were added sequentially to a reaction vessel at room temperature, and the mixture was stirred at 100° C. for 18 hr. After this reaction mixture was cooled to about 45° C., ethyl iodide (3.0 mL, 37.8 mmol) was added dropwise thereto, and the mixture was stirred at 45° C. for 5 hr. After the reaction mixture was cooled to room temperature, 5% aqueous potassium carbonate solution was added thereto, and the product was extracted with toluene. The resulting organic layer was washed sequentially with 5% aqueous potassium carbonate solution and 20% brine, and then concentrated under reduced pressure. The resulting crude compound [16] was used in the next step assuming that the yield was 100%.

The crude compound [16] prepared by the same process was concentrated to dryness for measuring NMR and MS.

¹H-NMR (CDCl₃) δ: 8.82 (1H, s), 7.98 (1H, s), 7.37-7.14 (5H, m), 4.85 (1H, d, J=15.7 Hz), 4.23 (2H, q, J=7.1 Hz), 4.20 (1H, d, J=15.7 Hz), 3.71 (1H, q, J=7.1 Hz), 3.27-3.17 (1H, m), 3.11-3.02 (1H, m), 2.06-1.98 (1H, m), 1.95-1.85 (1H, m), 1.30 (3H, t, J=7.1 Hz), 1.21 (3H, d, J=7.1 Hz).

MS: m/z=319 [M+H]⁺

Step 2

[Chem. 153]

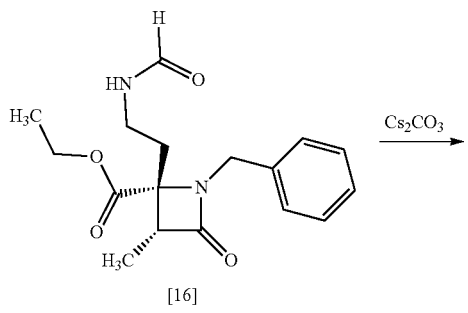

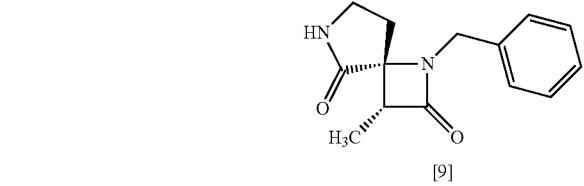

Under nitrogen atmosphere, the crude compound [16] (equivalent to 3.05 mmol), acetonitrile (5 mL) and cesium carbonate (1.49 g, 4.58 mmol) were added sequentially to a reaction vessel at room temperature, and the mixture was stirred at room temperature for 4 hr. To the reaction mixture was added 25% aqueous potassium hydrogen sulfate solution (5 mL), and the product was extracted three times with chloroform (5 mL). The resulting organic layers were combined, washed with saturated aqueous sodium bicarbonate (5 mL), and concentrated under reduced pressure. The concentrated residue was purified by thin layer silica gel chromatography (eluent: ethyl acetate) to give RR-MDDO [9] (638 mg, 2.61 mmol) in a yield of 85.6%.

Using RR-MDDO [9] prepared by the same process, NMR and MS were measured.

¹H-NMR (CDCl₃) δ: 7.33-7.26 (5H, m), 5.92 (1H, brs), 4.85 (1H, d, J=15.5 Hz), 3.99 (1H, d, J=15.5 Hz), 3.27-3.18 (2H, m), 3.16-3.10 (1H, m), 2.07-1.99 (2H, m), 1.28 (3H, d, J=7.6 Hz).

MS: m/z=245 [M+H]⁺

[Example 8] Preparation of SR-MDBN-DSU (Compound [11-1])

[Chem. 154]

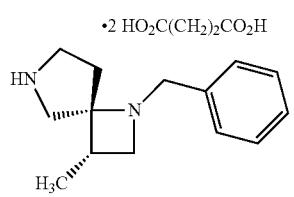

Step 1

[Chem. 155]

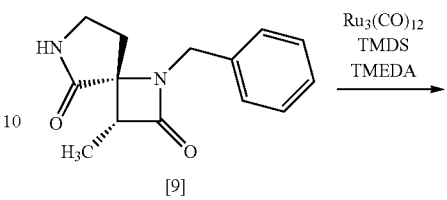

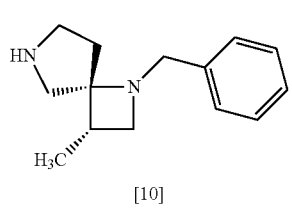

Under nitrogen atmosphere, RR-MDDO [9] (1.0 g, 4.09 mmol), toluene (10 mL), triruthenium dodecacarbonyl (261 mg, 0.41 mmol), TMDS (5.49 g, 40.9 mmol) and TMEDA (0.061 mL, 0.41 mmol) were added sequentially to a reaction vessel, and the mixture was stirred at 70° C. for 40 hr. After this reaction mixture was cooled to room temperature and concentrated under reduced pressure, 2 M hydrochloric acid (10 mL) and THF (10 mL) were added to the resulting concentrated residue, and the layers were separated. To the resulting aqueous layer were added CPME (10 mL) and 25% aqueous sodium hydroxide solution (5 mL), the layers were separated. The resulting organic layer was washed with saturated brine (5 mL) and concentrated under reduced pressure. To this concentrated residue was added 2-propanol (10 mL) to give a solution of the crude SR-MDBN [10] in 2-propanol (equivalent to 4.09 mmol). The resulting solution of SR-MDBN [10] in 2-propanol was used in the next step assuming that the yield was 100%.

The crude SR-MDBN [10] prepared by the same process was concentrated to dryness for measuring NMR and MS.

¹H-NMR (CDCl₃) δ: 7.34-7.20 (5H, m), 3.62 (1H, d, J=12.9 Hz), 3.59 (1H, d, J=12.9 Hz), 3.21 (1H, dd, J=7.5, 6.6 Hz), 2.99 (1H, d, J=12.1 Hz), 2.95 (1H, d, J=12.1 Hz), 2.84 (2H, t, J=7.3 Hz), 2.68 (1H, t, J=5.8 Hz), 2.43-2.35 (1H, m), 2.22-2.15 (1H, m), 1.81-1.74 (2H, m), 1.13 (3H, d, J=6.9 Hz).

MS: m/z=217 [M+H]⁺

Step 2

[Chem. 156]

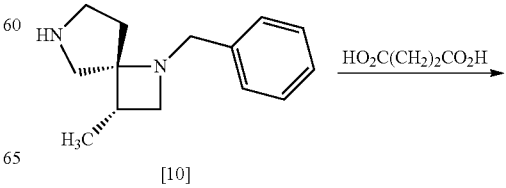

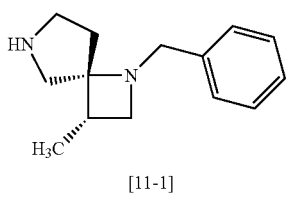

[11-1]

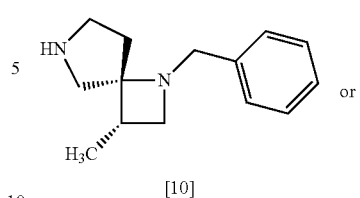

[10]

Under nitrogen atmosphere, succinic acid (966 mg, 8.18 mmol) and 2-propanol (5 mL) were added to a reaction vessel, and the mixture was heated to 70° C. To this suspension, the solution of crude SR-MDBN [10] in 2-propanol (equivalent to 4.09 mmol) was added dropwise at 70° C., the mixture was cooled to room temperature and then stirred for 8 hr. The precipitated solid was collected on the filter, the resulting solid was washed twice with 2-propanol (3 mL), and dried at 40° C. under reduced pressure to give SR-MDBN-DSU [11-1] (1.25 g, 2.77 mmol) in a yield of 67.7%.

Using SR-MDBN-DSU [11-1] prepared by the same process, NMR and melting point were measured, and elemental analysis was performed.

$^1$H-NMR (D$_2$O) δ: 7.43-7.38 (5H, m), 4.30 (1H, d, J=12.1 Hz), 4.24 (1H, d, J=12.1 Hz), 3.96 (1H, dd, J=10.1, 8.9 Hz), 3.85 (1H, d, J=14.5 Hz), 3.77 (1H, d, J=14.5 Hz), 3.45-3.33 (3H, m), 2.99-2.91 (1H, m), 2.89-2.81 (1H, m), 2.53-2.47 (1H, m), 1.17 (3H, d, J=7.3 Hz).

Melting Point: 126° C. to 128° C.

Elemental analysis: C, 58.4 wt %, H, 7.1 wt % and N, 6.1 wt %

(Theoretical value: C, 58.4 wt %, H, 7.1 wt % and N, 6.2 wt %)

Using SR-MDBN-DSU [11-1] prepared by the same process, the diffraction angle 2θ and the diffraction intensity were measured by the powder X-ray diffractometry. The resulting spectrum is shown in FIG. 5.

Figure 5:
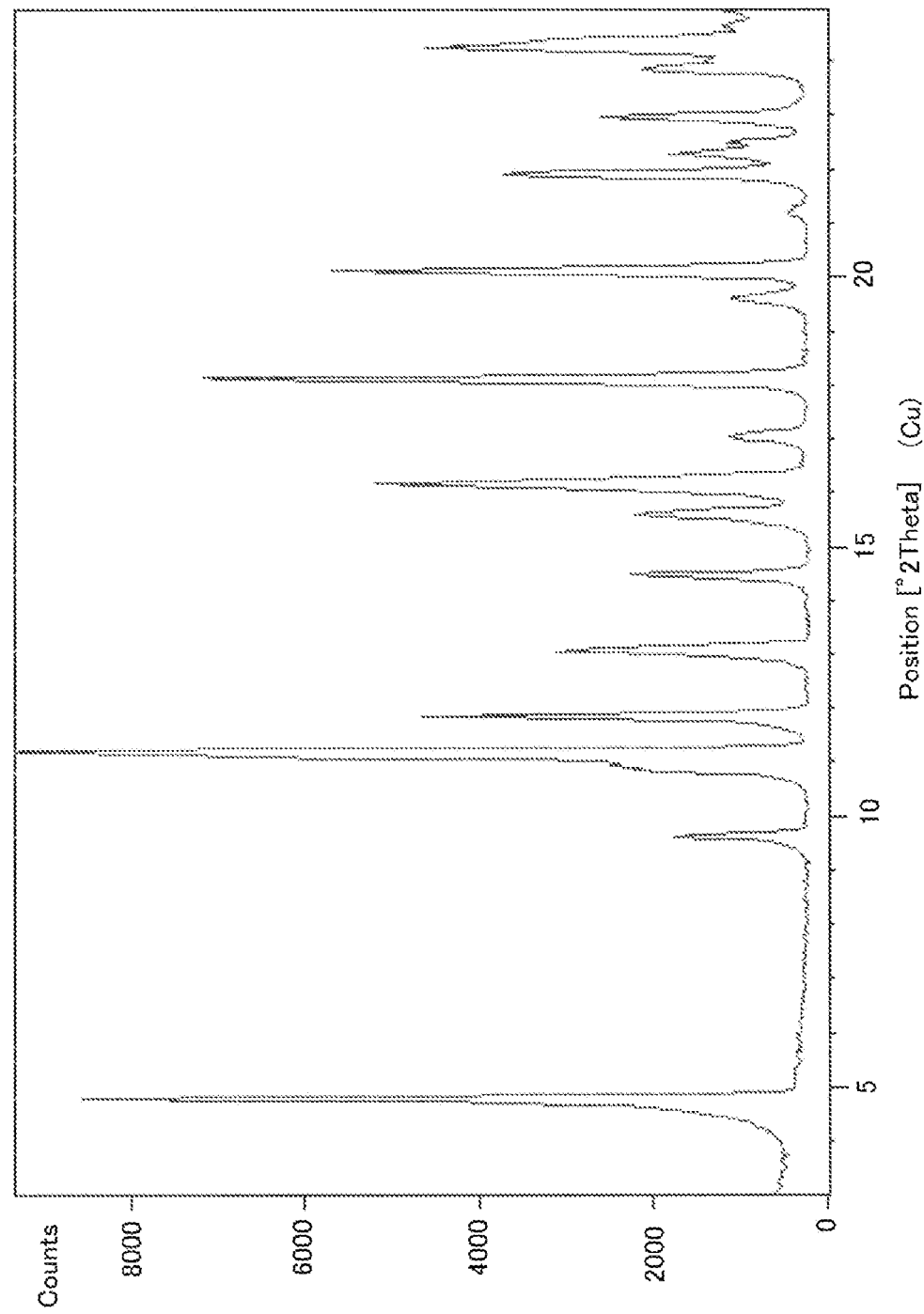
FIG. 5 shows a multiple record for powder X-ray diffraction pattern of SR-MDBN-DSU [11-1]. Diffraction intensity (cps: counts per second) is shown in the vertical axis, and diffraction angle 2θ (°) is shown in the horizontal axis.

The respective peaks in FIG. 5 are as shown in the following table.

TABLE 5

| Diffraction angle [2θ (°)] | Relative intensity [%] | Diffraction intensity [cps] |
|---|---|---|
| 4.8029 | 84.94 | 8145.72 |
| 9.6302 | 15.96 | 1530.79 |
| 10.8332 | 19.99 | 1917.06 |
| 11.1933 | 100.00 | 9590.10 |
| 11.8635 | 46.66 | 4474.68 |
| 13.0866 | 28.70 | 2752.50 |
| 14.4786 | 21.34 | 2046.30 |
| 15.6090 | 20.59 | 1974.60 |
| 16.1689 | 51.86 | 4973.37 |
| 17.0568 | 9.32 | 893.48 |
| 18.1269 | 74.24 | 7119.23 |
| 19.6147 | 9.35 | 896.81 |
| 20.1328 | 57.36 | 5501.07 |
| 21.1796 | 2.35 | 224.89 |
| 21.9108 | 36.80 | 3528.73 |
| 22.2909 | 16.57 | 1589.02 |
| 22.5258 | 8.99 | 861.74 |
| 22.9718 | 25.26 | 2421.98 |
| 23.8514 | 20.16 | 1933.47 |
| 24.2442 | 45.40 | 4354.10 |

Each dibenzyl derivative (Compound [21]) of SR-MDBN [10] and SR-MDBN-DSU [11-1] was prepared as follows, and measured by HPLC.

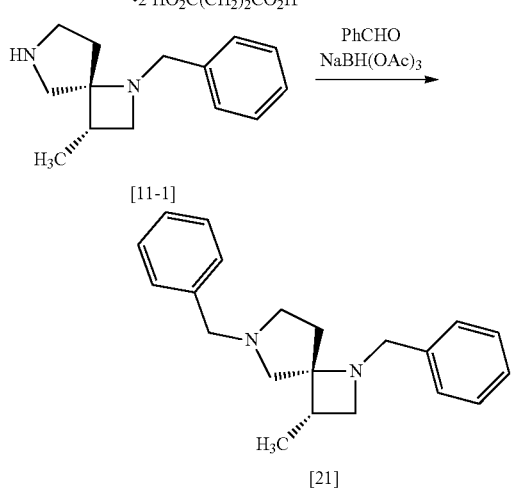

Under nitrogen atmosphere, to a solution of SR-MDBN-DSU [11-1] (72 mg, 0.16 mmol) or the crude SR-MDBN [10] (34 mg, equivalent to 0.16 mmol) and benzaldehyde (0.024 mL, 0.24 mmol) in DMF (1 mL) was added sodium triacetoxyborohydride (67 mg, 0.32 mmol) at room temperature, and the mixture was stirred at the same temperature for 1 hr. To the reaction mixture was added 2 M hydrochloric acid (1 mL), and the mixture was washed with toluene (2 mL). To the resulting aqueous layer was added 2M aqueous sodium hydroxide solution (2 mL) and the product was extracted three times with ethyl acetate (2 mL). The combined organic layer was washed with saturated brine (3 mL), dried over anhydrous sodium sulfate, and concentrated under reduced pressure. An aliquot of the resulting concentrated residue was measured by HPLC.

The measuring instrument and condition for HPLC are shown below.

Instrument: Nexera system (Shimadzu)

Condition:

Column: CHIRALCEL OJ-RH: 3 um, 4.6 mm×150 mm (Daicel)

Column temperature: 25° C.

Flow rate: 0.8 mL/min

Analysis time: 15 min

Detector wavelength: UV (210 nm)

Mobile phase: Methanol/diethylamine=100/0.1 (v/v)

The retention time of the compound [21] measured under above described HPLC measuring condition was about 5.2 min. The retention time of each stereoisomer was about 4.4 min for RR form, about 7.2 min for SS form and 8.6 min for RS form.

Figure 6:
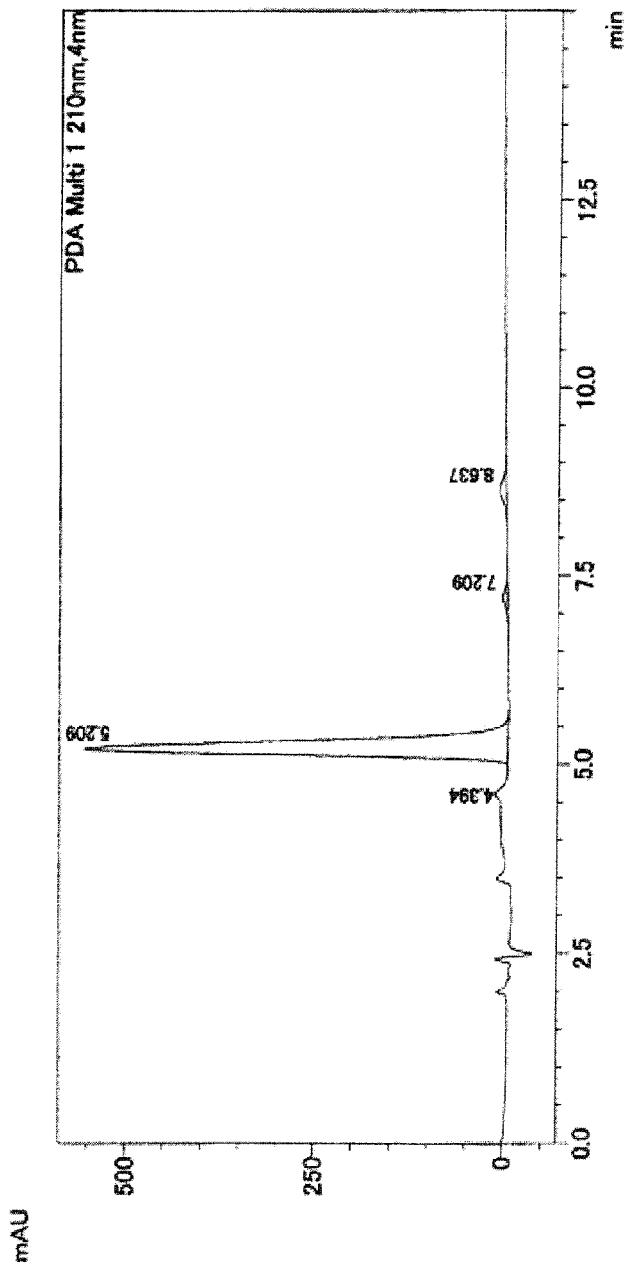
FIG. 6 shows analytical results of HPLC for compound [21] obtained from a crude SR-MDBN [10] obtained in Example 8-Step 1. Absorbance (AU) is shown in the vertical axis, and retention time (min) is shown in the horizontal axis.

The result of HPLC analysis of the compound [21] obtained from the crude SR-MDBN [10] in Example 8-Step 1 is shown in FIG. 6 and in the following table.

TABLE 6

|   | Retention time (min) | Area | Height | % Area | Configuration |
|---|---|---|---|---|---|
| 1 | 4.394 | 10041 | 1534 | 0.144 | RR |
| 2 | 5.209 | 6683427 | 559633 | 95.812 | SR |
| 3 | 7.209 | 101904 | 6111 | 1.461 | SS |
| 4 | 8.637 | 180223 | 8900 | 2.584 | RS |

Figure 7:
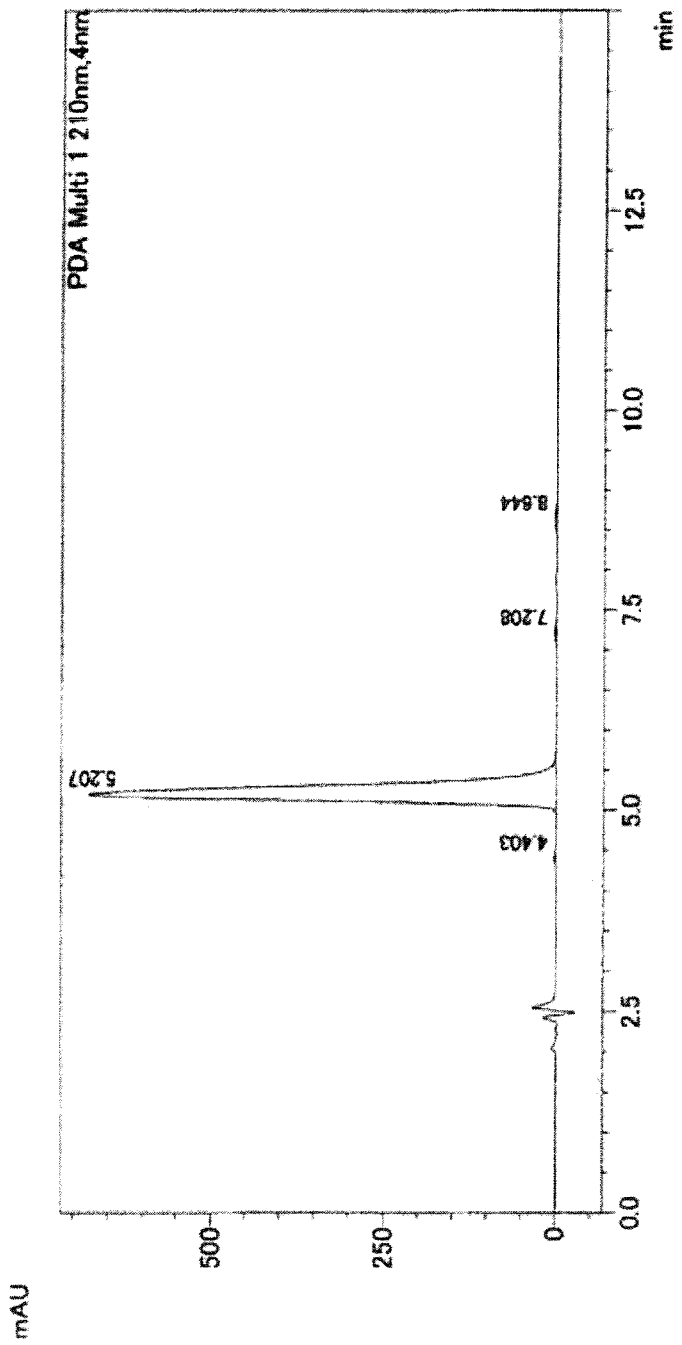
FIG. 7 shows analytical results of HPLC for compound [21] obtained from SR-MDBN-DSU [11-1] obtained via the crystallization step of Example 8-Step 2. Absorbance (AU) is shown in the vertical axis, and retention time (min) is shown in the horizontal axis.

The result of HPLC analysis of the compound [21] obtained from the SR-MDBN-DSU [11-1] which was obtained via crystallization step of Example 8-Step 2 is shown in FIG. 7 and in the following table.

TABLE 7

|   | Retention time (min) | Area | Height | % Area | Configuration |
|---|---|---|---|---|---|
| 1 | 4.403 | 14724 | 1644 | 0.171 | RR |
| 2 | 5.207 | 8475065 | 677373 | 98.481 | SR |
| 3 | 7.208 | 42110 | 2810 | 0.489 | SS |
| 4 | 8.644 | 73894 | 3732 | 0.859 | RS |

The crystallization step of SR-MDBN-DSU [11-1] is useful for removal of its enantiomer, RS-MDBN. The enantiomer ratio in the crude SR-MDBN [10] was [SR-MDBN/RS-MDBN=95.81%/2.59% (HPLC Area percentage)], while the enantiomer ratio in SR-MDBN [11-1] which was obtained via the crystallization step was [SR-MDBN/RS-MDBN=98.48%/0.86% (HPLC Area percentage)].

[Example 8-2] Preparation of SR-MDBN Monosuccinate

To a solution of SR-MDBN (446 mg, 2.06 mmol) in 2-propanol (2.9 mL) was added succinic acid (243 mg, 2.06 mmol) at room temperature. The mixture was stirred at room temperature, and then sonicated to precipitate a crystal. The precipitated crystal was filtered and washed with 2-propanol (2 mL), and then dried under reduced pressure at room temperature. SR-MDBN monosuccinate (467 mg, 1.39 mmol) was obtained in the yield of 67.8%.

The obtained SR-MDBN monosuccinate was measured by differential scanning calorimetry and elemental analysis.

Figure 8:
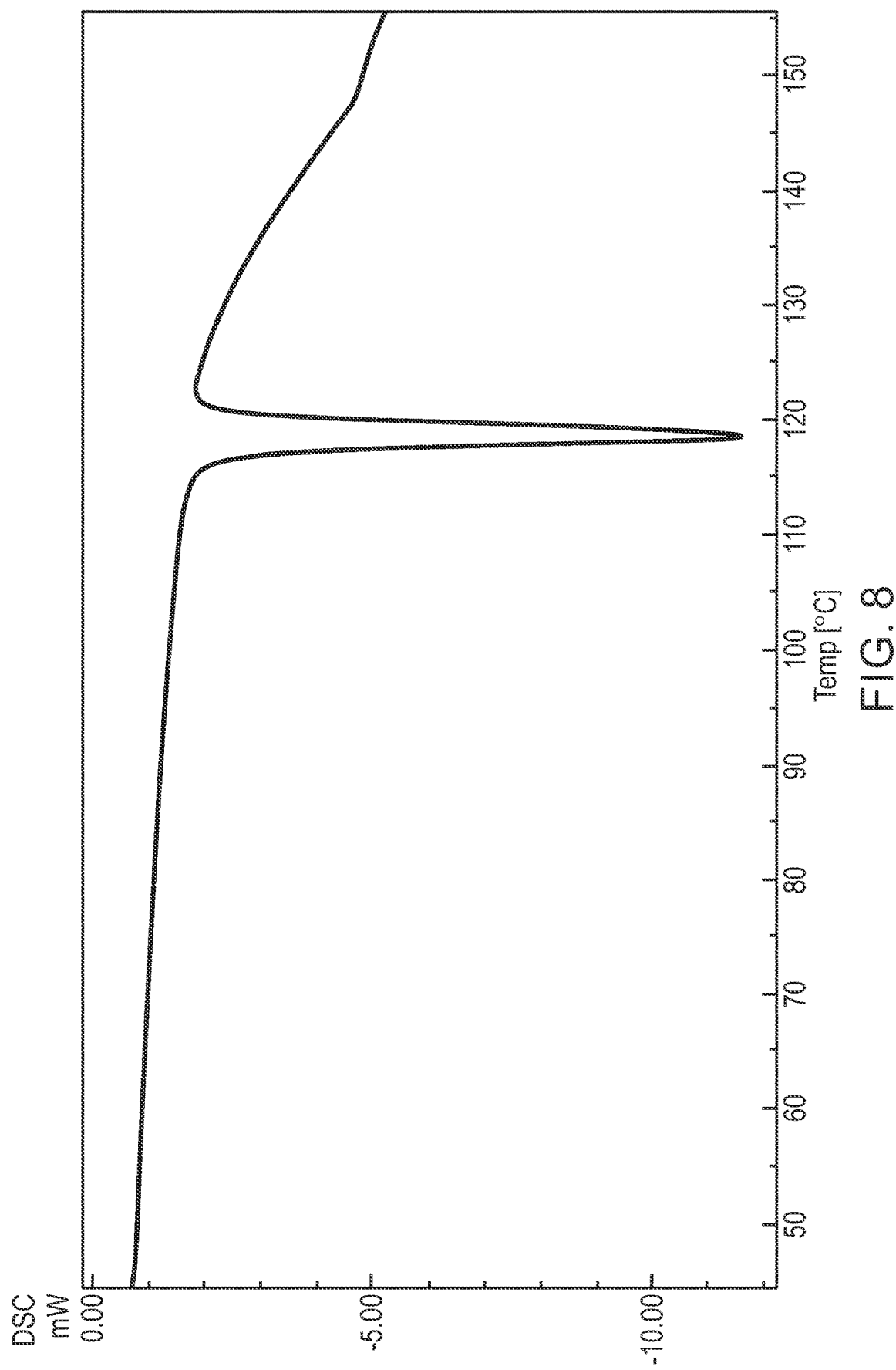
FIG. 8 shows a differential scanning calorimetry (DSC) curve for SR-MDBN monosuccinate obtained in Example 8-2.

Differential Scanning Calorimetry:

Measurement was conducted with a differential scanning calorimeter DSC-60A (manufactured by Shimadzu Corporation) at the rate of temperature increase of 5° C./min (sealed aluminum pan). A DSC curve obtained in the measurement is shown in FIG. 8. Enthalpy of endothermic peaks on the DSC curve was 97.56 J/g, the endothermic temperature was 118.53° C., and the extrapolated onset temperature was 117.25° C.

Elemental analysis: C, 64.69 wt %, H, 7.78 wt %, N, 8.34 wt %

(Theoretical value: C, 64.65 wt %, H, 7.84 wt %, N, 8.38 wt %)

[Example 9] Purification of SR-MDBN-DSU (Compound [11-1])

[Chem. 158]

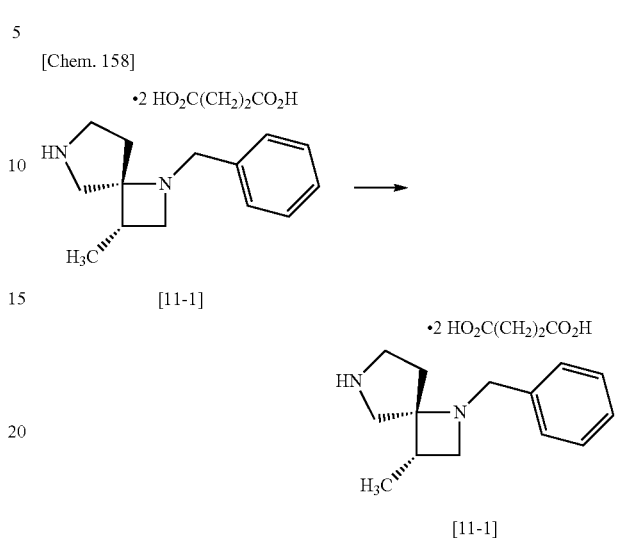

Under nitrogen atmosphere, crude SR-MDBN-DSU [11-1](3.00 g, 6.63 mmol) and 2-propanol (18 mL) were added to a reaction vessel, and the mixture was stirred at room temperature for 2.5 hr. A solid was collected on a filter, and the obtained solid was washed with 2-propanol (9 mL), and then was dried under a reduced pressure at 50° C. to give SR-MDBN-DSU [11-1] (2.74 g, 6.06 mmol) in a yield of 91.3%.

NMR was performed for the obtained SR-MDBN-DSU [11-1].

$^1$H-NMR (DMSO-$D_6$) δ: 11.99 (4H, brs), 7.33-7.21 (5H, m), 3.69 (1H, d, J=12.9 Hz), 3.48 (1H, d, J=12.9 Hz), 3.24 (1H, d, J=12.7 Hz), 3.23-3.17 (1H, m), 3.11-3.05 (2H, m), 2.93 (1H, d, J=12.7 Hz), 2.64 (1H, dd, J=6.9, 3.7 Hz), 2.33 (8H, s), 2.31-2.23 (2H, m), 2.02-1.95 (1H, m), 1.15 (3H, d, J=6.9 Hz).

HPLC analysis was performed for SR-MDBN-DSU [11-1]obtained in Example 9.

A measuring instrument and conditions of HPLC are shown as follows.

Measuring instrument: LC-10 system (Shimadzu Corporation)

Conditions:

Column: CHIRALPAK IE-3: 3 um, 4.6 mm×250 mm (Daicel Corporation)

Column temperature: 40° C.

Flow rate: 1.0 mL/min.

Time for analysis: 30 min.

Detection wavelength: UV (220 nm)

Mobile phase: n-hexane/ethanol/isopropylamine=95/5/0.1 (volume ratio)

A retention time for the compound [11-1] under the above HPLC conditions was about 16.4 minutes. A retention time for the enantiomer, RS-MDBN-DSU, was about 21.9 minutes.

The step for purifying SR-MDBN-DSU [11-1] was effective for removal of its enantiomer, RS-MDBN-DSU. The enantiomer ratio in the crude SR-MDBN-DSU [11-1] was [SR-MDBN-DSU/RS-MDBN-DSU=98.2%/1.8% (HPLC area percentage)], while the enantiomer ratio in SR-MDBN

[11-1] after the purification step was [SR-MDBN-DSU/RS-MDBN-DSU=>99.9%/<0.1% (HPLC area percentage)].

The results of HPLC analysis for crude SR-MDBN-DSU [11-1] in Example 9 are shown in FIG. 9 and the following table.

TABLE 8

| | Retention time (min) | Area | Hight | % Area | Configuration |
|---|---|---|---|---|---|
| 1 | 16.354 | 15790968 | 438277 | 98.167 | SR |
| 2 | 18.507 | 4568 | 0 | 0.028 | |
| 3 | 21.854 | 290240 | 11127 | 1.804 | RS |

The results of HPLC analysis for SR-MDBN-DSU [11-1] after the purification step in Example 9 are shown in FIG. 10 and the following table.

TABLE 9

| | Retention time (min) | Area | Hight | % Area | Configuration |
|---|---|---|---|---|---|
| 1 | 16.680 | 15541643 | 278621 | 99.938 | SR |
| 2 | 21.884 | 6429 | 441 | 0.041 | RS |
| 3 | 22.443 | 3236 | 231 | 0.021 | |

[Example 10] Preparation of SR-MDBN (Compound [10])

[Chem. 159]

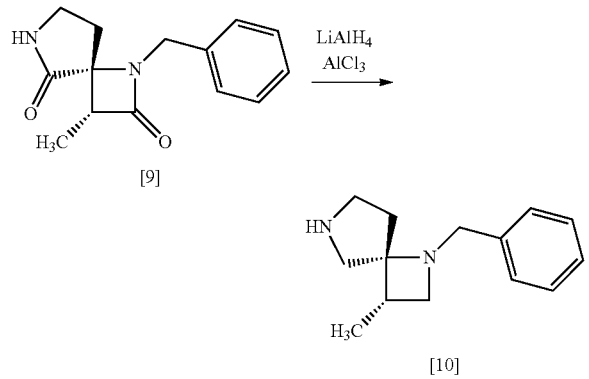

Under nitrogen atmosphere, aluminium chloride (820 mg, 6.15 mmol) and THF (1 mL) were added to a reaction vessel at 0° C. A solution of 1 M lithium aluminium hydride in THF (6.1 mL, 6.15 mmol) was added dropwise to the mixture at the temperature below 10° C., and the mixture was stirred at room temperature for 1 hr. To the reaction mixture, a solution of RR-MDDO [9] (500 mg, 2.05 mmol) in THF (2 mL) was added dropwise at −15° C. to −10° C., and the mixture was stirred at −10° C. for 1 hr, then at 40° C. overnight. After the reaction mixture was cooled to 0° C., saturated aqueous solution of potassium sodium tartrate (10 mL) was added dropwise to the reaction mixture. Then 25% aqueous sodium hydroxide solution (5 mL) was added thereto and the product was extracted twice with CPME (5 mL). The resulting organic layers were combined, washed with saturated brine (5 mL) and concentrated under reduced pressure. To this concentrated residue was added 2-propanol (5 mL) to give a solution of crude SR-MDBN [10] in 2-propanol (equivalent to 2.05 mmol).

The crude SR-MDBN [10] prepared by the same process was concentrated to dryness for measuring NMR and MS.

$^1$H-NMR (CDCl$_3$) δ: 7.34-7.20 (5H, m), 3.62 (1H, d, J=12.9 Hz), 3.59 (1H, d, J=12.9 Hz), 3.21 (1H, dd, J=7.5, 6.6 Hz), 2.99 (1H, d, J=12.1 Hz), 2.95 (1H, d, J=12.1 Hz), 2.84 (2H, t, J=7.3 Hz), 2.68 (1H, t, J=5.8 Hz), 2.43-2.35 (1H, m), 2.22-2.15 (1H, m), 1.81-1.74 (2H, m), 1.13 (3H, d, J=6.9 Hz).

MS: m/z=217 [M+H]$^+$

Example 11

(A) Preparation of SR-MDBN (Compound [10])

[Chem. 160]

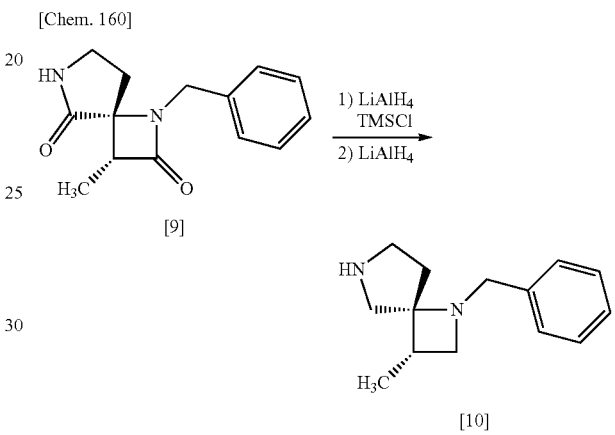

Under nitrogen atmosphere, chlorotrimethylsilane (22.2 g, 205 mmol) and toluene (60 mL) were added to a reaction vessel at room temperature, and then a 10% solution of lithium aluminum hydride in THF (83.0 mL, 205 mmol) was added dropwise at −10° C. to 0° C. to the mixture. The mixture was stirred at the same temperature for 0.5 hr. A solution of RR-MDDO [9] (20.0 g, 81.9 mmol) in THF (100 mL) was added dropwise at −10° C. to 0° C. to the reaction mixture, and the mixture was stirred at the same temperature for 1 hr. A 10% solution of lithium aluminum hydride in THF (19.9 mL, 49.1 mmol) was added dropwise at −5° C. to 0° C. to the reaction mixture, and then the mixture was stirred at 50° C. for 20 hr. The reaction mixture was cooled to 0° C., and then thereto was added dropwise 2-propanol (40 mL). The mixture was stirred for 2.5 hr. The mixture was added dropwise to a mixture of 50% aqueous solution of potassium sodium tartrate (300 mL) and 8N aqueous potassium hydroxide (40 mL), and was stirred at room temperature overnight. The organic layer obtained by separation was washed with 50% aqueous solution of potassium sodium tartrate (100 mL), and was concentrated under a reduced pressure. 2-Propanol (60 mL) was added to the concentrated residue and the mixture was concentrated, which was repeated twice to give a solution of crude SR-MDBN [10] in 2-propanol (equivalent to 81.9 mmol).

A part of the solution of crude SR-MDBN [10] in 2-propanol synthesized in the same manner was concentrated and dried, and then NMR and MS were performed.

$^1$H-NMR (DMSO-D$_6$) δ: 7.28-7.17 (5H, m), 3.56 (1H, d, J=13.9 Hz), 3.52 (1H, d, J=13.2 Hz), 3.20 (1H, brs), 3.09-3.05 (1H, m), 2.80 (1H, d, J=11.3 Hz), 2.73-2.67 (3H, m), 2.56-2.53 (1H, m), 2.28-2.20 (1H, m), 2.09-2.02 (1H, m), 1.69-1.63 (1H, m), 1.06 (3H, d, J=6.9 Hz).

MS: m/z=217 [M+H]+

(B) Preparation of SR-MDBN (Compound [10])

[Chem. 161]

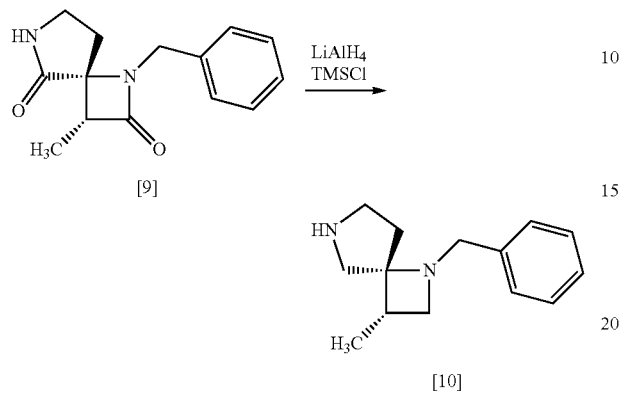

SR-MDBN [10] was prepared in the following alternative manner. Under nitrogen atmosphere, THF (535 mL) was cooled to 0-5° C., then a 15% solution of lithium aluminum hydride in toluene/THF (374 mL, 1.314 mol) was added dropwise. The mixture was stirred for 10 min at 0-5° C., then chlorotrimethylsilane (142.8 g, 1.314 mol) was added dropwise and the mixture was stirred for 10 min at 0-5° C. A solution of RR-MDDO [9] (107.0 g, 0.438 mol) in THF (535 mL) was added dropwise. After 30 min the cooling was stopped and the mixture was heated to 40-50° C. The mixture was stirred at the same temperature for 1 hr. The mixture was then heated to reflux and stirred at that temperature for 14 hrs. The reaction mixture was cooled to 0-5° C., and then thereto was added tert-butyl methyl ether (2140 mL, first 400 mL added dropwise). Then a saturated aqueous solution of Rochelle salt (1740 mL, first 150 mL added dropwise while the temperature was kept at 0-5° C.) and water (670 mL) was added. After addition the reaction mixture was allowed to warm to 15-20° C. and then stirred at 20° C. for 1 hr. The organic layer obtained by separation was concentrated under reduced pressure. 2-Propanol was added to the concentrated residue and the mixture was concentrated, which was repeated twice to give a solution of crude SR-MDBN [10] in 2-propanol (equivalent to 0.417 mmol).

[Example 12] Preparation of SR-MDOP (Compound [14])

[Chem. 162]

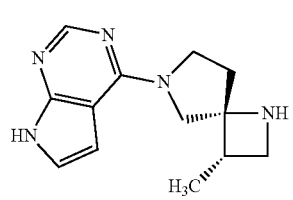

Step 1

[Chem. 163]

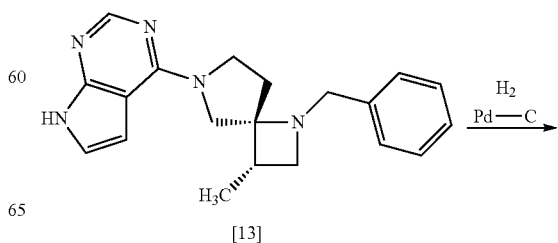

Under nitrogen atmosphere, to tripotassium phosphate (14.1 g, 66.3 mmol) was added purified water (30 mL). To this solution, SR-MDBN-DSU [11-1] (5.0 g, 11.0 mmol), CPPY [12] (1.73 g, 11.3 mmol) and tert-butanol (15 mL) were added sequentially at 30° C. to 40° C. The reaction mixture was stirred at 75° C. to 85° C. for 2.5 hr, and then cooled to room temperature. The layers of this reaction mixture were separated to give a solution of the crude SR-MDBP [13] in aqueous tert-butanol (43.16 g, equivalent to 11.0 mmol). The resulting solution of the crude SR-MDBP [13] in aqueous tert-butanol was used in the next step assuming that the yield was 100%.

The crude SR-MDBP [13] prepared by the same process was concentrated to dryness for measuring NMR and MS.

$^1$H-NMR (DMSO-$d_6$) δ: 11.57 (1H, s), 8.09 (1H, s), 7.29-7.15 (5H, m), 7.10 (1H, t, J=2.8 Hz), 6.57 (1H, brs), 3.75-3.53 (6H, m), 3.23 (1H, dd, J=7.4, 6.5 Hz), 2.70 (1H, t, J=5.8 Hz), 2.36 (1H, dt, J=19.5, 7.2 Hz), 2.29-2.22 (1H, m), 2.14-2.07 (1H, m), 1.07 (3H, d, J=7.2 Hz). MS: m/z=344 [M+H]+

Step 2

[Chem. 164]

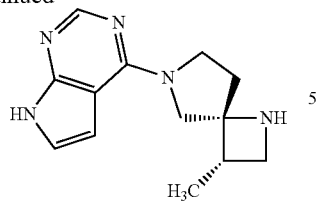

[14]

To the solution of the crude SR-MDBP [13] in aqueous tert-butanol (43.16 g, equivalent to 11.0 mmol) were added sequentially purified water (3.7 mL), acetic acid (1.32 g, 22.0 mmol) and 10% palladium on carbon (Kawaken Fine Chemicals Co., Ltd. Type M, 52.6% water-content, 370 mg). The reaction vessel was filled with hydrogen, and the mixture was stirred at 55° C. for 7 hr at atmospheric pressure. The reaction solution was cooled to room temperature, and then the reaction vessel was filled with nitrogen. To the solution were added toluene (17 mL) and 8 M aqueous sodium hydroxide solution (15.5 mL, 44.0 mmol), and the mixture was stirred at 45° C. for 6 hr. After the reaction mixture was cooled to room temperature, 10% palladium on carbon was filtered off. The reaction vessel and 10% palladium on carbon were washed with a mixture of tert-butanol and toluene (1:1, 7 mL). The filtrate combined with the washings, and the layers were separated. The resulting organic layer was washed with 10% brine (7 mL), and concentrated under reduced pressure. A procedure of an addition of toluene (17 mL) to the concentrated residue followed by concentration was repeated three times. And then, toluene (20 mL) was added to the concentrated residue again, and the mixture was stirred at 15° C. to 30° C. for 1 hr, then at 0° C. to 10° C. for 1 hr. The precipitated solid was collected on the filter, and the resulting solid was washed with toluene (5 mL). The resulting wet solid was dried under reduced pressure to give SR-MDOP [14] (2.45 g, 10.07 mmol) in a yield of 91.5%.

Using SR-MDOP [14] prepared by the same process, NMR and MS were measured.

$^1$H-NMR (DMSO-$d_6$) δ: 11.57 (brs, 1H), 8.07 (s, 1H), 7.10 (d, 1H, J=3.2 Hz), 6.58 (d, 1H, J=3.2 Hz), 3.92-3.59 (m, 4H), 3.49 (dd, 1H, J=8.3, 7.2 Hz), 2.93 (dd, 1H, J=7.2, 6.1 Hz), 2.61-2.53 (m, 2H), 2.12-2.01 (m, 2H), 1.10 (d, 3H, J=6.9 Hz).

MS: m/z=244 [M+H]$^+$

[Example 13] Preparation of Compound A (Compound [17]) 1-Ethanolate (Compound [20])

[Chem. 165]

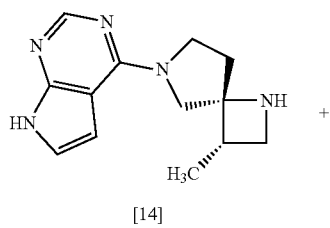

[14]

+

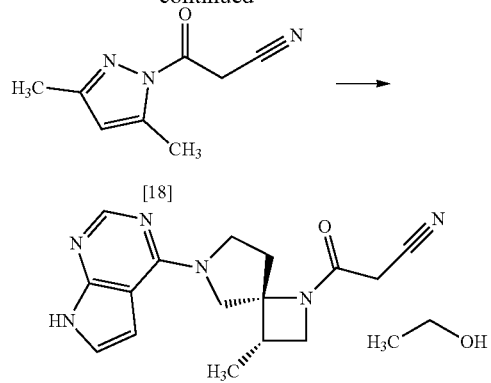

Under nitrogen atmosphere, to SR-MDOP [14] (5.00 g, 20.5 mmol) were added acetonitrile (60 mL) and triethylamine (416 mg, 4.11 mmol), followed by an addition of a solution of DPCN [18] (3.69 g, 22.6 mmol) in acetonitrile (35 mL) dropwise at 45° C. The dropping funnel used for the dropping was washed with acetonitrile (5.0 mL), and the washings were added to the reaction mixture. The reaction mixture was stirred at 45° C. for 3 hr, and then cooled to room temperature. To the reaction mixture were added 5% aqueous sodium bicarbonate (25 mL), 10% brine (25 mL) and ethyl acetate (50 mL) and the mixture was stirred. Then, the organic layer was separated. The solvent in the organic layer was removed under reduced pressure. A procedure of an addition of THF (50 mL) to the concentrated residue followed by concentration was repeated four times. THF (50 mL) was added to the concentrated residue, and then, water was added to the mixture so that the water content was adjusted to 5.5 wt. %. The precipitated insoluble materials were filtered off. The reaction vessel and the filter cake were washed with THF (15 mL). The filtrate was combined with the washings, and then the solvent in the filtrate was removed under reduced pressure. To the concentrated residue were added ethanol (50 mL) and a crystal (5.1 mg) of Compound A (Compound [17]) previously prepared according to the process of Example 11 described below, and the mixture was stirred at room temperature for 1 hr. The solvent was removed under reduced pressure, and ethanol (50 mL) was added to the residue, and the mixture was concentrated again. To the concentrated residue was added ethanol (15 mL), and the mixture was stirred at room temperature for 1 hr. The precipitated solid was collected on the filter, and the resulting solid was washed with ethanol (20 mL). The resulting wet solid was dried under reduced pressure to give Compound A (Compound [17]) 1-ethanolate [20] (6.26 g, 17.6 mmol) in a yield of 85.5%.

Using Compound A (Compound [17]) 1-ethanolate prepared by the same process, NMR and MS were measured.

$^1$H-NMR (DMSO-$d_6$) δ: 11.59 (brs, 1H), 8.08 (s, 1H), 7.11 (dd, 1H, J=3.5, 2.3 Hz), 6.58 (dd, 1H, J=3.5, 1.8 Hz), 4.34 (t, 1H, J=5.1 Hz), 4.16 (t, 1H, J=8.3 Hz), 4.09-3.92 (m, 3H), 3.84-3.73 (m, 1H), 3.71 (d, 1H, J=19.0 Hz), 3.65 (d, 1H, J=19.0 Hz), 3.58 (dd, 1H, J=8.2, 5.9 Hz), 3.44 (dq, 2H, J=6.7, 5.1 Hz), 2.69-2.60 (m, 2H), 2.23-2.13 (m, 1H), 1.12 (d, 3H, J=7.1 Hz), 1.06 (t, 3H, J=6.7 Hz).

MS: m/z=311 [M+H]$^+$

Using Compound A (Compound [17]) 1-ethanolate prepared by the same process, the diffraction angle 2θ and the diffraction intensity were measured by the powder X-ray diffractometry. The resulting spectrum is shown in FIG. 11.

The respective peaks in FIG. 11 are as shown in the following table.

TABLE 10

| Diffraction angle [2θ (°)] | Relative intensity [%] | Diffraction intensity [cps] |
|---|---|---|
| 8.2697 | 100.00 | 5765.29 |
| 10.0967 | 7.73 | 445.63 |
| 11.0161 | 4.77 | 275.16 |
| 11.9986 | 19.17 | 1105.32 |
| 12.6933 | 63.30 | 3649.39 |
| 12.9629 | 58.64 | 3380.72 |
| 13.8549 | 25.71 | 1482.08 |
| 14.8506 | 4.53 | 261.35 |
| 16.5910 | 10.63 | 613.11 |
| 17.0458 | 10.84 | 624.86 |
| 18.1156 | 6.92 | 399.14 |
| 20.0496 | 64.61 | 3724.97 |
| 22.1288 | 6.60 | 380.77 |
| 23.1059 | 13.68 | 788.68 |
| 24.0968 | 38.33 | 2209.75 |

[Example 14] Purification of Compound A (Compound [17])

[Chem. 166]

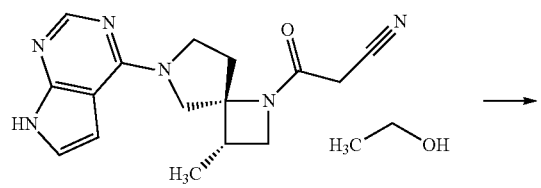

Under nitrogen atmosphere, Compound A (Compound [17]) 1-ethanolate [20] (4.00 g, 11.2 mmol) and 1-butanol (32 mL) were mixed, and the mixture was dissolved at 110° C. After the solution was cooled to 85° C., a crystal (4.0 mg) of Compound A (Compound [17]) which was previously prepared by the same process as this process was added, and the mixture was stirred at 85° C. for 2 hr, 75° C. for 1 hr, and then at room temperature for 16 hr. The precipitated solid was collected on the filter, and the resulting solid was washed sequentially with 1-butanol (8.0 mL) and ethyl acetate (8.0 mL). The resulting wet solid was dried under reduced pressure to give Compound A (Compound [17]) (3.18 g, 10.2 mmol) in a yield of 91.3%.

Using Compound A (Compound [17]) prepared by the same process, NMR and MS were measured.

$^1$H-NMR (DMSO-$d_6$) δ: 11.59 (brs, 1H), 8.08 (s, 1H), 7.11 (dd, 1H, J=3.5, 2.5 Hz), 6.58 (dd, 1H, J=3.5, 1.8 Hz), 4.16 (t, 1H, J=8.3 Hz), 4.09-3.93 (m, 3H), 3.84-3.73 (m, 1H), 3.71 (d, 1H, J=19.0 Hz), 3.65 (d, 1H, J=19.0 Hz), 3.58 (dd, 1H, J=8.2, 5.9 Hz), 2.69-2.59 (m, 2H), 2.23-2.13 (m, 1H), 1.12 (d, 3H, J=7.2 Hz).

MS: m/z=311 [M+H]$^+$

A single crystal X-ray structure analysis of Compound A (Compound [17]) prepared by the same process was performed.

(1) Process for Preparing Single Crystal

To 10 mg of Compound A (Compound [17]) in a LaPha Robovial 2.0 mL wide-mouthed vial was added 0.5 mL of chloroform, and the vial was capped. Compound A (Compound [17]) was completely dissolved. In order to evaporate the solvent slowly, a hole was made on the septum attached to the cap with a TERUMO syringe needle, and the vial was stood still at room temperature. The resulting single crystal was used for the structure analysis.

(2) Instrument

Beamline: SPring-8 BL32B2

Detector: Rigaku R-AXIS V diffractometer (3) Measuring Method

The radiant light of 0.71068 Å was irradiated to the single crystal to measure X-ray diffraction data.

(4) Assay Method

Using the X-ray anomalous scattering effect of the chlorine atom in the resulting Compound A (Compound [17]) chloroform-solvate, the absolute configuration of Compound A (Compound [17]) was confirmed as (3S,4R). Based on the obtained absolute configuration of Compound A (Compound [17]), the absolute configuration of each process intermediate was identified.

[Example 15] Preparation of Compound A (Compound [17])

[Chem. 167]

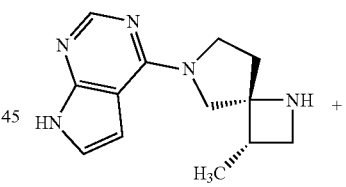

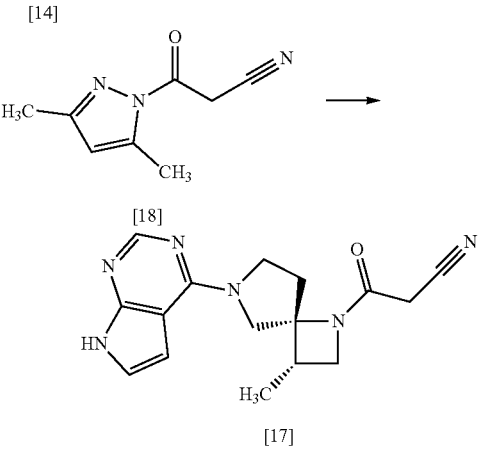

Under nitrogen atmosphere, acetonitrile (900 mL) was added to SR-MDOP [14] (90.0 g, 370 mmol), and then to the mixture was added dropwise a solution of DPCN [18] (63.5 g, 389 mmol) in acetonitrile (540 mL) at 70° C. to 80° C. The dropping funnel used was washed with acetonitrile (90 mL), and the washing was added to the reaction mixture. The reaction mixture was stirred at 70° C. to 80° C. for 1.5 hr, and then to the mixture was added 1-butanol (900 mL). The solvent was removed under a reduced pressure. 1-Butanol (900 mL) was added to the concentrated residue, and the mixture was concentrated again. 1-Butanol was added to the concentrated residue so that the total amount of the mixture was adjusted to be 2.1 L, and then the mixture was dissolved with heating at 90° C. to 100° C. This solution was cooled to 60° C. to 70° C., and then thereto was added a crystal of Compound A (90 mg) that was prepared in advance in the same manner as this procedure. The mixture was stirred at 60° C. to 70° C. for 2 hr, and was then cooled to 30° C. over 4 hr. The mixture was stirred at 20° C. to 30° C. for 1 hr, and was then stirred at 0° C. to 5° C. for 4 hrs. The precipitated solid was collected on a filter, and the resulted solid was washed with sequentially 1-butanol (180 mL) and ethyl acetate (180 mL). The resulted wet solid was dried under a reduced pressure to give Compound A [17] (104 g, 335 mmol) in a yield of 90.5%.

NMR and MS were performed for Compound A that was synthesized in the same manner as this procedure.

$^1$H-NMR (DMSO-d$_6$) δ: 11.60 (s, 1H), 8.09 (s, 1H), 7.12 (dd, 1H, J=3.0, 2.7 Hz), 6.58 (brs, 1H), 4.16 (t, 1H, J=8.4 Hz), 4.11-3.91 (m, 3H), 3.88-3.72 (m, 1H), 3.68 (d, 2H, J=2.1 Hz), 3.57 (dd, 1H, J=8.4, 6.0 Hz), 2.70-2.56 (m, 2H), 2.24-2.10 (m, 1H), 1.12 (d, 3H, J=7.2 Hz).

MS: m/z=311 [M+H]$^+$

[Example 16] Purification of Compound A (Compound [17])

Under nitrogen atmosphere, Compound A (Compound [17]) (100 g, 322 mmol) that was prepared in Example 15 was mixed with 1-butanol (1.8 L), and was dissolved at 90° C. to 100° C. The solution was filtered at 85° C. to 100° C., and the vessel that had contained the solution and the filtered residue were washed with 1-butanol (200 mL). The washing was added to the filtrate. The filtrate was cooled to 60° C. to 70° C., and then thereto was added a crystal of Compound A (100 mg) that was prepared in advance in the same manner as this procedure. This mixture was stirred at 60° C. to 70° C. for 2 hr, and was then cooled to 30° C. over 3 hr. The mixture was stirred at 20° C. to 30° C. for 1 hr, and was then stirred at 0° C. to 5° C. for 4 hr. The precipitated solid was collected on a filter, and the resulted solid was washed with sequentially 1-butanol (200 mL) and ethyl acetate (200 mL). The resulted wet solid was dried under a reduced pressure to give Compound A (Compound [17]) (91.7 g, 295 mmol) in 91.7% yield. The resulted compound was analyzed with powder X-ray diffraction, etc. to confirm Compound A.

NMR and MS were performed for Compound A that was synthesized in the same manner as this procedure.

$^1$H-NMR (DMSO-d$_6$) δ: 11.60 (s, 1H), 8.09 (s, 1H), 7.12 (dd, 1H, J=2.7, 2.4 Hz), 6.59 (brs, 1H), 4.16 (t, 1H, J=8.2 Hz), 4.11-3.91 (m, 3H), 3.86-3.72 (m, 1H), 3.68 (d, 2H, J=2.1 Hz), 3.58 (dd, 1H, J=8.1, 6.0 Hz), 2.71-2.56 (m, 2H), 2.27-2.09 (m, 1H), 1.12 (d, 3H, J=6.9 Hz).

MS: m/z=311 [M+H]$^+$

[Example 17] Preparation of RR-AOPA (Compound [22])

[Chem. 168]

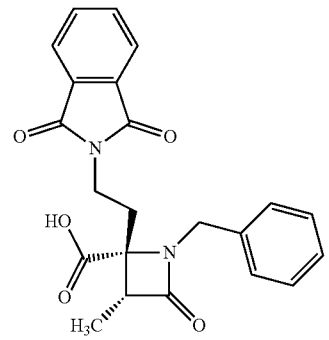

[22]

Step 1

[Chem. 169]

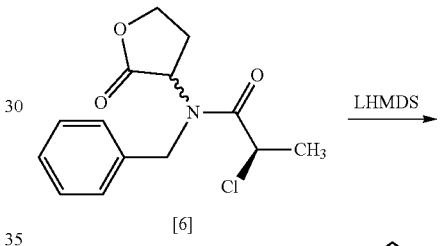

Under nitrogen atmosphere, to a solution of R-CPBL [6] (25.0 g, 88.7 mmol) in THF (100 mL) was added dropwise a 24% solution of lithium hexamethyldisilazide in THF (66.3 g, 93.2 mmol) at −10° C. to 0° C., and the mixture was stirred at the same temperature for 1 hr. This reaction mixture was added dropwise to 2M hydrochloric acid (100 mL), and the product was extracted with toluene (200 mL). The obtained organic layer was washed sequentially with 5% aqueous sodium bicarbonate (125 mL) and water (125 mL), and then was concentrated under a reduced pressure. Toluene (125 mL) was added to the concentrated residue and the mixture was concentrated, which was repeated twice to give a solution of RR-AOBL [7] in toluene (69.1 g, equivalent to 88.7 mol). The obtained solution of RR-AOBL [7] in toluene was estimated to be obtained in a yield of 100% and was used for the next step.

A part of the solution of crude RR-AOBL [7] in toluene synthesized in the same manner was concentrated and dried, and then NMR and MS were performed.

$^1$H-NMR (DMSO-D$_6$) δ: 7.36-7.25 (5H, m), 4.54 (1H, d, J=15.7 Hz), 4.35-4.30 (1H, m), 4.24-4.18 (1H, m), 4.13 (1H, d, J=15.7 Hz), 3.60 (1H, q, J=7.4 Hz), 2.46-2.35 (2H, m), 1.10 (3H, d, J=7.4 Hz).

MS: m/z=246 [M+H]$^+$

Step 2

[Chem. 170]

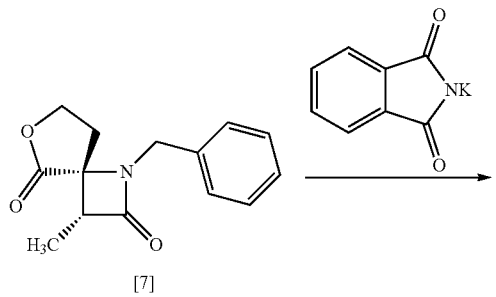

[7]

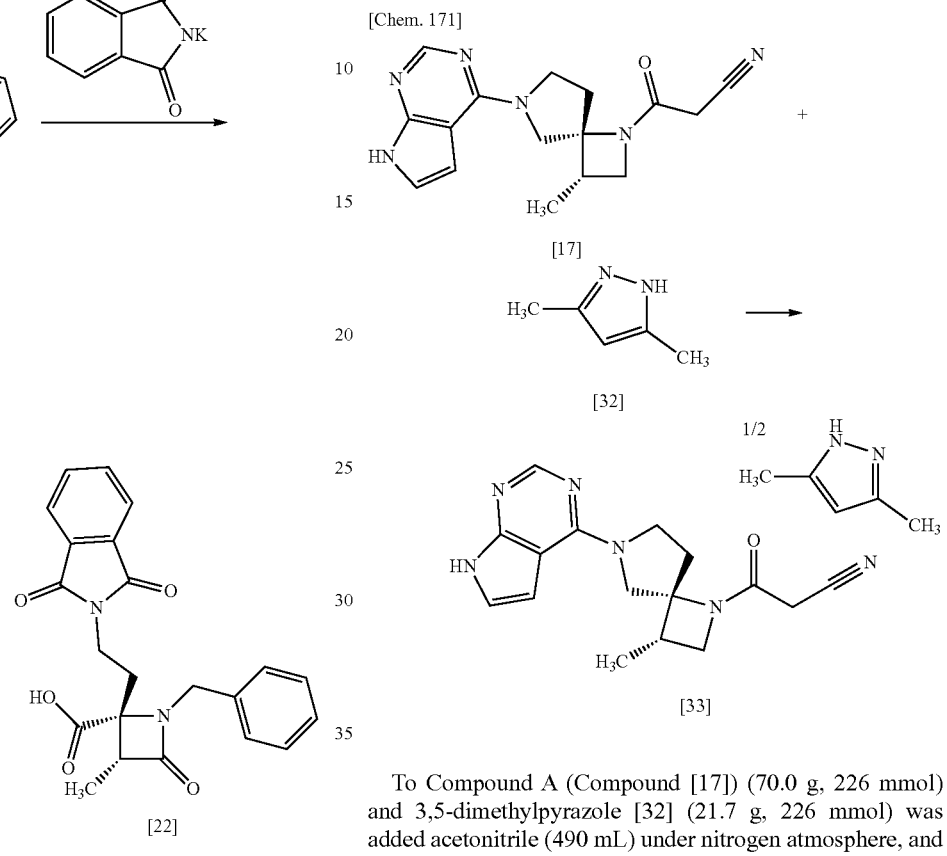

[22]

Under nitrogen atmosphere, a solution of crude RR-AOBL [7] in toluene (69.1 g, equivalent to 88.7 mmol), DMSO (100 mL), and potassium phthalimide (18.1 g, 97.6 mmol) were sequentially added to a reaction vessel at room temperature, and the mixture was stirred with heating at 90° C. to 110° C. overnight. The reaction mixture was cooled to around room temperature, and then the product was extracted after the addition of water (100 mL) and toluene (100 mL). To the obtained aqueous layer was added a 5% aqueous solution of potassium hydrogen sulfate (500 mL), and the mixture was extracted with ethyl acetate (150 mL) twice, and then concentrated under a reduced pressure. The concentrated residue was purified through silica gel column chromatography (chloroform:methanol=9:1) to give RR-AOPA [22] (25.5 g, 65.0 mol) in a yield of 63.7% from R-CPBL [6].

NMR and MS were performed for the obtained RR-AOPA [22].

$^1$H-NMR (DMSO-D$_6$) δ: 13.45 (1H, brs), 7.84-7.81 (4H, m), 7.39-7.31 (4H, m), 7.24 (1H, t, J=7.2 Hz), 4.63 (1H, d, J=16.1 Hz), 4.33 (1H, d, J=16.1 Hz), 3.64-3.57 (1H, m), 3.52-3.44 (1H, m), 3.36 (1H, q, J=7.5 Hz), 2.30-2.15 (2H, m), 1.09 (3H, d, J=7.5 Hz).

MS: m/z=393 [M+H]$^+$

[Example 18] Preparation of a Co-Crystal (2:1, Molar Ratio) (Compound [33]) of Compound a (Compound [17]) with 3,5-Dimethylpyrazole (Seed Crystal)

[Chem. 171]

To Compound A (Compound [17]) (70.0 g, 226 mmol) and 3,5-dimethylpyrazole [32] (21.7 g, 226 mmol) was added acetonitrile (490 mL) under nitrogen atmosphere, and the mixture was dissolved with heating at 80° C. The mixture was stirred at 65° C. for 2 hrs. After precipitation of a crystal was observed, the mixture was gradually cooled to room temperature. After the mixture was stirred under ice cooling for 2 hrs, a precipitated solid was collected on a filter, and the obtained solid was washed with ice-cooled acetonitrile (140 mL). The obtained wet solid was dried under reduced pressure to give a co-crystal (2:1, molar ratio) (Compound [33]) of Compound A (Compound [17]) with 3,5-dimethylpyrazole (75.3 g, 210 mmol) in the yield of 93.1%.

NMR, elemental analysis, and differential scanning calorimetry were measured for the synthesized co-crystal (2:1, molar ratio) of Compound A (Compound [17]) with 3,5-dimethylpyrazole.

$^1$H-NMR (DMSO-d$_6$) δ: 11.98 (br s, 0.5H), 11.59 (br s, 1H), 8.08 (s, 1H), 7.11 (dd, 1H, J=3.5, 2.2 Hz), 6.58 (dd, 1H, J=3.5, 1.4 Hz), 5.73 (s, 0.5H), 4.16 (t, 1H, J=8.3 Hz), 4.09-3.93 (m, 3H), 3.84-3.74 (m, 1H), 3.70 (d, 1H, J=19.0 Hz), 3.65 (d, 1H, J=19.0 Hz), 3.58 (dd, 1H, J=8.2, 5.9 Hz), 2.70-2.58 (m, 2H), 2.22-2.12 (m, 1H), 2.12 (s, 3H), 1.12 (d, 3H, J=7.2 Hz).

Elemental analysis: C, 61.9 wt %, H, 6.1 wt %, N, 27.2 wt %

(Theoretical value: C, 62.0 wt %, H, 6.2 wt %, N, 27.4 wt %)

Differential Scanning Calorimetry:

Measurement was conducted with a differential scanning calorimeter DSC-60A (manufactured by Shimadzu Corporation) at the rate of temperature increase of 5° C./min (sealed aluminum pan). A DSC curve obtained in the measurement is shown in FIG. 12. Enthalpy of endothermic peaks on the DSC curve was 100.26 J/g, the endothermic temperature was 173.66° C., and the extrapolated onset temperature was 172.36° C. The resulting spectrum is shown in FIG. 12.

The diffraction angle 2θ and the diffraction intensity were measured by the powder X-ray diffractometry for the co-crystal (2:1, molar ratio) of Compound A (Compound [17]) with 3,5-dimethylpyrazole. The resulting spectrum is shown in FIG. 13.

The respective peaks in FIG. 13 are as shown in the following table.

TABLE 11

| Diffraction angle [2θ (°)] | Relative intensity [%] | Diffraction intensity [cps] |
| --- | --- | --- |
| 4.5995 | 22.59 | 1219.62 |
| 6.5864 | 6.80 | 367.17 |
| 7.7159 | 12.60 | 680.20 |
| 9.2996 | 3.43 | 185.09 |
| 11.1525 | 4.05 | 218.54 |
| 12.6288 | 100.00 | 5398.64 |
| 13.2491 | 52.15 | 2815.46 |
| 13.8436 | 1.87 | 101.04 |
| 14.2405 | 18.90 | 1020.43 |
| 14.6304 | 8.80 | 475.04 |
| 15.1842 | 15.26 | 823.69 |
| 16.0529 | 68.62 | 3704.73 |
| 17.0279 | 6.45 | 348.43 |
| 17.4374 | 6.06 | 327.35 |
| 18.0485 | 3.67 | 197.88 |
| 18.6535 | 39.95 | 2156.69 |
| 19.1303 | 45.91 | 2478.47 |
| 19.3693 | 26.84 | 1449.11 |
| 19.6389 | 6.22 | 335.68 |
| 20.3423 | 28.14 | 1519.44 |
| 20.9117 | 45.96 | 2481.20 |
| 21.8334 | 5.48 | 295.84 |
| 22.8850 | 40.22 | 2171.23 |
| 23.3477 | 6.21 | 335.04 |
| 23.9286 | 18.49 | 998.22 |
| 24.4043 | 16.04 | 866.13 |
| 24.7252 | 29.15 | 1573.95 |

[Example 19] Preparation of a Co-Crystal (2:1, Molar Ratio) (Compound [33]) of Compound A (Compound [17]) with 3,5-Dimethylpyrazole

[Chem. 172]

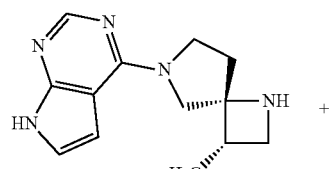

[14]

-continued

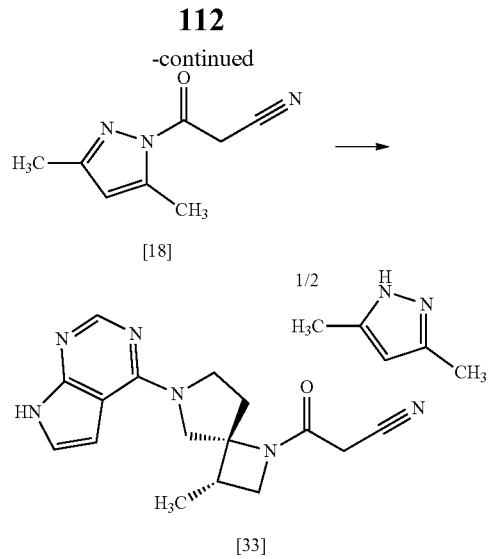

To SR-MDOP [14] (800 g, 3.29 mol) was added acetonitrile (8.0 L) under nitrogen atmosphere, and then to the mixture was added dropwise a solution of DPCN [18] (563 g, 3.45 mol) in acetonitrile (4.8 L) at 75° C. The dropping funnel used was washed with acetonitrile (0.8 L), and the washings were added to the reaction mixture. After the reaction mixture was stirred at 75° C. for 1.5 hrs, the reaction solution was concentrated under reduced pressure to 8.0 L. To the residue was added at 65° C. the co-crystal (2:1, molar ratio) (Compound [33]) of Compound A (Compound [17]) with 3,5-dimethylpyrazole (80 mg) synthesized in Example 18. After stirring at 65° C. for 2 hrs, the mixture was stirred for 2 hrs under ice cooling. The precipitated solid was collected on a filter, and the resulting solid was washed with ice-cooled acetonitrile (2.4 L). The wet solid was dried under reduced pressure to give a co-crystal (2:1, molar ratio) (Compound [33]) of Compound A (Compound [17]) with 3,5-dimethylpyrazole (1070 g, 2.99 mol) in the yield of 90.8%.

NMR, elemental analysis, and differential scanning calorimetry were measured for the synthesized co-crystal (2:1, molar ratio) of Compound A (Compound [17]) with 3,5-dimethylpyrazole.

$^1$H-NMR (DMSO-$d_6$) δ: 11.99 (br s, 0.5H), 11.59 (br s, 1H), 8.11 (s, 1H), 7.11 (s, 1H), 6.58 (d, 1H, J=3.0 Hz), 5.73 (s, 0.5H), 4.16 (t, 1H, J=8.4 Hz), 4.10-3.92 (m, 3H), 3.85-3.74 (m, 1H), 3.70 (d, 1H, J=19.1 Hz), 3.65 (d, 1H, J=19.1 Hz), 3.57 (dd, 1H, J=7.9, 6.1 Hz), 2.70-2.58 (m, 2H), 2.22-2.14 (m, 1H), 2.12 (s, 3H), 1.12 (d, 3H, J=6.9 Hz).

Elemental analysis: C, 62.0 wt %, H, 6.2 wt %, N, 27.2 wt %

(Theoretical value: C, 62.0 wt %, H, 6.2 wt %, N, 27.4 wt %)

Differential Scanning Calorimetry:

Measurement was conducted with a differential scanning calorimeter DSC-60A (manufactured by Shimadzu Corporation) at the rate of temperature increase of 5° C./min (sealed aluminum pan). A DSC curve obtained in the measurement is shown in FIG. 14. Enthalpy of endothermic peaks on the DSC curve was 78.02 J/g, the endothermic temperature was 173.81° C., and the extrapolated onset temperature was 172.02° C. The resulting spectrum is shown in FIG. 14.

The diffraction angle 2θ and the diffraction intensity were measured by the powder X-ray diffractometry for the synthesized co-crystal (2:1, molar ratio) of Compound A (Compound [17]) with 3,5-dimethylpyrazole. The resulting spectrum is shown in FIG. 15.

The respective peaks in FIG. 15 are as shown in the following table.

TABLE 12

| Diffraction angle [2θ (°)] | Relative intensity [%] | Diffraction intensity [cps] |
|---|---|---|
| 4.6074 | 12.69 | 341.47 |
| 6.5985 | 6.20 | 166.76 |
| 7.7215 | 9.57 | 257.49 |
| 9.3039 | 2.93 | 78.86 |
| 11.1582 | 2.08 | 56.00 |
| 12.6252 | 100.00 | 2690.94 |
| 13.2478 | 72.85 | 1960.46 |
| 13.8405 | 4.03 | 108.35 |
| 14.2414 | 16.75 | 450.87 |
| 14.6317 | 18.63 | 501.35 |
| 15.1837 | 27.93 | 751.46 |
| 16.0555 | 97.64 | 2627.45 |
| 17.0293 | 4.96 | 133.42 |
| 17.4558 | 4.29 | 115.36 |
| 18.0432 | 4.82 | 129.78 |
| 18.6385 | 45.15 | 1214.91 |
| 19.1352 | 29.44 | 792.08 |
| 19.3755 | 30.43 | 818.96 |
| 19.6628 | 4.02 | 108.11 |
| 20.3391 | 29.67 | 798.38 |
| 20.9048 | 35.47 | 954.60 |
| 21.8601 | 3.95 | 106.37 |
| 22.8816 | 36.84 | 991.38 |
| 23.3272 | 7.46 | 200.72 |
| 23.9114 | 23.73 | 638.46 |
| 24.4128 | 13.76 | 370.22 |
| 24.7091 | 29.29 | 788.13 |

Example 20

(A) Purification of Compound A (Compound [17])

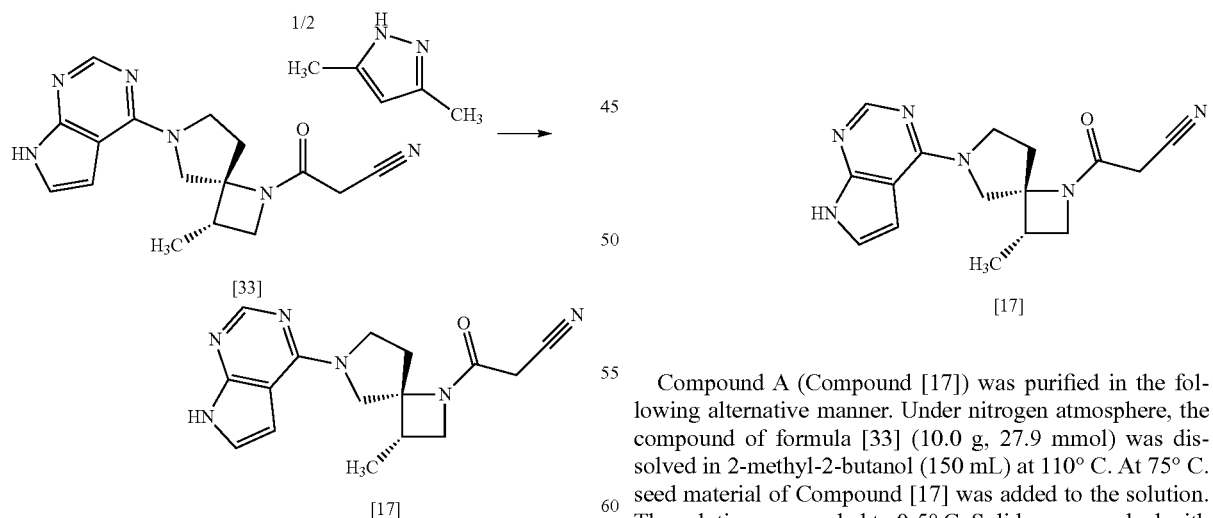

The co-crystal (2:1, molar ratio) (Compound [33]) of Compound A (Compound [17]) with 3,5-dimethylpyrazole (5.00 g, 14.0 mmol), BHT (0.15 g), and 1-butanol (40 mL) were mixed under nitrogen atmosphere, and dissolved at 110° C. After the mixture was cooled to 85° C., the crystal (5 mg) of Compound A (Compound [17]) prepared preliminarily was added to the mixture. After stirring at 85° C. for 2 hrs, the mixture was gradually cooled to room temperature and stirred at room temperature for 3 hrs. The precipitated solid was collected on a filter, and the resulting solid was washed sequentially with 1-butanol (10 mL) and ethyl acetate (10 mL). The resulting wet solid was dried under reduced pressure to give Compound A (Compound [17]) (3.96 g, 12.8 mmol) in the yield of 91.5%.

NMR and MS were measured for Compound A (Compound [17]) that was synthesized in the same manner.

$^1$H-NMR (DMSO-$d_6$) δ: 11.58 (br s, 1H), 8.08 (s, 1H), 7.11 (dd, 1H, J=3.5, 2.3 Hz), 6.58 (dd, 1H, J=3.5, 1.6 Hz), 4.16 (t, 1H, J=8.4 Hz), 4.10-3.94 (m, 3H), 3.84-3.74 (m, 1H), 3.70 (d, 1H, J=19.0 Hz), 3.65 (d, 1H, J=18.7 Hz), 3.58 (dd, 1H, J=8.2, 5.9 Hz), 2.70-2.59 (m, 2H), 2.23-2.12 (m, 1H), 1.12 (d, 3H, J=7.2 Hz).

MS: m/z=311 [M+H]$^+$ (B) Purification of Compound A (Compound [17])

[Chem. 174]

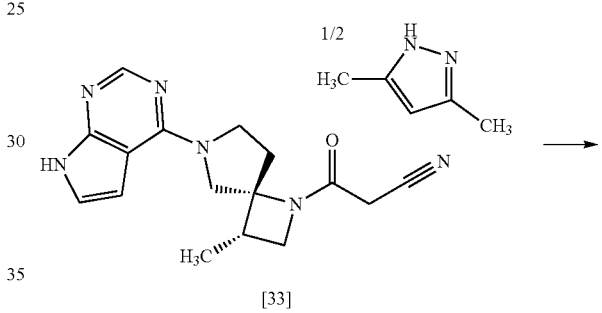

Compound A (Compound [17]) was purified in the following alternative manner. Under nitrogen atmosphere, the compound of formula [33] (10.0 g, 27.9 mmol) was dissolved in 2-methyl-2-butanol (150 mL) at 110° C. At 75° C. seed material of Compound [17] was added to the solution. The solution was cooled to 0-5° C. Solids were washed with 2-methyl-2-butanol (20 mL) and then with ethyl acetate (20 mL). The precipitated solid was collected on the filter, and the resulting solid was washed with 2-methyl-2-butanol (20 mL) and then with ethyl acetate (20 mL). The resulting wet solid was dried under reduced pressure to give Compound [17] (7.6 g, 24 mmol).

[Example 21] Preparation of
Boc-Dab(MeOCO)—OH (Compound [24])

[Chem. 175]

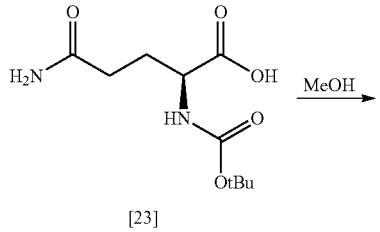

[23]

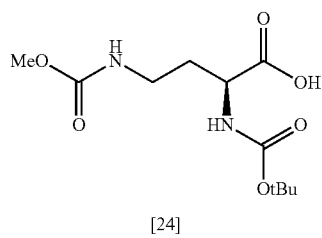

[24]

Sodium hydroxide (60.0 g, 1.5 mmol) was added to methanol (600 mL). The mixture was heated to 40° C. for 45 minutes, until all solids had dissolved. To the resulting solution was added Boc-Gln-OH (Compound [23]) (62.82 g, 250 mmol) in portions with the aid of methanol (30 mL). The resulting solution was stirred at 40° C. for 30 minutes. Bromine (15.4 mL, 300 mmol) was added dropwise. After 90 minutes of stirring, an additional portion of bromine (10.2 mL, 200 mmol) was added dropwise. The reaction mixture was stirred for 30 minutes and subsequently allowed to cool to ambient temperature.

The solvent was evaporated to afford a solid, which was dissolved in water (250 mL) followed by addition of ethyl acetate (315 mL). The mixture was stirred vigorously, and aqueous hydrogen chloride (2 M, 290 mL) was added dropwise until the aqueous phase had a pH of up to 2. The phases were separated, and the aqueous phase was extracted with ethyl acetate (315 mL). The combined organic phases were concentrated to afford crude product [24] (71.31 g) of up to 95% purity.

The compound was used in the next step without further purification.

[Example 22] Preparation of
Boc-Dab(MeOCO)—OH (Compound [24])

[Chem. 176]

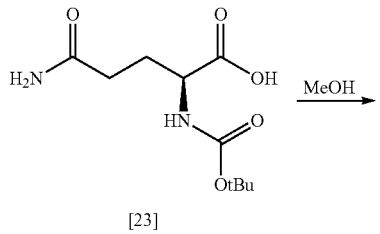

[23]

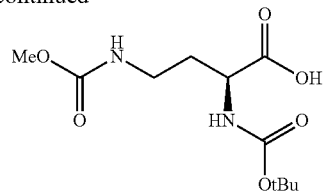

[24]

Solid sodium hydroxide (194.9 g, 4.87 mol) was added portionwise at 10-20° C. to methanol (6 L). To the solution was added Boc-Gln-OH [23] (600 g, 2.44 mol) at 20-25° C. The reaction mixture was heated to 40-45° C. To the reaction mixture was added an aqueous solution of sodium hypochlorite (158.4 g/L, 1.26 L, 199.6 g, 2.68 mol) at 40-45° C. over 1 hour. The mixture was stirred at 40-45° C. for 1-3 hours.

The reaction mixture was cooled to 20-25° C., and a solution of sodium sulfite (61.4 g, 0.49 mol) in water (300 mL) was added. The mixture was stirred for 10 minutes before it was concentrated. 2-Propyl acetate (1.8 L) was added in portions to the evaporation residue and the mixture was concentrated to dryness. To the evaporation residue were added water (300 mL) and 2-propyl acetate (3 L). The pH was adjusted to 2-3 with aqueous hydrogen chloride (2 M, 2.75 L; pH 2.56) at 20-25° C. The phases were separated, and the aqueous phase was extracted with 2-propyl acetate (2×1.5 L). The organic phases were combined and washed with water (1.2 L). The phases were separated, and the organic phase was concentrated to yield Boc-Dab (MeOCO)—OH [24] (669.4 g, 2.42 mol) with HPLC purity 96.3 area-%.

The compound was used in the next step without further purification.

$^1$H NMR (600 MHz, DMSO-d$_6$) δ 12.47 (brs, 1H), 7.15-7.05 (m, 2H), 3.88 (td, J=9.1, 4.7 Hz, 1H), 3.50 (s, 3H), 3.06-2.96 (m, 2H), 1.87-1.78 (m, 1H), 1.70-1.60 (m, 1H), 1.38 (s, 9H). The compound displays a minor rotameric form: 6.81-6.68 (m), 3.82-3.75 (m), 1.34 (s).

LC-MS: m/z=275 [M−H]$^-$

[Example 23] Preparation of methyl (S)-2-amino-4-((methoxycarbonyl)amino)butanoate hydrochloride (Compound [25])

[Chem. 177]

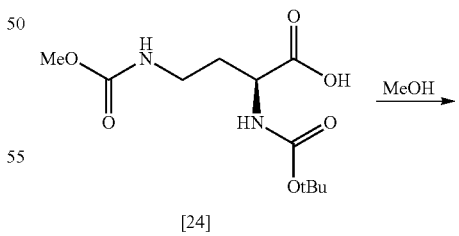

[24]

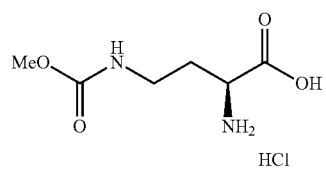

[25]

Methanol (3.5 L) was added to Compound [24] (669 g, 2.42 mol) concentrate at 10-20° C. The mixture was cooled to 15-20° C. Methanolic hydrogen chloride (42.19 weight-%, 864 g, 9.99 mol) was added while maintaining the temperature at 15-20° C. The reaction mixture was stirred at 15-20° C.

Nitrogen gas was bubbled through the reaction mixture for 30 minutes to remove the hydrogen chloride. The reaction mixture was evaporated to dryness. Methanol (1 L) was added to the residue, which was concentrated to dryness to yield Compound [25] (555.9 g, 2.42 mol) with HPLC purity 89.7 area-%.

[Example 24] Preparation of methyl (S)-2-amino-4-((methoxycarbonyl)amino)butanoate hydrochloride (Compound [25])

[Chem. 178]

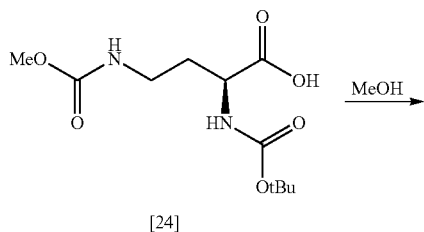

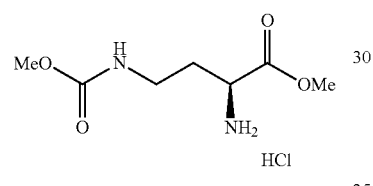

Methanol (285 mL) was cooled to −10° C., and acetyl chloride (174 mL) was added dropwise over 30 minutes. The resulting methanolic hydrogen chloride solution was stirred at 0° C., and Compound [24] (up to 95% purity, 71.31 g, 245 mmol) dissolved in methanol (143 mL) was added. After 1 hour of stirring, the mixture was allowed to reach 20° C. The mixture was stirred for 2 hours, after which LC-MS analysis indicated full consumption of Compound [24].

The reaction mixture was concentrated. Toluene (200 mL) was added, and the solution was concentrated. This was repeated with another portion of toluene (200 mL) to yield Compound [25]. The compound was used in the next step without further purification.

[Example 25] Preparation of methyl (S)-2-amino-4-((methoxycarbonyl)amino)butanoate hydrochloride (Compound [25])

[Chem. 179]

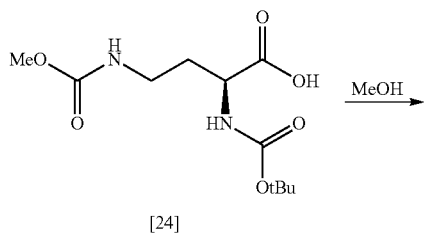

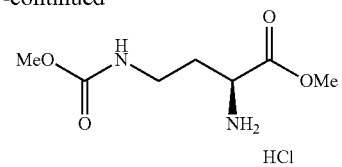

Compound [24] (12.4 g, 40.6 mmol) was dissolved in MeOH (60 mL). Thionyl chloride (5.9 mL, 81 mmol) was added to the mixture keeping the temperature between 15° C. and 20° C. The reaction was stirred at 15-20° C. for 21 hours, after which nitrogen gas was bubbled through the mixture for 30 minutes. The resulting mixture was evaporated to dryness. Methanol (40 mL) was added, and the solution was evaporated to dryness. The residue was co-evaporated with toluene (2×50 mL) to afford Compound [25], which was used in the next step without further purification.

$^1$H NMR (600 MHz, DMSO-$d_6$) δ 8.62 (brs, 3H), 7.26 (t, J=5.8 Hz, 1H), 4.02 (t, J=6.6 Hz, 1H), 3.74 (s, 3H), 3.52 (s, 3H), 3.17-3.08 (m, 2H), 2.01-1.88 (m, 2H).

[Example 26] Preparation of methyl (S)-2-(benzylamino)-4-((methoxycarbonyl)amino)butanoate hydrochloride (Compound [26-2])

[Chem. 180]

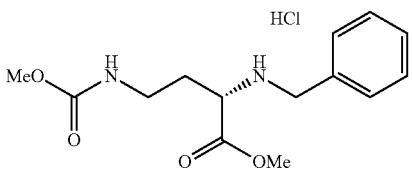

Step 1

[Chem. 181]

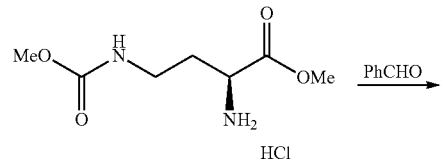

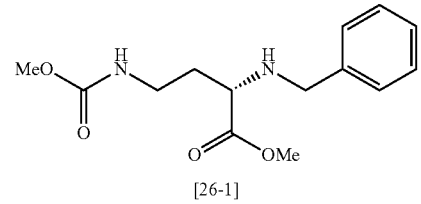

Methanol (1.853 L) was added to Compound [25] (185.3 g, 817.5 mmol) followed by the addition of triethylamine (136.7 mL, 981.0 mmol) and benzaldehyde (91.4 mL, 899 mmol). The mixture was stirred at 20-25° C. for 90 minutes and cooled to between −20° C. and −15° C. To the mixture was added sodium borohydride (46.35 g, 122.6 mmol) portionwise. The mixture was heated to 20-25° C., and the reaction was continued for 21 hours.

The reaction mixture was quenched with water (1.85 L) and stirred for 15 minutes. Methanol was distilled off at 40° C., and 2-propyl acetate (1.85 L) was added to the residue. After separation of the phases, the aqueous emulsion layer was extracted with 2-propyl acetate (1.85 L). The emulsion was filtered off. The combined organic layers were washed with aqueous sodium hydrogen carbonate (20%, 1.85 L) and brine (1.85 L). The organic solution was concentrated to yield the crude amine [26-1] (methyl (S)-2-(benzylamino)-4-((methoxycarbonyl)amino)butanoate) (197.3 g, 703.8 mmol) with purity 92.7 area-%.

$^1$H NMR (600 MHz, CDCl$_3$) δ 7.35-7.29 (m, 4H), 7.28-7.25 (m, 1H), 5.49 (brs, 1H), 3.82 (d, J=12.9 Hz, 1H), 3.73 (s, 3H), 3.65 (s, 3H), 3.61 (d, J=12.9 Hz, 1H), 3.43-3.36 (m, 1H), 3.30 (dd, J=9.0, 4.5 Hz, 1H), 3.28-3.23 (m, 1H), 1.95-1.87 (m, 1H), 1.75-1.65 (m, 1H).

$^{13}$C NMR (151 MHz, CDCl$_3$) δ 175.4, 157.1, 139.6, 128.6, 128.5, 127.4, 59.4, 52.4, 52.1 (2C), 39.1, 32.8.

Step 2

[Chem. 182]

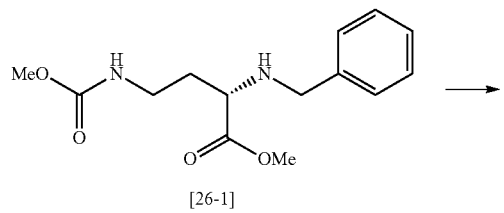

[26-1]

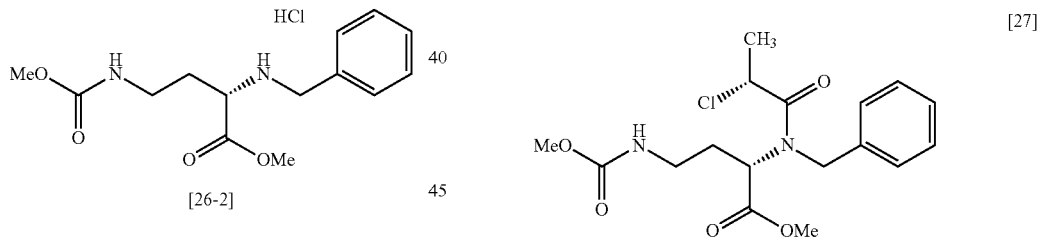

[26-2]

To the crude amine [26-1] (590.4 g, 2.11 mol) was added 2-propyl acetate (5.9 L). The mixture was heated to 50° C., and a solution of hydrogen chloride in 2-propyl acetate (17.3 weight-%, 1,066 g, 184.5 g, 5.06 mol) was added dropwise. The resulting suspension was stirred at 50° C. for 15 minutes and cooled to 0-5° C. and stirred for 1 hour.

The suspension was filtered, and the filter cake was washed with cold 2-propyl acetate (2×500 mL) and dried at 45-50° C. under vacuum to yield crude Compound [26-2] (520.6 g, 1.64 mol) with purity 97.5 area-%.

$^1$H NMR (600 MHz, DMSO-d$_6$) δ 10.37 (brs, 1H), 9.85 (brs, 1H), 7.63-7.53 (m, 2H), 7.46-7.37 (m, 3H), 7.26 (t, J=5.9 Hz, 1H), 4.20 (d, J=13.0 Hz, 1H), 4.13 (d, J=13.1 Hz, 1H), 4.06-4.00 (m, 1H), 3.72 (s, 3H), 3.52 (s, 3H), 3.16 (dq, J=13.6, 5.9 Hz, 1H), 3.07 (dq, J=13.7, 6.9 Hz, 1H), 2.18 (dq, J=13.5, 7.3 Hz, 1H), 2.05 (dq, J=14.0, 7.8 Hz, 1H).

$^{13}$C NMR (151 MHz, DMSO-d$_6$) δ 168.9, 156.7, 131.5, 130.5 (2C), 129.1, 128.6 (2C), 56.4, 52.9, 51.4, 49.1, 36.5, 29.0.

LC-MS: m/z=281 [M+H]$^+$

Step 3

[Chem. 183]

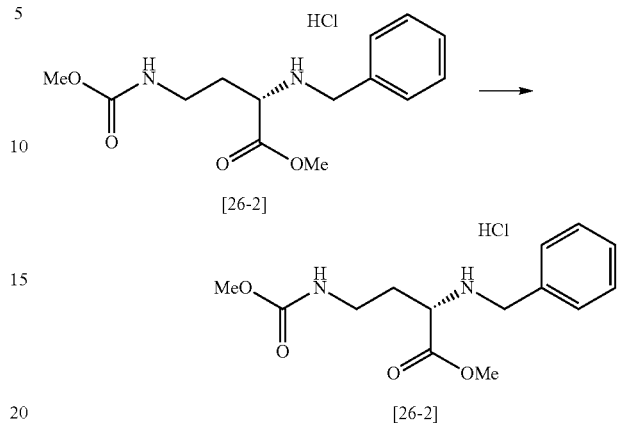

[26-2]

The crude hydrogen chloride salt [26-2] (1.100 kg) was added to 2-propanol (14 L). The mixture was refluxed and stirred for 15 minutes before it was cooled to 0-5° C. and stirred for 1 hour.

The solid was filtered off and washed with cold 2-propyl acetate (2×500 mL), followed by drying at 45-50° C. under vacuum to yield Compound [26-2] (1.063 kg) with 99.5 area-% HPLC purity.

[Example 27] Preparation of methyl (S)-2-((R)—N-benzyl-2-chloropropanamido)-4-((methoxycarbonyl)amino)butanoate (Compound [27])

[Chem. 184]

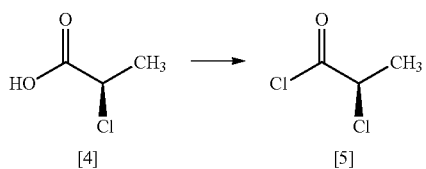

[27]

Step 1

[Chem. 185]

(Chem. 185 structures)

[4]    [5]

To (2R)-2-chloropropionic acid [4] (162 g, 1.49 mol) was added thionyl chloride (119.2 mL, 195.3 g, 1.642 mol) over 45 minutes at 60-65° C. The mixture was heated to 85° C. and stirred for 2 hours followed by heating to 100° C. for 3 hours.

The reaction mixture was distilled at atmospheric pressure with a flow of nitrogen gas. The main fractions were collected at 105-110° C. to yield Compound [5] (118.24 g, 931.3 mmol) as a liquid with HPLC purity 99 area-% and enantiomeric purity 96.5 area-% by chiral HPLC.

$^1$H NMR (600 MHz, CDCl$_3$) δ 4.66 (q, J=7.0 Hz, 1H), 1.82 (d, J=7.1 Hz, 3H).

Step 2

[Chem. 186]

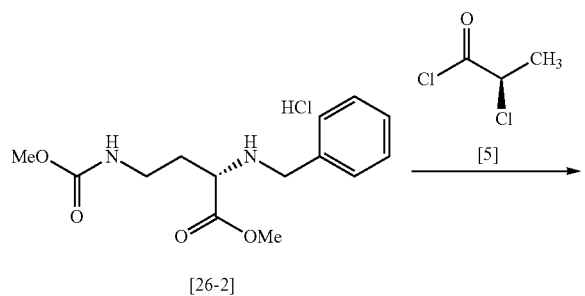

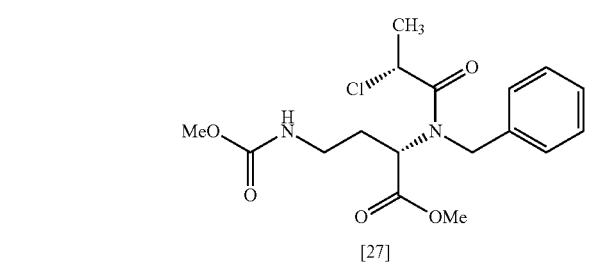

To a suspension of Compound [26-2] (250.0 g, 789.2 mmol) in toluene (1.25 L) was added a solution of potassium carbonate (327.1 g, 2.367 mol) in water (300 mL). The mixture was stirred at 20-25° C. until all solids had dissolved. The mixture was cooled to between −5 and 0° C., and a solution of Compound [5] (110 g, 868 mmol) in toluene (220 mL) was added dropwise while maintaining the temperature of the reaction mixture below 0° C. The reaction mixture was stirred between −5° C. and 0° C. for 3 hours, after which additional Compound [5] (20.04 g, 157.8 mmol) in toluene (40 mL) was added, while maintaining the temperature of the reaction mixture below 0° C.

Water (1.25 L) was added to the reaction mixture. After 15 minutes stirring, the phases were separated, and the aqueous phase was extracted with toluene (2×500 mL). The combined organic phases were filtered, and the solvent was evaporated under reduced pressure to yield Compound [27] (312.79 g, 843.46 mmol) with HPLC purity 97.90 area-%.

$^1$H NMR (600 MHz, CDCl$_3$) δ 7.59-7.13 (m, 5H), 4.92-4.26* [m, 5H; 4.86 (d, J=17.0 Hz), 4.80-4.62 (m), 4.58-4.53 (d, J=16.9 Hz), 4.52 (q, J=6.6 Hz), 4.49-4.44 (m), 4.30 (t, J=6.8 Hz)], 3.70* (s, 2.3H), 3.64 (s, 3H), 3.55* (s, 0.7H), 3.28-3.01 (m, 2H), 2.28 (dq, J=13.9, 6.8 Hz, 1H), 2.01-1.84 (m, 1H), 1.76* (d, J=6.4 Hz, 0.7H), 1.64* (d, J=6.5 Hz, 2.3H). *Denotes rotameric peaks.

LC-MS: m/z=371 [M+H]$^+$

[Example 28] Preparation of methyl (S)-2-((R)—N-benzyl-2-chloropropanamido)-4-((methoxycarbonyl)amino)butanoate (Compound [27])

[Chem. 187]

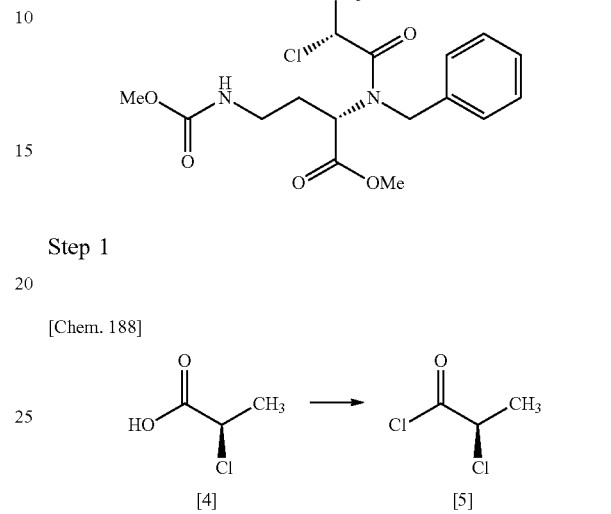

Step 1

[Chem. 188]

Oxalyl chloride (13.0 mL, 150 mmol) was added dropwise over 15 minutes to a solution of N,N-dimethylformamide (23.2 mL, 300 mmol) in acetonitrile (300 mL), while maintaining the temperature between −10° C. and 0° C. After 45 minutes of stirring at 0° C., (2R)-2-chloropropionic acid [4](11.0 mL, 125 mmol) was added dropwise. The mixture was stirred for 30 minutes, and then cooled to −10° C.

Step 2

[Chem. 189]

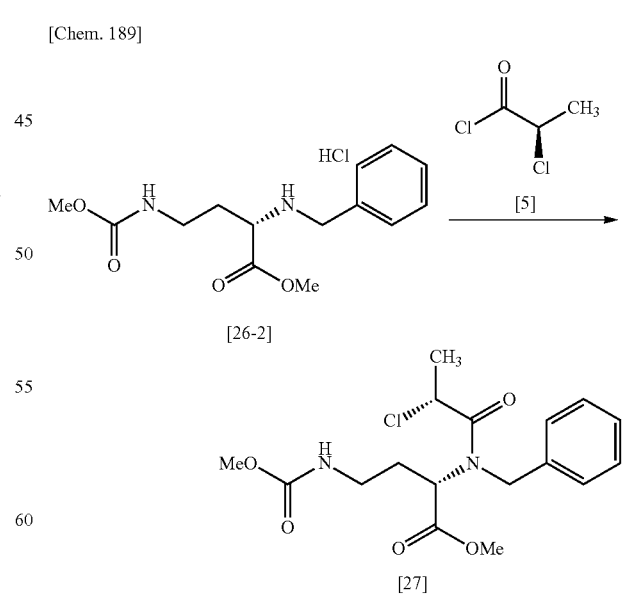

N,N-Diisopropylethylamine (17.4 mL, 100 mmol) and 2,6-lutidine (34.8 mL, 300 mmol) were added to a suspension of Compound [26-2] (33.35 g, 100 mmol) in acetonitrile (85 mL) at 0° C. The resulting solution was added dropwise over 10-15 minutes to the reaction mixture obtained in step 1, which contained the acid chloride [5], keeping the internal temperature below 0° C. The mixture was stirred for 30 minutes.

The reaction mixture was quenched by dropwise addition of aqueous hydrogen chloride (2 M, 200 mL) followed by addition of toluene (165 mL) and ethyl acetate (165 mL). The biphasic mixture was stirred vigorously for 10 minutes. The organic phase was separated from the acidic aqueous phase, dried over sodium sulfate, filtered and concentrated to afford the crude product (39.5 g). Acetonitrile (100 mL) was added, and the mixture was concentrated. HPLC analysis showed that the product [27] was formed in a 97:3 ratio of diastereoisomers.

[Example 29] Preparation of RR-MDDO (Compound [9])

[Chem. 190]

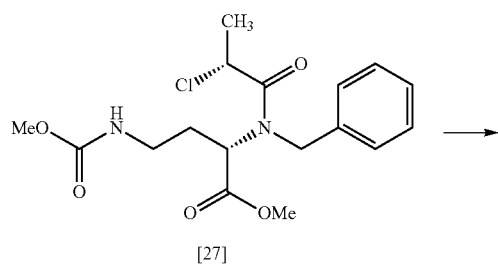

[27]

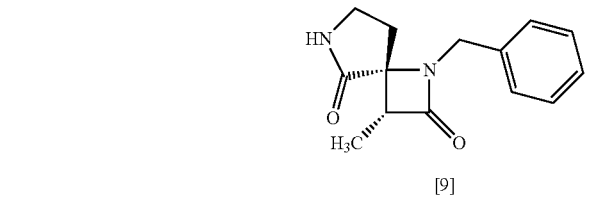

[9]

Acetonitrile (240 mL) was added to Compound [27] (24.07 g, 63.1 mmol, calculated as 100% theoretical yield from the acylation step). Cesium carbonate (61.7 g, 189.3 mmol) was added. The resulting suspension was stirred vigorously at 20-25° C. for 15 hours. MeOH (48 mL) was added.

The suspension was concentrated to half volume. The cesium salts were filtered off and washed with toluene (3×40 mL), and the filtrate was concentrated to up to 25 mL. The solution was clarified by addition of Tonsil® (3 g) filter aid, which was subsequently filtered off. The resulting solution was subjected to crystallization between 2° C. and 6° C. overnight. The precipitate was filtered off and washed with toluene (3×4 mL). The product was dried under reduced pressure at 30° C. to yield Compound [9] (9.31 g, 38.1 mmol) with HPLC purity 98.85 area-% and enantiomeric purity 99.55 area-% by chiral HPLC.

[Example 30] Preparation of RR-MDDO(Compound [9])

[Chem. 191]

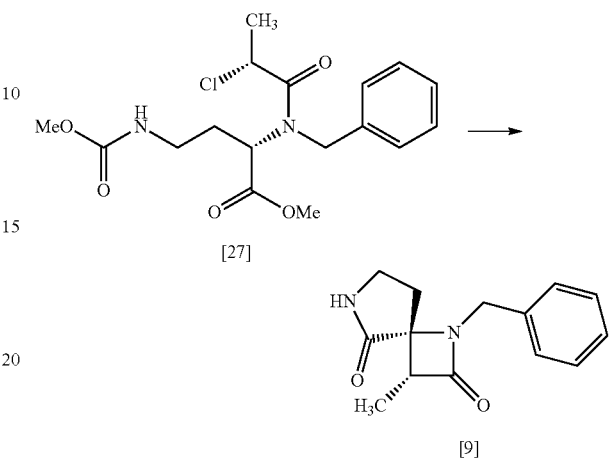

Lithium 2-methyl-2-butoxide in heptane (40 weight-%, 401.33 mL, 1.245 mol) was added over 20 minutes to acetonitrile (535 mL) keeping the temperature between −10° C. and −5° C. A solution of Compound [27] (167.5 g, 415.2 mmol) in acetonitrile (230 mL) was added dropwise over 60 minutes. The mixture was stirred at 0-5° C. for 5 hours.

The mixture was cooled to below 0° C., and aqueous sodium chloride (saturated, 330 mL) and 2-propyl acetate (790 mL) were added to the mixture. Next, an aqueous solution of citric acid (50 weight-%, 159 g) was added for adjustment to pH 5-6. After 20 minutes of stirring, the phases were separated, and the aqueous phase was extracted with 2-propyl acetate (2×263 mL). The combined organic phase was concentrated to half volume under reduced pressure and washed with aqueous sodium chloride (saturated, 263 mL). The organic phase was concentrated, and toluene (800 mL) was added. The solution was concentrated to 6 mL per gram of product, based on 100% theoretical yield.

The resulting solution was heated to 60° C. before it was allowed to cool. It was seeded at 40° C. and cooled to 20-25° C. Then heptane (304 mL, 3 mL per gram) was added dropwise to the stirred mixture. After complete addition, the mixture was stirred for 1 hour at 20° C. The precipitated solid was filtered off. The solid was washed with a mixture of toluene and heptane (1:2) (202 mL) and dried under reduced pressure at 40° C. to yield Compound [9](70.39 g, 288.1 mmol) with HPLC purity 98.53 area-% and enantiomeric purity 97.93 area-% by chiral HPLC.

The product was stirred in toluene (1.5 mL per gram of product) at 50° C. for 1 hour. The solid was filtered off at 20° C. and rinsed with toluene (2×15 mL) and dried under reduced pressure at 40° C. The product [9] (64.79 g, 265.2 mmol) was obtained with HPLC purity 99.78 area-% and enantiomeric purity 99.56 area-% by chiral HPLC.

$^1$H NMR (600 MHz, CDCl$_3$) δ 7.34-7.26 (m, 5H), 6.51 (brs, 1H), 4.86 (d, J=15.5 Hz, 1H), 3.99 (d, J=15.5 Hz, 1H), 3.27 (q, J=7.5 Hz, 1H), 3.24-3.20 (m, 1H), 3.15 (ddt, J=10.0, 8.1, 2.3 Hz, 1H), 2.05 (ddd, J=13.3, 6.8, 2.5 Hz, 1H), 2.01 (dt, J=13.3, 8.6 Hz, 1H), 1.29 (d, J=7.5 Hz, 3H).

$^{13}$C NMR (151 MHz, CDCl$_3$) δ 174.2, 169.8, 136.4, 128.8 (2C), 128.3 (2C), 127.8, 65.8, 55.8, 44.5, 38.3, 30.7, 9.8.

LC-MS: m/z=245 [M+H]$^+$

[Example 31] Preparation of SR-MDBN (Compound [10])

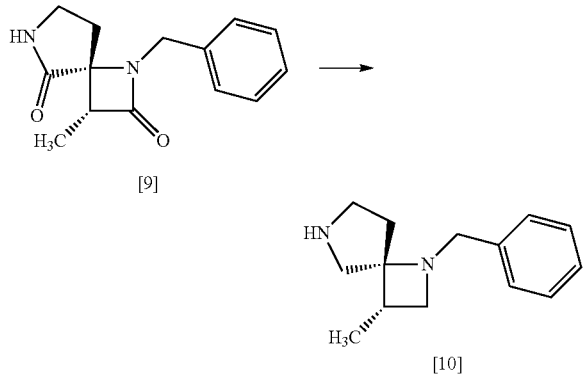

A solution of lithium aluminum hydride in tetrahydrofuran/toluene (2.4:1) (15 weight-%, 217.5 mL, 193.55 g, 765 mmol) was added dropwise to dry tetrahydrofuran (374 mL) at a temperature between −5° C. and 0° C. After 10 minutes of stirring, trimethylsilyl chloride (83.11 g, 97.1 mL, 765 mmol) was added dropwise, and the mixture was stirred for 10 minutes while maintaining the temperature between −5° C. and 0° C. Then a solution of Compound [9] (74.8 g, 306.2 mmol) in dry tetrahydrofuran (748 mL) was added dropwise. After 30 minutes, the cooling was discontinued, and the reaction mixture was heated to 45-50° C. The reaction mixture was stirred for 2 hours, before additional lithium aluminum hydride in tetrahydrofuran/toluene (2.4:1) (15 weight-%, 87 mL, 77.4 g, 306.2 mmol) was added dropwise at 45-50° C. After another 18 hours stirring, additional lithium aluminum hydride in tetrahydrofuran/toluene (2.4:1) (15 weight-%, 43.5 mL, 38.7 g, 153 mmol) was added dropwise at 45-50° C., and the resulting mixture was stirred at the same temperature for 19 hours.

The reaction mixture was cooled to 0° C., before water (46.5 mL) was added dropwise. Tetrahydrofuran (500 mL) was added to the resulting slurry. Then aqueous sodium hydroxide (15 weight-%, 46.5 mL, 6.98 g, 174 mmol) was added, and additional water (139.5 mL) was added to the suspension. The mixture was allowed to reach ambient temperature, before Celite (Registered trademark) filter aid and sodium sulfate (60 g) were added. The stirring was continued for 15 minutes. The solids were filtered off through a bed of Celite (Registered trademark) filter aid. The filter cake was washed with tetrahydrofuran (4×250 mL), and the filtrate was concentrated under reduced pressure to yield the product [10] (64.71 g, 299.1 mmol) with HPLC purity 92.37 area-% and enantiomeric purity 99.45 area-% by chiral GC.

$^1$H NMR (600 MHz, CDCl$_3$) δ 7.33-7.27 (m, 4H), 7.23-7.19 (m, 1H), 3.62 (d, J=13.1 Hz, 1H), 3.58 (d, J=13.0 Hz, 1H), 3.20 (dd, J=7.5, 6.5 Hz, 1H), 2.95 (s, 2H), 2.82 (dd, J=7.7, 6.7 Hz, 2H), 2.66 (dd, J=6.5, 5.5 Hz, 1H), 2.39 (pd, J=7.1, 5.4 Hz, 1H), 2.17 (dt, J=13.1, 7.5 Hz, 1H), 1.76 (dt, J=13.4, 6.8 Hz, 1H), 1.12 (d, J=7.0 Hz, 3H), 1.68 (brs, 1H).

$^{13}$C NMR (151 MHz, CDCl$_3$) δ 139.2, 128.7, 128.4, 126.9, 75.7, 57.8, 55.7, 48.9, 45.6, 35.9, 35.8, 15.6.

LC-MS: m/z=217 [M+H]$^+$

[Example 32] Preparation of (3S,4R)-1-benzyl-3-methyl-1,6-diazaspiro[3.4]octane oxalate (Compound [11-2])

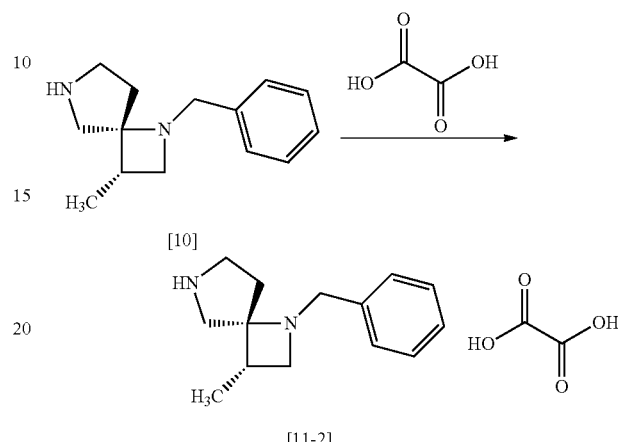

A solution of oxalic acid (0.082 g) in tetrahydrofuran (1.5 mL) was added dropwise to a solution of Compound [10] (0.180 g) in tetrahydrofuran (2.0 mL).

The formed precipitate was filtered off and dried under reduced pressure to afford Compound [11-2] (0.204 g).

$^1$H NMR (600 MHz, DMSO-d$_6$) δ 7.33-7.27 (m, 4H), 7.26-7.21 (m, 1H), 3.74 (d, J=13.0 Hz, 1H), 3.52 (d, J=13.0 Hz, 1H), 3.29 (d, J=12.7 Hz, 1H), 3.24 (ddd, J=11.4, 7.8, 5.5 Hz, 1H), 3.16-3.09 (m, 2H), 3.02 (d, J=12.7 Hz, 1H), 2.68 (dd, J=6.7, 3.8 Hz, 1H), 2.36-2.27 (m, 1H), 2.03 (ddd, J=12.9, 7.2, 5.5 Hz, 1H), 1.16 (d, J=7.1 Hz, 3H).

$^{13}$C NMR (151 MHz, DMSO-d$_6$) δ 164.2, 137.8, 128.4, 128.2, 126.9, 73.6, 56.2, 53.7, 46.1, 43.5, 34.6, 30.2, 15.9.

[Example 33] Preparation of (3S,4R)-1-benzyl-3-methyl-1,6-diazaspiro[3.4]octane hemi-oxalate (Compound [11-3])

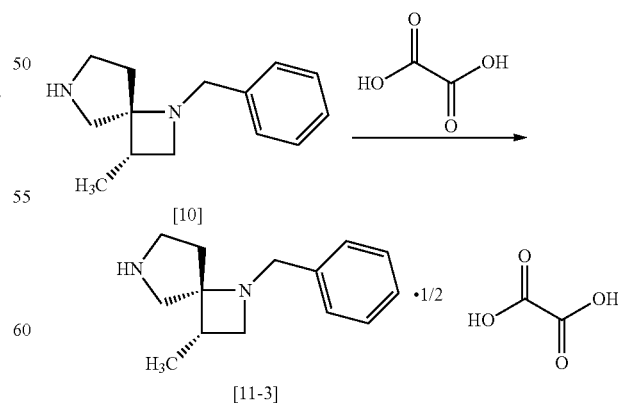

Step 1

Compound [10] (52.47 g, 218.3 mmol) was dissolved in 2-propanol (367 mL), and the mixture was heated to 60° C.

A solution of oxalic acid (9.83 g, 109.1 mmol) in 2-propanol (157 mL) was added dropwise over 2 hours, while maintaining the temperature at 60° C. After complete addition, the mixture was stirred at 60° C. for 25 minutes, before it was seeded with crystals of Compound [11-3].

After an additional 35 minutes of stirring at 60° C., the formed suspension was filtered at the same temperature, and the solid was washed with 2-propanol (2×25 mL) at 20-25° C. The product was dried under reduced pressure at 40° C. to afford Compound [11-3] (48.65 g, 186.14 mmol) with HPLC purity 99.12 area-% and enantiomeric purity 99.6 area-% by chiral HPLC.

$^1$H NMR (600 MHz, D$_2$O) δ 7.45-7.36 (m, 5H), 3.76 (d, J=12.2 Hz, 1H), 3.71 (d, J=12.2 Hz, 1H), 3.52 (d, J=13.2 Hz, 1H), 3.42 (t, J=7.9 Hz, 1H), 3.33 (ddd, J=12.5, 7.8, 5.0 Hz, 1H), 3.27-3.20 (m, 2H), 2.86 (dd, J=7.7, 4.9 Hz, 1H), 2.48 (ddt, J=11.7, 9.4, 7.9 Hz, 2H), 2.24 (ddd, J=13.5, 6.9, 5.0 Hz, 1H), 1.17 (d, J=7.2 Hz, 3H).

$^{13}$C NMR (151 MHz, D$_2$O) δ 176.25, 138.73, 132.28 (2C), 131.62 (2C), 130.73, 76.91, 58.99, 57.34, 48.48, 46.69, 37.54, 34.33, 17.38.

Step 2A

Slurry stirring of (3S,4R)-1-benzyl-3-methyl-1,6-diazaspiro[3.4]octane hemi-oxalate (Compound [11-3])

[Chem. 195]

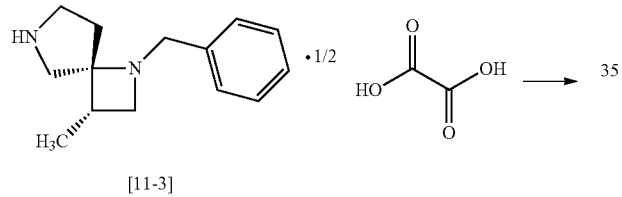

[11-3]

The hemi-oxalate [11-3] (48.5 g, 185.6 mmol) was stirred in a mixture of water and 2-propanol (1:24, 303 mL) for 5 hours at 20-25° C. The mixture was cooled to between −5° C. and 0° C. and stirred for 1 hour.

The suspension was filtered at 0° C. and washed with cold 2-propanol (2×8 mL). The solid was dried under reduced pressure at 40° C. to yield the product [11-3] (45.95 g, 175.8 mmol) with HPLC purity 99.50 area-% and enantiomeric purity 99.93 area-% by chiral GC.

Step 2B

Recrystallization of (3S,4R)-1-benzyl-3-methyl-1,6-diazaspiro[3.4]octane hemi-oxalate (Compound [11-3])

[Chem. 196]

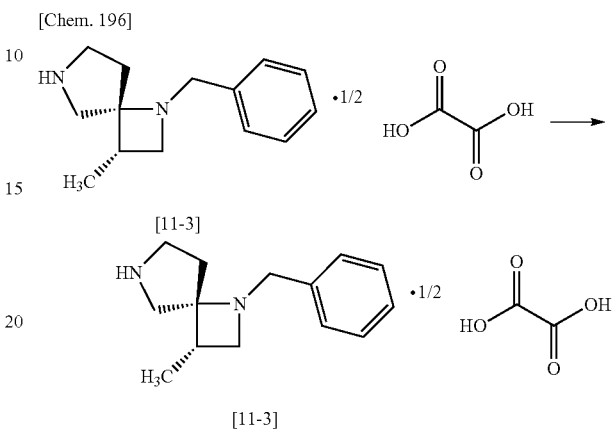

[11-3]

The hemi-oxalate [11-3] (5 g, 19.1 mmol) was dissolved in a mixture of 2-propanol (34 mL) and water (0.75 mL) at reflux temperature. After total dissolution it was evaporated to half volume. 2-Propanol (20 mL) was added then evaporated. This was repeated twice and the mixture was stirred in 2-propanol (15 mL) for 1 hr at 0-5° C. The product was filtered and washed twice with 2-propanol (1.5 mL). The solid was dried under reduced pressure at 40° C. to yield the recrystallized product [11-3] (4.755 g, 18.2 mmol).

Example 34

(A) Preparation of SR-MDBP (Compound [13])

[Chem. 197]

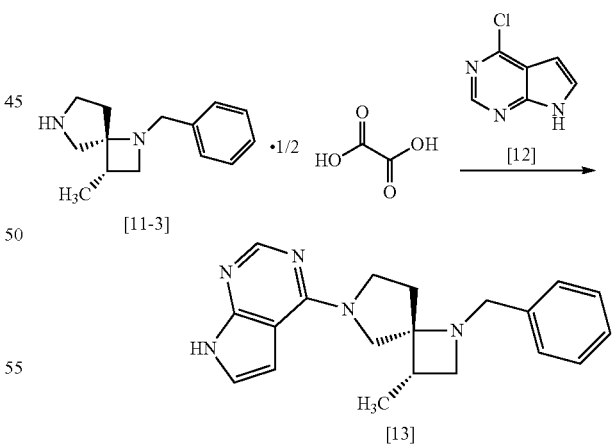

[13]

Potassium phosphate (8.12 g, 38.3 mmol) was added to a mixture of Compound [11-3], (5.00 g, 19.1 mmol), CPPY [12](2.95 g, 19.2 mmol), water (20 mL), and 2-propanol (25 mL). The reaction mixture was stirred at 75° C. for 4.5 hours and cooled to 30° C.

The aqueous layer was removed, and the resulting solution of crude SR-MDBP [13] in aqueous 2-propanol was used in the next step assuming a yield of 100%.

(B) Preparation of SR-MDBP (Compound [13])

[Chem. 198]

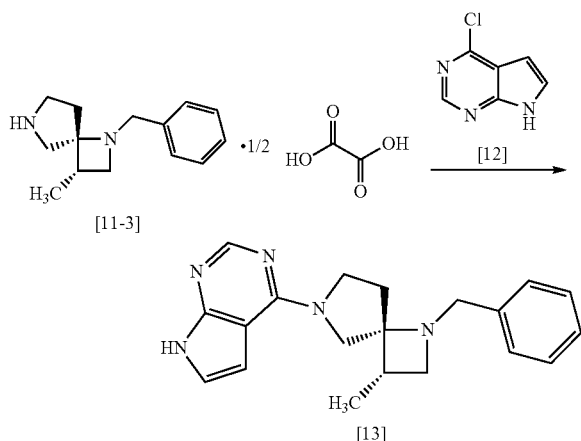

Compound [13] was prepared in the following alternative manner. Potassium phosphate (8.12 g, 38.3 mmol) and a 45% aqueous solution of potassium hydroxide (5.01 g, 40.2 mmol) was added to a mixture of Compound [11-3] (10.0 g, 38.3 mmol), CPPY [12] (5.91 g, 38.5 mmol), water (40 mL), and 2-propanol (50 mL). The reaction mixture was stirred at 75° C. for 18 hours and cooled to 40° C.

The aqueous layer was removed, and the resulting solution of crude SR-MDBP [13] in aqueous 2-propanol was used in the next step assuming a yield of 100%.

Example 35

(A) Preparation of SR-MDOP (Compound [14])

[Chem. 199]

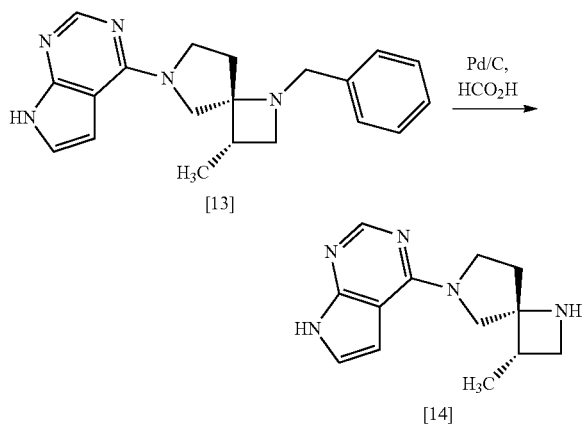

To the solution of crude SR-MDBP [13] (19.1 mmol) in aqueous 2-propanol was sequentially added purified water (15 mL), formic acid (3.61 mL, 95.7 mmol), and 5% palladium on carbon (0.67 g, 53 wt-% moisture). The reaction mixture was stirred at 55° C. for 15 hours.

The reaction mixture was cooled to room temperature, and the palladium on carbon was filtered off and rinsed with a mixture of 2-propanol and water (9:1, 12 mL). To the combined filtrate was added aqueous sodium hydroxide (8 M, 15 mL), sodium chloride (7.5 g), 2-propanol (15 mL), and toluene (55 mL). The layers were separated, and the organic layer was washed with brine (20 weight-%, 10 mL) and concentrated. The residue (25 g) was diluted with a mixture of toluene and 2-propanol (1:1, 35 mL) and filtered. The resulting solution was concentrated at 50° C. to a residue (~25 g). Two cycles of adding toluene (35 mL) and concentrating at 50° C. to a residue (~25 g) were performed during which solids formed.

Toluene was added to the concentrated slurry (~25 g) to adjust the total weight of the slurry to 48 g. The slurry was kept at 4° C. for 16 hours and then stirred at 0° C. for 30 minutes. The slurry was filtered, and the filter cake was washed with toluene (14 mL). The solid was dried at 50° C. under reduced pressure to give SR-MDOP [14] (4.21 g, 17.3 mmol).

(B) Preparation of SR-MDOP (Compound [14])

[Chem. 200]

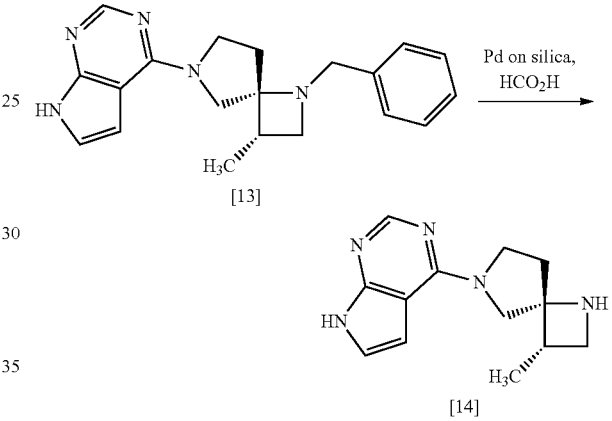

Compound [14] was prepared in the following alternative manner. To the solution of crude SR-MDBP [13] (76.5 mmol) in aqueous 2-propanol was added purified water (77 mL), formic acid (11.5 mL, 306 mmol), and then palladium on silica gel (Pd content 0.20 mmol/g, 3.8 g, 0.765 mmol). The reaction mixture was stirred at 55° C. for 22 hours.

The reaction mixture was cooled to room temperature, and the palladium on silica gel was filtered off and rinsed with a mixture of 2-propanol and water (9:1, 60 mL). To the combined filtrate was added aqueous sodium hydroxide (8 M, 57 mL), sodium chloride (29.1 g), and toluene (199 mL). The layers were separated, and the organic layer was washed with brine (20 weight-%, 38 mL) and concentrated. The residue (70 g) was diluted with a mixture of toluene and 2-propanol (1:1, 140 mL) and concentrated. The residue (100 g) was diluted with a mixture of toluene and 2-propanol (1:1, 140 mL) and filtered. The resulting solution was concentrated. The residue (80 g) was diluted with toluene (140 mL) and concentrated until precipitation was seen. The mixture was stirred at 50° C. for 1 hr and concentrated to a residue of 120 g. The residue was diluted with toluene (140 mL), concentrated to a residue of 120 g, and diluted by toluene (92 mL). The slurry was kept at 4° C. for 4 days and then stirred at 0° C. for 90 minutes. The slurry was filtered, and the filter cake was washed with toluene (50 mL). The solid was dried at 50° C. under reduced pressure to give SR-MDOP [14] (17.3 g, 71.1 mmol).

[Example 36] Preparation of SR-ZMDB-OX (Compound [29])

[Chem. 201]

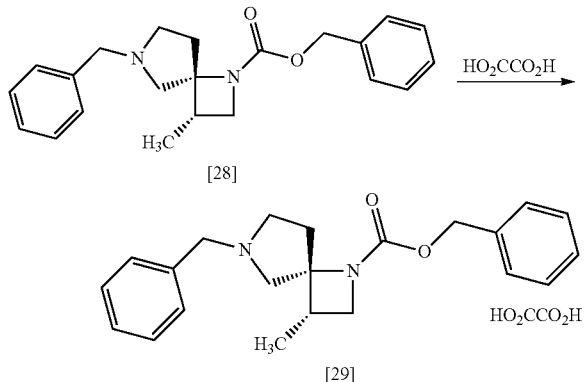

[28]

[29]

A solution of SR-ZMDB [28] (10.0 g, 28.5 mmol), Compound [28] which was synthesized according to the procedures in Examples 42 to 50, in tetrahydrofuran (40 mL) and toluene (10 mL) was added dropwise to a stirred solution of oxalic acid (2.84 g, 31.4 mmol) in tetrahydrofuran (50 mL) at 50° C. under nitrogen. When approximately 50% of the SR-ZMDB [28] had been added, the reaction mixture was seeded with Compound [29] (5 mg), and the addition continued to completion. The resulting mixture was aged for 30 minutes at 50° C., diluted with tetrahydrofuran (20 mL) and cooled to 20° C. Additional tetrahydrofuran (20 mL) was added. Stirring was continued at 20° C. for 11 hours.

The crystallization mixture was aged at 0° C. for 1 hour, and the precipitated solid was filtered off. The resulting solid was washed with cold tetrahydrofuran (40 mL). The solid was dried under reduced pressure at 30° C. to yield Compound [29] (11.1 g, 25.2 mmol).

$^1$H-NMR (D$_2$O, internal reference d$_4$-TMSP) δ 7.71-7.05 (m, 10H), 5.30-4.98 (m, 2H), 4.56-1.98 (m, 11H), 1.28-0.98 (m, 3H).

$^{13}$C NMR (151 MHz, DMSO-d$_6$) δ 164.2, 154.2, 153.9, 136.6, 136.5, 133.2, 132.7, 130.0, 129.8, 128.8, 128.7, 128.5, 128.4, 128.2, 127.9, 127.6, 73.6, 73.4, 66.1, 65.6, 57.6, 55.5, 55.1, 52.6, 52.4, 51.7, 51.2, 37.3, 36.5, 35.5, 34.6, 15.2, 15.0.

Elemental analysis: C, 65.5 weight-%, H, 6.3 weight-% and N, 6.3 weight-%

Theoretical value: C, 65.4 weight-%, H, 6.4 weight-% and N, 6.4 weight-%

[Example 37] Preparation of (3S,4R)-3-methyl-1,6-diazaspiro [3.4] octane oxalate (Compound [30-1])

[Chem. 202]

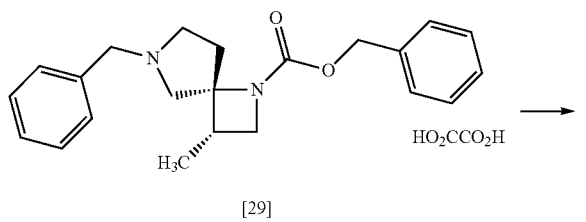

[29]

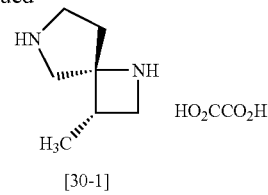

[30-1]

A slurry of SR-ZMDB-OX [29] (50 mg, 0.11 mmol) and 10% palladium on carbon (5 mg, moisture content 53.4 weight-%) in water (1 mL) and 2-methylpropan-2-ol (1 mL) was treated with hydrogen (3 bar) at 30° C. for 2 hours.

The hydrogen atmosphere was changed to an argon atmosphere, and the mixture was filtered through Celite (Registered trademark) with the aid of water (0.5 mL). The combined filtrates were concentrated to dryness under reduced pressure to yield Compound [30-1] (24 mg, 0.11 mmol).

$^1$H NMR (600 MHz, D$_2$O, internal reference d$_4$-TMSP) δ 4.17 (dd, J=10.7, 8.8 Hz, 1H), 3.99 (dd, J=14.2, 1.4 Hz, 1H), 3.73 (d, J=14.2 Hz, 1H), 3.65 (dd, J=10.7, 6.9 Hz, 1H), 3.58 (ddd, J=12.7, 8.7, 4.2 Hz, 1H), 3.48 (ddd, J=12.2, 9.8, 7.1 Hz, 1H), 3.17 (dqd, J=8.8, 7.3 Hz, 6.9 Hz, 1H), 2.84 (dddd, J=15.1, 7.2, 4.2, 1.4 Hz, 1H), 2.50 (dt, J=15.0, 9.3 Hz, 1H), 1.29 (d, J=7.3 Hz, 3H).

$^{13}$C NMR (151 MHz, D$_2$O) δ 175.9, 78.0, 51.6, 51.1, 46.7, 37.8, 37.4, 16.6.

[Example 38] Preparation of (3S,4R)-3-methyl-1,6-diazaspiro [3.4] octane oxalate (Compound [30-1])

[Chem. 203]

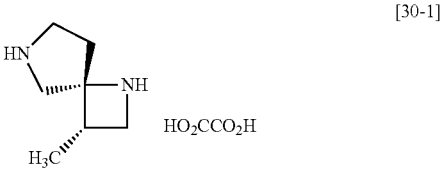

Step 1

[Chem. 204]

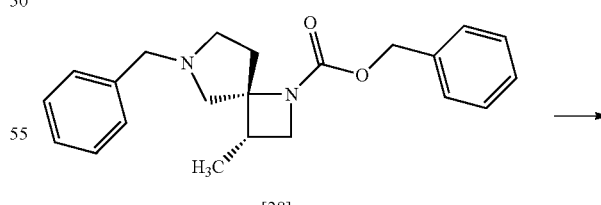

[28]

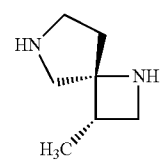

[31]

A mixture of SR-ZMDB [28] (350 mg, 1.00 mmol) and 10% palladium on carbon (35 mg, moisture content 53.4 weight-%,) in ethanol (3 mL) was treated with hydrogen (3 bar) at 50° C. for 2 hours.

Step 2

[Chem. 205]

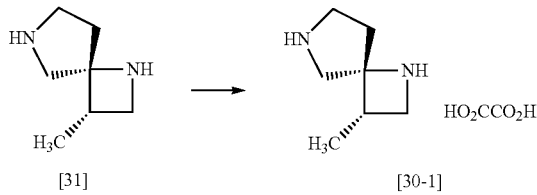

The hydrogen atmosphere was replaced with an argon atmosphere. The reaction mixture from Step 1 was filtered through a 0.2 μm PTFE syringe filter with the aid of ethanol (0.75 mL) and added dropwise to a stirred solution of oxalic acid (100 mg. 1.10 mmol) in ethanol (0.75 mL). The resulting mixture was warmed to 50-60° C. for 5 minutes and aged at 20° C. for 20 hours.

The mixture was filtered, and the collected solid was washed with ethanol (0.30 mL) and dried under reduced pressure at 50° C. to give Compound [30-1] (205 mg, 0.947 mmol).

$^1$H NMR (600 MHz, $D_2O$, internal reference $d_4$-TMSP) δ 4.17 (dd, J=10.7, 8.8 Hz, 1H), 3.99 (dd, J=14.2, 1.4 Hz, 1H), 3.73 (d, J=14.2 Hz, 1H), 3.65 (dd, J=10.7, 6.9 Hz, 1H), 3.58 (ddd, J=12.7, 8.7, 4.2 Hz, 1H), 3.48 (ddd, J=12.2, 9.8, 7.1 Hz, 1H), 3.17 (dqd, J=8.8, 7.3 Hz, 6.9 Hz, 1H), 2.84 (dddd, J=15.1, 7.2, 4.2, 1.4 Hz, 1H), 2.50 (dt, J=15.0, 9.3 Hz, 1H), 1.29 (d, J=7.3 Hz, 3H).

$^{13}$C NMR (151 MHz, $D_2O$) δ 175.9, 78.0, 51.6, 51.1, 46.7, 37.8, 37.4, 16.6.

[Example 39] Preparation of (3S,4R)-3-methyl-1,6-diazaspiro[3.4]octane disuccinate (Compound [30-2])

[Chem. 206]

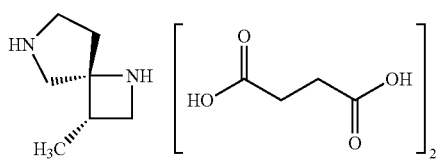

Step 1

[Chem. 207]

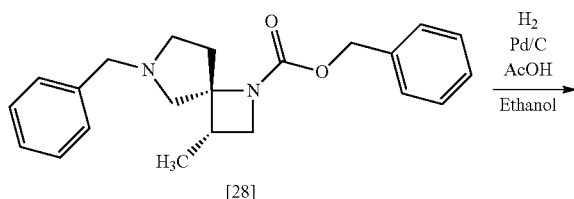

-continued

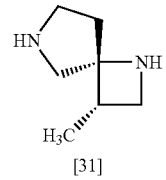

SR-ZMDB [28] (5.38 kg, 15.4 mol) was dissolved in anhydrous ethanol (31.6 kg). 10% Palladium on carbon (0.248 kg) was added followed by glacial acetic acid (2.29 kg, 38.1 mol) and water (0.284 kg). The reactor system was inerted by several cycles of evacuation-nitrogen purge before hydrogen gas (2.8-3.1 bar) was applied for 18 hours.

The pressure was released, and the reactor purged with nitrogen. The catalyst was filtered off on a bed of Celite (Registered trademark) filter aid, which had been saturated with ethanol. The filter cake was washed with ethanol (10 kg). The filtrate was concentrated to 30-35 L under reduced pressure to give a crude product [31].

Step 2

[Chem. 208]

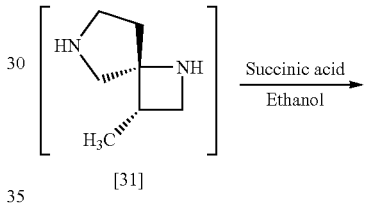

Succinic acid (4.261 kg, 36.08 mol) was dissolved in anhydrous ethanol (49.7 kg). Approximately 5% of the crude product [31] from Step 1 was added. When precipitation of product had commenced (with or without seeding), the remaining concentrate was added. The mixture was agitated for 1 hour at 20-25° C. followed by 2 hours at −2 to 2° C.

The product was filtered off and washed with cold ethanol (2×13.7 kg). The product was dried under reduced pressure to furnish Compound [30-2] (5.143 kg, 14.19 mol) with HPLC purity 99.3 area-%.

$^1$H NMR (600 MHz, $D_2O$, internal reference $d_4$-TMSP) δ 4.18 (dd, J=10.7, 8.9 Hz, 1H), 3.97 (dd, J=14.3, 1.4 Hz, 1H), 3.74 (d, J=14.3 Hz, 1H), 3.64 (dd, J=10.8, 6.8 Hz, 1H), 3.58 (ddd, J=12.6, 8.6, 4.2 Hz, 1H), 3.47 (ddd, J=12.3, 9.9, 7.1 Hz, 1H), 3.15 (ddd, J=8.9, 7.3, 6.8 Hz, 1H), 2.84 (dddd, J=15.1, 7.1, 4.3, 1.4 Hz, 1H), 2.56-2.47 (m, 9H), 1.28 (d, J=7.3 Hz, 3H).

$^{13}$C NMR (151 MHz, $D_2O$) δ 182.8, 78.0, 51.6, 51.1, 46.8, 37.8, 37.6, 34.3, 16.6.

[Example 40] Preparation of SR-MDOP (Compound [14])

[Chem. 209]

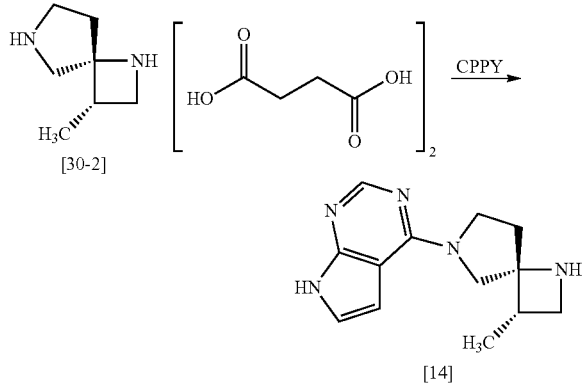

CPPY [12] (1.697 kg, 11.05 mol) and Compound [30-2] (4.000 kg, 11.04 mol) were mixed, and molten 2-methyl-propan-2-ol (13.0 kg) was added. The resulting slurry was warmed to 28° C. A solution of potassium phosphate (4.92 kg, 23.2 mol) in water (13.0 kg) was added followed by aqueous potassium hydroxide (45 weight-%, 5.5 kg, 44 mol). The reaction mixture was stirred at 40-50° C. for 22 hours.

Toluene (16 L) was added, and the temperature of the reaction mixture was lowered to 20-30° C. The organic layer was washed with a mixture of brine (saturated, 12.2 kg) and water (4.1 kg). The organic layer was concentrated under reduced pressure to a volume of not more than 16 L. 2-Methylpropan-2-ol (7.42 kg) and toluene (8 L) were added to the reactor, and the mixture was concentrated under reduced pressure to a volume of not more than 16 L. 2-Methylpropan-2-ol (9.04 kg) and toluene (10 L) were added to the residue. The mixture was filtered at 35-40° C., and the solution was concentrated under reduced pressure to a volume of not more than 16 L. The residue was heated to 45-50° C., and toluene (16 L) was added. The mixture was aged at 45-50° C. for 1 hour, before it was concentrated under reduced pressure to a volume of not more than 16 L. Toluene (16 L) was added to the slurry, which was aged at 0-5° C. for more than 1 hour.

The formed precipitate was filtered off, and the filter cake washed with toluene (8 L) and heptane (8 L). The solid was dried under reduced pressure at 50° C. for 20 hours to yield SR-MDOP [14] (2.445 kg, 10.05 mol) with HPLC purity 95.25%.

[Example 41] Preparation of Compound [17]

[Chem. 210]

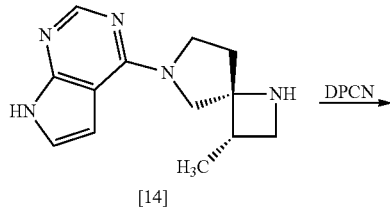

-continued

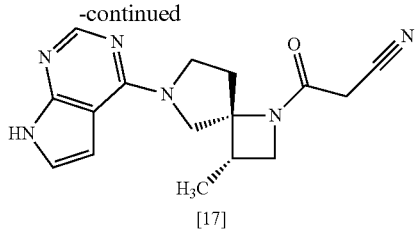

Compound [14] (2.38 kg, 9.78 mol) was suspended in acetonitrile (22.4 kg). Triethylamine (98.8 g, 0.976 mol) was added, and the slurry was heated to 45-55° C. A solution of DPCN [18] (1.68 kg, 10.3 mol) in acetonitrile (13.4 kg) was added during 1 hour with the aid of additional acetonitrile (2.2 kg). The reaction mixture was stirred for 2.5 hours at 45-55° C.

Ethanol (2 L) was charged to the reaction mixture, which was concentrated under reduced pressure to a volume of not more than 24 L. Ethanol (24 L) was added to the residue, and the solution was heated to 35-40° C. The resulting solution was polish filtered through a fine filter with the aid of ethanol (2 L). The resulting clear solution was concentrated under reduced pressure to a volume of not more than 24 L. Ethanol (24 L) was added to the resulting slurry. The slurry was concentrated under reduced pressure to a volume of not more than 24 L. Ethanol (4 L) was added to the slurry. The slurry was concentrated under reduced pressure to a volume of 19 L. The crystallization mixture was aged at 0-10° C. for 2 hours.

The formed precipitate was filtered off, and the filter cake was washed with ethanol (10 L). The product was dried under reduced pressure for 20 hours to furnish an ethanol solvate of Compound [17] (3.11 kg, 8.73 mol) with HPLC purity 99.85%.

Butan-1-ol (43.7 kg) was added to the ethanol solvate of Compound [17] (3.10 kg). The mixture was warmed to 90-95° C. and aged for 2 hours. The solution was cooled to 70-72° C. in 1 hour, seeded with Compound [17] (14.6 g, 47.0 mmol) and cooled to 8° C. over a period of 12 hours.

The formed precipitate was filtered off, and the filter cake washed with butan-1-ol (5.2 kg) and ethyl acetate (6 L). The solid was dried under reduced pressure at 55-65° C. for 22 hours to yield Compound [17] (2.46 kg, 7.93 mol) with HPLC purity 99.91 area-%.

[Example 42] Preparation of S-MABB-HC (Compound [36])

[Chem. 211]

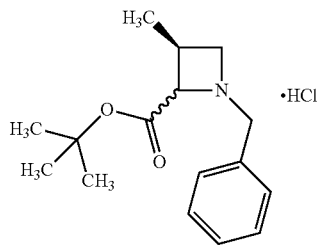

Step 1

[Chem. 212]

[37] → TBBA → [38]

S-BAPO [37] (35.0 g, 212 mmol) was added to water (175 mL) at room temperature under nitrogen atmosphere. To the resulting suspension were added toluene (53 mL) and potassium carbonate (32.2 g, 233 mmol) at room temperature. To the resulting solution was added dropwise TBBA (434.4 g, 223 mmol) at room temperature, and then the used dropping funnel was washed with toluene (17 mL) and the washings were added to the reaction mixture. The reaction mixture was stirred at 65° C. for 21 hours, and then cooled to room temperature. After toluene (105 mL) was added to the reaction mixture and then the mixture was stirred, the organic layer was separated out. The organic layer was washed with water (175 mL), aqueous layer was removed, and then the solvent was removed out of the organic layer in vacuo. Toluene (105 mL) was added to the residue and the toluene solution was concentrated. The operation was repeated two more times to give a toluene solution of S-BBMO [38] (74.0 g, 212 mmol in theory). The given toluene solution of S-BBMO [38] was used in the next step, assuming that the yield was 100%.

A crude product of S-BBMO [38] which was prepared by the same process was evaporated to dryness and then measured about NMR and MS.

$^{1}$H-NMR (DMSO-$d_6$) δ: 7.36-7.13 (5H, m), 4.26 (1H, dd, J=6.8, 3.9 Hz), 3.72 (2H, dd, J=14.2, 6.8 Hz), 3.47-3.38 (1H, m), 3.30-3.08 (3H, m), 2.79 (1H, sext, J=6.8 Hz), 1.35 (9H, s), 0.96 (3H, d, J=6.8 Hz).

MS: m/z=280 [M+H]$^+$

Step 2

[Chem. 213]

[38] →

To the toluene solution of S-BBMO [38] (74.0 g, 212 mmol) were added toluene (200 mL), tetrahydrofuran (35 mL), and then triethylamine (25.7 g, 254 mmol) at room temperature under nitrogen atmosphere. To the mixture was added dropwise methanesulfonyl chloride (26.7 g, 233 mmol) at 0° C., and then the used dropping funnel was washed with toluene (10 mL) and the washings were added to the reaction mixture. The reaction mixture was stirred at room temperature for 2 hours and further at 65° C. for 22 hours, and then cooled to room temperature. After sodium bicarbonate water (105 mL) was added to the reaction mixture and then the mixture was stirred, the organic layer was separated out. The organic layer was washed with water (105 mL), aqueous layer was removed, and then the solvent was removed out of the organic layer in vacuo. Toluene (105 mL) was added to the residue, and the toluene solution was concentrated. The operation was repeated two more times to give a toluene solution of R-BCAB [39] (75.3 g, 212 mmol in theory). The given toluene solution of R-BCAB was used in the next step, assuming that the yield was 100%.

A crude product of R-BCAB which was prepared by the same process was evaporated to dryness and then measured about NMR and MS.

$^{1}$H-NMR (DMSO-$d_6$) δ: 7.28-7.11 (5H, m), 4.24-4.11 (1H, m), 3.80 (2H, d, J=3.6 Hz), 3.24 (2H, d, J=3.6 Hz), 2.98-2.78 (2H, m), 1.46-1.37 (12H, m).

MS: m/z=298 [M+H]$^+$

Step 3

[Chem. 214]

[39] → [40]

To the toluene solution of R-BCAB [39] (75.3 g, 212 mmol) were added tetrahydrofuran (88.0 mL) and 1,3-dimethyl-3,4,5,6-tetrahydro-2(1H)-pyrimidinone (42.0 mL) at room temperature under nitrogen atmosphere. To the resulting solution was added dropwise a solution of lithium bis(trimethylsilyl)amide/tetrahydrofuran (195 mL, 233 mmol) at 0° C., and then the used dropping funnel was washed with tetrahydrofuran (17.0 mL) and the washings were added to the reaction mixture. The reaction mixture was stirred at 0° C. for 1 hour, and then warmed to room temperature. After water (175 mL) and toluene (175 mL) were added to the reaction mixture and then the mixture was stirred, the organic layer was separated out. The resulting organic layer was washed with aqueous ammonium chloride (175 mL) and then water (175 mL), and the solvent was removed out of the organic layer in vacuo. Ethyl acetate (175 mL) was added to the residue and the ethyl acetate solution was concentrated. The operation was repeated two more times to give an ethyl acetate solution of S-MABB [40] (66.5 g, 212 mmol in theory). The given ethyl acetate solution of S-MABB was used in the next step, assuming that the yield was 100%.

A crude product of S-MABB [40] which was prepared by the same process was evaporated to dryness and then measured about NMR and MS.

$^1$H-NMR (DMSO-d$_6$) δ: 7.28-7.25 (10H, m), 3.75 (1H, d, J=12.7 Hz), 3.68 (1H, d, J=1.4 Hz), 3.66 (1H, d, J=6.7 Hz), 3.46 (2H, d, J=12.7 Hz), 3.30-3.17 (2H, m), 2.95 (1H, dd, J=6.2, 1.2 Hz), 2.77 (1H, dd, J=6.1, 2.2 Hz), 2.65-2.55 (1H, m), 2.48-2.40 (2H, m), 1.35 (9H, s), 1.35 (9H, s), 1.12 (3H, d, J=7.2 Hz), 1.09 (3H, d, J=6.2 Hz).

MS: m/z=262 [M+H]$^+$

Step 4

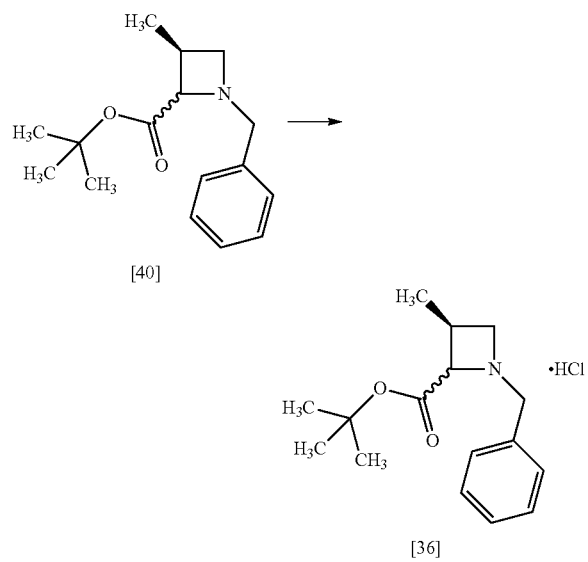

[Chem. 215]

[40]

[36]

To the ethyl acetate solution of S-MABB [40] (66.5 g, 212 mmol in theory) were added ethyl acetate (175 mL) and active carbon (3.5 g) under nitrogen atmosphere, and then the mixture was stirred at room temperature for 2 hours. The active carbon was removed by filtration, and the residue on the filter was washed with ethyl acetate (175 mL). The washings were added to the filtrate. To the solution was added S-MABB-HC crystal (17.5 mg) that was prepared according to the method described herein at 0° C., and then 4 M hydrogen chloride/ethyl acetate (53.0 mL, 212 mmol) was dropped thereto at 0° C. The reaction mixture was stirred at 0° C. for 17 hours, and then the precipitated solid was collected on a filter, and washed with ethyl acetate (70 mL). The resulting wet solid was dried in vacuo to give S-MABB-HC [36] (48.3 g, 162 mmol, yield: 76.4%).

S-MABB-HC [36] which was prepared by the same process was measured about NMR, MS, and Cl-content.

$^1$H-NMR (DMSO-d$_6$) δ: 11.08 (1H, br s), 10.94 (1H, br s), 7.52-7.42 (10H, m), 5.34 (1H, t, J=8.4 Hz), 4.90 (1H, br s), 4.45-4.10 (5H, m), 3.92-3.49 (3H, br m), 3.10-2.73 (2H, br m), 1.35 (9H, s), 1.29 (9H, s), 1.24 (3H, d, J=6.7 Hz), 1.17 (3H, d, J=7.4 Hz).

MS: m/z=262 [M+H-HCl]$^+$

Cl content (ion chromatography): 11.9% (in theory: 11.9%)

[Example 43] Preparation of S-MACB-HC (Compound [41])

[Chem. 216]

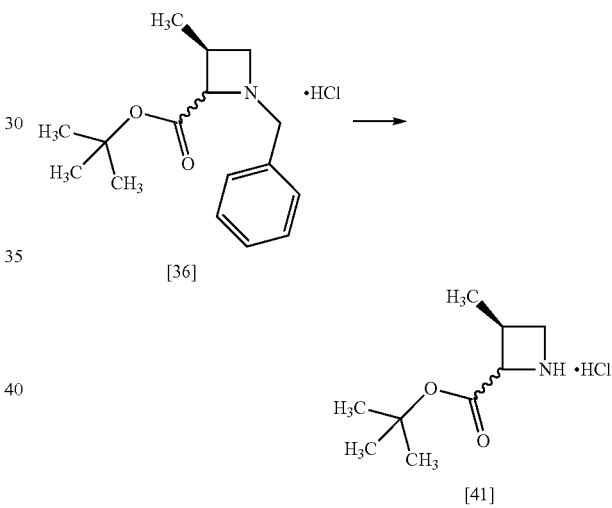

[36]

[41]

To a solution of S-MABB-HC [36] (5.0 g, 16.8 mmol) in methanol (15.0 mL) was added 5% palladium carbon (made by Kawaken Fine Chemicals Co., Ltd., PH type, 54.1% water-content 1.0 g) at room temperature under nitrogen atmosphere. The reaction vessel was filled with hydrogen, the reaction mixture was stirred at hydrogen pressure of 0.4 MPa at room temperature for 12 hours, the hydrogen in the reaction vessel was replaced with nitrogen, and then the 5% palladium carbon was removed by filtration. The reaction vessel and the 5% palladium carbon were washed with methanol (10 mL). The washings were added to the filtrate to give a methanol solution of S-MACB-HC [41](24.8 g, 16.8 mmol in theory). The given methanol solution of S-MACB-HC [41] was used in the next step, assuming that the yield was 100%.

A crude product of S-MACB-HC [41] which was prepared by the same process was evaporated to dryness and then measured about NMR and MS.

$^1$H-NMR (DMSO-d$_6$) δ: 9.60 (br s, 1H), 4.97 (d, 1H, J=9.2 Hz), 4.61 (d, 1H, J=8.4 Hz), 4.01 (dd, 1H, J=10.0, 8.4 Hz), 3.78-3.74 (m, 1H), 3.54 (dd, 1H, J=9.6, 8.4 Hz), 3.35

(dd, 1H, J=10.0, 6.0 Hz), 3.15-3.03 (m, 1H), 3.00-2.88 (m, 1H), 1.49 (s, 9H), 1.47 (s, 9H), 1.22 (d, 3H, J=6.8 Hz), 1.14 (d, 3H, J=7.2 Hz).

MS: m/z=172 [M+H]$^+$ (free form)

[Example 44] Preparation of S-ZMAB (Compound [42])

[Chem. 217]

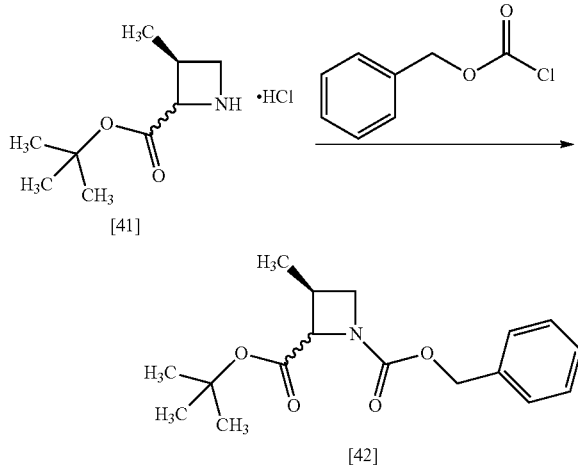

To the methanol solution of S-MACB-HC [41] (24.8 g, 16.8 mmol in theory) was added dropwise N,N-diisopropylethylamine (4.8 g, 36.9 mmol) at room temperature under nitrogen atmosphere, and then the used dropping funnel was washed with tetrahydrofuran (2.5 mL) and the washings were added to the reaction mixture. To the resulting reaction mixture was added dropwise benzyl chloroformate (3.0 g, 17.6 mmol) at 0° C., and then the used dropping funnel was washed with tetrahydrofuran (2.5 mL) and the washings were added to the reaction mixture. The reaction mixture was stirred at 0° C. for 1 hour, and then the solvent was removed in vacuo. After toluene (25.0 mL) and an aqueous solution of citric acid (25.0 mL) was added to the residue and then the mixture was stirred, the organic layer was separated out. The resulting organic layer was washed with sodium bicarbonate water (25.0 mL) and then water (25.0 mL), and the solvent in the organic layer was removed out of the organic layer in vacuo. Toluene (15.0 mL) was added to the residue and the toluene solution was concentrated. The operation was repeated one more time to give a toluene solution of S-ZMAB [42] (6.9 g, 16.8 mmol in theory). The given toluene solution of S-ZMAB [42] was used in the next step, assuming that the yield was 100%.

A crude product of S-ZMAB [42] which was prepared by the same process was evaporated to dryness and then measured about NMR and MS.

$^1$H-NMR (CDCl$_3$) δ: 7.38-7.28 (m, 10H), 5.16-5.04 (m, 4H), 4.60 (d, 1H, J=9.2 Hz), 4.18-4.12 (m, 2H), 4.04 (t, 1H, J=8.6 Hz), 3.66 (dd, 1H, J=7.6, 7.2 Hz), 3.50 (dd, 1H, J=8.0, 5.2 Hz), 3.05-2.94 (m, 1H), 2.60-2.50 (m, 1H), 1.43 (br s, 18H), 1.33 (d, 3H, J=6.5 Hz), 1.15 (d, 3H, J=7.2 Hz).

MS: m/z=328 [M+Na]$^+$

[Example 45] Preparation of RS-ZMBB (Compound [43])

[Chem. 218]

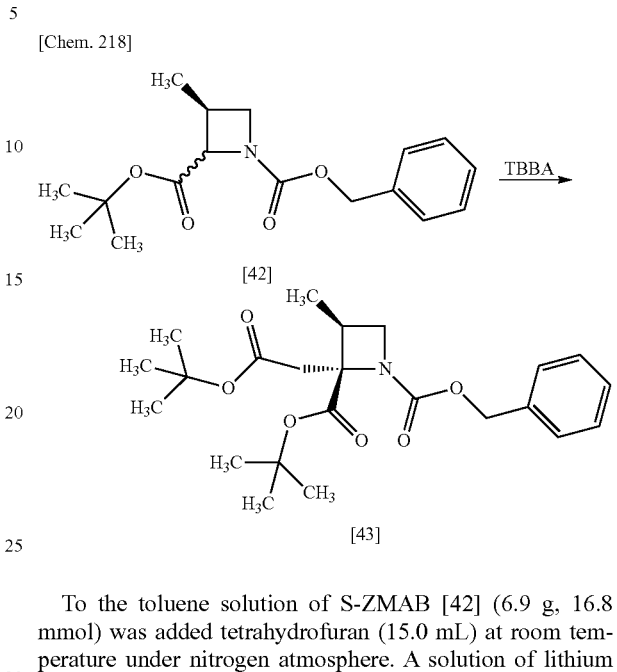

To the toluene solution of S-ZMAB [42] (6.9 g, 16.8 mmol) was added tetrahydrofuran (15.0 mL) at room temperature under nitrogen atmosphere. A solution of lithium bis(trimethylsilyl)amide/tetrahydrofuran (14.7 mL, 17.6 mmol) was added dropwise to the toluene solution at −70° C. The used dropping funnel was washed with tetrahydrofuran (2.5 mL) and the washings were added to the reaction mixture. The reaction mixture was stirred at −70° C. for 6 hours, and then a solution of TBBA (3.4 g, 17.6 mmol) in tetrahydrofuran (2.5 mL) was added dropwise to the reaction mixture at −70° C. The used dropping funnel was washed with tetrahydrofuran (2.5 mL) and the washings were added to the reaction mixture. The reaction mixture was stirred at −70° C. for 1 hour, and then warmed to room temperature. To the reaction mixture were added an aqueous ammonium chloride (25 mL) and toluene (25 mL) and then the mixture was stirred, the organic layer was separated out. The resulting organic layer was washed with an aqueous solution of citric acid (25 mL×2), sodium bicarbonate water (25 mL), and then water (25 mL), and then the solvent was removed out of the organic layer in vacuo. Acetonitrile (15 mL) was added to the residue and the acetonitrile solution was concentrated. The operation was repeated two more times. Acetonitrile (15 mL) and active carbon (0.25 g) were added to the residue, the mixture was stirred at room temperature for 2 hours. The active carbon was removed by filtration, and the reaction vessel and the residue on the filter was washed with acetonitrile (10 mL). The washings were added to the filtration, and then the filtration was concentrated in vacuo to give an acetonitrile solution of RS-ZMBB [43] (13.2 g, 16.8 mmol in theory). The given acetonitrile solution of RS-ZMBB [43] was used in the next step, assuming that the yield was 100%.

A crude product of RS-ZMBB [43] which was prepared by the same process was evaporated to dryness and then measured about NMR and MS.

$^1$H-NMR (DMSO-d$_6$) δ: 7.38-7.29 (m, 5H), 5.09-4.96 (m, 2H), 3.91 (t, 0.4H, J=8.0 Hz), 3.79 (t, 0.6H, J=8.0 Hz), 3.55 (t, 0.4H, J=7.2 Hz), 3.46 (t, 0.6H, J=7.5 Hz), 3.14-3.04 (m,

1H), 2.83-2.72 (m, 2H), 1.38 (br s, 9H), 1.37 (br s, 3.6H), 1.34 (br s, 5.4H), 1.12-1.09 (m, 3H).

MS: m/z=420 [M+H]⁺

[Example 46] Preparation of RS-ZMAA-DN·2H₂O (Compound [44])

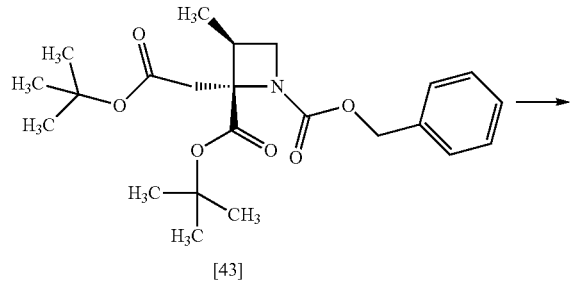

[43]

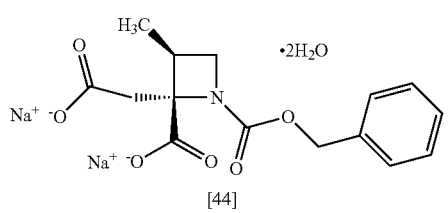

[44]

To the acetonitrile solution of RS-ZMBB [43] (13.2 g, 16.8 mmol in theory) was added acetonitrile (15 mL) at room temperature under nitrogen atmosphere. p-Toluenesulfonic acid mono-hydrate (6.4 g, 33.6 mmol) was added to the solution at room temperature. The reaction mixture was stirred at 50° C. for 12 hours, and then cooled to room temperature, and water (7.5 mL) was added dropwise to the reaction mixture. The reaction mixture was cooled to 0° C., and then 4 mol/L aqueous sodium hydroxide (17.6 mL, 70.5 mmol) was added dropwise thereto. After stirring the reaction mixture at room temperature for 1 hour, acetonitrile (75 mL) was added dropwise thereto at room temperature, and the reaction mixture was stirred for 3 hours. The precipitated solid was collected on a filter, and washed with a mixture of acetonitrile:water=4:1 (10 mL) and then acetonitrile (10 mL). The resulting wet solid was dried in vacuo to give RS-ZMAA-DN·2H₂O [44] (5.2 g, 13.4 mmol, yield: 85.4%).

RS-ZMAA-DN·2H₂O [44] which was prepared by the same process was measured about NMR, MS, Na-content, and water-content.

¹H-NMR (DMSO-d₆) δ: 7.32-7.22 (m, 5H), 4.97 (d, 1H, J=12.7 Hz), 4.84 (d, 1H, J=12.7 Hz), 3.79 (t, 1H, J=8.0 Hz), 3.29 (d, 1H, J=14.8 Hz), 3.16-3.12 (m, 1H), 2.17-2.09 (m, 2H), 1.07 (d, 3H, J=6.9 Hz).

MS: m/z=352 [M+H]⁺ (anhydrate)

Na content (ion chromatography): 13.3% (after correction of water content) (13.1% in theory)

Water content (Karl Fischer's method): 9.8% (9.3% in theory)

[Example 47] Preparation of RS-ZMAA (Compound [45])

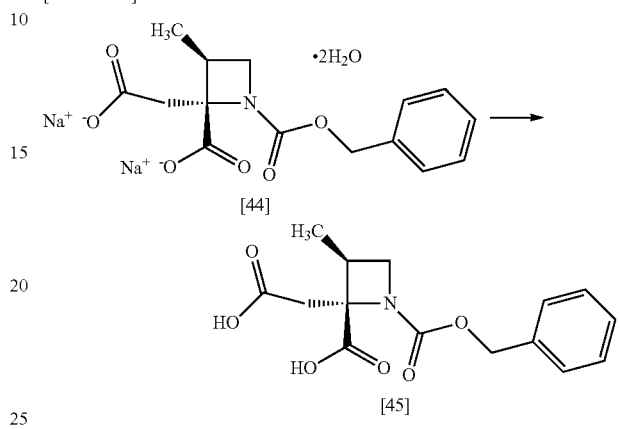

[44]

[45]

To 1 mol/L hydrochloric acid (180 mL) were added RS-ZMAA-DN·2H₂O [44] (30 g, 77.5 mmol) and acetonitrile (60 mL), and the mixture was stirred at room temperature for about 15 minutes. After ethyl acetate (240 mL) was added to the reaction mixture and then the mixture was stirred, the organic layer was separated out. The organic layer was washed with 10% brine (60 mL×2). The organic layer was stirred with magnesium sulfate (6 g), the magnesium sulfate was removed by filtration, and the residue on the filter was washed with ethyl acetate (60 mL). The filtrate and the washings are combined, and the solvent was removed out in vacuo. Tetrahydrofuran (240 mL) was added to the residue and the tetrahydrofuran solution was concentrated. The operation was repeated two more times. Tetrahydrofuran (60 mL) was added to the residue to give a tetrahydrofuran solution of RS-ZMAA [45]. The given tetrahydrofuran solution of RS-ZMAA [45] was used in the next step, assuming that the yield was 100%.

RS-ZMAA [45] which was prepared by the same process was measured about NMR and MS.

¹H-NMR (DMSO-D₆) δ: 7.35-7.28 (m, 5H), 5.06-4.94 (m, 2H), 3.86 (dt, 1H, J=48.4, 7.9 Hz), 3.50 (dt, 1H, J=37.9, 7.4 Hz), 3.16-3.02 (br m, 1H), 2.91-2.77 (br m, 2H), 1.08 (d, 3H, J=6.9 Hz)

MS: m/z=308 [M+H]⁺

[Example 48] Preparation of RS-ZMOO (Compound [46])

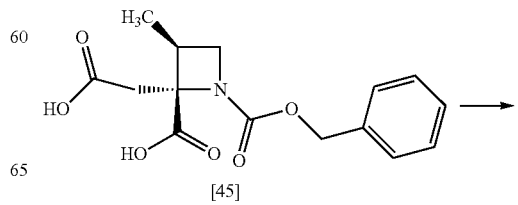

[45]

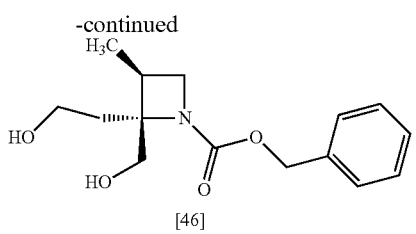

[46]

To the tetrahydrofuran solution of RS-ZMAA [45] (25.8 mmol in theory) was added tetrahydrofuran (50 mL) under nitrogen atmosphere. Boron trifluoride etherate complex (4.40 g) was added dropwise thereto at 0° C. to 5° C. The used dropping funnel was washed with tetrahydrofuran (5 mL) and the washings were added to the reaction mixture. To the reaction mixture was added dropwise 1.2 mol/L borane-tetrahydrofuran complex (43.0 mL) at 0° C. to 5° C., and the reaction mixture was stirred at 0° C. to 5° C. for about 30 minutes, and then further stirred at room temperature overnight. To the reaction mixture was added dropwise 1.2 mol/L borane-tetrahydrofuran complex (21.1 mL) at 0° C. to 5° C., and then the reaction mixture was stirred at room temperature overnight. After stirring, water (40 mL) was added dropwise to the reaction mixture at 0° C. to 15° C. To the reaction mixture was added sodium bicarbonate (5.42 g) at 0° C. to 15° C. The sodium bicarbonate left in the vessel was washed with water (10 mL), and the washings were added to the reaction mixture. The reaction mixture was stirred at room temperature for 2 hours, and then toluene (50 mL) was added thereto and the reaction mixture was further stirred. The organic layer was separated out. The resulting organic layer was washed with 10% brine (20 mL×1), a mixture (×3) of 5% sodium bicarbonate water (20 mL) and 10% brine (20 mL), a mixture (×1) of 5% aqueous potassium hydrogensulfate (10 mL) and 10% brine (10 mL), and then 10% brine (20 mL×2). The organic layer was stirred with magnesium sulfate (8.9 g), the magnesium sulfate was removed by filtration, and the residue on the filter was washed with toluene (20 mL). The washings were added to the filtration, and then the filtrate was concentrated in vacuo. To the concentrated residue was added toluene (80 mL). The solution was concentrated in vacuo, and toluene (15 mL) was added thereto to give a toluene solution of RS-ZMOO [46]. The given toluene solution of RS-ZMOO [46] was used in the next step, assuming that the yield was 100%.

RS-ZMOO [46] which was prepared by the same process was measured about NMR and MS.

$^1$H-NMR (CDCl$_3$) δ: 7.39-7.30 (m, 5H), 5.10 (s, 2H), 4.15-4.01 (br m, 2H), 3.83-3.73 (br m, 3H), 3.48 (dd, 1H, J=8.3, 6.4 Hz), 2.59-2.50 (br m, 1H), 2.46-2.40 (br m, 1H), 2.07-1.99 (m, 1H), 1.14 (d, 3H, J=7.2 Hz)

MS: m/z=280 [M+H]$^+$

[Example 49] Preparation of RS-ZMSS (Compound [47])

[Chem. 222]

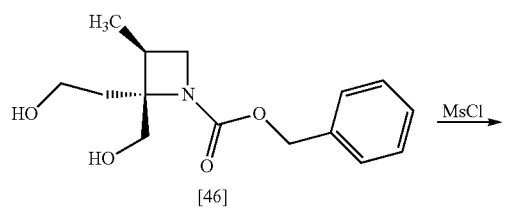

[46] MsCl→

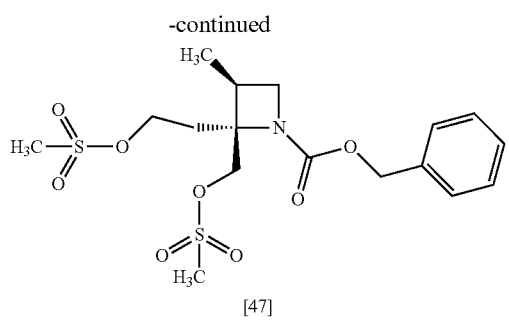

[47]

To the toluene solution of RS-ZMOO [46] (23.7 mmol in theory) was added toluene (55 mL) under nitrogen atmosphere. And, triethylamine (5.27 g) was added dropwise thereto at −10° C. to 10° C., and the used dropping funnel was washed with toluene (1.8 mL) and the washings were added to the reaction mixture. To this reaction mixture was added dropwise methanesulfonyl chloride (5.69 g) at −10° C. to 10° C., and then the used dropping funnel was washed with toluene (1.8 mL) and the washings were added to the reaction mixture. The reaction mixture was stirred at 0° C. to 10° C. for about 2 hours, and then water (28 mL) was added dropwise thereto at 0° C. to 20° C. The reaction mixture was stirred at 0° C. to 20° C. for about 30 minutes, and then, the organic layer was separated out. The resulting organic layer was washed twice with 10% brine (18 mL). The organic layer was stirred with magnesium sulfate (2.75 g), the magnesium sulfate was removed by filtration, and the residue on the filter was washed with toluene (18 mL). The washings were added to the filtrate, and then the solvent was removed from the filtrate in vacuo. To the concentrated residue was added toluene up to 18 mL to give a toluene solution of RS-ZMSS [47]. The given toluene solution of RS-ZMSS [47] was used in the next step, assuming that the yield was 100%.

RS-ZMSS [47] which was prepared by the same process was measured about NMR and MS.

$^1$H-NMR (DMSO-D$_6$) δ: 7.37-7.27 (br m, 5H), 5.10-4.98 (m, 2H), 4.58-4.22 (br m, 4H), 3.84 (dt, 1H, J=45.6, 8.1 Hz), 3.48-3.33 (br m, 1H), 3.17-3.10 (m, 6H), 2.81-2.74 (br m, 1H), 2.22-2.12 (m, 2H)

MS: m/z=436 [M+H]$^+$

[Example 50] Preparation of SR-ZMDB (Compound [28])

[Chem. 223]

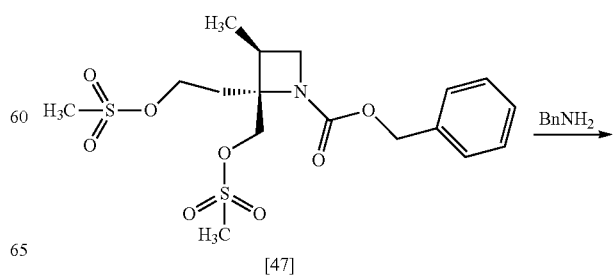

[47] BnNH$_2$→

-continued

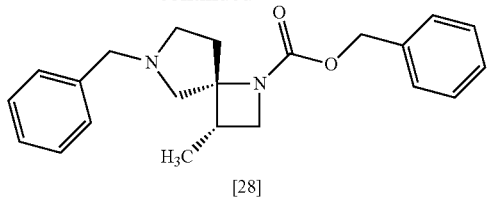

[28]

To a toluene solution of RS-ZMSS [47] (23.7 mmol in theory) was added toluene (55 mL) under nitrogen atmosphere. And, benzylamine (17.8 g) was added dropwise thereto at room temperature, and the used dropping funnel was washed with toluene (9.2 mL) and the washings were added to the reaction mixture. The reaction mixture was stirred at room temperature for about 1 hour, at 55° C. to 65° C. for about 3 hours, and then at 70° C. to 80° C. for 6 hours. After the reaction mixture was cooled to room temperature, 10% NaCl (28 mL) was added dropwise thereto, and the reaction mixture was stirred at room temperature for about 30 minutes. After toluene (37 mL) was added to the reaction mixture and then the mixture was stirred, the organic layer was separated out. The resulting organic layer was washed with a mixture (×2) of 10% brine (18 mL) and acetic acid (2.84 g), and then 10% brine (11 mL×1). The solvent of the organic layer was removed in vacuo to a half volume, and acetic anhydride (1.45 g) was added to the concentrated residue at room temperature. The mixture was stirred for about 3 hours. To the reaction mixture were added dropwise a solution of potassium hydrogensulfate (3.87 g) and water (92 mL) at room temperature. The reaction mixture was stirred, and then the aqueous layer was separated out. The resulting aqueous layer was washed with toluene (18 mL), and toluene (73 mL) and then sodium bicarbonate (6.56 g) were added to the aqueous layer at room temperature, and the mixture was stirred. The organic layer was separated out, and washed with 10% brine (11 mL). The organic layer was stirred with magnesium sulfate (2.75 g), the magnesium sulfate was removed by filtration. The residue on the filter was washed with toluene (18 mL), and the washings were added to the filtrate, and then the filtrate was concentrated in vacuo. Toluene (44 mL) was added to the concentrated residue to give a toluene solution of SR-ZMDB [28]. The given toluene solution of SR-ZMDB [28] was used in the next step, assuming that the yield was 100%.

$^1$H-NMR (CDCl$_3$) δ: 7.35-7.20 (m, 10H), 5.08 (d, 2H, J=23.6 Hz), 3.94 (q, 1H, J=7.9 Hz), 3.73-3.42 (br m, 2H), 3.30-3.23 (m, 1H), 3.05 (dd, 1H, J=19.7, 9.5 Hz), 2.79 (dt, 1H, J=69.6, 6.1 Hz), 2.57-2.32 (br m, 4H), 1.96-1.89 (m, 1H), 1.09 (d, 3H, J=6.9 Hz)

MS: m/z=351 [M+H]$^+$

INDUSTRIAL APPLICABILITY

The compounds of the present invention are useful as synthetic intermediates for preparing Compound A (Compound [17]). The processes for preparation in the present invention provide a method for stably preparing Compound A (Compound [17]) in a good chemical and optical purity. The processes for preparation in the present invention stably provide Compound A (Compound [17]) in a good yield, and are also useful for an industrially large scale synthesis. The processes for preparation of synthetic intermediates of Compound A (Compound [17]) in the present invention provide a method for stably preparing RR-MDDO and SR-MDBN-DSU, the synthetic intermediates of Compound A (Compound [17]), in a good chemical and optical purity.

The invention claimed is:
1. A process for preparing a compound of formula [17]:

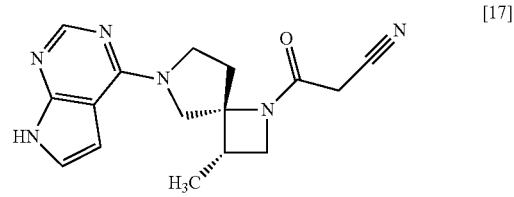 [SMILES: C[C@H]1CN(C(=O)CC#N)[C@]12CCN(c1ncnc3[nH]ccc13)C2]

[17]

or its salt with using a compound of formula [31]:

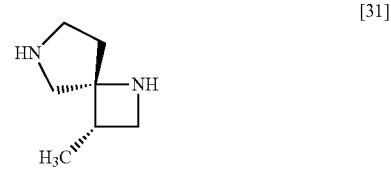

[31]

or its salt with an organic acid, comprising the following steps of:
(1) reacting a compound of formula [31] or its salt with an organic acid with a compound of formula [12]:

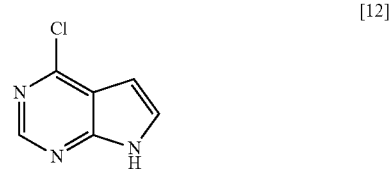

[12]

or its salt to give a compound of formula [14]:

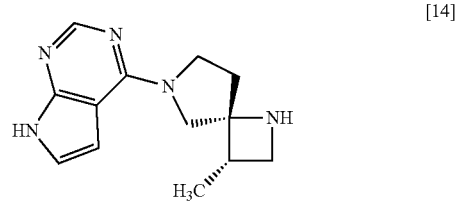 [SMILES: C[C@H]1CN[C@]12CCN(c1ncnc3[nH]ccc13)C2]

[14]

or its salt; and
(2) cyanoacetylating a compound of formula [14] or its salt to give a compound of formula [17] or its salt.
2. The process of claim 1, further comprising the step of adding an organic acid to a compound of formula [31] to give a salt of a compound of formula [31] with an organic acid.
3. The process of claim 1, wherein the salt with an organic acid is a disuccinate or an oxalate.
4. The process of claim 1, further comprising the step of obtaining a compound of formula [31] or its salt with an organic acid from a compound of formula [28]:

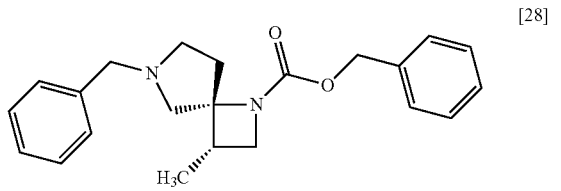 [SMILES: C[C@H]1CN(C(=O)OCc2ccccc2)[C@]12CCN(Cc1ccccc1)C2] [28]
or its salt with an organic acid.
5. The process of claim 4, further comprising the step of adding an organic acid to a compound of formula [28] to give a salt of a compound of formula [28] with an organic acid.
6. The process of claim 5, wherein the salt of a compound of formula [28] with an organic acid is an oxalate.
* * * * *